US008669050B2

(12) United States Patent
James et al.

(10) Patent No.: US 8,669,050 B2
(45) Date of Patent: Mar. 11, 2014

(54) NUCLEIC ACID MARKERS FOR USE IN DETERMINING PREDISPOSITION TO NEOPLASM AND/OR ADENOMA

(75) Inventors: Robert James, Wattle Park (AU); Julianne Henry, McLaren Flat (AU); Jan Kazenwadel, Belair (AU); Nick Van Host Pellekaan, Greenhill (AU); Anne MacPherson, Kingswood (AU); Susan O'Connor, Prospect (AU)

(73) Assignee: Clinical Genomics Pty. Ltd., New South Wales (AU)

( * ) Notice: Subject to any disclaimer, the term of this patent is extended or adjusted under 35 U.S.C. 154(b) by 394 days.

(21) Appl. No.: 10/800,322

(22) Filed: Mar. 12, 2004

(65) Prior Publication Data

US 2005/0053967 A1    Mar. 10, 2005

Related U.S. Application Data

(63) Continuation of application No. PCT/AU02/01258, filed on Sep. 13, 2002.

(60) Provisional application No. 60/322,288, filed on Sep. 14, 2001.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

| 5,702,886 A | 12/1997 | Vogelstein et al. |
| 2003/0235820 A1 | 12/2003 | Mack et al. |
| 2004/0038220 A1* | 2/2004 | Markowitz ........................ 435/6 |
| 2005/0233353 A1 | 10/2005 | Markowitz |
| 2006/0134668 A1 | 6/2006 | Markowitz |

FOREIGN PATENT DOCUMENTS

| WO | WO 00/37643 | | 6/2000 |
| WO | 00/55180 A2 | | 9/2000 |
| WO | 00/73348 A2 | | 12/2000 |
| WO | 01/02568 A2 | | 1/2001 |
| WO | 01/22920 A2 | | 4/2001 |
| WO | WO 01/49870 A2 | * | 7/2001 |
| WO | WO 0149875 | | 7/2001 |
| WO | 02/29086 A2 | | 4/2002 |
| WO | WO 02/40720 | | 5/2002 |
| WO | PCT/AU02/01258 | * | 9/2002 |
| WO | WO 02068677 | | 9/2002 |

OTHER PUBLICATIONS

Resnick et al., 1999, Molecular Diagnosis, 4: 219-232).*
Schmittgen et al., 2003, Int. J. Cancer 107: 323-329.*
Loisseau et al., Neuroscience Letter, 1999, 263: 173-176.*
Hoshikawa et al. Physical Genomics, vol. 12, pp. 209-219, 2003.*
Chan. Integrating Transcriptomics and Proteomics. 2007. pp. 1-5. Obtained from www.genpromag.com on Mar. 10, 2007.*
Blast 2 Sequences results comparing instant SEQ ID No. 7 to gi: 38638697, KIAA1199 mRNA.*
GenBank record NM_018689, dated Feb. 10, 2008, *Homo sapiens* KIAA1199, mRNA, GI: 38638697.*
Blast 2 Sequences results comparing instant SEQ ID No. 7 to gi: 6330400, *Homo sapiens* mRNA for KIAA1199 protein.*
GenBank record AB033025, dated Nov. 11, 1999, *Homo sapiens* mRNA for KIAA1199 protein, partial cds.*
NCBI Map Viewer. Map of chromosome 15, region displayed 78831K-78931K; printed from www.ncbi.nlm.nih.gov on Feb. 18, 2009. 2 pages.*
Blast results. SEQ ID No. 7 versus GenBank AB0330025. printed from blast.ncbi.nlm.nih.gov on Feb. 18, 2009, 1 page.*
Blast 2 Sequences results comparing instant SEQ ID No. 7 to gi: 38638697, KIAA1199 mRNA; obtained May 20, 2008.*
Blast 2 Sequences results comparing instant SEQ ID No. 7 to gi: 6330400, *Homo sapiens* mRNA for KIAA1199 protein; obtained May 20, 2008.*
GenBank Accession No. AC012324.7, *Homo sapiens* chromosome 16 clone RP11-92P14 (2001).
GenBank Accession No. AC079240.6, *Homo sapiens* chromosome 4 clone RP11-808H17 (2001), Waterston R.H.
GenBank Accession No. AC004024.2, *Homo sapiens* 12q24.2 PAC RPCI1-128M12 (2000), Muzny D. et al.
GenBank Accession No. AF117829.1, *Homo sapiens* 8q21:3: RICK gene (1999), Platzer M. et al.

(Continued)

*Primary Examiner* — Juliet Switzer
(74) *Attorney, Agent, or Firm* — Scully, Scott, Murphy & Presser, P.C.

(57) ABSTRACT

The present invention relates generally to novel nucleic acid molecules, the levels and/or patterns of expression of which are indicative of the onset, predisposition to the onset and/or progression of a neoplasm and to derivatives, homologues or analogues of said molecules. More particularly, the present invention is directed to novel nucleic acid molecules, the levels of expression of which are indicative of the onset and/or progression of a gastrointestinal tract neoplasm, such as an adenoma, and to derivatives, homologues or analogues of said molecules. The present invention is further directed to isolated proteins encoded thereby and to derivatives, homologues, analogues, chemical equivalents and mimetics thereof. The molecules of the present invention are useful in a range of prophylactic, therapeutic and/or diagnostic applications including, but not limited to, those relating to the diagnosis and/or treatment of colorectal neoplasms such as colorectal adenomas. In a related aspect, the present invention is directed to a method of screening a subject for the onset, predisposition to the onset and/or progression of a neoplasm by screening for modulation in the level of expression of one or more nucleic acid molecule markers.

14 Claims, 4 Drawing Sheets

(56) References Cited

OTHER PUBLICATIONS

GenBank Accession No. AC004459.1, *Homo sapiens* BAC clone CTA-273G1 from 8q21 (2000), Bradshaw H. et al.
GenBank Accession No. AC023302.5, *Homo sapiens* clone RP11-28H5 (2001), Birren B. et al.
GenBank Accession No. AL138715.11, Human DNA sequence from clone RP11-77P19 on chromosome 13 (2000), Blakey S.
GenBank Accession No. AP000542.1, *Homo sapiens* genomic DNA, chromosome 22q11.2, Cat eye syndrome region (2000), Shimizu N.
GenBank Accession No. AC023150.5, *Homo sapiens* chromosome 4 clone RP11-709L9 (2001), Waterston R.H.
GenBank Accession No. AC008381.8, *Homo sapiens* chromosome 5 clone CTC-216O13 (2001).
GenBank Accession No. AF345934.1, *Homo sapiens* regenerating gene type IV mRNA (2001), Violette S. et al.
Hartupee J.C. et al., "Isolation and Characterization of a cDNA Encoding a Novel Member of the Human Regenerating Protein Family: Reg IV¹", *Biochimica et Biophysica Acta* 1518(3):287-293 (2001).
GenBank Accession No. NM_032044.1, *Homo sapiens* regenerating gene type IV (REG-IV) (2001), Hartupee J.C. et al.
Shinozaki S. et al., "Upregulation of Reg 1α and GW112 in the Epithelium of Inflamed Colonic Mucosa", *Gut* 48(5):623-629 (2001).
GenBank Accession No. NM_006418.2, *Homo sapiens* differentially expressed in hematopoietic lineages (GW112) (2001), Shinozaki S. et al.
GenBank Accession No. NM_001046.1, *Homo sapiens* solute carrier family 12 (sodium/potassium/chloride transporters), member 2 (SLC12A2) (2000), Payne J.A. et al.
Payne J.A. et al., "Primary Structure, Functional Expression, and Chromosomal Localization of the Bumetanide-Sensitive Na—K—Cl Contransporter in Human Colon", *The Journal of Biological Chemistry* 270(30):17977-17985 (1995).
GenBank Accession No. AC007860.6, *Homo sapiens* 12p13 BAC RPCI11-709E21 (1999), Muzny D. et al.
GenBank Accession No. AC012519.9, *Homo sapiens* 3 BAC RP11-1036F1 (2000), Muzny D. et al.
GenBank Accession No. AJ238592.1, *Homo sapiens* SLAP gene promoter region (1999), Witter K. et al.
GenBank Accession No. AF235100.3, *Homo sapiens* chromosome 8 map 8q24.3 PAC RP6-98A24 containing part of the thyroglobulin (TG) gene and part of the gene fro Src-like adapter protein (2000), Blechschmidt K. et al.
GenBank Accession No. AC004687.1, *Homo sapiens* chromosome 17, clone lhRPC.1171_I_10 (1998), B. et al.
GenBank Accession No. AL049766.14, Human DNA sequence from clone RP4-686N3 on chromosome 20q13.2-13. Contains the 3' part of the gene for a novel ATP dependent RNA helicase (contains conserved C-terimal helicase domains and DEAD/DEAH boxes), the KIAA1404 gene (2001), Corby N.
GenBank Accession No. AP000866.4, *Homo sapiens* genomic DNA, chromosome 11q, clone:RP11-677M14 (2001), Hattori M. et al.
GenBank Accession No. AK022999.1, *Homo sapiens* cDNA FLJ12937 fis, clone NT2RP2005020 (2000), Isogai T. et al.
GenBank Accession No. AL050021.1, *Homo sapiens* mRNA, cDNA DKFZp564D016 (from clone DKFZp564D016) (2000), Wambutt R. et al.
GenBank Accession No. AK023154.1, *Homo sapiens* cDNA FLJ13092 fis, clone NT2RP3002147 (2000), Isogai T. et al.
EMBL Accession No. AC013410.5, *Homo sapiens* BAC clone RP11-495I2 from 2 (2001), Edwards J. et al.
EMBL Accession No. AL445248.7, Human DNA sequence from clone RP11-277A4 on chromosome 1 (2000), Cobley V.
EMBL Accession No. AL078591.18, Human DNA sequence from clone RP1-19819 on chromosome 6q12-13. Contains the gene KIAA1411 (2000), Babbage A.
EMBL Accession No. L13616.1, Human focal adhesion kinase (FAK) mRNA (1994), Whitney G.S. et al.

Whitney G.S. et al., "Human T and B Lymphocytes Express a Structurally Conserved Focal Adhesion Kinase pp125FAK", *DNA and Cell Biology* 12(9):823-830 (1993).
Tommerup N. et al., "Isolation and Fine Mapping of 16 Novel Human Zinc Finger-Encoding cDNAs Identify Putative Candidate Genes for Developmental and Malignant Disorders", *Genomics* 27(2):259-264 (1995).
EMBL Accession No. U09848.1, Human zinc finger protein (NF139) mRNA (1995), Tommerup N. et al.
Zendman A.J.W. et al., "TM7XN1, a Novel Human EGF-TM7-Like cDNA, Detected with mRNA Differential Display Using Human Melanoma Cell Lines with Different Metastatic Potential", *FEBS Letter* 446(2-3):292-298 (1999).
GenBank Accession No. AJ011001.1, *Homo sapiens* mRNA for TM7XN1 protein (1999), Zendman A.J. et al.
EMBL Accession No. AK025080.1, *Homo sapiens* cDNA: FLJ21427 fis, clone COL04177 (2000), Sugano S. et al.
EMBL Accession No. AK025039.1, *Homo sapiens* cDNA: FLJ21386 fis, clone COL03414 (2000), Sugano S. et al.
GenBank Accession No. XM_015882.1, *Homo sapiens* hypothetical protein FLJ22792 (FLJ22792) (2001).
EMBL Accession No. Z99943.1, Human DNA sequence from PAC 313L4 on chromosome 1q24 (1999), Pearce A.
EMBL Accession No. AK024700.1, *Homo sapiens* cDNA: FLJ21047 fis, clone CAS00253 (2000), Sugano S. et al.
GenBank Accession No. NM_001675.1, *Homo sapiens* activating transcription factor 4 (tax-responsive enhancer element B67) (ATF4) (2000), Tsujimoto A. et al.
Tsujimoto A. et al., "Isolation of cDNAs for DNA-Binding Proteins Which Specifically Bind to a Tax-Responsive Enhancer Element in the Long Terminal Repeat of Human T-Cell Leukemia Virus Type I", *Journal of Virology* 65(3):1420-1426 (1991).
Karpinski B.A. et al., "Molecular Cloning of Human CREB-2: An ATF/CREB Transcription Factor that Can Negatively Regulate Transcription from the cAMP Response Element", *Proceedings of the National Academy of Sciences USA* 89:4820-4824 (1992).
EMBL Accession No. AC022489.7, *Homo sapiens* chromosome 4 clone RP11-671P3 from 4, (2001), Waterston R.H.
GenBank Accession No. AL356738.4, *Homo sapiens* chromosome X clone RP13-228121, (2001), Mclay K.
GenBank Accession No. AC005829.1, *Homo sapiens* chromosome 17, clone hRPK.259_G_18 (1998), Birren B. et al.
Bast, Jr. R.C. et al., "2000 Update of Recommendations for the Use of Tumor Markers in Breast and Colorectal Cancer: Clinical Practice Guidelines of the American Society of Clinical Oncology", *Journal of Clinical Oncology* 19(6):1865-1878 (2001).
Van Laethem J.L., "Use of Genetic Markers During Endoscopic Screening and Follow-Up of Gastrointestinal Precancerous Lesions", *Acta Gastro-Enterologica Belgica* 58(2):187-192 (1995).
SEQ ID No. 13 of PCT International Publication No. WO 00/55371, published Sep. 21, 2000.
SEQ ID No. 17 of PCT International Publication No. WO 00/76530, published Dec. 21, 2000.
SEQ ID No. 7050 of PCT International Publication No. WO 01/075067, published Oct. 11, 2001.
SEQ ID Nos. 1047 and 3703 of PCT International Publication No. WO 99/38972, published Aug. 5, 1999.
U.S. Appl. No. 60/272,206, filed Feb. 27, 2001, Mack, et al.
U.S. Appl. No. 60/281,149, filed Apr. 2, 2001, Mack, et al.
U.S. Appl. No. 60/284,555, filed Apr. 17, 2001, Mack, et al.
Willis, A.E., "Translational Control of Growth Factor and Proto-Oncogene Expression" The International Journal of Biochemistry and Cell Biology (Jan. 1999) pp. 73-86, vol. 31, No. 1.
Van Der Veldon, A.W. et al., "The Role of the 5' Untranslated region of an mRNA in Translation Regulation During Development" The International Journal of Biochemistry and Cell Biology (Jan. 1999) pp. 87-106, vol. 31, No. 1.
Chou, K.C., "Prediction of Protein Signal Sequences and Their Cleavage Sites" Proteins: Structure, Function, and Genetics (Jan. 2001) pp. 136-139, vol. 42, No. 1.
Kopreski, M.S. et al., "Detection of Tumor Messenger RNA in the Serum of Patients with Malignant Melanoma" Clinical Cancer Research (Aug. 1999) pp. 1961-1965, vol. 5.

(56) References Cited

OTHER PUBLICATIONS

Hasselman, D.O. et al, "Detection of Tumor-Associated Circulating mRNA in Serum, Plasma and Blood Cells from Patients with Disseminated Malignant Melanoma" Oncology Reports (2001) pp. 115-118, vol. 8.

Sozzi, G. et al., "Analysis of Circulating Tumor DNA in Plasma at Diagnosis and During Follow-Up of Lung Cancer Patients" Cancer Research (Jun. 15, 2001) pp. 4675-4678, vol. 61.

Chou, K.C., "Prediction of Signal Peptides Using Scaled Window" Peptides (2001) pp. 1973-1979, vol. 22.

Gygi, S.P. et al., "Correlation Between Protein and mRNA Abundance in Yeast" Molecular and Cellular Biology (Mar. 1999) pp. 1720-1730, vol. 19, No. 3.

Mignone, F. et al., "Untranslated Regions of mRNAs" Genome Biology (2002) pp. 1-10, vol. 3, No. 3.

Eddy, S.R., "Non-Coding RNA Genes and the Modern RNA World" Nature Reviews Genetics (Dec. 2001) pp. 919-929, vol. 2, issue 12.

Chan, E.C. et al., "Identification of Novel Genes that are Differentially Expressed in Human Colorectal Carcinoma" Biochemica at Biophysica Acta (Sep. 30, 1998) pp. 200-204, vol. 1407, No. 3.

Tanaka, M. et al., "Human Calgizzarin; One Colorectal Cancer-related Gene Selected by a Large Scale Random cDNA Sequencing and Northern Blot Analysis" Cancer Letters (1995) pp. 195-200, vol. 89, No. 2.

EMBL Database Accession No. AC023150, "*Homo sapiens* BAC Clone RP11-709L9 from 4, Complete Sequence" (Feb. 14, 2000) XP002630967, 2 pages.

EMBL Database Accession No. AF097021, "*Homo sapiens* GW112 Protein (GW112) mRNA, Complete cds" (Nov. 12, 1998) XP002631418, 2 pages.

Partial European Search Report dated Apr. 4, 2011 issued in corresponding European Application No. EP 10 18 1428.3, 3 pages.

European Search Report dated Apr. 1, 2011 issued in corresponding European Application No. EP 10 18 1375.6, 4 pages.

European Search Report dated Apr. 21, 2011 issued in corresponding European Application No. EP 10 18 1372.3, 4 pages.

European Search Report dated Apr. 11, 2011 issued in corresponding European Application No. EP 10 18 1361.6, 4 pages.

European Search Report dated Apr. 7, 2011 issued in corresponding European Application No. EP 10 18 1360.8, 4 pages.

\* cited by examiner

SEQUENCE LISTING

<160> NUMBER OF SEQ ID NOS: 338

<210> SEQ ID NO 1
<211> LENGTH: 289
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 1
aatcaaactc gaactcagga ttaagaatct cactcaaanc ngctcaacta catggaaact      60
gaacaacctg ctcctgaatg actactgggt acataacgaa atgaaggcag aaataaagat     120
gttctttgaa accaacgaga acaaagacac aacataccag aatctctggg acncattcaa     180
agcantgtgt agagggaaat ttatagcact aaatgcccac aagagaaagc aggaaagatc     240
caaaattgac accctaacat cacaattaaa agaactagaa aaaaaaaa                  289

<210> SEQ ID NO 2
<211> LENGTH: 1584
<212> TYPE: DNA
<213> ORGANISM: mammalian

<400> SEQUENCE: 2
cggggcagct ctgaggaaca aggtggaagc tcagagcgct ggtctccacc ctggtgcccc      60
tgggctggtg ctggcagtgg gagccgtggc tgtggatgag agacatagac gagagagtga     120
gatggcctgg tttgccctct acctcctgag ccttctctgg ctacagctg ggactagtac      180 ccagacccag agttcatgct ccgttccctc agcacaggag cccttggtca atggaataca     240
agtactcatg gagaactcgg tgacttcatc agcctaccca aaccccagca tcctgattgc     300
catgaatctg gccggagcct acaacttgaa ggcccagaag ctcctgactt accagctcat     360
gtccagcgac aacaacgatc taaccattgg gcacctcggc ctcaccatca tggccctcac     420
ctcctcctgc cgagaccctg gggataaagt atccattcta caaagacaaa tggagaactg     480
ggcaccttcc agcccaacg ctgaagcatc agccttctat gggcccagtc tagcgatctt     540
ggcactgtgc cagaagaact ctgaggcgac cttgccgata gccgtccgct ttgccaagac     600
cctgctggcc aactcctctc ccttcaatgt agacacagga gcaatggcaa ccttggctct     660
gacctgtatg tacaacaaga tccctgtagg ttcagaggaa ggttacagat ccctgtttgg     720
tcaggtacta aaggatattg tggagaaaat cagcatgaag atcaaagata tggcatcat     780 tggagacatc tacagtactg gcctcgccat gcaggctctc tctgtaacac ctgagccatc     840
taaaaaggaa tggaactgca agaagactac ggatatgata ctcaatgaga ttaagcaggg     900
gaaattccac aacccatgt ccattgctca atcctccct tccctgaaag gcaagacata      960
cctagatgtg ccccaggtca cttgtagtcc tgatcatgag gtacaaccaa ctctacccag    1020
caaccctggc cctggcccca cctctgcatc taacatcact gtcatataca ccataaataa    1080
ccagctgagg ggggttgagc tgctcttcaa cgagaccatc aatgttagtg tgaaaagtgg    1140
gtcagtgtta cttgttgtcc tagaggaagc acagcgcaaa aatccatgt tcaaatttga    1200 aaccacaatg acatcttggg gccttgtcgt ctcttctatc aacaatatcg cggaaaatgt    1260
taatcacaag acatactggc agtttcttag tggtgtaaca cctttgaatg aagggggttgc    1320 tgactacata cccttcaacc acgagcacat cacagccaat tcacacagt actaacgaag     1380

```
aggtgggttc agcttctatc aaacatctcc aaaggatggg tgaaatttt tccacttcat    1440 tttaaatcta tgcaaaaaag cgaatgcctg tgatgctacc atattcctgg taaaaacatg   1500
gagaaccact atgtagaata aaaatgcaaa gttcactgga gtctcaacat ctatgactca   1560
tgaaaataaa attttcatct tctc                                          1584
```

<210> SEQ ID NO 3
<211> LENGTH: 417
<212> TYPE: PRT
<213> ORGANISM: mammalian

<400> SEQUENCE: 3

```
Met Ala Trp Phe Ala Leu Tyr Leu Leu Ser Leu Leu Trp Ala Thr Ala
1               5                   10                  15

Gly Thr Ser Thr Gln Thr Gln Ser Ser Cys Ser Val Pro Ser Ala Gln
            20                  25                  30

Glu Pro Leu Val Asn Gly Ile Gln Val Leu Met Glu Asn Ser Val Thr
        35                  40                  45

Ser Ser Ala Tyr Pro Asn Pro Ser Ile Leu Ile Ala Met Asn Leu Ala
    50                  55                  60

Gly Ala Tyr Asn Leu Lys Ala Gln Lys Leu Leu Thr Tyr Gln Leu Met
65                  70                  75                  80

Ser Ser Asp Asn Asn Asp Leu Thr Ile Gly His Leu Gly Leu Thr Ile
                85                  90                  95

Met Ala Leu Thr Ser Ser Cys Arg Asp Pro Gly Asp Lys Val Ser Ile
            100                 105                 110

Leu Gln Arg Gln Met Glu Asn Trp Ala Pro Ser Ser Pro Asn Ala Glu
        115                 120                 125

Ala Ser Ala Phe Tyr Gly Pro Ser Leu Ala Ile Leu Ala Leu Cys Gln
    130                 135                 140

Lys Asn Ser Glu Ala Thr Leu Pro Ile Ala Val Arg Phe Ala Lys Thr
145                 150                 155                 160

Leu Leu Ala Asn Ser Ser Pro Phe Asn Val Asp Thr Gly Ala Met Ala
                165                 170                 175

Thr Leu Ala Leu Thr Cys Met Tyr Asn Lys Ile Pro Val Gly Ser Glu
            180                 185                 190

Glu Gly Tyr Arg Ser Leu Phe Gly Gln Val Leu Lys Asp Ile Val Glu
        195                 200                 205

Lys Ile Ser Met Lys Ile Lys Asp Asn Gly Ile Gly Asp Ile Tyr
    210                 215                 220

Ser Thr Gly Leu Ala Met Gln Ala Leu Ser Val Thr Pro Glu Pro Ser
225                 230                 235                 240

Lys Lys Glu Trp Asn Cys Lys Lys Thr Thr Asp Met Ile Leu Asn Glu
                245                 250                 255

Ile Lys Gln Gly Lys Phe His Asn Pro Met Ser Ile Ala Gln Ile Leu
            260                 265                 270

Pro Ser Leu Lys Gly Lys Thr Tyr Leu Asp Val Pro Gln Val Thr Cys
        275                 280                 285

Ser Pro Asp His Glu Val Gln Pro Thr Leu Pro Ser Asn Pro Gly Pro
    290                 295                 300

Gly Pro Thr Ser Ala Ser Asn Ile Thr Val Ile Tyr Thr Ile Asn Asn
305                 310                 315                 320

Gln Leu Arg Gly Val Glu Leu Leu Phe Asn Glu Thr Ile Asn Val Ser
                325                 330                 335

Val Lys Ser Gly Ser Val Leu Leu Val Val Leu Glu Glu Ala Gln Arg
```

```
                340             345             350
Lys Asn Pro Met Phe Lys Phe Glu Thr Thr Met Thr Ser Trp Gly Leu
            355                 360                 365
Val Val Ser Ser Ile Asn Asn Ile Ala Glu Asn Val Asn His Lys Thr
        370                 375                 380
Tyr Trp Gln Phe Leu Ser Gly Val Thr Pro Leu Asn Glu Gly Val Ala
385                 390                 395                 400
Asp Tyr Ile Pro Phe Asn His Glu His Ile Thr Ala Asn Phe Thr Gln
            405                 410                 415
Tyr
```

<210> SEQ ID NO 4
<211> LENGTH: 353
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 4

```
aaccttcgat ctcctgacga gtttattgtt ggccaaaacc aggctttgat tgaaccagga      60
tgaatgcggg tgttggaagt agaatatata tatacatata aaattgaaac tggcgatgga     120
atatgagagg agccctctgg aaananaagg acanaccctg tgctttcatg aaagtgaaga     180
tctggctgaa ccagttccac aaggttactt gtatacatag cctgagttta aaaggctgtg     240
cccacttcna gaatgtcatt gntagacttt gaaatttcta actgcctacc tgcataaaga     300
aaataaaatc ttttanatca aaaaaaaaaa ngccctatag tgggtcgaat nag            353
```

<210> SEQ ID NO 5
<211> LENGTH: 191
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 5

```
atctacaacc ttcgatctcg tgacgagttt attgttggct naaaccaggc tttgattgaa      60
ccaggatgaa tgcgggtgtt ggaagtagaa tatatatata catataaaat tggttgggag     120
ccacgtgtcc agtgtgtgtt gatcttgctt gattcagctg cttgtacaga actggcgatg     180
gattttntttt t                                                          191
```

<210> SEQ ID NO 6
<211> LENGTH: 287
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 6

```
ttttcctgcc cggtaaaaag caaaagctca atanntangt cataaatggg caaattgtag      60
tggataacat gctgtgtgca aactgaggtg gatttcaaga tgcatagttc tggaaacaat     120
aagggagatg gtaatcctat ggtccttagg cagtcangcc agaaaaggga tgcttttana     180
ttctaaataa cacatattat aaaaggaatt atgatatgat gtcntctgaa ggtgcccaca     240
```

-continued

| | |
|---|---|
| tgaaattaaa atgtctngga aaatgaattg tgtaatataa gatgata | 287 |

<210> SEQ ID NO 7
<211> LENGTH: 3671
<212> TYPE: DNA
<213> ORGANISM: mammalian

<400> SEQUENCE: 7

| | |
|---|---|
| aagcggctct caaccgaaac ctccccaggg gctacagtgg cctttccatg tggctttctc | 60 |
| acagcatgtt ggctgtgttc caatggtgaa agtccacaga gagagagaga gacccagtgg | 120 |
| aaggcacatc atttttctaa acgactcctg gaagttacac ttctgctcca tcctgggact | 180 |
| acagggcaca taacaccatg ccagctaatt ttatgtgtgt gtgtgtgtgt gtgtgtgtgt | 240 |
| gtgtgtgtgt gtgcgtagac gggatctcat catcttgccc aggttagtct tggactcctg | 300 |
| gactcaagtg atcctcccat ctcaacctcc aaaagtgctg ggttacaggc atgagtcact | 360 |
| gcacctggct ggaaatttgt taatagccta tgttgaaggg gtagctgaaa tcacctcacc | 420 |
| atcctctggg tttccagagc acctccattc ttatagccca tgtgagtcgt atggtggggt | 480 |
| gtggttctat gtccttttctc gccctctgtc tgggactgcc gagagagcag gtctcatgtc | 540 |
| atttatttgt agagtctcag ggcctattgc aggatctgac agagtcaatg actgctacct | 600 |
| ttgcggaatg aatgaataaa atcattaatg gctgaatgtg gctggctttt ccacgccttc | 660 |
| ccacagctgg ggtacttaat attggctgag gcaactactt ttaaactgtt ggtatttctc | 720 |
| tttaataaaa tcttgggaaa accttgactt tcatgtcatt ttactttggg acttttttcca | 780 |
| aaatccaggc tttattttc atcaaacaca tgtcatgatc atgctcttag ggagtcttta | 840 |
| caaaccatca tcatgctctt gagggaatct tttgaaaacc ttactttaga tcagagttag | 900 |
| agaagaaatt cacattctaa tagatttgca gggtaattga tattctcgcc atctctgttc | 960 |
| atatttgaaa tatttcagta ctcgatgtag gggcaaaaac attgagttta caccttctaa | 1020 |
| taactttcca aaaacctgtt ataaagtaaa actgctgatt cagaggtttg gggatctctg | 1080 |
| gggatacagc tcagccttgg ggcccagggc ctaccgtagc tgggctacac cttcctctcc | 1140 |
| agcttcttgt ccagctgctt ctccccttctg ttttagactc tagcaacatc ctaggattgt | 1200 |
| tatggtcctg ttgatgcaat gctgcttctt gccatcttgc tgctgtaaat gctgctttct | 1260 |
| ctgctcaatc atctagcaaa ctaccattca ttcttcctga ccctgctgag gcatcccctt | 1320 |
| ctctgtgaag agttccctct ctccttctcc aatgtatcag taagctattg ctgtgtaata | 1380 |
| aaccacccc aaggcagtgg cttgaaacaa ctgtgtatta ttgtcctgtg ggtcaaccag | 1440 |
| ctggttctgc tgatccggac aggcttggct aatctcaact ctgttttgta tctatcggca | 1500 |
| gaacaactgg aggctggctg gtctaggatg gcctcattta tgtgtttggc attggctagc | 1560 |
| tctcaattca gtggatgagg gtgactggac catgcgtctc tcatcaccca gtagactagc | 1620 |
| ctgggttttgt tctcgaggtg actgatgctg ttctgtgaga gagaaggaaa gcatgcatgg | 1680 |
| cctctggagg cctggatctc aaaacccaat ggcacaccag cacttctgct gctttctttt | 1740 |
| ggctgaagcc aggtcagttc atgttcaagg ggaggagatt tagactctac cttttaatgg | 1800 |
| gagaagctgc atagttacat tgcaaaagac aaggatctga ggggaggaga aaggatgag | 1860 |
| tggaatggtt gattgatttt tgtgatcaat ccaccacacc cacctttgat agaggtactt | 1920 |
| actctgtagt acaattggcc ttccatactg tggggttccat acctatagat tcaaccaatt | 1980 |
| gcaaactgaa atatttgaa atatgtttgc atctgcactg aacatgtaca gactattttt | 2040 |
| cttgtcctta caggataata atacgggata acaactattg acaaagcatt tacattgtat | 2100 |

-continued

| | |
|---|---|
| taggtattat aagtaatcta gagatgattt aaagtataca ggaggatgta tgtatgttat | 2160 |
| atgcaaatac tacactcttt tatattaggg acttgagcat ctggagagtg tggtatctga | 2220 |
| gggagttcct ggaactaatg tgcagatgcc aagggacaac tgtactattg tacttggaag | 2280 |
| tactcatggg gtcatattgc attgtttctt tgagtcctaa ttctgccaac atggcctggt | 2340 |
| gcttgcatta atcagctttc taatctctga gtaacaaggc acagtaacaa ggagcagtaa | 2400 |
| caaggcacag ggctggcacc tgagagtgga ggtacccagg aggcagacac cataaggcgg | 2460 |
| gaaagggaca tatgtacaga atcatggctg catgtcctga agcctggctt aagccatcaa | 2520 |
| cggctgctgg gcaggggcca aagccctgtt atccctttcg cccttcctga tggctctgcc | 2580 |
| tctgccttca gctgggcgtg gcaggcccc acccaccgag gctccagccc ttacccacag | 2640 |
| tgtcagcaat gcagcctcca gaggatgtgc tcaggccctg cccacacacc cggatgttga | 2700 |
| caggggcatg actccagcgc cagctctaat ggatggtctc atcgctttta aataatgac | 2760 |
| catggggcgt gggctggcga gagcagtgac atcactttcc tgcaattctg ggtcagttcc | 2820 |
| tgctgctttt ctctgtatgt ttgaatgact gaaataaatc tattggttgg atatatttcc | 2880 |
| tggaagactt ctgacatgtt cacatgccta tcttggaatg tggtcaggag agcaatggct | 2940 |
| ttggacttag aggtcctggg ttcaagattc tgctactagc ttgctgtatg aacttggact | 3000 |
| agcaacttaa cttctccagg cctgtgtttt ctcatttgta caatgatggg aggaataccc | 3060 |
| ttggttttgt aaaggaatgg tgaggacgaa ctgggatctc ttgtcagaga cactgtcttm | 3120 |
| gtcagtttgg gctgctataa caagttccag cagattaggt ggcttgttaa cagcagaaat | 3180 |
| atatttctca cagttctgga ggctagaagt ccaagctcag gatgccagca tggttgggct | 3240 |
| ctggagggct cctaaacacc attattcttc attcacgctt ctcagagccc taaggaagag | 3300 |
| agtgattcct cagctcaatt gtgaactgct cctgccactc tgtacttcct cgtgtaaaga | 3360 |
| arccagactt tacatcatgg gtgaccactc ccgcagagtt gtacagaacc tcccttgggg | 3420 |
| ccacaggatg gctggattct gtcccctcat atacaaggag gttattggga cagcatttct | 3480 |
| ccctagaaca agagtgtata tttcagaaag ctatggatga cttcccatgg tcatcagatc | 3540 |
| actaggcagg aatgctattc tcctgataga tgtgtggaaa gtattcaatt caattttgac | 3600 |
| ccaaagttct aggcactgga ttaagaaatg ccaaacccaa aacgtttaac tttagaatta | 3660 |
| aaaaaaaaa a | 3671 |

<210> SEQ ID NO 8
<211> LENGTH: 357
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 8

| | |
|---|---|
| gaattgtagc tatgacntac cttcttacat ggcacgttga gccatgtaag gaaaatgttn | 60 |
| ggttttgta gaaggtacag aaatatttt tcatatggtc atttctctta gcagtcttta | 120 |
| taaagctaag aatagaatat aaaaattcta ccaaatgagc tataaaaata gttatgattg | 180 |
| cctgaattta tttctaacaa cttcctgact aagttcagac acccaggata gttgctttta | 240 |
| ataaaacatg cttatttca nggttttct ttagaaaggg atatgtgtca gggagatgaa | 300 |
| agaatgtatt cttttcttgc atttgggtga cctgtaagtt taccccctggg gtaaatg | 357 |

<210> SEQ ID NO 9

```
<211> LENGTH: 244
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 9
ctttgacctt atggctcccc cagaagcaat tcagcccaac aggaggacag cttcaaccca      60
ttacgatttc atctctgccc caaccactca gcagcaagca cctgttacct gtccacccccc    120 accccttccc ccaaactgcc tttgaaaaat ccctaaccta tgagctttga ataagatgag    180 tacgaantttt catcgcccat gtggcgtggc cggcctcgtg tctattaaat tcttttttcta  240 ctgc                                                                  244

<210> SEQ ID NO 10
<211> LENGTH: 342
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 10
actgcaaaca accaagaagc acgtgaannt tgctcaacat cattaagcat caggtaaatt      60
caaatcaatg ccacagttag ataacacttc atactcacta ggatggctat aactaggaaa    120
aaaaaaggcg ttggctggga tgcagacaac ttgaaatcct catacattgc caataggact    180
ataaaatggt acagccattt tggaaaacag tctggtagta cctcatgaca ttcactgtgt    240
gatccagcaa ttccactaga tgttacttaa gacaaggaaa atatgatgtc cacataaaaa    300
cttatacaaa tgttcataag agcattagtc acaatagcaa aa                        342

<210> SEQ ID NO 11
<211> LENGTH: 440
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 11
tgtacccaca ccaggnttcc agtgaaacag tgggctangg gactgggccg cccacagaca      60
ctgaggaggg tgtataaaga gtcagcggct gaggccctga caagcctgtg cttgcgctgc    120
gggcatttat tcagtataga tttaatgaca aaggtcttga gtcaacacac ttgtggggaa    180
ttcacatggt cgtgcttgcg cccaccccca cccccgcta gtcttgcatg cagatgattt     240
aggccaggtt ccatggtcta agtaaactaa cttacttaga tgagtttctt tacatcccct   300
tgttacctaa cctaaagttt caggcaccag ataagacaat ctggcttgcc ttcagccaaa    360 tcttttttccg aagcttttgt aaaaccttcc agccttccaa gaaggttaca tctttctaca  420
atttttccac cccctgactg                                                440

<210> SEQ ID NO 12
<211> LENGTH: 211
<212> TYPE: DNA
<213> ORGANISM: mammalian
<220> FEATURE:
<221> NAME/KEY: misc_feature
<222> LOCATION: ()..()
```

<223> OTHER INFORMATION: "n" is an unknown nucleotide

<400> SEQUENCE: 12

```
aaggcccagg atggttaagt gacttgacna ataccacaca gtgagggtag ccggtgtgag      60
tgagagtcca anttcttaac tacaaagctt tactgtctcc aacttatgtt attagacccc     120
agnttnacat gatataaaac ttaatnctat gttctggggc tttnatctga ggtgctcang     180
acatctcacc tttttattct ttatcaatcc a                                    211
```

<210> SEQ ID NO 13
<211> LENGTH: 230
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 13

```
aactgaccag agaaacagtt gtgttttttc agcttggaca atgcagtttc taaccttgtt      60
cattgtgttc gttggtgggc tgggttcttt atccaagtag aaatttataa taagcactgt     120
taaaaagttt ctggagattc catgtacaga nnanttatga atatacaatg taagtagaaa     180
atgaatccat ttaactatct ataaaactac tatctcctaa ccccccctctg                230
```

<210> SEQ ID NO 14
<211> LENGTH: 875
<212> TYPE: DNA
<213> ORGANISM: mammalian

<400> SEQUENCE: 14

```
actctgcctc tgaagagatt atgaaaaaat ccaaatttca gcaaaattat atggttgttt      60
tcagtacctc tgaaggtgct atatcaagaa ttctcatgct actctttgag aaaacagatt     120
gcgtttttac ctagaaaatc aactgcaagg cattttata accttacccc aagtaaaaaa     180
aatacattga aatatactaa taaatgcaga ctacattact tgaaaatgg taatacagaa     240
tgccactttt aatatttgaa aatatgaatt tttggtagaa ataatgtaaa ataaagcttc     300
tggtaagcct taggcagtta aatttacatc agtgtaaagt aggatgaaaa tctgtaaaaa     360
ataaaaacaa aaaacaaac aaaaacctac accaaaaaaa ccctaacatc caccaatgca     420
tacatattga tctttgtgct gggaaaatct aaagcagaac attttggtaa acttgatagt     480
tatttatttt gactatattg gcatgttgat aaaactactt atatttaatt tgagtgaaac     540
atgtccacat tattaaaagt gttgctttgt actatgaatg atggatgtaa agtcttgatc     600
ctcatccaaa taaatatggc aacactttct tctgcttctt tcaagctgag gcattctgaa     660
agctcaaatt tgaagtgaga gggacttaac atcagagcct gaaaaaccaa gaagaatgag     720
gtaggatggt cagctctgaa gctcagggtg gcctggggaa actcaatata atgatgtcaa     780
ctatgaagct tactgggtaa aactacaaat aggccgatct catttcacag aggtaagccg     840
acactccctt ttccaagaaa gtaaaaaaaa aaaaa                                875
```

<210> SEQ ID NO 15
<211> LENGTH: 421
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

```
<400> SEQUENCE: 15
agatggcagg tgagagctcc ttgaaaacaa aaacattcta ctatttgaat gcaaagtgtt      60
cttctttgcc tgtgatgttt cctaatctgt gaaatcatac tggacctcga agctgtctat     120
taaaaaaata gcaaagtggc tgggcatggt ggctcatgac tatagtagtt ctagcacttt     180
gagaggctga gcggggtgga tcatttgagg ccaggatttc gaaccagcct ggccaatatg     240
cgaaacccca tctctactaa aantacaaaa attagccagg tgtggtggca tctgtctgta     300
gtcccaccta ttcgggaggc tgaggcacaa gaatcatttg agctcaggag gcagaggttg     360
cagtgagcca aaattgcacc actgcactcc atcctgggca acagagtgag gctctgtctg     420
a                                                                     421

<210> SEQ ID NO 16
<211> LENGTH: 290
<212> TYPE: DNA
<213> ORGANISM: mammalian

<400> SEQUENCE: 16
ctacctgact tcaaactata ctacaaggct acagtaacca aaacagcatg gtactggtac      60
caaaacagag atatagacca atggaacaga acagagccct cagaaataat gccacatatc     120
tacaaccatc tgatctttga caaacctgac aaaaacaaga atggggaaaa ggattccctc     180
tttaataaat ggtgctggga aaactggcag ccatatgtag aaagctgaaa ctggatccct     240
tccttacacc ttatacaaaa attaattcaa gatggattaa agacttaaat                290

<210> SEQ ID NO 17
<211> LENGTH: 620
<212> TYPE: DNA
<213> ORGANISM: mammalian

<400> SEQUENCE: 17
gctagcatgg agaagaaatc ccacagagac acagttcttc taaacagaaa cttcagttac      60
tttagagatt attataaggc cagatttttc tgatctgatt gtatgcttta cctgaatcca     120
ctcaagctgt ggttttgagg ggcatgctgt ttgcattttt acacgggagc ttaacctcag     180
agagactcca ggacagattg ataacactga catttggtca aactattctt agttatcaca     240
gcaaactgtt gctaaataca tatcccagtg aagctatccc agagcttttg ctatactgg      300 gaagctaaat ttaaacaaca acaaaatata tatatatatc tccttattac aaaagaagc      360 ttttttcactg ctatatctgt aagttttaa tgccttccta gaggtgtgtt ttgctccttc     420
aagtagaaag cttagaactc tgatttttta aaaataagca atgattgaga gtaattaaaa     480
ggtttgcata atcactgtgg taaagtttaa agccaacaaa tagttgatga gctaaagtta     540
gtcttggaga aagataaact agttgtaaac taaacatgag tttgcagtag aatagaaaag     600
gatgaactag aaaaaaaaaa                                                 620

<210> SEQ ID NO 18
<211> LENGTH: 656
<212> TYPE: DNA
<213> ORGANISM: mammalian

<400> SEQUENCE: 18
cgcggatcca gacgctgcgt tgctggcttt gatgaaact gatggcgatg aatgaacact       60
gcgtttgctg tgcttgaggt acagaggaca cacatcgtag acaggcctgt gtcatgtttc     120
cttacagtcg tttttttacag agaaaagggg cattgttttt tcacttgctt tctcaacagt    180
```

```
tcctgtgaat aaatgaaaca tttcggagct ccctgagagc aagacgctag catggtgctc    240
tgccaggaca ggtttccctg aaggaagctg ctcacactcg agatgagcct ctcagggcag    300
gacctcttcc caagccctgc acacccaccc ctgcagccct tttggctccc cttttccctg    360
tgcctcagca ctcctttcct ggttgcagat aacgaactaa ggttgcctaa agggcagatc    420
tgccctctcc atgtcttcgt cctggcaaac agggtcgtct taaaattatg cgctaattct    480
gtatgggagc actcaaaagg cattacttag agattgaaat ttcaaactat ctctagtttt    540
tcaatggaaa tatatcagct agggaaaaac catcaagctc attattattt tttgatcttc    600
agttgtattt ttgtgaatat tttaatacat cttttttcaat ttctgaaaaa aaaaaa      656

<210> SEQ ID NO 19
<211> LENGTH: 641
<212> TYPE: DNA
<213> ORGANISM: mammalian

<400> SEQUENCE: 19
gcatttgctg aacacagaga aacccaggag aggagatcag cagttttctt tcactctact     60
tgatctgtca gatttaccca cagaaagcca gtcaggatcc cttaagagtc tttaggccca    120
gaatggagtc ctcagggctg caggggactg tggtgctaac aattaaactg ttcaagactt    180
taaagagttg aagggactaa atgggtatcc ctagcatggc ctcctagatg ggaattaact    240
ggcaactcct aytgtgccat tcccagtatg tgtgcttccc tttagcctcc catagaattg    300
gctgaaacac cctaccaccg ttttctgttt ccccactacc acacctgtgt tatgggtgtc    360
agcctgtgag tccttgaacc cttccagagg ctcccaakg gagggtgatc actgcccttc    420 cataaaggc tgaggaaagc caagtgagaa gattcaatta atttgggcaa gttatttaac    480
atctgaacct gttttctct tmattgttta ttacttacct tgtccaaaaa ggtcataaag    540
ggtaagggct ttttctgttc cacctctgta ctatatttat ccccaacaaa tatctgcccc    600
tgaggacctc aataaaggtt tggtcaagtg aaaaaaaaaa a                        641

<210> SEQ ID NO 20
<211> LENGTH: 2306
<212> TYPE: DNA
<213> ORGANISM: mammalian

<400> SEQUENCE: 20
atgctgcagg atttcttgtc atagtctcag aagttctgaa atgtcacttc tgccatgctc     60
tattgagaaa gtcacaaagg cccatctgga atggaggtga aaatagttag actccacttt    120
ggtgtcagtt gcarcataca tctataggga gggaagaaat tgatgacacc gtctttggag    180
actgtcaacc gtacctgttc tacatttctc ctaatttccg ctccatctgt ttatccttcc    240
atccatttat ccatctatcc atccactcat ccatttgtct gcccatcagt actttcattc    300
atctacccat ccatctgtct acccacacag ccatccaccc atctatccat ccttctatcc    360
attcattcat taaacaacta ctcaaagact gctatgagcc aatcattatt ctgggtgcta    420
ctgatacatt gctgaaaaga gcctcatgag gataataaat tagtagggga gacagggagg    480
ctaacaaata tgtaagtata cagtttcaaa ctgtgataat tgtaattaat cacaccaagc    540
ttatgactga aaacgaatt gttcaattac tagtaggtcc caaagttct cttttgagaga    600 atgtcactga aaatgaatga taattggtca ggagaggatg ggaaaagacc ctttcatgca    660
gttagagaag catgaaacaa atttgtcttt gctcagttgt aacaacatga gtgagacttt    720
ccctgaacaa tcttctaaaa atataatcat tacctcttct taggttccct attccctttc    780
```

```
tcttcttgct ctttcactgt gacatttaac acatctgaaa tatcaagttc tctatttact      840
tctgggtttg tttattatat gtcataccca ctaaaatgta agtttcttga aaatggagat      900
atttgttaaa taaatgcatg aattgtgttc agcctttcta ataatatttt attgtattta      960
tactgtatt tataaactac ttttagatct aatattctat ttagtgtgta tcaagagcat     1020
tggatggatg ttgaggaaac ctatrttcta tatttcatcc tgccactaac ctcctgcttg     1080
actctgaaca aattgcatgg tggccttctg tcagtttcct catacctaga acaaggatgt     1140
tgacttctgt ttgcttctat tattctaagg atccataatt tcttttcatt tttgtacagt     1200
gaaataatta gagaaggacc caagacttaa atcaattgac cttattcaca taagagaagg     1260
ccagagggga aagaaagaa aagattctta caggcagcag ggctcacaag gcatgttctg      1320
tgggtgaact tgtattttct tcataaggag agaaaaacaa gaaacaaaac aaaacaaaac     1380
aaaaacttct tcctccagga cttgggtact aacacaaaag attcaacaaa cagttttgt      1440
tttctgtgcc aataaaattt tatatgaaag acaggaggta caaaaacaaa gatcagattc     1500
atctgatctt tttaaaaatt ttttaattta atttaagttt caggacatgt gtgcaggacg     1560
tgcaggtttg ttacataggt gaacgtgtac catggtggtt tgctgtacct gtcaacccat     1620
cacctaggat taagccccgc atgcattact tatttatcct gatgtgctcc ctctccatgc     1680
cctaccgaca ggccccagtt tgtgttgttc cccttcttgc atgtccaagt gttctcactg     1740
ttcagctccc acttgtaagt gagaacatgt ggtgttcaac aaatgctttt taaagctaac     1800
cagtatgtgg tctggcctgt gatgatctgg cttagttatc catgcagaaa tgatttctat     1860
gaggggtttg gagaagaaaa aaagtcagga aatttagcct agtagacagg aaaagccayc     1920
gcagcaggtc acttctgttg ccaccatcga ggcagcttaa ccaggtggcc atggcatgag     1980
cagcatggtg gagggtccc atcagtgagt aacacagaaa tggagcccctt tacctctgta     2040
agtgtgttct gcaggtaggc acagcaacag taggactaag gcacaaggag ggtttctgga     2100
aggtgagaag gtctcatacc agatggggag gagcaccagg agccatttca aactgaacta     2160
caagtccaaa gacagctggt gagtcacccc cagggaatca agtgtgattg ttacttagaa     2220
ccaagcggat ggcctggaaa ataggaaacc cttgttctta ggcataaacg tgcacatata     2280
ttctgatagc taggaaaaaa aaaaaa                                          2306

<210> SEQ ID NO 21
<211> LENGTH: 263
<212> TYPE: DNA
<213> ORGANISM: mammalian

<400> SEQUENCE: 21
gtgggcagtt tgctttacag ggaagacggg ataggcagaa atatgcagaa gtggagattt       60
tcccccaaat tcacacagag gagtaaaaga gctttagact gatagtcaga ggtatgagtt      120
ttgygatgac tttttaatag acacttacca agaaagaatc tagtacagat gaagctctga      180
atttattccc tgtcatttct ttagtaaarac tttattgagc aaggcatatt ccacaaactg      240
ggatttagct gtaaaaaaaa aaa                                              263

<210> SEQ ID NO 22
<211> LENGTH: 245
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
```

<400> SEQUENCE: 22

```
cacatagcan ntacagcctt gccctcctgg ccccagtgag cgtaatgtct caccatgcca      60
aagtactttt atcttaaatt gcttattttt ttgtttattt ttttaactga ctctgtttac     120
aaaattaacc ttttatctag tgacagctag atttgtcac atttgtcatc tatggacact      180
gattttagt tgtttatatg ggtaagttat tattgntttc cttatttaag aaaacaggac      240
tgagg                                                                 245
```

<210> SEQ ID NO 23
<211> LENGTH: 253
<212> TYPE: DNA
<213> ORGANISM: mammalian

<400> SEQUENCE: 23

```
ggtccgccga gagagggcgg agcaggaggc tcttactggt gagtgcaaag agctggaaaa      60
gaagaacgag gctctaaaag agagggcgga ttccctggcc aaggagatcc agtacctgaa     120
agatttgata gaagaggtcc gcaaggcaag ggggaagaaa agggtccct agttgaggat      180
agtcaggagc gtcaatgtgc ttgtacatag agtgcgtgta gcatgtgtgt tccaataaat     240
tattttgtag gga                                                        253
```

<210> SEQ ID NO 24
<211> LENGTH: 459
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 24

```
gccctcctgt ttcaacttgc cacaaggcta cagtaaccca acagcatgg tgctggtaca       60
agaacagaca catagacaaa tgaacagaa cagagaaccg agaaatgaga ccacacacct      120
acaactaact gatcttcggc aaacctgaca aaaacaagca atggggaaag gattccggtt     180
caataaatgg tgcttgggat aactggctag ccatgtgcag aagatgaaac cgctcccttg     240
cttacactat atccaaagat taactcaaga tggattaaga ctgacatgta aaccccact      300
atgaanctct gaaagacact taggcaatgc cttcagggct tangcatggg gcaagntttc     360
atgatgagac cgcccaaaag caattgcaac aaaagccaaa attgacaaat gggggcttaa     420
taaatttaag aactgtgccc gtggaagaac tttcacnga                            459
```

<210> SEQ ID NO 25
<211> LENGTH: 457
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 25

```
aagggtaatg ataccaatga gggttggttt attatcaaac ctgaatagct gtggtttctc      60
cagtaaaatat tttcttctac tgaacatgga gccattatta agagtgtgt gttttttatt    120
atgtacattt gtatatttt ttgcttgttt gatgttctat ttttctaata gttttcttt       180
agtttcttaa agttgtgata ctagattan attctgatgc taacttgcaa atcaggttgg      240
tctctgctgg gtctctcctg cttttatttt actttaagga caagtgtagt tgtcgtccac    300
```

| | |
|---|---:|
| cacctttcaa aaaatgtgaa actgccctgc ctcccctttt tgctgacaac actgtgtaca | 360 |
| ttgaccactt cctaccatac tttatgttgt aaaatcaaac tcttttgtgg tacattatct | 420 |
| catgcttctg canattcgaa taaatctatg gctccga | 457 |

<210> SEQ ID NO 26
<211> LENGTH: 261
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 26

| | |
|---|---:|
| ctgccggtag cccgattcta atcctgcctc cctcacttat tctttgtgtt actttgggca | 60 |
| aagtacgtat tctgctctgt aaaatggagg tagtaatacc acctacctct taagtttaac | 120 |
| tattattagt gaatgaagct attttccaca gttctaaact ttaaaggtta aaatctgagt | 180 |
| gaagcaaaaa tcagcacctc tttcctaatt caaacnttca aacacctatc tacnttagga | 240 |
| ctttggacct ncntttaatt a | 261 |

<210> SEQ ID NO 27
<211> LENGTH: 2470
<212> TYPE: DNA
<213> ORGANISM: mammalian

<400> SEQUENCE: 27

| | |
|---|---:|
| attaggttac ccacagcttg gaagagatag agttgaaatg caaaaccgag ttgaaattta | 60 |
| aaaccaactt atctgattcc aaaaccagta cagagcaccg aggccttgat ttgataggct | 120 |
| atggagtttg aatttaattc agaagacagt ggacagccac tgatagtatt tgaacagggc | 180 |
| aatgatagga tcagtgctgt gtctaggaag attgttcttg aaatgacaga gagctttaga | 240 |
| atggtgaaag actaaagact agttagaagt ctgctgtaat ggttccaact ccagagacat | 300 |
| agaaaagata ggtctcccaaa gacaagtgat ggcatagtct ttgctcagcc agagtctcta | 360 |
| ggaaaatggt ggtgccgtta actgaaatag gttaagttaa gagaggttat tggcttaggg | 420 |
| tggagtgcag ggagaatatg atatttaggt ttggtatatt taagtttgag atatcagtag | 480 |
| gacttcaaat aaataaagtc taacaagcat tttgaagtat agaagatttg acttcagaga | 540 |
| ccaatttgga aatcataatt aaagatactg gagtgaataa gaacctcaga agagaggtaa | 600 |
| tagagatcag agagtacatc tttaggaaac atacatattt aaacagaaga agaggaagaa | 660 |
| aagtaagagg aagaggcaac aagtgaggac aatcagagaa gtggaagaac tagaatagta | 720 |
| ttatgtcatg agcaacacgc gaagagtcaa gaagcgcgta tttattgggt cagaagtaat | 780 |
| ttagggctgt tgtcttgct gtagcatcag tcccttctt aggaaacaac tgacaccatt | 840 |
| aagttcaaac acattcattt ttctatttca actctgttag ggaggaaatt cagcaatcaa | 900 |
| gaaaactgtt ttcctgttaa agatgtgttt ggtagtcaca ttttcatttt aagctaatga | 960 |
| gagctctcaa ttttactgcc agcaaaagaa agcaacattt tgaagtattt ctctatgtca | 1020 |
| ttggaggttt agttcccaag aaagctcttg ttatgtccgt gcttctgccc ttttactctg | 1080 |
| tgcttcttcc tgtggtctgt caagtctccc ttcattagat ttagtacctg aaaccgatgc | 1140 |
| ccagaagcca ggtcacaagc ccaatatgca ttgcattgtc tcttcaagcc ttagttacct | 1200 |
| aatttgtgga acgggtggta ctaataaagg gagagtaaaa tagctaatga aggattataa | 1260 |
| agcactttgc taatataaaa tgcaacatca aagctgaata ataatcttaa tttagggtga | 1320 |

| | |
|---|---|
| agggttccat tagcagagta aaaataaaaa ggacaaaggg tagtgttgct ttgtaccttg | 1380 |
| ataacagtgt acaaatcaaa agtgctgcta ttgatcctca ttgccctgtg aactctcaac | 1440 |
| ccaggaattt ggctcccctc cctaactctc taagtacttc ccttacccac tcagtgtggt | 1500 |
| gatggcacct ccctgaatct cctgacaaat gcgaacagga actcctattc atcagagcca | 1560 |
| acttgataac tgagaagatt cctctctcat ttatcagcct ttgattatct ttttgtgtct | 1620 |
| cttactattt gcgcttagca agaaaaataa agaggtttga acaattaaga agtaacaaag | 1680 |
| agctcatagt tcacaaagag caagtcaaag gatgtctgga atatttgaac atacaactgc | 1740 |
| ctttggcatg aggtggccta catacattct caggggcagg ataggctgga gagctgatca | 1800 |
| agctgccggg aagctgaagc aaaggcaggg tggtggaatc aaatgtctct tcaactgaag | 1860 |
| actttaaaac ttgggcttta gctgggatta caggtgtgag ccaccgcacc cagccaggtg | 1920 |
| tcatgcactt tggcgtacct atttctaaga caaatatgtt ctcatgtaaa tgtattcaag | 1980 |
| tgtgttccca tggctcacac aagctgccca attatgatat ctcctcaagc aggaacaggg | 2040 |
| tccagacaat tccttttggc tgaactagga ctgaacttaa tcccagactg actcagcttc | 2100 |
| tctgttaaca ttgttttgaaa ttctgatatc cctccagagg ttgtttctaa cgagtgctta | 2160 |
| gtgtgaagta cgaatcacaa agaaatggac caaagtggac ctgggagacc aaaagctcac | 2220 |
| gttttcaaca ttaatttagc acacatttat tgactgcctt ttatgttaga gcattgtgct | 2280 |
| atgcgggatt ataaagaaac ccctgccctc aatttagtaa gtgagagtat aggccaggca | 2340 |
| tggtggctca cacctgtaat ctcagcactt tgggaggcca aggcaggaag atcacttgag | 2400 |
| gccagaagtt tgagaccagt ctgggcaaca tagcaagacc ccatctctgt ttattaaaaa | 2460 |
| aaaaaaaaaa | 2470 |

<210> SEQ ID NO 28
<211> LENGTH: 2178
<212> TYPE: DNA
<213> ORGANISM: mammmalian

<400> SEQUENCE: 28

| | |
|---|---|
| attaggttac ccacagcttg gaagagatag agttgaaatg caaaaccgag ttgaaattta | 60 |
| aaaccaactt atctgattcc aaaaccagta cagagcaccg aggccttgat ttgataggct | 120 |
| atggagtttg aatttaattc agaagacagt ggacagccac tgatagtatt tgaacagggc | 180 |
| aatgatagga tcagtgctgt gtctaggaag attgttcttg aaatgacaga gagctttaga | 240 |
| atggtgaaag actaaagact agttagaagt ctgctgtaat ggttccaact ccagagacat | 300 |
| agaaaagata ggtctcccaaa gacaagtgat ggcatagtct ttgctcagcc agagtctcta | 360 |
| ggaaaatggt ggtgccgtta actgaaatag gttaagttaa gagaggttat tggcttaggg | 420 |
| tggagtgcag ggagaatatg atatttaggt ttggtatatt taagtttgag atatcagtag | 480 |
| gacttcaaat aaataaagtc taacaagcat tttgaagtat agaagatttg acttcagaga | 540 |
| ccaatttgga aatcataatt aaagatactg gagtgaataa gaacctcaga agagaggtaa | 600 |
| tagagatcag agagtacatc tttaggaaac atacatattt aaacagaaga agaggaagaa | 660 |
| aagtaagagg aagaggcaac aagtgaggac aatcagagaa gtggaagaac tagaatagta | 720 |
| ttatgtcatg agcaacacgc gaagagtcaa gaagcgcgta tttattgggt cagaagtaat | 780 |
| ttagggctgt ttgtcttgct gtagcatcag tcccttttctt aggaaacaac tgacaccatt | 840 |
| aagttcaaac acattcattt ttctatttca actctgttag ggaggaaatt cagcaatcaa | 900 |
| gaaaactgtt ttcctgttaa agatgtgttt ggtagtcaca ttttttcattt aagctaatga | 960 |

-continued

| | |
|---|---|
| gagctctcaa ttttactgcc agcaaaagaa agcaacattt tgaagtattt ctctatgtca | 1020 |
| ttggaggttt agttcccaag aaagctcttg ttatgtccgt gcttctgccc ttttactctg | 1080 |
| tgcttcttcc tgtggtctgt caagtctccc ttcattagat ttagtacctg aaaccgatgc | 1140 |
| ccagaagcca ggtcacaagc ccaatatgca ttgcattgtc tcttcaagcc ttagttacct | 1200 |
| aatttgtgga acgggtggta ctaataaagg gagagtaaaa tagctaatga aggattataa | 1260 |
| agcactttgc taatataaaa tgcaacatca aagctgaata ataatcttaa tttagggtga | 1320 |
| agggttccat tagcagagta aaaataaaaa ggacaaaggg tagtgttgct ttgtaccttg | 1380 |
| ataacagtgt acaaatcaaa agtgctgcta ttgatcctca ttgccctgtg aactctcaac | 1440 |
| ccaggaattt ggctcccctc cctaactctc taagtacttc ccttacccac tcagtgtggt | 1500 |
| gatggcacct ccctgaatct cctgacaaat gcgaacagga actcctattc atcagagcca | 1560 |
| acttgataac tgagaagatt cctctctcat ttatcagcct ttgattatct ttttgtgtct | 1620 |
| cttactattt gcgcttagca agaaaaataa agaggtttga acaattaaga agtaacaaag | 1680 |
| agctcatagt tcacaaagag caagtcaaag gatgtctgga atatttgaac atacaactgc | 1740 |
| ctttggcatg aggtggccta catacattct caggggcagg ataggctgga gagctgatca | 1800 |
| agctgccggg aagctgaagc aaaggcaggg tggtggaatc aaatgtctct tcaactgaag | 1860 |
| actttaaaac ttgggcttta gctgggcgca gtagctcaca cctgtaatcc cagcactttg | 1920 |
| ggaggtcaag tcgggtagat cacttgaggt caggagttcg agaccagcct ggccaacatg | 1980 |
| gagaaacccc gtctctacta aaaatacaaa aattagccag gcataatggt gggtgcctgt | 2040 |
| aatccagcta cttgggaggc tgaggcagga gaatcacttg aacctgggag gtgaggttgc | 2100 |
| agtgagccaa gatcgcacca ctgcactcca gcctgggcaa caaagcgaga ctctatctat | 2160 |
| ctcaaaaaaa aaaaaaaa | 2178 |

<210> SEQ ID NO 29
<211> LENGTH: 2548
<212> TYPE: DNA
<213> ORGANISM: mammalian

<400> SEQUENCE: 29

| | |
|---|---|
| attaggttac ccacagcttg aagagatag agttgaaatg caaaaccgag ttgaaattta | 60 |
| aaaccaactt atctgattcc aaaaccagta cagagcaccg aggccttgat ttgataggct | 120 |
| atggagtttg aatttaattc agaagacagt ggacagccac tgatagtatt tgaacagggc | 180 |
| aatgatagga tcagtgctgt gtctaggaag attgttcttg aaatgacaga gagctttaga | 240 |
| atggtgaaag actaaagact agttagaagt ctgctgtaat ggttccaact ccagagacat | 300 |
| agaaaagata ggtctccaaa gacaagtgat ggcatagtct ttgctcagcc agagtctcta | 360 |
| ggaaaatggt ggtgccgtta actgaaatag gttaagttaa gagaggttat tggcttaggg | 420 |
| tggagtgcag ggagaatatg atatttaggt ttggtatatt taagtttgag atatcagtag | 480 |
| gacttcamat aaataaagtc taacaagcat tttgaagtat agaagatttg acttcagaga | 540 |
| ccaatttgga aatcataatt aaagatactg gagtgaataa gaacctcaga agagaggtaa | 600 |
| tagagatcag agagtacatc tttaggaaac atacatattt aaacagaaga gaggaagaa | 660 |
| aagtaagagg aagaggcaac aagtgaggac aatcagagaa gtggaagaac tagaatagta | 720 |
| ttatgtcatg agcaacacgc gaagagtcaa gaagcgcgta tttattgggt cagaagtaat | 780 |
| ttagggctgt ttgtcttgct gtagcatcag tccctttctt aggaaacaac tgacaccatt | 840 |
| aagttcaaac acattcattt ttctatttca actctgttag ggaggaaatt cagcaatcaa | 900 |

-continued

| | |
|---|---|
| gaaaactgtt ttcctgttaa agatgtgttt ggtagtcaca ttttcattt aagctaatga | 960 |
| gagctctcaa tttactgcc agcaaaagaa agcaacattt tgaagtattt ctctatgtca | 1020 |
| ttggaggttt agttcccaag aaagctcttg ttatgtccgt gcttctgccc ttttactctg | 1080 |
| tgcttcttcc tgtggtctgt caagtctccc ttcattagat ttagtacctg aaaccgatgc | 1140 |
| ccagaagcca ggtcacaagc ccaatatgca ttgcattgtc tcttcaagcc ttagttacct | 1200 |
| aatttgtgga acgggtggta ctaataaagg gagagtaaaa tagctaatga aggattataa | 1260 |
| agcactttgc taatataaaa tgcaacatca aagctgaata ataatcttaa tttagggtga | 1320 |
| agggttccat tagcagagta aaaataaaaa ggacaaaggg tagtgttgct ttgtaccttg | 1380 |
| ataacagtgt acaaatcaaa agtgctgcta ttgatcctca ttgccctgtg aactctcaac | 1440 |
| ccaggaattt ggctccctc cctaactctc taagtacttc ccttacccac tcagtgtggt | 1500 |
| gatggcacct ccctgaatct cctgacaaat gcgaacagga actcctattc atcagagcca | 1560 |
| acttgataac tgagaagatt cctctctcat ttatcagcct ttgattatct ttttgtgtct | 1620 |
| cttactattt gcgcttagca agaaaaataa agaggtttga caattaaga agtaacaaag | 1680 |
| agctcatagt tcacaaagag caagtcaaag gatgtctgga atatttgaac atacaactgc | 1740 |
| ctttggcatg aggtggccta catacattct caggggcagg ataggctgga gagctgatca | 1800 |
| agctgccggg aagctgaagc aaaggcaggg tggtggaatc aaatgtctct tcaactgaag | 1860 |
| actttaaaac ttgggcttta gctgggcgca gtagctcaca cctgtaatcc cagcactttg | 1920 |
| ggaggtcaag tgatctgcct gcctcggtcc cccaaagtgc tgggattaca ggtgtgagcc | 1980 |
| accgcaccca gccaggtgtc atgcactttg gcgtacctat ttctaagaca aatatgttct | 2040 |
| catgtaaatg tattcaagtg tgttcccatg gctcacacaa gctgcccaat tatgatatct | 2100 |
| cctcaagcag gaacagggtc cagacaattc cttttggctg aactaggact gaacttaatc | 2160 |
| ccagactgac tcagcttctc tgttaacatt gtttgaaatt ctgatatccc tccagaggtt | 2220 |
| gtttctaacg agtgcttagt gtgaagtacg aatcacaaag aaatggacca agtggacct | 2280 |
| gggagaccaa aagctcacgt tttcaacatt aatttagcac acattttattg actgcctttt | 2340 |
| atgttagagc attgtgctat gcgggattat aaagaaaccc ctgcccctcaa tttagtaagt | 2400 |
| gagagtatag ccaggcatg gtggctcacg cctgtaatct cagcactttg ggaggccaag | 2460 |
| gcaggaagat cacttgaggc cagaagtttg agaccagtct gggcaacata gcaagacccc | 2520 |
| atctctgttt attaaaaaaa aaaaaaaa | 2548 |

<210> SEQ ID NO 30
<211> LENGTH: 1691
<212> TYPE: DNA
<213> ORGANISM: mammalian

<400> SEQUENCE: 30

| | |
|---|---|
| agcatggcgt gatctcggct cactgcaacc tccgcttccc aggttccagc gattctcctg | 60 |
| cctcagcctc ccaagtagct gggattacag aaaaatggat ggacatgttt tactgcctga | 120 |
| acgctggtgc cagttaggcc aacagtcatg tggcaatggc tatgaattgc aagcattgct | 180 |
| gattgttatc tgctgctact gcctttgagc tggagcggaa cagatcaaca tgggccaaac | 240 |
| aagagcctct ttggagattt ctctactgct tcaagcacac agattccaag tttagaagct | 300 |
| caagagaagc acagcctgac caatcagaat ccctcctggg aggctttcca caaatgctga | 360 |
| gggaagatcg gtagtgtcac tttttgtaaaa acgtgagcca gaagctgtag gaaatgctga | 420 |
| actctcgctg ggtcgtgaaa gtccatcacg atggtaaaac tacaagacac agtaagtgat | 480 |

```
ttgcaccaaa tctcatgtcc atcctttgcc agaatcatcc acaatcttca catgccataa      540
gacaaaccca gcctcacttc cagaagatcc agagctccca ttttttaagg gtgtgacctg      600
gaactagctc attagttcat cctagaagac cctaggattt attgttatta tttgcctttt      660
ttggtagagg gagaagcatc cctttgcaga caatcatcgt ggtccacgtt ataaaggggt      720
tagccctgtg cttgacggat tgcctactac actttattaa agcccattac aatttccaac      780
atttgtcata tgaaaatgcc ttctaacaaa taccagcttg ttagagaatg ctgttagca      840 ggataaattg gtcttgcttt gctcctacct cgtcaactcc aaccctagca cctaatcaaa      900
ctttgacaat caaaaccctatataggtttc ctaatggatg caaaacaggt ggggaaagca      960
cggtccgctg cagtagcatc cagagaacac aaaatatatc aacttccact cccacagtac     1020
aggcttgctt ccccacaaaa ctggacaaga agcagagcta atgaaccat ctctttctgt      1080 gcaagctatt accagctaaa tgacttaaaa aaaaaaatcc agagcagccc gggttgagct     1140
tccatcctaa tgaaatgcag tctggttgaa gtgttgctgg ttatacaagg cccggtgcag     1200
aaatcctgat caaagcctct ggcatctga agtcatcagt aattcgacag cctatttggg      1260
tgaaaagagc tcctttctgg ctgtttcact tcaggcccac cccagagagg ggcacaactc     1320
aagcaaacaa gactgctggc aactcaagat gcctcttccc aagatgtgac atgaaacaca     1380
agtcagcagc agcagccgga tgcagcgatc aggtttcgcg gggggagcag ctgtgtacat     1440
cacacatgct atttgcatgt atgtcatctg ttctggtgag gctgagacat gtttcacaga     1500
gacatgagca gtggcctttt gacctgtatg aggctgagag cagctctccc caggagccac     1560
tgctcttcca gagaaggagc agtgacagtg taagcaatga tgaaacgag gtgctcctgg      1620 tcactcttgg atttcattaa atattgcctg ataaaaaaaa aaaaaaaaaa aaaaaaaaa      1680 aaaaaaaaaa a                                                          1691

<210> SEQ ID NO 31
<211> LENGTH: 358
<212> TYPE: DNA
<213> ORGANISM: mammalian

<400> SEQUENCE: 31
tagcggataa caatttcaca caggatggat tggtccttta catgccagct ttgcttgtga       60
atccttgctt ttttcctctc atcagcctta agtttaggcg tttgttgttc tccagtgatg      120
tagacagttc ccttcacaag tcacagttct tcccataaat gaggcccgct gacctctgcg      180
ggactttaaa aatctattca gatatttccg agtaagtggc tttgtttaaa ttcttcctgt      240
gtctttcttt attccttaat tggttggtgg aaagaagaga tgcttgggaa ccttgggttc      300
ttaggtttgg attcttttaat aatatctaaa aagctaaatt ttaaatacca gctttacg      358

<210> SEQ ID NO 32
<211> LENGTH: 6075
<212> TYPE: DNA
<213> ORGANISM: mammalian

<400> SEQUENCE: 32
gggggaggag ccaagatggc cgaataggaa cagctccggt ctacagctcc cagcgtgagc       60
gacgcagaag acggtgattt ctgcatttcc atctgaggta ccgggttcat ctcactaggg      120
agtgccagac agtgggcgca ggccagtgtg tgtgcgcacc gtgcgcgagc cgaagcaggg      180
cgaggcattg cctcacctgg gaagcgcaag gggtcaggga gttccctttc tgagtcaaag      240
aaaggggtga cggtcgcacc tggaaaatcg ggtcactccc acccgaatat tgcgcttttc      300
```

```
agaccggctt aagaaacggc gcaccacgag actatatccc acacctggct cggagggtcc    360
tacgcccacg gaatctcgct gattgctagc acagcagtct gagatcaaac tgcaaggcgg    420
caacgaggct gggggagggg cgcccgccat tgcccaggct tgcttaggta aacaaagcag    480
ccgggaagct cgaactgggt ggagcccacc acagctcaag gaggcctgcc tgcctctgta    540
ggctccacct ctgggggcag ggcacagaca acaaaaaga cagcagtaac ctctgcagac    600
ttaagtgtcc ctgtctgaca gctttgaaga gagcagtggt tctcccagca cgcagctgga    660
gatctgagaa cgggcagaca gactgcctcc tcaagtgggt ccctgactcc tgaccccga    720 gcagcctaac tgggaggcac cccccagcag gggcacactg acacctcaca cggcagggta    780
ttccaacaga cctgcagctg agggtcctgt ctgttagaag aaaactaac aaccagaaag     840 gacatctaca ccgaaaaccc atctgtacat caccatcatc aaagaccaaa agtagataaa    900
accacaaaga tgggaaaaaa cagaacagaa aaactggaaa ctctaaaacg cagagcgcct    960
ctcctcctcc aaaggaacgc agttcctcac cagcaacaga acaaagctgg atggagaatg   1020
attttgacga gctgagagaa gaaggcttca gacgatcaaa ttactctgag ctacgggagg   1080
acattcaaac caaaggcaaa gaagttgaaa actttgaaaa aaatttagaa gaatgtataa   1140
ctagaatatc caatacagag aagtgcttaa aggagctgat ggagctgaaa accaaggctc   1200
gagaactacg tgaagaatgc agaagcctca ggagccgatg cgatcaactg aagaaaggg    1260 tatcagcaat ggaagatgaa atgaatgaaa tgaagcgaga agggaagttt agagaaaaaa   1320
gaataaaaag aaatgagcaa agcctccaag aaatatggga ctatgtgaaa agaccaaatc   1380
tacgtctgat tggtgtacct gaaagtgatg tggagaatgg aaccaagttg gaaaacactc   1440
tgcaggatat tatccaggag aacttcccca atctagcaag gcaggccaac gttcagattc   1500
aggaaataca gagaacgcca caaagatact cctcgagaag agcaactcca agacacataa   1560
ttgtcagatt caccaaagtt gaaatgaagg aaaaaatgtt aagggcagcc agagagaaag   1620
gtcgggttac cctcaaaggg aagcccatca gactaacagc ggatctctcg gcagaaaccc   1680
tacaagccag aagagagtgg gggccaatat tcaacattct aaagaaaag aattttcaac    1740 ccagaatttc atatccagcc aaactaagct tcataagtga aggagaaata aaatacttta   1800
tagacaagca aatgttgaga gattttgtca ccaccaggcc tgccctaaaa gagctcctga   1860
aggaagcgct aaacatggaa aggaacaacc ggtaccagcc gctgcaaaat catgccaaaa   1920
tgtaaagacc atcgagacta ggaagaaact gcatcaacta atgagcaaaa tcaccagcta   1980
acatcataat gacaggatca aattcacaca taacaatatt aactttaaat ataaatggac   2040
taaattctgc aattaaaaga cacagactgg caagttggat aaagagtcaa gacccatcag   2100
tgtgctgtat tcaggaaacc catctcacgt gcagagacac ataggctc aaaataaaag     2160 gatggaggaa gatctaccaa gccaatggaa acaaaaaaa ggcagggg tt gcaatcctag    2220 tctctgataa aacagacttt aaaccaacaa agatcaaaag agacaaagaa ggccattaca   2280
taatggtaaa gggatcaatt caacaagagg agctaactat cctaaatatt tatgcaccca   2340
atacaggagc acccagattc ataaagcaag tcctcagtga cctacaaaga gacttagact   2400
cccacacatt aataatggga gactttaaca ccccactgtc aacattagac agatcaacga   2460
gacagaaagt caacaaggat acccaggaat tgaactcagc tctgcaccaa gcagacctaa   2520
tagacatcta cagaactctc caccccaaat caacagaata tacatttttt tcagcaccac   2580
accacaccta ttccaaaatt gaccacatag ttggaagtaa agctctcctc agcaaatgta   2640
aaagaacaga aattataaca aactatctct cagaccacag tgcaatcaaa ctagaactca   2700
```

```
ggattaagaa tctcactcaa agccgctcaa ctacatggaa actgaacaac ctgctcctga   2760
atgactactg ggtacataac gaaatgaagg cagaaataaa gatgttcttt gaaaccaacg   2820
agaacaaaga caccacatac cagaatctct gggacgcatt caaagcagtg tgtagaggga   2880
aatttatagc actaaatgcc tacaagagaa agcaggaaaa atccaaaatt gacaccctaa   2940
catcacaatt aaaagaacta gaaaagcaag agcaaacaca ttcaaaagct agcagaaggc   3000
aagaaataac taaaatcaga gcagaactga aggaaataga gacacaaaaa acccttcaaa   3060
aaatcaatga atccaggagc tggttttttg aaaggatcaa caaaattgat agaccgctat   3120
caagactaat aaagaaaaaa agagagaaga atcaaataga cacaataaaa aatgataaag   3180
gggatatcac caccgatccc acagaaatac aaactaccat cagagaatac tacaaacacc   3240
tctacgcaaa taaactagaa aatctagaag aaatggatac attcctcgac acatacactc   3300
tcccaagact aaaccaggaa gaagttgaat ctctgaatag accaataaca ggctctgaaa   3360
ttgtggcaat aatcaatagt ttaccaacca aaaagagtcc aggaccagat ggattcacag   3420
ccgaattcta ccagaggtac atggaggaac tggtaccatt ccttctgaaa ctattccaat   3480
caatagaaaa agagggaatc ctccctaact cattttatga ggccagcatc attctgatac   3540
caaagccggg cagagacaca accaaaaaag agaattttag accaatatcc ttgatgaaca   3600
ttgatgcaaa aatcctcaat aaaatactgg caaaccgaat ccagcagcac atcaaaaagc   3660
ttatccacca tgatcaagtg ggcttcatcc ctgggatgca aggctggttc aatatacgca   3720
aatcaataaa tgtaatccag catataaaca gagccaatga caaaaaccac atgattatct   3780
caatagatgc agaaaaagcc tttgacaaaa ttcaacaacc cttcatgcta aaaactctca   3840
ataaattagg tattgatggg acgtatttca aaataataag agctatctat gacaaaccca   3900
cagccaatat catactgaat gggcaaaaac tggaagcatt ccctttgaaa accggcacaa   3960
gacagggatg ccctctctca ccgctcctat tcaacatagt gttggaagtt ctggccaggg   4020
caatcaggca ggagaaggaa ataaagggta ttcaattagg aaaagaggaa gtcaaattgt   4080
ccctgtttgc agacgacatg attgtatatc tagaaaaccc catcgtctca gcccaaaatc   4140
tccttaagct gataagcaac ttcagcaaag tctcaggata caaaatcaat gtacaaaaat   4200
cacaagcatt cttatacacc aacaacagac aaacagagag ccaaatcatg ggtgaactcc   4260
cattcgtaat tgcttcaaag agaataaaat acctaggaat ccaacttaca agggatgtga   4320
aggacctctt caaggagaac tacaaaccac tgctcaagga aataaaagag gacacaaaca   4380
aatggaagaa cattccatgc tcatgggtag gaagaatcaa tatcgtgaaa atggccatac   4440
tgcccaaggt aatttacaga ttcaatgcca tccccatcaa gctaccaatg actttcttca   4500
cagaattgga aaaaactact ttaaagttca tatggaacca aaaaagagcc cgcattgcca   4560
agtcaatcct aagccaaaag aacaaagctg gaggcatcac actacctgac ttcaaactat   4620
actacaaggc tacagtaacc aaaacagcat ggtactggta ccaaaacaga gatatagatc   4680
aatggaacag aacagagccc tcagaaataa tgccgcatat ctacaactat ctgatctttg   4740
acaaacctga gaaaacaag caatgggaa aggattccct atttaataaa tggtgctggg   4800
aaaactggct agccatatgt agaaagctga aactggatcc cttccttaca ccttatacaa   4860
aaatcaattc aagatggatt aaagatttaa acgttaaacc taaaaccata aaaccctag   4920 aagaaaacct aggcattacc attcaggaca taggcgtggg caaggacttc atgtccaaaa   4980
caccaaaagc aatggcaaca aaagacaaaa ttgacaaatg ggatctaatt aaactaaaga   5040
gcttctgcac agcaaaagaa actaccatca gagtgaacag gcaacctaca acatgggaga   5100
```

-continued

```
aaattttcgc aacctactca tctgacaaag ggctaatatc cagaatctac aatgaactca    5160
aacaaattta caagaaaaaa acaaacaacc ccatcaaaaa gtgggcgaag gacatgaaca    5220
gacacttctc aaaagaagac atttatgcag ccaaaaaaca catgaagaaa tgctcatcat    5280
cactggccat cagagaaatg caaatcaaaa ccactatgag atatcatctc acaccagtta    5340
gaatggcaat cattaaaaag tcaggaaaca acaggtgctg gagaggatgc ggagaaatag    5400
gaacactttt acactgttgg tgggactgta aactagttca accattgtgg aagtcagtgt    5460
ggcgattcct cagggatcta gaactagaaa taccatttga cccagccatc ccattactgg    5520
gtatataccc aaatgagtat aaatcatgct gctataaaga cacatgcaca cgtatgttta    5580
ttgcggcact attcacaata gcaaagactt ggaaccaacc gaaatgtcca acaatgatag    5640
actggattaa gaaaatgtgg cacatataca ccatggaata ctatgcagcc ataaaaaatg    5700
atgagttcat atcctttgta gggacatgga tgaaattgga aaccatcatt ctcagtaaac    5760
tatcgcaaga acaaaaaacc aaacaccgca tattctcact cataggtggg aattgaacaa    5820
tgagatcaca tggacacagg aaggggaata tcacactctg gggactgtgg tggggtcggg    5880 ggaggggggga gggatagcat tgggagatat acctaatgct agatgacaca ttagtgggtg    5940
cagcgcacca gcatggcaca tgtatacata tgtaactaac ctgcacaatg tgcacatgta    6000
ccctaaaact tagagtataa taaaaaaaaa aaaaaaaaaa aaaaaaaaaa aaaaaaaaa    6060 aaaaaaaaaa aaaaa                                                    6075
```

<210> SEQ ID NO 33
<211> LENGTH: 41
<212> TYPE: PRT
<213> ORGANISM: mammalian

<400> SEQUENCE: 33

Met Gly Lys Asn Arg Thr Glu Lys Leu Glu Thr Leu Lys Arg Arg Ala
1               5                   10                  15

Pro Leu Leu Leu Gln Arg Asn Ala Val Pro His Gln Gln Asn Lys
            20                  25                  30

Ala Gly Trp Arg Met Ile Leu Thr Ser
        35                  40

<210> SEQ ID NO 34
<211> LENGTH: 1275
<212> TYPE: PRT
<213> ORGANISM: mammalian

<400> SEQUENCE: 34

Met Thr Gly Ser Asn Ser His Ile Thr Ile Leu Thr Leu Asn Ile Asn
1               5                   10                  15

Gly Leu Asn Ser Ala Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Ala Gly Val Ala Ile Leu Val Ser Asp
65                  70                  75                  80

Lys Thr Asp Phe Lys Pro Thr Lys Ile Lys Arg Asp Lys Glu Gly His
                85                  90                  95

Tyr Ile Met Val Lys Gly Ser Ile Gln Gln Glu Glu Leu Thr Ile Leu
            100                 105                 110

-continued

Asn Ile Tyr Ala Pro Asn Thr Gly Ala Pro Arg Phe Ile Lys Gln Val
            115                 120                 125
Leu Ser Asp Leu Gln Arg Asp Leu Asp Ser His Thr Leu Ile Met Gly
130                 135                 140
Asp Phe Asn Thr Pro Leu Ser Thr Leu Asp Arg Ser Thr Arg Gln Lys
145                 150                 155                 160
Val Asn Lys Asp Thr Gln Glu Leu Asn Ser Ala Leu His Gln Ala Asp
            165                 170                 175
Leu Ile Asp Ile Tyr Arg Thr Leu His Pro Lys Ser Thr Glu Tyr Thr
            180                 185                 190
Phe Phe Ser Ala Pro His His Thr Tyr Ser Lys Ile Asp His Ile Val
            195                 200                 205
Gly Ser Lys Ala Leu Leu Ser Lys Cys Lys Arg Thr Glu Ile Ile Thr
            210                 215                 220
Asn Tyr Leu Ser Asp His Ser Ala Ile Lys Leu Glu Leu Arg Ile Lys
225                 230                 235                 240
Asn Leu Thr Gln Ser Arg Ser Thr Thr Trp Lys Leu Asn Asn Leu Leu
            245                 250                 255
Leu Asn Asp Tyr Trp Val His Asn Glu Met Lys Ala Glu Ile Lys Met
            260                 265                 270
Phe Phe Glu Thr Asn Glu Asn Lys Asp Thr Thr Tyr Gln Asn Leu Trp
            275                 280                 285
Asp Ala Phe Lys Ala Val Cys Arg Gly Lys Phe Ile Ala Leu Asn Ala
            290                 295                 300
Tyr Lys Arg Lys Gln Glu Arg Ser Lys Ile Asp Thr Leu Thr Ser Gln
305                 310                 315                 320
Leu Lys Glu Leu Glu Lys Gln Glu Gln Thr His Ser Lys Ala Ser Arg
            325                 330                 335
Arg Gln Glu Ile Thr Lys Ile Arg Ala Glu Leu Lys Glu Ile Glu Thr
            340                 345                 350
Gln Lys Thr Leu Gln Lys Ile Asn Glu Ser Arg Ser Trp Phe Phe Glu
            355                 360                 365
Arg Ile Asn Lys Ile Asp Arg Pro Leu Ser Arg Leu Ile Lys Lys Lys
            370                 375                 380
Arg Glu Lys Asn Gln Ile Asp Thr Ile Lys Asn Asp Lys Gly Asp Ile
385                 390                 395                 400
Thr Thr Asp Pro Thr Glu Ile Gln Thr Thr Ile Arg Glu Tyr Tyr Lys
            405                 410                 415
His Leu Tyr Ala Asn Lys Leu Glu Asn Leu Glu Glu Met Asp Thr Phe
            420                 425                 430
Leu Asp Thr Tyr Thr Leu Pro Arg Leu Asn Gln Glu Glu Val Glu Ser
            435                 440                 445
Leu Asn Arg Pro Ile Thr Gly Ser Glu Ile Val Ala Ile Ile Asn Ser
            450                 455                 460
Leu Pro Thr Lys Lys Ser Pro Gly Pro Asp Gly Phe Thr Ala Glu Phe
465                 470                 475                 480
Tyr Gln Arg Tyr Met Glu Glu Leu Val Pro Phe Leu Leu Lys Leu Phe
            485                 490                 495
Gln Ser Ile Glu Lys Glu Gly Ile Leu Pro Asn Ser Phe Tyr Glu Ala
            500                 505                 510
Ser Ile Ile Leu Ile Pro Lys Pro Gly Arg Asp Thr Thr Lys Lys Glu
            515                 520                 525
Asn Phe Arg Pro Ile Ser Leu Met Asn Ile Asp Ala Lys Ile Leu Asn
            530                 535                 540

```
Lys Ile Leu Ala Asn Arg Ile Gln Gln His Ile Lys Lys Leu Ile His
545                 550                 555                 560

His Asp Gln Val Gly Phe Ile Pro Gly Met Gln Gly Trp Phe Asn Ile
                565                 570                 575

Arg Lys Ser Ile Asn Val Ile Gln His Ile Asn Arg Ala Asn Asp Lys
            580                 585                 590

Asn His Met Ile Ile Ser Ile Asp Ala Glu Lys Ala Phe Asp Lys Ile
        595                 600                 605

Gln Gln Pro Phe Met Leu Lys Thr Leu Asn Lys Leu Gly Ile Asp Gly
    610                 615                 620

Thr Tyr Phe Lys Ile Ile Arg Ala Ile Tyr Asp Lys Pro Thr Ala Asn
625                 630                 635                 640

Ile Ile Leu Asn Gly Gln Lys Leu Glu Ala Phe Pro Leu Lys Thr Gly
                645                 650                 655

Thr Arg Gln Gly Cys Pro Leu Ser Pro Leu Leu Phe Asn Ile Val Leu
            660                 665                 670

Glu Val Leu Ala Arg Ala Ile Arg Gln Glu Lys Glu Ile Lys Gly Ile
        675                 680                 685

Gln Leu Gly Lys Glu Glu Val Lys Leu Ser Leu Phe Ala Asp Asp Met
    690                 695                 700

Ile Val Tyr Leu Glu Asn Pro Ile Val Ser Ala Gln Asn Leu Leu Lys
705                 710                 715                 720

Leu Ile Ser Asn Phe Ser Lys Val Ser Gly Tyr Lys Ile Asn Val Gln
                725                 730                 735

Lys Ser Gln Ala Phe Leu Tyr Thr Asn Asn Arg Gln Thr Glu Ser Gln
            740                 745                 750

Ile Met Gly Glu Leu Pro Phe Val Ile Ala Ser Lys Arg Ile Lys Tyr
        755                 760                 765

Leu Gly Ile Gln Leu Thr Arg Asp Val Lys Asp Leu Phe Lys Glu Asn
    770                 775                 780

Tyr Lys Pro Leu Leu Lys Glu Ile Lys Glu Asp Thr Asn Lys Trp Lys
785                 790                 795                 800

Asn Ile Pro Cys Ser Trp Val Gly Arg Ile Asn Ile Val Lys Met Ala
                805                 810                 815

Ile Leu Pro Lys Val Ile Tyr Arg Phe Asn Ala Ile Pro Ile Lys Leu
            820                 825                 830

Pro Met Thr Phe Phe Thr Glu Leu Glu Lys Thr Thr Leu Lys Phe Ile
        835                 840                 845

Trp Asn Gln Lys Arg Ala Arg Ile Ala Lys Ser Ile Leu Ser Gln Lys
    850                 855                 860

Asn Lys Ala Gly Gly Ile Thr Leu Pro Asp Phe Lys Leu Tyr Tyr Lys
865                 870                 875                 880

Ala Thr Val Thr Lys Thr Ala Trp Tyr Trp Tyr Gln Asn Arg Asp Ile
                885                 890                 895

Asp Gln Trp Asn Arg Thr Glu Pro Ser Glu Ile Met Pro His Ile Tyr
            900                 905                 910

Asn Tyr Leu Ile Phe Asp Lys Pro Glu Lys Asn Lys Gln Trp Gly Lys
        915                 920                 925

Asp Ser Leu Phe Asn Lys Trp Cys Trp Glu Asn Trp Leu Ala Ile Cys
    930                 935                 940

Arg Lys Leu Lys Leu Asp Pro Phe Leu Thr Pro Tyr Thr Lys Ile Asn
945                 950                 955                 960

Ser Arg Trp Ile Lys Asp Leu Asn Val Lys Pro Lys Thr Ile Lys Thr
```

965                 970                 975
Leu Glu Glu Asn Leu Gly Ile Thr Ile Gln Asp Ile Gly Val Gly Lys
            980                 985                 990

Asp Phe Met Ser Lys Thr Pro Lys Ala Met Ala Thr Lys Asp Lys Ile
        995                 1000                1005

Asp Lys Trp Asp Leu Ile Lys Leu Lys Ser Phe Cys Thr Ala Lys
    1010                1015                1020

Glu Thr Thr Ile Arg Val Asn Arg Gln Pro Thr Thr Trp Glu Lys
    1025                1030                1035

Ile Phe Ala Thr Tyr Ser Ser Asp Lys Gly Leu Ile Ser Arg Ile
    1040                1045                1050

Tyr Asn Glu Leu Lys Gln Ile Tyr Lys Lys Thr Asn Asn Pro
    1055                1060                1065

Ile Lys Lys Trp Ala Lys Asp Met Asn Arg His Phe Ser Lys Glu
    1070                1075                1080

Asp Ile Tyr Ala Ala Lys Lys His Met Lys Lys Cys Ser Ser Ser
    1085                1090                1095

Leu Ala Ile Arg Glu Met Gln Ile Lys Thr Thr Met Arg Tyr His
    1100                1105                1110

Leu Thr Pro Val Arg Met Ala Ile Ile Lys Lys Ser Gly Asn Asn
    1115                1120                1125

Arg Cys Trp Arg Gly Cys Gly Glu Ile Gly Thr Leu Leu His Cys
    1130                1135                1140

Trp Trp Asp Cys Lys Leu Val Gln Pro Leu Trp Lys Ser Val Trp
    1145                1150                1155

Arg Phe Leu Arg Asp Leu Glu Leu Glu Ile Pro Phe Asp Pro Ala
    1160                1165                1170

Ile Pro Leu Leu Gly Ile Tyr Pro Asn Glu Tyr Lys Ser Cys Cys
    1175                1180                1185

Tyr Lys Asp Thr Cys Thr Arg Met Phe Ile Ala Ala Leu Phe Thr
    1190                1195                1200

Ile Ala Lys Thr Trp Asn Gln Pro Lys Cys Pro Thr Met Ile Asp
    1205                1210                1215

Trp Ile Lys Lys Met Trp His Ile Tyr Thr Met Glu Tyr Tyr Ala
    1220                1225                1230

Ala Ile Lys Asn Asp Glu Phe Ile Ser Phe Val Gly Thr Trp Met
    1235                1240                1245

Lys Leu Glu Thr Ile Ile Leu Ser Lys Leu Ser Gln Glu Gln Lys
    1250                1255                1260

Thr Lys His Arg Ile Phe Ser Leu Ile Gly Gly Asn
    1265                1270                1275

<210> SEQ ID NO 35
<211> LENGTH: 374
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 35
gtgatttaat acgactcact atagggcttt ttttttttta ctcattttaa ataaattnga    60
atgaattttc ttcctaaaat aatgttagct gatgctggtt ctttcccgca ctttcagaaa   120 caaatatnc ntnttnttta catatcaaaa gngatnccta agattaaatc cctttgtaac   180

```
ctcctggata caaagagtcc tttgngccac agtaggacag caggaccttt attnaattnc      240 tatncttat  ttgncagaat tcaacagctg gtaaaaagac tctaagcagg tattttagg       300 aagatcttaa aataaggata tattgttttt gaaattccaa caatgaatag actcttttt      360 ggctattttg agcc                                                        374

<210> SEQ ID NO 36
<211> LENGTH: 935
<212> TYPE: DNA
<213> ORGANISM: mammalian

<400> SEQUENCE: 36
tgatataagt ttagccacac tttgatttgg gttcattttt tgttttgttt ttttcaatca      60
tgatattcag aaaaatccag gatccaaaat gtggcgtttt tctaagaatg aaaattatat     120
gtaagctttt aagcatcatg aagaacaatt tatgttcaca ttaagatacg ttctaaaggg     180
ggatggccaa ggggtgacat cttaattcct aaactacctt agctgcatag tggaagagga     240
gagcatgaag caaagaattc caggaaaccc aagaggctga gaattctttt gtctaccata     300
gaattattat ccagactgga attttgtgtt gttagaacac cctcagttg caatatgcta     360 atcccacttt acaaagaata taaaagctat attttgaaga cttgagttat ttcagaaaaa     420
actacagccc tttttgtctt acctgccttt tactttcgtg tggatatgtg aagcattggg     480
tcgggaacta gctgtagaac acaactaaaa actcatgtct tttttcacag aataatgtgc     540
cagttttttg tagcaatgat atttctcttg gaagcagaaa tgctttgtac cagagcacct     600
ccaaactgca ttgaggagaa gttccagaac catccccttt ttccattttt atataattta     660
taaagaaaga ttaaagccat gttgactatt ttacagccac tggagttaac taacccttcc     720
ttgtatctgt cttcccagga gagaatgaag caaaacagga atttggttttt cttttgatgt     780 ccagttacac catccattct gttaattttg aaaaaatata ccctcccttt agtttgttgg     840
gggatataaa ttattctcag gaagaatata atgaactgta cagttacttt gacctattaa     900
aaaggtgtta ccagcaaaaa aaaaaaaaaa aaaaa                                935

<210> SEQ ID NO 37
<211> LENGTH: 302
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 37
tgatttaata cgactcacta tagggctttt ttttttttac tagtcttgct ancggnctgt      60
caattttgtt gatcttttca aaaanccagg ncctggattc attaattttt tgaagggttt     120
tttnggtctn tatctcctcc agttctgctc tgatcttagt tatttcttgc cttctgctac     180
cntttngaat gngttngctc tngcttttct agttctttna atngggangt tagggngtca     240
attttanatc tttcctgctt tctcttgggg ncattaaggg ctataaattn ccctgtncac     300
ac                                                                    302

<210> SEQ ID NO 38
<211> LENGTH: 1200
<212> TYPE: DNA
<213> ORGANISM: mammalian

<400> SEQUENCE: 38
```

```
aagatatuaaa agctccagaa acgttgactg ggaccactgg agacactgaa gaaggcaggg      60
gcccttagag tcttggttgc caaacagatt tgcagatcaa ggagaaccca ggagtttcaa     120
agaagcgcta gtaaggtctc tgagatcctt gcactagcta catcctcagg gtaggaggaa     180
gatggcttcc agaagcatgc ggctgctcct attgctgagc tgcctggcca aacaggagt     240
cctgggtgat atcatcatga acccagctg tgctcctgga tggttttacc acaagtccaa     300
ttgctatggt tacttcagga agctgaggaa ctggtctgat gccgagctcg agtgtcagtc     360
ttacggaaac ggagcccacc tggcatctat cctgagttta aggaagcca gcaccatagc     420
agagtacata agtggctatc agagaagcca gccgatatgg attggcctgc acgacccaca     480
gaagaggcag cagtggcagt ggattgatgg ggccatgtat ctgtacagat cctggtctgg     540
caagtccatg ggtgggaaca agcactgtgc tgagatgagc tccaataaca acttttaac     600
ttggagcagc aacgaatgca caagcgcca acacttcctg tgcaagtacc gaccatagag     660
caagaatcaa gattctgcta actcctgcac agccccgtcc tcttcctttc tgctagcctg     720
gctaaatctg ctcattattt cagaggggaa acctagcaaa ctaagagtga aagggcccct     780
actacactgg ctttttttagg cttagagaca gaaactttag cattggccca gtagtggctt     840
ctagctctaa atgtttgccc cgccatccct ttccacagta tccttcttcc ctcctcccct     900
gtctctggct gtctcgagca gtctagaaga gtgcatctcc agcctatgaa acagctgggt     960
cttttggccat aagaagtaaa gatttgaaga cagaaggaag aaactcagga gtaagcttct    1020
agacccccttc agcttctaca cccttctgcc ctctctccat gcctgcacc ccaccccagc    1080
cactcaactc ctgcttgttt ttcctttggc cataggaagg tttaccagta gaatccttgc    1140
taggttgatg tgggccatac attcctttaa taaaccattg tgtacataag aaaaaaaaaa    1200

<210> SEQ ID NO 39
<211> LENGTH: 158
<212> TYPE: PRT
<213> ORGANISM: mammalian

<400> SEQUENCE: 39

Met Ala Ser Arg Ser Met Arg Leu Leu Leu Leu Ser Cys Leu Ala
1               5                   10                  15

Lys Thr Gly Val Leu Gly Asp Ile Ile Met Arg Pro Ser Cys Ala Pro
                20                  25                  30

Gly Trp Phe Tyr His Lys Ser Asn Cys Tyr Gly Tyr Phe Arg Lys Leu
            35                  40                  45

Arg Asn Trp Ser Asp Ala Glu Leu Glu Cys Gln Ser Tyr Gly Asn Gly
    50                  55                  60

Ala His Leu Ala Ser Ile Leu Ser Leu Lys Glu Ala Ser Thr Ile Ala
65                  70                  75                  80

Glu Tyr Ile Ser Gly Tyr Gln Arg Ser Gln Pro Ile Trp Ile Gly Leu
                85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
        115                 120                 125

Cys Ala Glu Met Ser Ser Asn Asn Asn Phe Leu Thr Trp Ser Ser Asn
    130                 135                 140

Glu Cys Asn Lys Arg Gln His Phe Leu Cys Lys Tyr Arg Pro
145                 150                 155

<210> SEQ ID NO 40
```

```
<211> LENGTH: 497
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 40
tttcacttgt cgcaccaggc gtatttcctc tggaatntaa cgagtgtggc aaggccttca      60
gccacagttc caatctcatc ctccatcagc gcatccactc tggagagaaa ccttatgaat     120
gtaatgagtg cgggaaggcc ttcagccaga gctcggacct caccaagcat cagagaattc     180
acacggggga gaaaccctat gaatgtagtg aatgtnnaaa agctttcaac cgaaactcat     240
acctgatttt gcatcggaga attcacactc gagaaaagcc ctacaagtgc actaagtgtg     300
gcaaggcctt cacccgcagc tccaccctca ctctgcatca cagaatccat gccagagaga     360
gagcctctga gtacagccca gcctcccttg atgcatttgg cgcgttcctg aaaagttgtg     420
tgtaaaggaa gaatttgcca tcaagccatt tcccctttttg tttctaaatt atttcanaga     480
tgtgtgctct ggangga                                                    497

<210> SEQ ID NO 41
<211> LENGTH: 451
<212> TYPE: DNA
<213> ORGANISM: mammalian

<400> SEQUENCE: 41
gctcccgaag tgatacggag gttaggatgc tacttgctgc aaacaagccc tactttggcc      60
aacatcctgc ttatttctca aaaaagaggg acagtgaaaa caaaaacgac attgggacat     120
gctgctcaag gtagttatat atacgataag ttgtatatat gatcactggt agcctaccaa     180
agctgtagaa atctaggact gtgctaatca gtatcaaacc aaagatttct atctcttccc     240
gaaagagagg gtatgtgcac cagtctacag ttccaaagga ctgcaacaaa tgtagatggt     300
tctgtcctca tccctgagat cagttctact gaaatggcaa caacaactcc aaatacatct     360
ctcccttctt gaaatcccta agcactatc gcactcctaa atgcatttct cccaagttag     420
cacttgattg atctgtcttt aatccttcat t                                    451

<210> SEQ ID NO 42
<211> LENGTH: 469
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 42
cccttcccct cttctctcag ttttggacaa gtgacaaacc attttgcccc ctcactcttc      60
ttttttaact gttaaaccaa aggaaagcac aaatgaagga aatcctgtgt aaagcattga     120
gaaggaaaga agcctggagc agcctctcct gtccacagcc aggggttagg tctgcaggcc     180
cgtctgcggt ccccatcgag catcaagggg acgcntgtgt gtgcatgcaa gtgaccccga     240
aaacaaccac agccgtcaca tggtcctcct gaagttgggg caccctcctc tcagcaccaa     300 aatggcccccc actccttcgt gtcctcccgc tatctccaaa tcggacgttc tttctagctt     360 gagatttttta ttttttccaca tctgtagtgc catgaagcga ttctgtcttt gacttccaat     420
ggcaaacctg ggtgatcggg aacaagcacg ttgtaccctt ggctggaca                469
```

<210> SEQ ID NO 43
<211> LENGTH: 1584
<212> TYPE: DNA
<213> ORGANISM: mammalian

<400> SEQUENCE: 43

| | | | | | |
|---|---|---|---|---|---|
| cggggcagct | ctgaggaaca | aggtggaagc | tcagagcgct | ggtctccacc | ctggtgcccc | 60 |
| tgggctggtg | ctggcagtgg | gagccgtggc | tgtggatgag | agacatagac | gagagagtga | 120 |
| gatggcctgg | tttgccctct | acctcctgag | ccttctctgg | gctacagctg | ggactagtac | 180 |
| ccagacccag | agttcatgct | ccgttccctc | agcacaggag | cccttggtca | atggaataca | 240 |
| agtactcatg | gagaactcgg | tgacttcatc | agcctaccca | aaccccagca | tcctgattgc | 300 |
| catgaatctg | gccggagcct | acaacttgaa | ggcccagaag | ctcctgactt | accagctcat | 360 |
| gtccagcgac | aacaacgatc | taaccattgg | gcacctcggc | ctcaccatca | tggccctcac | 420 |
| ctcctcctgc | cgagaccctg | gggataaagt | atccattcta | caaagacaaa | tggagaactg | 480 |
| ggcaccttcc | agcccaacg | ctgaagcatc | agccttctat | gggcccagtc | tagcgatctt | 540 |
| ggcactgtgc | cagaagaact | ctgaggcgac | cttgccgata | gccgtccgct | ttgccaagac | 600 |
| cctgctggcc | aactcctctc | ccttcaatgt | agacacagga | gcaatggcaa | ccttggctct | 660 |
| gacctgtatg | tacaacaaga | tccctgtagg | ttcagaggaa | ggttacagat | ccctgtttgg | 720 |
| tcaggtacta | aaggatattg | tggagaaaat | cagcatgaag | atcaaagata | tggcatcat | 780 |
| tggagacatc | tacagtactg | gcctcgccat | gcaggctctc | tctgtaacac | ctgagccatc | 840 |
| taaaaaggaa | tggaactgca | agaagactac | ggatatgata | ctcaatgaga | ttaagcaggg | 900 |
| gaaattccac | aaccccatgt | ccattgctca | aatcctccct | tccctgaaag | gcaagacata | 960 |
| cctagatgtg | ccccaggtca | cttgtagtcc | tgatcatgag | gtacaaccaa | ctctacccag | 1020 |
| caaccctggc | cctggcccca | cctctgcatc | taacatcact | gtcatataca | ccataaataa | 1080 |
| ccagctgagg | ggggttgagc | tgctcttcaa | cgagaccatc | aatgttagtg | tgaaaagtgg | 1140 |
| gtcagtgtta | cttgttgtcc | tagaggaagc | acagcgcaaa | aatcctatgt | tcaaatttga | 1200 |
| aaccacaatg | acatcttggg | gccttgtcgt | ctccttctatc | aacaatatcg | cggaaaatgt | 1260 |
| taatcacaag | acatactggc | agtttcttag | tggtgtaaca | cctttgaatg | aaggggttgc | 1320 |
| tgactacata | cccttcaacc | acgagcacat | cacagccaat | ttcacacagt | actaacgaag | 1380 |
| aggtgggttc | agcttctatc | aaacatctcc | aaaggatggg | tgaaattttt | tccacttcat | 1440 |
| tttaaatcta | tgcaaaaaag | cgaatgcctg | tgatgctacc | atattcctgg | taaaaacatg | 1500 |
| gagaaccact | atgtagaata | aaaatgcaaa | gttcactgga | gtctcaacat | ctatgactca | 1560 |
| tgaaaataaa | attttcatct | tctc | | | | 1584 |

<210> SEQ ID NO 44
<211> LENGTH: 417
<212> TYPE: PRT
<213> ORGANISM: mammalian

<400> SEQUENCE: 44

Met Ala Trp Phe Ala Leu Tyr Leu Leu Ser Leu Leu Trp Ala Thr Ala
1               5                   10                  15

Gly Thr Ser Thr Gln Thr Gln Ser Cys Ser Val Pro Ser Ala Gln
            20                  25                  30

Glu Pro Leu Val Asn Gly Ile Gln Val Leu Met Glu Asn Ser Val Thr
        35                  40                  45

Ser Ser Ala Tyr Pro Asn Pro Ser Ile Leu Ile Ala Met Asn Leu Ala

Gly Ala Tyr Asn Leu Lys Ala Gln Lys Leu Leu Thr Tyr Gln Leu Met
65                  70                  75                  80

Ser Ser Asp Asn Asn Asp Leu Thr Ile Gly His Leu Gly Leu Thr Ile
                85                  90                  95

Met Ala Leu Thr Ser Ser Cys Arg Asp Pro Gly Asp Lys Val Ser Ile
            100                 105                 110

Leu Gln Arg Gln Met Glu Asn Trp Ala Pro Ser Pro Asn Ala Glu
        115                 120                 125

Ala Ser Ala Phe Tyr Gly Pro Ser Leu Ala Ile Leu Ala Leu Cys Gln
    130                 135                 140

Lys Asn Ser Glu Ala Thr Leu Pro Ile Ala Val Arg Phe Ala Lys Thr
145                 150                 155                 160

Leu Leu Ala Asn Ser Ser Pro Phe Asn Val Asp Thr Gly Ala Met Ala
                165                 170                 175

Thr Leu Ala Leu Thr Cys Met Tyr Asn Lys Ile Pro Val Gly Ser Glu
            180                 185                 190

Glu Gly Tyr Arg Ser Leu Phe Gly Gln Val Leu Lys Asp Ile Val Glu
        195                 200                 205

Lys Ile Ser Met Lys Ile Lys Asp Asn Gly Ile Gly Asp Ile Tyr
210                 215                 220

Ser Thr Gly Leu Ala Met Gln Ala Leu Ser Val Thr Pro Glu Pro Ser
225                 230                 235                 240

Lys Lys Glu Trp Asn Cys Lys Lys Thr Thr Asp Met Ile Leu Asn Glu
                245                 250                 255

Ile Lys Gln Gly Lys Phe His Asn Pro Met Ser Ile Ala Gln Ile Leu
            260                 265                 270

Pro Ser Leu Lys Gly Lys Thr Tyr Leu Asp Val Pro Gln Val Thr Cys
        275                 280                 285

Ser Pro Asp His Glu Val Gln Pro Thr Leu Pro Ser Asn Pro Gly Pro
    290                 295                 300

Gly Pro Thr Ser Ala Ser Asn Ile Thr Val Ile Tyr Thr Ile Asn Asn
305                 310                 315                 320

Gln Leu Arg Gly Val Glu Leu Leu Phe Asn Glu Thr Ile Asn Val Ser
                325                 330                 335

Val Lys Ser Gly Ser Val Leu Leu Val Val Leu Glu Glu Ala Gln Arg
            340                 345                 350

Lys Asn Pro Met Phe Lys Phe Glu Thr Thr Met Thr Ser Trp Gly Leu
        355                 360                 365

Val Val Ser Ser Ile Asn Asn Ile Ala Glu Asn Val Asn His Lys Thr
370                 375                 380

Tyr Trp Gln Phe Leu Ser Gly Val Thr Pro Leu Asn Glu Gly Val Ala
385                 390                 395                 400

Asp Tyr Ile Pro Phe Asn His Glu His Ile Thr Ala Asn Phe Thr Gln
                405                 410                 415

Tyr

<210> SEQ ID NO 45
<211> LENGTH: 247
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

```
<400> SEQUENCE: 45 actgtcccg gggcgcagac cctgnactcg gggacttggg atgttcctct tggtgtcata    60
ttccaactca gattgagccc tacattgtgc tgcacctggt ccatacggag ttgaatcaga   120
cctggttccc gcctccccca aggctcatgg tccttggagg acccgttgca gggcgaggtc   180
aagaagagtt ctgacctgga tggcccatag acctgacgtc ccagaatcca tgctttcttc   240
attttgc                                                             247

<210> SEQ ID NO 46
<211> LENGTH: 454
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 46
ctcctgatat agcaacaaag cctgggcaac ctttgttcct ggattctatt tctcctaaaa    60
aatcttttaa gactcgaaaa caaaagtctt cttcaaaggc tgaatacaat ttaactgcat   120
gcaaatgcct cctttgcaag aggaaatata gttcacaaat aatgcttaaa agacatatgc   180
ntattgtcca caagataact cttttctgaa caaactctaa aagagaaaaa ggccctaata   240
atactgccaa cagttcagaa ataacagtta aagttgaacc agcagattct gtagaatctt   300
cccccccttc cattacccat tctccacaga atgaattaaa gggaacaaat cattcaaatg   360
aaaaaaagaa cacaccggca gcacagaaaa ataaagttaa acaagactct gaaagcccta   420
aatcaactag tccgtcggct gcaggtggcc agca                               454

<210> SEQ ID NO 47
<211> LENGTH: 382
<212> TYPE: DNA
<213> ORGANISM: mammalian

<400> SEQUENCE: 47
acacccatgg gaggtcatgc ctgatctgta cttctacaga gatcctgaag agattgaaaa    60
agaagagcag gctgctgctg agaaggcagt gaccaaggag gaatttcagg gtgaatggac   120
tgctcccgct cctgagttca ctgctactca gcctgaggtt gcagactggt ctgaaggtgt   180
acaggtgccc tctgtgccta ttcagcaatt ccctacttga agactggagc gctcagcctg   240
ccacggaaga ctggtctgca gctcccactg ctcaggccac tgaatgggta ggagcaacca   300
ctgactggtc ttaagctgtt cttgcatagg ctcttaagca gcatggaaaa atgggttgat   360
ggaaaataaa catcagtttc ca                                            382

<210> SEQ ID NO 48
<211> LENGTH: 361
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 48 tgttttgct atgctcntcc cctttcttc cctttctctg tgaagcagcc attttatta      60 nnttcctgtt tatcactcat gcatgcatat gttattgag gatgttggca ttcaagcaaa   120
tatatgggtt aacattcttt ttgtcatccc tatacgaaag atatacccag tatactctat   180
```

```
tgggtggggt tttttcctta aaatattcag tagatctctc cagttagcac atagttatct    240
tatagataga acatatacat ataccctttn ttaactatgc tattaaaata tagctttcag    300
taccttgata attattttgg gattgaaaaa ctactggaaa tcaactcaat catgtgaaag    360
c                                                                   361

<210> SEQ ID NO 49
<211> LENGTH: 475
<212> TYPE: DNA
<213> ORGANISM: mammalian

<400> SEQUENCE: 49
acacatctgc tcctgctctc tctcctccag cgaccctagc catgagaacc ctcaccatcc     60
tcactgctgt tctcctcgtg gccctccagg ccaaggctga gccactccaa gctgaggatg    120
atccactgca ggcaaaagct tatgaggctg atgcccagga gcagcgtggg gcaaatgacc    180
aggactttgc cgtctccttt gcagaggatg caagctcaag tcttagagct ttgggctcaa    240
caagggcttt cacttgccat tgcagaaggt cctgttattc aacagaatat tcctatggga    300
cctgcactgt catgggtatt aaccacagat tctgctgcct ctgagggatg agaacagaga    360
gaaatatatt cataatttac tttatgacct agaaggaaac tgtcgtgtgt cccatacatt    420
gccatcaact tgtttcctc atctcaaata aagtcctttc agcaaaaaaa aaaaa          475

<210> SEQ ID NO 50
<211> LENGTH: 100
<212> TYPE: PRT
<213> ORGANISM: mammalian

<400> SEQUENCE: 50

Met Arg Thr Leu Thr Ile Leu Thr Ala Val Leu Leu Val Ala Leu Gln
 1               5                  10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
        35                  40                  45

Phe Ala Val Ser Phe Ala Glu Asp Ala Ser Ser Ser Leu Arg Ala Leu
    50                  55                  60

Gly Ser Thr Arg Ala Phe Thr Cys His Cys Arg Arg Ser Cys Tyr Ser
65                  70                  75                  80

Thr Glu Tyr Ser Tyr Gly Thr Cys Thr Val Met Gly Ile Asn His Arg
                85                  90                  95

Phe Cys Cys Leu
            100

<210> SEQ ID NO 51
<211> LENGTH: 515
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 51
nggggccgta ggcgattnca acagctgatn tttattttc ttcttgattc tcttctacag      60
tttccaaatt ctctacaatg aacatgtact tctttttaat atcaaaagac aaaagaattg    120
gtacgtaaaa agaacatcct tcccatcttc aaggtcaaga ttgaacgctg actcctgcag    180
gaagtcttcc aggattccca ggcaggaatg atggctccct gtcctgtag ctccaggagt     240
```

| | |
|---|---|
| tcttgcttca cgcacgcctc acataccana ctgaatgttg gcaggaggag tgaccaggtc | 300 |
| ggtcatctgt gtccctacca cctacaacag gccagcaatc tacccgtgtg tgtttgttgg | 360 |
| acagaattaa ccatgatggg cggccgaggg cgcctggagc tatttggggg cttggagaga | 420 |
| acctcttagg agagtgtcag gctctaggcc agtgtcacca gaggaggtca gtctcagtcc | 480 |
| ttggagtcgt cctgtgtgaa attgttatcc cgcta | 515 |

<210> SEQ ID NO 52
<211> LENGTH: 340
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 52

| | |
|---|---|
| ctacttttc cngtaggact tattgcanag ctttgctggt tttgtaaaat ggatggaaga | 60 |
| ctttgtattt atactgtgat tttgaacaga ttatgcaaca ttggaaggaa ggctgtnctt | 120 |
| tgatggtttg aaggaactca ncantatgat gatctggttc caggggaaaa aaatagcttg | 180 |
| gttggtgtct agccccccaa cactttttgtn tcgttgtgta taaaagaaga aagactggca | 240 |
| tgtaccttca tttgcttagc tatttgagta tctagagaaa aattaaaatg caatgagtta | 300 |
| cgcantatac cctggcacac ttaataaatt aaacatttgt | 340 |

<210> SEQ ID NO 53
<211> LENGTH: 441
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 53

| | |
|---|---|
| tcgcaaatnn caacaccnac attatatttc cttctgacac ttggaaggta nccgaaattt | 60 |
| ctagaaatgg atccttctca caaagtagag accaagagaa aaactcattg attgggtttt | 120 |
| tacttctttc aaggactccn gaaatttcac tttgaactgc cgccaannga gntgttaaga | 180 |
| taacccacac tnaaactaaa ggctcnccca taggcttgat nnaaaaatga aggtaannt | 240 |
| ngtangtggg aatcngnnnt gaatnttgat cgtccnncng ccgngnagta ctnngnanaa | 300 |
| agcggncnat ngggtaangc gccngccccg nnnnanncnn cccactgtgc nnttaaccnc | 360 |
| ccatnccggn anancgacgc canncgcnnt nccaacccnn ngggngggnc ncnngcnncg | 420 |
| ccgcnngctc ccctacgacc a | 441 |

<210> SEQ ID NO 54
<211> LENGTH: 373
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 54

| | |
|---|---|
| ctggttcggg tgttacgcac acgtacttaa atgaaagcat gtggcatgtt catcgnataa | 60 |
| cacaatatga atacagggca tgcnttttgc agcagtgagt ctcttcagaa aacccttttc | 120 |
| tacagttagg gntgagttac ttcctatcaa gccnnnacgt gctaacaggc tcaatattcc | 180 |

| | |
|---|---:|
| tgaatgaaat atcaaactag tgacaagctt cctggtcttg agatgtcttc tcgntaagga | 240 |
| gatgggcctt ttggaggtan aggataaaat gaatganctc tgncctgatn ccgtattcta | 300 |
| gaactttgca tgacctttac tggcgncgcc tctttgaatg ttcttgaaan tttaaaacnt | 360 |
| ttctttntna ccn | 373 |

<210> SEQ ID NO 55
<211> LENGTH: 495
<212> TYPE: DNA
<213> ORGANISM: mammalian

<400> SEQUENCE: 55

| | |
|---|---:|
| gcttccattg cacgaagctc tcctaggcca aaaagatgtg caaagatcca ccttacaaag | 60 |
| tagaagaatc tgggtatgct ggtttcattt tgccaattga agtttatttt aaaaacaagg | 120 |
| aagaacctag gaaagtccgc tttgattatg acttattcct gcatcttgaa ggccatccgc | 180 |
| cagtgaatca cctccgttgt gaaaagctaa ctttcaacaa ccccacagag gactttaggg | 240 |
| agaaagttgc ttgaaggcag gaggggaccc taataggagt attcatacca gcagcagcag | 300 |
| cagcagcagt agcagcagca gcagcagcag cagcagcagc agtagcagca gcagcagcag | 360 |
| cagcagcggc agcagtagca gcagcagtag cagcagcagc agcagcagta gtccagtttt | 420 |
| tcaaagcctc acaattaatg aaggagccaa ggaaaacctt ttaagactcc agagacataa | 480 |
| agtgcttcaa agaaa | 495 |

<210> SEQ ID NO 56
<211> LENGTH: 2691
<212> TYPE: DNA
<213> ORGANISM: mammalian

<400> SEQUENCE: 56

| | |
|---|---:|
| gcttgcccgt cggtcgctag ctcgctcggt gcgcgtcgtc ccgctccatg gcgctcttcg | 60 |
| tgcggctgct ggctctcgcc ctggctctgg ccctgggccc cgccgcgacc ctggcgggtc | 120 |
| ccgccaagtc gccctaccag ctggtgctgc agcacagcag gctccggggc cgccagcacg | 180 |
| gccccaacgt gtgtgctgtg cagaaggtta ttggcactaa taggaagtac ttcaccaact | 240 |
| gcaagcagtg gtaccaaagg aaaatctgtg gcaaatcaac agtcatcagc tacgagtgct | 300 |
| gtcctggata tgaaaaggtc cctggggaga agggctgtcc agcagcccta ccactctcaa | 360 |
| acctttacga gaccctggga gtcgttggat ccaccaccac tcagctgtac acggaccgca | 420 |
| cggagaagct gaggcctgag atggaggggc ccggcagctt caccatcttc gcccctagca | 480 |
| acgaggcctg ggcctccttg ccagctgaag tgctggactc cctggtcagc aatgtcaaca | 540 |
| ttgagctgct caatgccctc cgctaccata tggtgggcag gcgagtcctg actgatgagc | 600 |
| tgaaacacgg catgacccta acctctatgt accagaattc caacatccag atccaccact | 660 |
| atcctaatgg gattgtaact gtgaactgtg cccggctcct gaaagccgac caccatgcaa | 720 |
| ccaacgggat ggtgcacctc atcgataagg tcatctccac catcaccaac acatccagc | 780 |
| agatcattga gatcgaggac accttgaga cccttcgggc tgctgtggct gcatcagggc | 840 |
| tcaacacgat gcttgaaggt aacggccagt acacgctttt ggccccgacc aatgaggcct | 900 |
| tcgagaagat ccctagtgag actttgaacc gtatcctggg cgaccagaa gccctgagag | 960 |
| acctgctgaa caaccacatc ttgaagtcag ctatgtgtgc tgaagccatc gttgcgggc | 1020 |
| tgtctgtaga gaccctggag ggcacgacac tggaggtggg ctgcagcggg gacatgctca | 1080 |
| ctatcaacgg gaaggcgatc atctccaata agacatcct agccaccaac ggggtgatcc | 1140 |

-continued

```
actacattga tgagctactc atcccagact cagccaagac actatttgaa ttggctgcag   1200
agtctgatgt gtccacagcc attgaccttt tcagacaagc cggcctcggc aatcatctct   1260
ctggaagtga gcggttgacc ctcctggctc ccctgaattc tgtattcaaa gatggaaccc   1320
ctccaattga tgcccataca aggaatttgc ttcggaacca cataattaaa gaccagctgg   1380
cctctaagta tctgtaccat ggacagaccc tggaaactct gggcggcaaa aaactgagag   1440
tttttgttta tcgtaatagc ctctgcattg agaacagctg catcgcggcc cacgacaaga   1500
gggggaggta cgggaccctg ttcacgatgg accgggtgct gacccccca atggggactg    1560 tcatggatgt cctgaaggga gacaatcgct ttagcatgct ggtagctgcc atccagtctg   1620
caggactgac ggagaccctc aaccgggaag gagtctacac agtctttgct cccacaaatg   1680
aagccttccg agccctgcca ccaagagaac ggagcagact cttgggagat gccaaggaac   1740
ttgccaacat cctgaaatac cacattggtg atgaaatcct ggttagcgga ggcatcgggg   1800
ccctggtgcg gctaaagtct ctccaaggtg acaagctgga agtcagcttg aaaaacaatg   1860
tggtgagtgt caacaaggag cctgttgccg agcctgacat catggccaca aatggcgtgg   1920
tccatgtcat caccaatgtt ctgcagcctc cagccaacag acctcaggaa agagggdatg   1980
aacttgcaga ctctgcgctt gagatcttca acaagcatc agcgttttcc agggcttccc    2040
agaggtctgt gcgactagcc cctgtctatc aaaagttatt agagaggatg aagcattagc   2100
ttgaagcact acaggaggaa tgcaccacgg cagctctccg ccaatttctc tcagatttcc   2160
acagagactg tttgaatgtt ttcaaaacca agtatcacac tttaatgtac atgggccgca   2220
ccataatgag atgtgagcct tgtgcatgtg ggggaggagg gagagagatg tacttttttaa   2280 atcatgttcc ccctaaacat ggctgttaac ccactgcatg cagaaacttg gatgtcactg   2340
cctgacattc acttccagag aggacctatc ccaaatgtgg aattgactgc ctatgccaag   2400
tccctggaaa aggagcttca gtattgtggg gctcataaaa catgaatcaa gcaatccagc   2460
ctcatgggaa gtcctggcac agttttttgta aagcccttgc acagctggag aaatggcatc   2520
attataagct atgagttgaa atgttctgtc aaatgtgtct cacatctaca cgtggcttgg   2580
aggcttttat ggggccctgt ccaggtagaa aagaaatggt atgtagagct tagatttccc   2640
tattgtgaca gagccatggt gtgtttgtaa taataaaacc aaagaaacat a            2691
```

<210> SEQ ID NO 57
<211> LENGTH: 683
<212> TYPE: PRT
<213> ORGANISM: mammalian

<400> SEQUENCE: 57

```
Met Ala Leu Phe Val Arg Leu Leu Ala Leu Ala Leu Ala Leu
1               5                  10                  15

Gly Pro Ala Ala Thr Leu Ala Gly Pro Ala Lys Ser Pro Tyr Gln Leu
            20                  25                  30

Val Leu Gln His Ser Arg Leu Arg Gly Arg Gln His Gly Pro Asn Val
        35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
```

-continued

```
               100                 105                 110
Val Gly Ser Thr Thr Thr Gln Leu Tyr Thr Asp Arg Thr Glu Lys Leu
            115                 120                 125

Arg Pro Glu Met Glu Gly Pro Gly Ser Phe Thr Ile Phe Ala Pro Ser
        130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
                180                 185                 190

Ser Met Tyr Gln Asn Ser Asn Ile Gln Ile His His Tyr Pro Asn Gly
            195                 200                 205

Ile Val Thr Val Asn Cys Ala Arg Leu Leu Lys Ala Asp His His Ala
        210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
        275                 280                 285

Pro Ser Glu Thr Leu Asn Arg Ile Leu Gly Asp Pro Glu Ala Leu Arg
    290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350

Ser Asn Lys Asp Ile Leu Ala Thr Asn Gly Val Ile His Tyr Ile Asp
        355                 360                 365

Glu Leu Leu Ile Pro Asp Ser Ala Lys Thr Leu Phe Glu Leu Ala Ala
    370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
        435                 440                 445

Leu Tyr His Gly Gln Thr Leu Glu Thr Leu Gly Gly Lys Lys Leu Arg
    450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
        515                 520                 525
```

```
Glu Thr Leu Asn Arg Glu Gly Val Tyr Thr Val Phe Ala Pro Thr Asn
            530                 535                 540

Glu Ala Phe Arg Ala Leu Pro Pro Arg Glu Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Ile Gly Ala Leu Val Arg Leu Lys Ser Leu
            580                 585                 590

Gln Gly Asp Lys Leu Glu Val Ser Leu Lys Asn Asn Val Val Ser Val
            595                 600                 605

Asn Lys Glu Pro Val Ala Glu Pro Asp Ile Met Ala Thr Asn Gly Val
            610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
                660                 665                 670

Val Tyr Gln Lys Leu Leu Glu Arg Met Lys His
            675                 680
```

<210> SEQ ID NO 58
<211> LENGTH: 380
<212> TYPE: DNA
<213> ORGANISM: mammalian

<400> SEQUENCE: 58

```
gagaatgaga atcttgtaga aaatggtgca gactccgatg aagatgataa cagcttcctc      60
aaacaacaat ctccacaaga acccaagtct ctgaattggt cgagttttgt agacaacacc     120
tttgctgaag aattcactac tcagaatcag aaatcccagg atgtggaact ctgggaggga     180
gaagtggtca agagctctc tgtggaagaa cagataaaga gaaatcggta ttatgatgag      240
gatgaggatg aagagtgaca aattgcaatg atgcttgggc cttaaattca tgttagtgtt     300
agcgagccac tgccctttgt caaaatgtga tgcacataag caggtatccc agcatgaaat     360
gtaatttact tggaagtaac                                                  380
```

<210> SEQ ID NO 59
<211> LENGTH: 2273
<212> TYPE: DNA
<213> ORGANISM: mammalian

<400> SEQUENCE: 59

```
gccagacctg ctcttgctgc tgctcaggta gaacatctgg gaggtcccctt gctgaccact     60
ggaagaagat gagctcgagc tattggagtg agacgagcag cagcagctgt ggaacccagc     120
agctcccaga ggtgctgcag tgccagcccc agcattacca ctgctaccat cagtcaagcc     180
aagcccagca gcctccagaa aaaatgtag tgtatgagcg agtgaggacc tacagtgggc      240
ccatgaacaa ggtggtgcag gccttggacc ccttcaactc acgggaagtg ctctcccctc     300
tcaaaaccac ctcctcctac caaaatttgg tttggagcga ccattctcag gaactccatt     360
ctccaacttt aaaatatct acatgtgccc aagtactct acatataacc caaaatactg       420
aacaggaact tcattctcca acagtgaaac ttactacata tccacagacc actattagga     480
aatatgtagt acaaaatcct gaacaggaac cactgtctca attcctaaga ggaagccatt     540
tcttcccagg aaacaatgtt atttatgaaa aaacaataag aaaagtggag aagctaaata     600
```

```
ctgatcaggg gtgccatcct caggctcaat gccatcatca cattatccaa cagccccagg    660
tcatccactc tgcacactgg caacaacctg attctagcca gcaaatccaa gccatcacag    720
gaaataatcc aatttctaca catattggaa atgaactgtg ccatagtgga tcaagccaga    780
tttgtgagca ggtgataatt caggatgatg gccctgaaaa attggacccc agatattttg    840
gagagttgct tgctgatctg agccgtaaga atacggatct atatcactgc ttattagaac    900
atttgcagag aattggagga agcaaacagg actttgagtc tacagatgag tcggaagaca    960
ttgaatcatt gattcctaaa ggattatcag agtttacaaa acagcaaata cgctacattc   1020
tgcagatgag gggtatgtct gataagtcac tccgactagt gctgtccaca tttagcaaca   1080
tacgggagga gcttggacat cttcaaaatg atttgacatc actggaaaat gacaagatga   1140
gacttgagaa agatttatca ttcaaagaca ctcaattaaa agagtacgaa gaactcttgg   1200
catcagtgag agcaaataat caccagcagc agcaaggact tcaagactca agttcaaaat   1260
gccaggcatt ggaagaaaac aatctctctc ttcgacatac actatcagac atggaataca   1320
gactaaaaga actggaatat tgtaaacgta atttagagca agagaatcaa aaccttagaa   1380
tgcaggtttc tgagacttgc acaggcccaa tgttgcaggc taaaatggat gagattggca   1440
accactacac ggagatggta aaaaacttga gaatggagaa agatagagag atctgcagac   1500
tgaggtccca attaaaccag taccataaag atgtttcaaa gagagaagga agttgtagtg   1560
acttccaatt taagcttcat gaactgacaa gcttgctgga agagaaggat ccctcataa   1620 agcgtcagtc agaggaactc tccaagttgc ggcaagaaat atattcctct cataaccaac   1680
cctccactgg tggaaggact actattacca ctaaaaagta caggacacaa tatccaatcc   1740
taggcctcct atatgatgac tacgaatata taccaccagg tagtgaaaca cagactattg   1800
tgattgagaa aacagaagac aaatacactt gtccatgaat ggatccactt taaagtatta   1860
caactcaaag ccgtttttt tgtgtgtgtg tgtctctgca ttagtacttt gttattttc    1920 catcactaaa ggccaatcag aatttggaac catgctgcta cccaagaaat ctaatggaat   1980
gaattagttc tgtagatgac aatttcttca cccatttatg agacctaaat cttttccata   2040
acactcatgt attcagtata acaacatact aactgaaaga gggacctgat tgtttaaagt   2100
ttgattgcag acactgtaga acataactca ttatgtttca gataaggtaa ctcctagata   2160
tcaaactaat ttgttggggt agagatttta caagtcatgc cattagaaga ttttctctga   2220
tattatatgt gcagttcagt tacaagatga aatcatgttt ttttaacaaa aaa          2273

<210> SEQ ID NO 60
<211> LENGTH: 2840
<212> TYPE: DNA
<213> ORGANISM: mammalian

<400> SEQUENCE: 60
cggcctctca tttctcctag cccttctgtt cttccttggc caagctgcag gggatttggg     60
ggatgtggga cctccaattc ccagccccgg cttcagctct ttcccaggtg ttgactccag    120
ctccagcttc agctccagct ccaggtcggg ctccagctcc agccgcagct taggcagcgg    180
aggttctgtg tcccagttgt tttccaattt caccggctcc gtggatgacc gtgggacctg    240
ccagtgctct gtttccctgc cagacaccac ctttcccgtg acagagtgg aacgcttgga     300 attcacagct catgttcttt ctcagaagtt tgagaaagaa ctttccaaag tgagggaata    360
tgtccaatta attagtttgt atgaaaagaa actgttaaac ctaactgtcc gaattgcat    420 catgggagaa ggatacattt cttacactga actggacttc gagctgataa ggtagaagtg    480
```

| | |
|---|---|
| aaggagatgg aaaaactggt catacagctg aaggagagtt ttggtggaag ctcagaaatt | 540 |
| gttgaccagc tggaggtgga gataagaaat atgactctct tggtagagaa gcttgagaca | 600 |
| ctagacaaaa acaatgtcct tgccattcgc cgagaaatcg tggctctgaa gaccaagctg | 660 |
| aaagagtgtg aggcctctaa agatcaaaac acccctgtcg tccaccctcc tcccactcca | 720 |
| gggagctgtg gtcatggtgg tgtggtgaac atcagcaaac cgtctgtggt tcagctcaac | 780 |
| tggagagggt tttcttatct atatggtgct tggggtaggg attactctcc ccagcatcca | 840 |
| aacaaaggac tgtattgggt ggcgccattg aatacagatg ggagactgtt ggagtattat | 900 |
| atactgtaca acacactgga tgatttgcta ttgtatataa atgctcgaga gttgcggatc | 960 |
| acctatggcc aaggtagtgg tacagcagtt tacaacaaca acatgtacgt caacatgtac | 1020 |
| aacaccggga atattgccag agttaacctg accaccaaca cgattgctgt gactcaaact | 1080 |
| ctccctaatg ctgcctataa taaccgcttt tcatatgcta atgttgcttg gcaagcatat | 1140 |
| tgactttgct gtggatgaga atggattgtg ggttatttat tcaactgaag ccagcactgg | 1200 |
| ttaacatggt gattagtaaa ctcaatgaca ccacacttca ggtgctaaac acttggtata | 1260 |
| ccaagcagta taaccatct gcttctaacg ccttcatggt atgtggggtt ctgtatgcca | 1320 |
| cccgtactat gaacaccaga acagaagaga ttttttacta ttatgacaca aacacaggga | 1380 |
| aagagggcaa actagacatt gtaatgcata agatgcagga aaaagtgcag agcattaact | 1440 |
| ataaccctt tgaccagaaa ctttatgtct ataacgatgg ttaccttctg aattatgatc | 1500 |
| tttctgtctt gcagaagccc cagtaagctg tttaggagtt agggtgaaag agaaaatgtt | 1560 |
| tgttgaaaaa atagtcttct ccacttactt agatatctgc agatatctaa gtaagtggag | 1620 |
| aagactattt tttcaacaaa cattttctct ttcacccctaa ctcctaaaca gcttactggg | 1680 |
| gcttctgcaa gacagaaaga tcataattca gaaggtaacc atcgttatag acataaagtt | 1740 |
| tctggtcaaa agggttatag ttaatgctct gcactttttc ctgcatctta tgcattacaa | 1800 |
| tgtctagttt gccctctttc cctgtgtttg tgtcataata gtaaaaaatc tcttctgttt | 1860 |
| ggcgtatagg gattctttgt acaggaaata ttgcccaatg actagtcctc atccatgtag | 1920 |
| caccactaat tcttccatgc ctggaagaaa cctggggact tagttaggta gattaatatc | 1980 |
| tggagctcct cgagggacca aatctccaac ttttttttcc cctcactagc acctggaatg | 2040 |
| atgctttgta tgtggcagat aagtaaattt ggcatgctta tatattctac atctgtaaag | 2100 |
| tgctgagttt tatggagaga ggccttttta tgcattaaat tgtacatggc aaataaatcc | 2160 |
| cagaaggatc tgtagatgag gcacctgctt tttcttttct ctcattgtcc accttactaa | 2220 |
| aagtcagtag aatcttctac ctcataactt ccttccaaag gcagctcaga agattagaac | 2280 |
| cagacttact aaccaattcc accccccacc aaccccttc tactgcctac tttaaaaaaa | 2340 |
| ttaatagttt tctatggaac tgatctaaga ttagaaaaat taattttctt taatttcatt | 2400 |
| atgaactttt atttacatga ctctaagact ataagaaaat ctgatggcag tgacaaagtg | 2460 |
| ctagcattta ttgttatcta ataaagacct tggagcatat gtgcaactta tgagtgtatc | 2520 |
| agttgttgca tgtaattttt gcctttgttt aagcctggaa cttgtaagaa atgaaaatt | 2580 |
| taatttttt ttctaggacg agctatagaa aagctattga gagtatctag ttaatcagtg | 2640 |
| cagtagttgg aaaccttgct ggtgtatgtg atgtgcttct gtgcttttga atgactttat | 2700 |
| catctagtct ttgtctatt ttcctttgat gttcaagtcc tagtctatag gattggcagt | 2760 |
| ttaaatgctt tactcccct tttaaaataa atgattaaaa tgtgcttcga aaaaaaaaa | 2820 |
| aaaaaaaaaa aaaaaaaaa | 2840 |

```
<210> SEQ ID NO 61
<211> LENGTH: 218
<212> TYPE: PRT
<213> ORGANISM: mammalian

<400> SEQUENCE: 61

Met Glu Lys Leu Val Ile Gln Leu Lys Glu Ser Phe Gly Gly Ser Ser
1               5                   10                  15
Glu Ile Val Asp Gln Leu Glu Val Glu Ile Arg Asn Met Thr Leu Leu
            20                  25                  30
Val Glu Lys Leu Glu Thr Leu Asp Lys Asn Asn Val Leu Ala Ile Arg
        35                  40                  45
Arg Glu Ile Val Ala Leu Lys Thr Lys Leu Lys Glu Cys Glu Ala Ser
    50                  55                  60
Lys Asp Gln Asn Thr Pro Val Val His Pro Pro Thr Pro Gly Ser
65                  70                  75                  80
Cys Gly His Gly Gly Val Val Asn Ile Ser Lys Pro Ser Val Val Gln
                85                  90                  95
Leu Asn Trp Arg Gly Phe Ser Tyr Leu Tyr Gly Ala Trp Gly Arg Asp
            100                 105                 110
Tyr Ser Pro Gln His Pro Asn Lys Gly Leu Tyr Trp Val Ala Pro Leu
        115                 120                 125
Asn Thr Asp Gly Arg Leu Leu Glu Tyr Tyr Ile Leu Tyr Asn Thr Leu
    130                 135                 140
Asp Asp Leu Leu Leu Tyr Ile Asn Ala Arg Glu Leu Arg Ile Thr Tyr
145                 150                 155                 160
Gly Gln Gly Ser Gly Thr Ala Val Tyr Asn Asn Asn Met Tyr Val Asn
                165                 170                 175
Met Tyr Asn Thr Gly Asn Ile Ala Arg Val Asn Leu Thr Thr Asn Thr
            180                 185                 190
Ile Ala Val Thr Gln Thr Leu Pro Asn Ala Ala Tyr Asn Asn Arg Phe
        195                 200                 205
Ser Tyr Ala Asn Val Ala Trp Gln Ala Tyr
    210                 215

<210> SEQ ID NO 62
<211> LENGTH: 439
<212> TYPE: DNA
<213> ORGANISM: mammalian

<400> SEQUENCE: 62
ggtgggtctg aatctagcac catgacggaa ctagagacag ccatgggcat gatcatagac     60
gtcttttccc gatattcggg cagcgagggc agcacgcaga ccctgaccaa gggggagctc    120
aaggtgctga tggagaagga gctaccaggc ttcctgcaga gtggaaaaga caaggatgcc    180
gtggataaat tgctcaagga cctggacgcc aatggagatg cccaggtgga cttcagtgag    240
ttcatcgtgt tcgtggctgc aatcacgtct gcctgtcaca agtactttga aaggcagga    300
ctcaaatgat gccctggaga tgtcacagat tcctgcagag ccatggtccc aggcttccca    360
aaagtgtttg ttggcaatta ttcccctagg ctgagcctgc tcatgtacct ctgattaata    420
aatgcttatg aaaaaaaaa                                                439

<210> SEQ ID NO 63
<211> LENGTH: 95
<212> TYPE: PRT
<213> ORGANISM: mammalian
```

<400> SEQUENCE: 63

| Met | Thr | Glu | Leu | Glu | Thr | Ala | Met | Gly | Met | Ile | Ile | Asp | Val | Phe | Ser |
|---|---|---|---|---|---|---|---|---|---|---|---|---|---|---|---|
| 1 | | | | 5 | | | | | 10 | | | | | 15 | |

| Arg | Tyr | Ser | Gly | Ser | Glu | Gly | Ser | Thr | Gln | Thr | Leu | Thr | Lys | Gly | Glu |
|---|---|---|---|---|---|---|---|---|---|---|---|---|---|---|---|
| | | | 20 | | | | | 25 | | | | | 30 | | |

| Leu | Lys | Val | Leu | Met | Glu | Lys | Glu | Leu | Pro | Gly | Phe | Leu | Gln | Ser | Gly |
|---|---|---|---|---|---|---|---|---|---|---|---|---|---|---|---|
| | | | 35 | | | | | 40 | | | | | 45 | | |

| Lys | Asp | Lys | Asp | Ala | Val | Asp | Lys | Leu | Leu | Lys | Asp | Leu | Asp | Ala | Asn |
|---|---|---|---|---|---|---|---|---|---|---|---|---|---|---|---|
| | | | 50 | | | | | 55 | | | | | 60 | | |

| Gly | Asp | Ala | Gln | Val | Asp | Phe | Ser | Glu | Phe | Ile | Val | Phe | Val | Ala | Ala |
|---|---|---|---|---|---|---|---|---|---|---|---|---|---|---|---|
| 65 | | | | | 70 | | | | | 75 | | | | | 80 |

| Ile | Thr | Ser | Ala | Cys | His | Lys | Tyr | Phe | Glu | Lys | Ala | Gly | Leu | Lys |
|---|---|---|---|---|---|---|---|---|---|---|---|---|---|---|
| | | | | 85 | | | | | 90 | | | | | 95 |

<210> SEQ ID NO 64
<211> LENGTH: 358
<212> TYPE: DNA
<213> ORGANISM: mammalian

<400> SEQUENCE: 64

```
gaccagatcc ctctccagtc ctggaacagc cagtcgtcct tgctggatgt gcaaccgggt    60
tccttccttc gagagcttcg aagatgactg cagccagtct ctctgcctca ataagccaac   120
catgtctttc aaggattaca tccaagagag gagtgacccg gtggagcaag gcaaaccagt   180
tatacctgca gctgtgctgg ccggcttcac aggaagtgga cctattcagc ttgtggcagt   240
ttctcctgga gcttgctatc agacaaatcc tgccagtcat tcatcagctg gactgggagac  300
ggatgggagt ttaagctcgc cgaccccgat gaggtggccc gccggtgggg aaagagga     358
```

<210> SEQ ID NO 65
<211> LENGTH: 207
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 65

```
actntggaca atctccacct tagctattcc cagggaaccc tngggggcaa ctgacatccc    60
tccaagatgt tctcctgatg tagcttgaga tataaaggaa aggccctgca caggtggctg   120
tttcttgtct gttatgtcag aggaacagtc ctgttcagaa aggggctctt ctgagcagaa   180
atgnntaata aactttgtgc tgatctg                                       207
```

<210> SEQ ID NO 66
<211> LENGTH: 4375
<212> TYPE: DNA
<213> ORGANISM: mammalian

<400> SEQUENCE: 66

```
ggtggcctct gtggccgtcc aggctagcgg cggcccgcag gcggcgggga gaaagactct    60
ctcacctggt cttgcggctg tggccaccgc cggccagggg tgtggagggc gtgctgccgg   120
agacgtccgc cgggctctgc agttccgccg ggggtcgggc agctatggag ccgcggccca   180
cggcgccctc ctccggcgcc ccgggactgg ccggggtcgg ggagacgccg tcagccgctg   240
cgctggccgc agccagggtg gaactgcccg gcacggctgt gccctcggtg ccggaggatg   300
ctgcgcccgc gagccgggac ggcggcgggg tccgcgatga gggccccgcg gcggccgggg   360
```

| | |
|---|---|
| acgggctggg cagacccttg gggcccaccc cgagccagag ccgtttccag gtggacctgg | 420 |
| tttccgagaa cgccgggcgg gccgctgctg cggcggcggc ggcggcggcg gcagcggcgg | 480 |
| cggctggtgc tggggcgggg gccaagcaga ccccgcgga cggggaagcc agcggcgaga | 540 |
| gcgagccagc taaaggcagc gaggaagcca agggccgctt ccgcgtgaac ttcgtggacc | 600 |
| cagctgcctc ctcgtcggct gaagacagcc tgtcagatgc tgccggggtc ggagtcgacg | 660 |
| ggcccaacgt gagcttccag aacggcgggg acacggtgct gagcgagggc agcagcctgc | 720 |
| actccggcgg cggcggcggc agtgggcacc accagcacta ctattatgat acccacacca | 780 |
| acacctacta cctgcgcacc ttcggccaca acaccatgga cgctgtgccc aggatcgatc | 840 |
| actaccggca cacagccgcg cagctgggcg agaagctgct ccggcctagc ctggcggagc | 900 |
| tccacgacga gctggaaaag gaaccttttg aggatggctt tgcaaatggg gaagaaagta | 960 |
| ctccaaccag agatgctgtg gtcacgtata ctgcagaaag taaggagtc gtgaagtttg | 1020 |
| gctggatcaa gggtgtatta gtacgttgta tgttaaacat ttgggggtgtg atgcttttca | 1080 |
| ttagattgtc atggattgtg ggtcaagctg gaataggtct atcagtcctt gtaataatga | 1140 |
| tggccactgt tgtgacaact atcacaggat tgtctacttc agcaatagca actaatggat | 1200 |
| ttgtaagagg aggaggagca tattatttaa tatctagaag tctagggcca gaatttggtg | 1260 |
| gtgcaattgg tctaatcttc gccttttgcca acgctgttgc agttgctatg tatgtggttg | 1320 |
| gatttgcaga aaccgtggtg gagttgctta aggaacattc catacttatg atagatgaaa | 1380 |
| tcaatgatat ccgaattatt ggagccatta cagtcgtgat tcttttaggt atctcagtag | 1440 |
| ctggaatgga gtgggaagca aaagctcaga ttgttctttt ggtgatccta cttcttgcta | 1500 |
| ttggtgattt cgtcatagga acatttatcc cactggagag caagaagcca aaagggtttt | 1560 |
| ttggttataa atctgaaata tttaatgaga actttgggcc cgattttcga gaggaagaga | 1620 |
| cttttctttc tgtatttgcc atcttttttc ctgctgcaac tggtattctg gctggagcaa | 1680 |
| atatctcagg tgatcttgca gatcctcagt cagccatacc caaaggaaca ctcctagcca | 1740 |
| ttttaattac tacattggtt tacgtaggaa ttgcagtatc tgtaggttct tgtgttgttc | 1800 |
| gagatgccac tggaaacgtt aatgacacta tcgtaacaga gctaacaaac tgtacttctg | 1860 |
| cagcctgcaa attaaacttt gattttcat cttgtgaaag cagtccttgt cctatggcc | 1920 |
| taatgaacaa cttccaggta atgagtatgg tgtcaggatt tacaccacta atttctgcag | 1980 |
| gtatattttc agccactctt tcttcagcat tagcatccct agtgagtgct cccaaaatat | 2040 |
| ttcaggctct atgtaaggac aacatctacc cagctttcca gatgtttgct aaaggttatg | 2100 |
| ggaaaaataa tgaacctctt cgtggctaca tcttaacatt cttaattgca cttggattca | 2160 |
| tcttaattgc tgaactgaat gttattgcac caattatctc aaacttcttc cttgcatcat | 2220 |
| atgcattgat caattttca gtattccatg catcacttgc aaaatctcca ggatggcgtc | 2280 |
| ctgcattcaa atactacaac atgtggatat cacttcttgg agcaattctt tgttgcatag | 2340 |
| taatgttcgt cattaactgg tgggctgcat tgctaacata tgtgatagtc cttgggctgt | 2400 |
| atatttatgt tacctacaaa aaaccagatg tgaattgggg atcctctaca caagccctga | 2460 |
| cttacctgaa tgcactgcag cattcaattc gtctttctgg agtggaagac cacgtgaaaa | 2520 |
| actttaggcc acagtgtctt gttatgacag gtgctccaaa ctcacgtcca gctttacttc | 2580 |
| atcttgttca tgatttcaca aaaaatgttg gtttgatgat ctgtggccat gtacatatgg | 2640 |
| gtcctcgaag acaagccatg aaagagatgt ccatcgatca agccaaatat cagcgatggc | 2700 |
| ttattaagaa caaaatgaag gcattttatg ctccagtaca tgcagatgac ttgagagaag | 2760 |

```
gtgcacagta tttgatgcag gctgctggtc ttggtcgtat gaagccaaac acacttgtcc   2820
ttggatttaa gaaagattgg ttgcaagcag atatgaggga tgtggatatg tatataaact   2880
tatttcatga tgcttttgac atacaatatg gagtagtggt tattcgccta aaagaaggtc   2940
tggatatatc tcatcttcaa ggacaagaag aattattgtc atcacaagag aaatctcctg   3000
gcaccaagga tgtggtagta agtgtggaat atagtaaaaa gtccgattta gatacttcca   3060
aaccactcag tgaaaaacca attacacaca aagttgagga gaggatggc aagactgcaa   3120 ctcaaccact gttgaaaaaa gaatccaaag gccctattgt gcctttaaat gtagctgacc   3180
aaaagcttct tgaagctagt acacagtttc agaaaaaaca aggaaagaat actattgatg   3240
tctggtggct ttttgatgat ggaggtttga ccttattgat accttacctt ctgacgacca   3300
agaaaaaatg gaaagactgt aagatcagag tattcattgg tggaaagata aacagaatag   3360
accatgaccg gagagcgatg gctactttgc ttagcaagtt ccggatagac ttttctgata   3420
tcatggttct aggagatatc aataccaaac caaagaaaga aatattata gcttttgagg   3480 aaatcattga gccatacaga cttcatgaag atgataaaga gcaagatatt gcagataaaa   3540
tgaaagaaga tgaaccatgg cgaataacag ataatgagct tgaactttat aagaccaaga   3600
cataccggca gatcaggtta aatgagttat taaaggaaca ttcaagcaca gctaatatta   3660
ttgtcatgag tctcccagtt gcacgaaaag gtgctgtgtc tagtgctctc tacatggcat   3720
ggttagaagc tctatctaag gacctaccac caatcctcct agttcgtggg aatcatcaga   3780
gtgtccttac cttctattca taaatgttct atacagtgga cagccctcca gaatggtact   3840
tcagtgccta gtgtagtaac ctgaaatctt caatgacaca ttaacatcac aatggcgaat   3900
ggtgactttt ctttcacgat ttcattaatt tgaaagcaca caggaaagct tgctccattg   3960
ataacgtgta tggagacttc ggttttagtc aattccatat ctcaatctta atggtgattc   4020
ttctctgttg aactgaagtt tgtgagagta gttttccttt gctacttgaa tagcaataaa   4080
agcgtgttaa cttttggtt gatgaaagaa gtacaaaaag cctttagcct tgaggtgcct   4140
tctgaaatta accaaatttc atccatatat cctcttttat aaacttatag aatgtcaaac   4200
tttgccttca actgttttta tttctagtct cttccacttt aaaacaaaat gaacactgct   4260
tgtcttcttc cattgaccat ttagtgttga gtactgtatg tgttttgtta attctataaa   4320
ggtatctgtt agatattaaa ggtgagaatt agggcaggtt aatcaaaaaa aaaaa       4375
```

<210> SEQ ID NO 67
<211> LENGTH: 1212
<212> TYPE: PRT
<213> ORGANISM: mammalian

<400> SEQUENCE: 67

Met Glu Pro Arg Pro Thr Ala Pro Ser Ser Gly Ala Pro Gly Leu Ala
1               5                   10                  15

Gly Val Gly Glu Thr Pro Ser Ala Ala Leu Ala Ala Ala Arg Val
            20                  25                  30

Glu Leu Pro Gly Thr Ala Val Pro Ser Val Pro Glu Asp Ala Ala Pro
        35                  40                  45

Ala Ser Arg Asp Gly Gly Val Arg Asp Glu Gly Pro Ala Ala Ala
    50                  55                  60

Gly Asp Gly Leu Gly Arg Pro Leu Gly Pro Thr Pro Ser Gln Ser Arg
65                  70                  75                  80

Phe Gln Val Asp Leu Val Ser Glu Asn Ala Gly Arg Ala Ala Ala Ala
                85                  90                  95

-continued

| | | | | | | | | | | | |
|---|---|---|---|---|---|---|---|---|---|---|---|
|Ala|Ala|Ala|Ala|Ala|Ala|Ala|Ala|Gly|Ala|Gly|Ala|Gly|
| | |100| | | |105| | |110| | |

Ala Lys Gln Thr Pro Ala Asp Gly Glu Ala Ser Gly Ser Glu Pro
    115             120             125

Ala Lys Gly Ser Glu Glu Ala Lys Gly Arg Phe Arg Val Asn Phe Val
130             135             140

Asp Pro Ala Ala Ser Ser Ala Glu Asp Ser Leu Ser Asp Ala Ala
145             150             155             160

Gly Val Gly Val Asp Gly Pro Asn Val Ser Phe Gln Asn Gly Gly Asp
                165             170             175

Thr Val Leu Ser Glu Gly Ser Ser Leu His Ser Gly Gly Gly Gly
        180             185             190

Ser Gly His His Gln His Tyr Tyr Tyr Asp Thr His Thr Asn Thr Tyr
        195             200             205

Tyr Leu Arg Thr Phe Gly His Asn Thr Met Asp Ala Val Pro Arg Ile
    210             215             220

Asp His Tyr Arg His Thr Ala Ala Gln Leu Gly Glu Lys Leu Leu Arg
225             230             235             240

Pro Ser Leu Ala Glu Leu His Asp Glu Leu Lys Glu Pro Phe Glu
        245             250             255

Asp Gly Phe Ala Asn Gly Glu Glu Ser Thr Pro Thr Arg Asp Ala Val
        260             265             270

Val Thr Tyr Thr Ala Glu Ser Lys Gly Val Val Lys Phe Gly Trp Ile
    275             280             285

Lys Gly Val Leu Val Arg Cys Met Leu Asn Ile Trp Gly Val Met Leu
    290             295             300

Phe Ile Arg Leu Ser Trp Ile Val Gly Gln Ala Gly Ile Gly Leu Ser
305             310             315             320

Val Leu Val Ile Met Met Ala Thr Val Val Thr Thr Ile Thr Gly Leu
        325             330             335

Ser Thr Ser Ala Ile Ala Thr Asn Gly Phe Val Arg Gly Gly Gly Ala
        340             345             350

Tyr Tyr Leu Ile Ser Arg Ser Leu Gly Pro Glu Phe Gly Gly Ala Ile
    355             360             365

Gly Leu Ile Phe Ala Phe Ala Asn Ala Val Ala Val Ala Met Tyr Val
370             375             380

Val Gly Phe Ala Glu Thr Val Val Glu Leu Leu Lys Glu His Ser Ile
385             390             395             400

Leu Met Ile Asp Glu Ile Asn Asp Ile Arg Ile Ile Gly Ala Ile Thr
        405             410             415

Val Val Ile Leu Leu Gly Ile Ser Val Ala Gly Met Glu Trp Glu Ala
        420             425             430

Lys Ala Gln Ile Val Leu Leu Val Ile Leu Leu Ala Ile Gly Asp
    435             440             445

Phe Val Ile Gly Thr Phe Ile Pro Leu Glu Ser Lys Lys Pro Lys Gly
        450             455             460

Phe Phe Gly Tyr Lys Ser Glu Ile Phe Asn Glu Asn Phe Gly Pro Asp
465             470             475             480

Phe Arg Glu Glu Glu Thr Phe Phe Ser Val Phe Ala Ile Phe Phe Pro
        485             490             495

Ala Ala Thr Gly Ile Leu Ala Gly Ala Asn Ile Ser Gly Asp Leu Ala
        500             505             510

Asp Pro Gln Ser Ala Ile Pro Lys Gly Thr Leu Leu Ala Ile Leu Ile
    515             520             525

```
Thr Thr Leu Val Tyr Val Gly Ile Ala Val Ser Val Gly Ser Cys Val
    530                 535                 540
Val Arg Asp Ala Thr Gly Asn Val Asn Asp Thr Ile Val Thr Glu Leu
545                 550                 555                 560
Thr Asn Cys Thr Ser Ala Ala Cys Lys Leu Asn Phe Asp Phe Ser Ser
                565                 570                 575
Cys Glu Ser Ser Pro Cys Ser Tyr Gly Leu Met Asn Asn Phe Gln Val
            580                 585                 590
Met Ser Met Val Ser Gly Phe Thr Pro Leu Ile Ser Ala Gly Ile Phe
        595                 600                 605
Ser Ala Thr Leu Ser Ser Ala Leu Ala Ser Leu Val Ser Ala Pro Lys
    610                 615                 620
Ile Phe Gln Ala Leu Cys Lys Asp Asn Ile Tyr Pro Ala Phe Gln Met
625                 630                 635                 640
Phe Ala Lys Gly Tyr Gly Lys Asn Asn Glu Pro Leu Arg Gly Tyr Ile
                645                 650                 655
Leu Thr Phe Leu Ile Ala Leu Gly Phe Ile Leu Ile Ala Glu Leu Asn
            660                 665                 670
Val Ile Ala Pro Ile Ile Ser Asn Phe Phe Leu Ala Ser Tyr Ala Leu
        675                 680                 685
Ile Asn Phe Ser Val Phe His Ala Ser Leu Ala Lys Ser Pro Gly Trp
    690                 695                 700
Arg Pro Ala Phe Lys Tyr Tyr Asn Met Trp Ile Ser Leu Leu Gly Ala
705                 710                 715                 720
Ile Leu Cys Cys Ile Val Met Phe Val Ile Asn Trp Trp Ala Ala Leu
                725                 730                 735
Leu Thr Tyr Val Ile Val Leu Gly Leu Tyr Ile Tyr Val Thr Tyr Lys
            740                 745                 750
Lys Pro Asp Val Asn Trp Gly Ser Ser Thr Gln Ala Leu Thr Tyr Leu
        755                 760                 765
Asn Ala Leu Gln His Ser Ile Arg Leu Ser Gly Val Glu Asp His Val
    770                 775                 780
Lys Asn Phe Arg Pro Gln Cys Leu Val Met Thr Gly Ala Pro Asn Ser
785                 790                 795                 800
Arg Pro Ala Leu Leu His Leu Val His Asp Phe Thr Lys Asn Val Gly
                805                 810                 815
Leu Met Ile Cys Gly His Val His Met Gly Pro Arg Arg Gln Ala Met
            820                 825                 830
Lys Glu Met Ser Ile Asp Gln Ala Lys Tyr Gln Arg Trp Leu Ile Lys
        835                 840                 845
Asn Lys Met Lys Ala Phe Tyr Ala Pro Val His Ala Asp Asp Leu Arg
    850                 855                 860
Glu Gly Ala Gln Tyr Leu Met Gln Ala Ala Gly Leu Gly Arg Met Lys
865                 870                 875                 880
Pro Asn Thr Leu Val Leu Gly Phe Lys Lys Asp Trp Leu Gln Ala Asp
                885                 890                 895
Met Arg Asp Val Asp Met Tyr Ile Asn Leu Phe His Asp Ala Phe Asp
            900                 905                 910
Ile Gln Tyr Gly Val Val Ile Arg Leu Lys Glu Gly Leu Asp Ile
        915                 920                 925
Ser His Leu Gln Gly Gln Glu Glu Leu Leu Ser Ser Gln Glu Lys Ser
    930                 935                 940
Pro Gly Thr Lys Asp Val Val Val Ser Val Glu Tyr Ser Lys Lys Ser
```

|     |     |     |     |     |     |     |     |     |     |     |     |     |     |     |
|-----|-----|-----|-----|-----|-----|-----|-----|-----|-----|-----|-----|-----|-----|-----|
|     |     | 945 |     |     | 950 |     |     |     | 955 |     |     |     | 960 |     |
| Asp | Leu | Asp | Thr | Ser | Lys | Pro | Leu | Ser | Glu | Lys | Pro | Ile | Thr | His | Lys |

```
                945                 950                 955                 960
Asp Leu Asp Thr Ser Lys Pro Leu Ser Glu Lys Pro Ile Thr His Lys
                    965                 970                 975
Val Glu Glu Glu Asp Gly Lys Thr Ala Thr Gln Pro Leu Leu Lys Lys
                980                 985                 990
Glu Ser Lys Gly Pro Ile Val Pro  Leu Asn Val Ala Asp  Gln Lys Leu
        995                 1000                1005
Leu Glu  Ala Ser Thr Gln Phe  Gln Lys Lys Gln  Gly Lys Asn Thr
    1010                1015                1020
Ile Asp  Val Trp Trp Leu Phe  Asp Asp Gly Gly  Leu  Thr Leu Leu
    1025                1030                1035
Ile Pro  Tyr Leu Leu Thr Thr  Lys Lys Lys Trp  Lys  Asp Cys Lys
    1040                1045                1050
Ile Arg  Val Phe Ile Gly Gly  Lys Ile Asn Arg  Ile  Asp His Asp
    1055                1060                1065
Arg Arg  Ala Met Ala Thr Leu  Leu Ser Lys Phe  Arg  Ile Asp Phe
    1070                1075                1080
Ser Asp  Ile Met Val Leu Gly  Asp Ile Asn Thr  Lys  Pro Lys Lys
    1085                1090                1095
Glu Asn  Ile Ile Ala Phe Glu  Glu Ile Ile Glu  Pro  Tyr Arg Leu
    1100                1105                1110
His Glu  Asp Asp Lys Glu Gln  Asp Ile Ala Asp  Lys  Met Lys Glu
    1115                1120                1125
Asp Glu  Pro Trp Arg Ile Thr  Asp Asn Glu Leu  Glu  Leu Tyr Lys
    1130                1135                1140
Thr Lys  Thr Tyr Arg Gln Ile  Arg Leu Asn Glu  Leu  Leu Lys Glu
    1145                1150                1155
His Ser  Ser Thr Ala Asn Ile  Ile Val Met Ser  Leu  Pro Val Ala
    1160                1165                1170
Arg Lys  Gly Ala Val Ser Ser  Ala Leu Tyr Met  Ala  Trp Leu Glu
    1175                1180                1185
Ala Leu  Ser Lys Asp Leu Pro  Pro Ile Leu Leu  Val  Arg Gly Asn
    1190                1195                1200
His Gln  Ser Val Leu Thr Phe  Tyr Ser
    1205                1210

<210> SEQ ID NO 68
<211> LENGTH: 441
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 68
agcggatnac aatttcacac aggagttgca ccatccgtta ccccgatccc ctnatcaagg      60
tgaatgatac cattcagatt gatttagaga ctggnaagat nctgattnna tcaagtttga    120
cattggttnt tttgngnatg ggggantggg aggngctaac ntaggaagaa tnggtgtgat    180
naccaacaga agaganggga ccntggatnt ttggangtgg gttaanggng aaaanatgcn    240
aatgggnaan aggtttggcn anttngantt tnnaanattt tttggtnatn gggaanggggg    300 aacaaacaan ggattttttt tnccngagga aaggggattn ngntnacaat nggtgaaaan    360
ananaaaaaa atgggggnaa aaaaganggg ggaaaggggc ntgggaaaan gnaaatttng    420
angaataaaa atgggngga t                                              441
```

<210> SEQ ID NO 69
<211> LENGTH: 258
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 69

```
gctgctgctg ctgctgctgc tgctgctgct gctaaagttc cagcaaaaaa gatcaccgcc    60
gcgagtaaaa aggctccagc ccanaaggtt cctgcccaga aagccacagg ccagaaagca   120
gcgcctgctc caaaagctca gaagggtcaa aaagctccag cccanaaagc acctgctcca   180
naggcatctg gcaagaaagc ataagtggca atcataaaaa gtaatanagg ttcttttga    240 cctgttaaaa aaaaaaaa                                                 258
```

<210> SEQ ID NO 70
<211> LENGTH: 240
<212> TYPE: DNA
<213> ORGANISM: mammalian

<400> SEQUENCE: 70

```
ctgctgctgc tgctgctgct gctgctaaag ttccagcaaa aaagatcacc gccgcgagta    60
aaaaggctcc agcccagaag gttcctgccc agaaagccac aggccagaaa gcagcgcctg   120
ctccaaaagc tcagaagggt caaaaagctc agcccagaa agcacctgct ccaaaggcat    180
ctggcaagaa agcataagtg gcaatcataa aaagtaataa aggttctttt tgacctgttg   240
```

<210> SEQ ID NO 71
<211> LENGTH: 267
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 71

```
aatgtaaagg gattngataa agaggtaaat gattcaaaaa ctacccatat agatattcca    60
agaataagct cttcccttgg aaaaaagcca agtttgactt ctgaatccag cattcatact   120
attactcctt cagttgttaa cttcactagt ttatttagta ataagccttt tttaaaactg   180
ggtgcagtat ctgcatcaga caaacacttg ccaagttgct gaaagcctaa gtactagttt   240
gcagtccaaa ccattaaaaa aaaaaaa                                       267
```

<210> SEQ ID NO 72
<211> LENGTH: 482
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 72

```
cccaaaccag aagatgcaca aggaggaaca tgaggtggct gtgctggggg cacccccag     60 caccatcctt ccaaggtcca ccgtgatcaa catccacagc gagacctccg tgcccgacca   120
tgtcgtctgg tccctgttca cacccctctt cttgaactgg tgctgtctgg gcttcatagc   180
attcgcctac tccgtgaagt ctagggacag gaagatggtt ggcgacgtga ccgggccca    240
```

| | |
|---|---|
| ggcctatgcc tccaccgcca agtgcctgaa catctgggcc ctgattctgg gcatcctcat | 300 |
| gaccattgga ttcatcctgt tactggtatt cggctctgtg acagtctacc atattatgtt | 360 |
| acagataata caggaaaaac ggggttacta ntagccgcca tagcctgcaa cctttgcact | 420 |
| cactgtgcaa tgctggccct gcacgctggg gctgttgccc tgccccttgg tctgccctag | 480 |
| at | 482 |

<210> SEQ ID NO 73
<211> LENGTH: 521
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 73

| | |
|---|---|
| gcgttgggag ctctccctat ggtcgacctg caggcggccg cgaattccta gtgattagcg | 60 |
| gataacaatt tcacacagga cgactccaag ttccatcata tttgagataa aggtttgaac | 120 |
| atatgaattt tgcggggaca caaccatgca gttcataaca tttgacatgt cctatcagtg | 180 |
| ctcacagaac ttgaatcagc tttttttaagt attacttatt tatttagaga tggtaacttg | 240 |
| ctatgttgtc cagattggtc tcaaactcct ggactcaagt gatcctccta cctcagcctc | 300 |
| ccaagtcact gggattatag acatgaacca cctcatctgg tttcaatcaa cttttttgtt | 360 |
| cttacccata aatataaatg gacagcacag gacaaccaga catttgagaa aaaccctagc | 420 |
| aagagcaacc aaaaaaaaaa agccctatag ngagtcgata aatcnattcc cgcggccgca | 480 |
| tggcggccgg aacatgcacg nggccattcn ccntagggag t | 521 |

<210> SEQ ID NO 74
<211> LENGTH: 523
<212> TYPE: DNA
<213> ORGANISM: mammalin
<220> FEATURE:
<221> NAME/KEY: misc_feature
<222> LOCATION: ()..()
<223> OTHER INFORMATION: "n" is an unknown nucleotide

<400> SEQUENCE: 74

| | |
|---|---|
| cgttgggagc tctccctatg gtcgacctgc aggcggccgc gaattcctag tgattagcgg | 60 |
| ataacaattt cacacaggac gactccaagc accagttccg gtggtacggg ggaataccag | 120 |
| tgaaatagtt tggttctccc tgaagcatct gcatattgaa agaacgcttt ccccactgtg | 180 |
| tgtcttctcc ccctcctcca gtaaaaacag tcccggctgg gtgctgtggc tcgcgtctgt | 240 |
| aatcccagca ctttgggagg ccgaggtggg cggatcacct aaggtcggga gttcgagacc | 300 |
| agcctggcca acatggtgga accccgtctc tgctaaaaat acaaaaaaat ttagccgtgc | 360 |
| ttggtggcac ctgtgatccc agctacttgg gaggctgagg cgggagaatc gcctgacctg | 420 |
| ggaactaagg caggagaatc cctggacctg gaggcaaagg ttgcagtggc caacgnacca | 480 |
| ttgnctctac ctggcacaca cnaactccgt ccaaaaaaaa gcn | 523 |

<210> SEQ ID NO 75
<211> LENGTH: 534
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 75

```
gttgggagct ctcccatatg gtcgacctgc aggcggccgc gaattcctag tgattaaccc     60
ctcaagaccc gtttagaggc cccaaggggt taactagtta ctcgagtgcg gccgcaagct    120
tcagagagct aaattgagtc tatcattatg gcaaagtctg acccaaaatt ttaatttgta    180
attttagcat gtgtctcatg cactttgggg agcgtcaaac taaatctaca attgccagaa    240
gccttgttac agtttaatgc acattaacta aaatgtgtac attttagtg ttcatgataa     300
atgcagttat gaccttatta cactttggc attctttaag aaagcacatt aagctttaat    360
ataagaaata tttaggttac acttgtgctc aagtaataat aaaacatttg tctttttga    420
tctcatacat tctctcctca ggtatggcca tctcctgacg cttgagccac cgcttgaatc    480
ggatcccgac atacacctga ctggaancac gcttcatcaa ttccgcgccg cagg          534
```

<210> SEQ ID NO 76
<211> LENGTH: 520
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 76

```
ccaagagtgg agcattcttc ccatgattcc cctgacactt ggctgaaagc attttgcact     60
aatttgcttt gtgcccgttc agacaatcta aaaagaaagg atgggggac aacaagtgtc    120
tattacacag aataaacagc ctctggcaaa tgaatacatt ttacacactt gtgcttttgg    180
agggatgggg tagtgatgag gggaagggga atggaggagg agaagtcaag gattagaggt    240
ctcttcagca tctcaggact gcctctctct ctctgtggtc acaggggtag gtttggtccc    300
atggcagaca tgaaactcaa gatcagccct ggcgtatacg ggttgggagg ccagngctgc    360
ctctggtggt ccccccaacc tgcaattcat attttgaatg ggttaaagcc tcttggcaat    420
acttttatcc tctaatgaaa agattgaacn ctttcccttg attatattta aatgttaccc    480
atataaatat actgcctgag gggangggta accctcttat                          520
```

<210> SEQ ID NO 77
<211> LENGTH: 524
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 77

```
ggtggcctcg agcaatctgg aggctgttgg aatatgaata gcggtaacag ctggggtata     60
tgagaaaata ttgactccta tctggccttc atcaactgac ctcgaaaagc ctcatgagat    120
gcttttctt aatgtgattt tgttcagcct cactgttttt accttaattt caactgccca    180
cacacttgac cgtgcagtca ggagtgactg gcttctcctt gtcctcattt atgcatgttt    240
ggaggagctg attcctgaac tcatatttaa tctctactgc cagggaaatg ctacattatt    300
tttctaattg gaagtataat tagagtgatg ttggtagggt agaaaagag ggagtccttg     360
atgcttccag gttaatcaga gctatgggtg ctcaggcttg tctttctaag tgacatatct    420
tatctaattc tcanatcagg gtttgaaacc ttggggggnct tttaaaattt aatccctcnt    480
tntttnggcc aaatgtccaa aaaaaggcta tatctttccc aatt                     524
```

```
<210> SEQ ID NO 78
<211> LENGTH: 524
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 78
tttctctttc aggtaggaaa atggaggcta agaaaagtta atttgtccga gggccctctg     60
atgatagtga aactgggatg gaacctctgc ctgcttgctt ctgaggtctg ggctcctaac    120
tactgctcta ctgcctcgag ccaagagatt tacgccctat taagcaattt gttgtgccga    180
taaattggaa gacacagcag ataagcaaac aactcaagca accaggtcag ttcctggagt    240
ttctgaattg ttgggaccaa ggggccgtgc agaggtaacc acagctggcg tagtgtggtt    300
gaggtagccc tattagcctt ttagttgctg ttactaattt atttctcagt ggtcaatgaa    360
ccaattgcca tcaatcactt tgtgtatagg tcatgtccca tggctctgac ccaggttgct    420
gctcagagtt ggcatcgtgg ctaaaatatt actagaggtc aaaatatgtg tgtgtttgtg    480
gtgattagtc aagnatctaa agaattgaca acattttggc atat                    524

<210> SEQ ID NO 79
<211> LENGTH: 198
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 79
gctgctaaac aactaatgct cctggaggca aaaaccccgg ccaggaaaag gagctggcgg     60
agaacaggga acanctggag attttacgtg ccaaatgcca agaactcaaa acacactcgg    120
atggcaaaat cgcagtggaa gttcataaat caattgtgaa tgaattaaaa agccaattac    180
agaaggaaaa aaaaaaaa                                                  198

<210> SEQ ID NO 80
<211> LENGTH: 615
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 80
cctanggaaa anttttagtg atgtctttgt naaagtcacc nnccagaatc taaaaatgct     60
gcgtatagtg gaaccttatg tgacctgggg atttccaaat ctgaagtctg tccgagaact    120
cattttgaaa cgtggacnag ccaaggtcaa naatangacc atccctctga cagacaatac    180
agtgattgan gagcacctgg ggaagtttgg ccgtcatttg cttggaagac ctcattcatg    240
aaattgcctt cccagggaag catttccagg agatctcatg gttcttgtgc cctttccacc    300
tctcagtggc ccgtcatgct accaaaaata gagtgggctt cctcaaggag atgggcacac    360
ctggctatcg gggtgaactg catnantcac ctcatccgtc anctnaacta aacccaggtg    420
aggcagggct gaaaactgnc cttgggctga cttttgatag gccatgcctt gccactntac    480
aaagttcttt angcattnac tagtattnaa gaagntncct agannttggg aggaatagag    540
```

```
gaggcnggta caatngatng agacctgctg ngatattnaa ngcctgatta ngacatgggg    600
ctctgcatag cccta                                                    615
```

<210> SEQ ID NO 81
<211> LENGTH: 252
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 81

```
catcnattaa tgggcaaaat naccagntna catcatantg acaggatcgt attacatata     60
nnantattaa ccttaaatgt aaataggcta antgcccnaa ttaaaagaca cagactggca    120
aactggatta agagtcaaga cccatcagtg tgctgaattc aggaaaccca tctcacatgc    180
agagacacac acaggctcaa aataaaggga tggaggaaga tctaccaagc aaatggaaag    240
caaaaaaaaa aa                                                       252
```

<210> SEQ ID NO 82
<211> LENGTH: 522
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 82

```
atttcccctt gagttcaccc acanccttta anaggaatgc attacccatg accnatgctg     60 anacccatg gggtntanca cnggacctan gaaagtctcn ngcagncaga tagcncatgg    120
tgtcnccaca caactagagc attctggaga ttgcccatan agggatgtga ggggaccgtn    180
tanatctntc ttgcttatnt natgcnctca cattccttca gcctcctgga gttcctgata    240
aaangaagcc agggtgtgga cattttttaa ctnttgattn tccannncnt tgnggatcac    300
ttgtacaccc actctttctt ntntgcctaa ttccgnntct tntggaacaa ntantntgcc    360
catgtatgtn tgtntctctt aacacnggtc natgaaantn tganttntgg cttgatgtnt    420
gttgcgtggc ctggaaccan ggagcaacac nctggncatn gttctgtgta ncngaaanta    480
tatttatgaa ncntgtgctt atcccantaa ngtcgcgtgt gt                      522
```

<210> SEQ ID NO 83
<211> LENGTH: 488
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 83

```
aagaagagct aactatccta aatatatatg cacccaatac aggagcaccc agattcataa     60
agcaagtcct tagagaccta caaagagact tanactccca cacaataata gtgggagact    120
ttaacacccc actgtcaaca ttanacagat cancganaca ganagttaac agggatatcc    180
gngaattgan ctcancgtgt gcaccangcg gacctaatan acatctacag actctccacc    240
ccaaatcaac agaatataca ttttttttcag caccacanca cactatattc caaaattgac    300
cacatagtgt ggaagtanng ctctcctcng caangtgtaa agagaacaga attttataac    360
```

```
aaacgtgtct ctcanaccac agtgcaatca anctagaact cnggattaag aaactcactn     420
aaaaccgtta nttgatggan actgaacacc ctgctctgat gactctgggt cttacgaagn    480
gaggcaaa                                                             488
```

<210> SEQ ID NO 84
<211> LENGTH: 504
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 84

```
ntgagagaag gcatgggatt ttnagcataa attcctgtta tgtgagtgct gtttgagttc     60
tgaagttcct atcaatatct gttcctgcaa gtgatctctg taagacccct tacatgctgg    120
tcttagttat tgttaaaatt gcaaggtttc ttcacaccct ctttgataag aagtgtttag    180
ctggcagagc tttcnttgac ttctgagtct agtgtgggtt ggcccatgac agtgggaaga    240
aatccaacat gttacatgga gaccttgtat gtaaacaaac tctgtagcct ttgaaagtgg    300
aactgctttt tacagttaaa gggctgctaa atggcttgca gatgagatct tctggctcac    360
cttgatcttc acatgaaccc attgtgacct atctggattc ctaggacctg tagttccatt    420
tgggtatatt agtgcctcag gaatgtgtnc tactggcaag catctcagaa attncgctgn    480 agggtanat anaggaagaa ttag                                            504
```

<210> SEQ ID NO 85
<211> LENGTH: 225
<212> TYPE: DNA
<213> ORGANISM: mammalian

<400> SEQUENCE: 85

```
tgccctgtct ggcagtcagc ttcccagaca gactatagac tataaatatg tctccatctg     60
ccttaccaag tgttttctta ctacaatgct gaatgactgg aaagaagaac tgatatggct    120
agttcagcta gctggtacag ataattcaaa actgctgttg gttttaattt tgtaacctgt    180
ggcctgatct gtaaataaaa cttacatttt tcgaaaaaaa aaaaa                    225
```

<210> SEQ ID NO 86
<211> LENGTH: 247
<212> TYPE: DNA
<213> ORGANISM: mammalian

<400> SEQUENCE: 86

```
gtttttagga actaaggtgt ttctctaaac acaaaatgtt gggtgaaact gggaacaact     60
ctcagaagct aatttatttg cttaaatgga aagtgtggga gccctaccct ctcttttgat    120
ctgccaagga tttcctctca gagctgttgc acagacagag attgtacttg gtaagatacc    180
aaacaagaca gatatggatc taaatttcta atgtgttcta tgggtttcaa ttccgaaaaa    240
aaaaaaa                                                              247
```

<210> SEQ ID NO 87
<211> LENGTH: 231
<212> TYPE: DNA
<213> ORGANISM: mammalian

<400> SEQUENCE: 87

```
gctgtacatt gttgcttgag agtctgtaca tttacgtcca gatttgtatt tgcactgtca     60
```

```
gtatggcaaa tgagtgaaaa atgtttaata cactattgga tttttatttt cctttttttg    120
attcagctta tacccgggct gaaaacctca atttatgttc atgacagtgg ggattttttt    180
aaatgtctac attctttcta ataaactgtt ggaagactta aaaaaaaaaa a             231
```

<210> SEQ ID NO 88
<211> LENGTH: 344
<212> TYPE: DNA
<213> ORGANISM: mammalian

<400> SEQUENCE: 88

```
atgcaaggat tgtgagtgac tctggggcct ctattgcaaa ttgttctagg gagaaatttg     60
cctgtcctgg tatcaagccc tggctggaag ccagagagag ggttacagaa agagattaag    120
gtgtcagtgc tggaggcaga agaggctatt gggcaatttg tttgcctggt tctaccgcac    180
acctgattta cacccagctt gtgaaaacct taccacaggt aaaatgccaa tagttgttct    240
actagagtgg tcaactttgt actgatttat ctcctacatt tttcaaacct tatgtaatgt    300
cttgttttta ataaacag ttttggaatg ttaaaaaaaa aaaa                       344
```

<210> SEQ ID NO 89
<211> LENGTH: 355
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 89

```
gtggacatgt tgaagctttg agatctgagc aggaggcagt gatgtccctg gtctattcag     60
ggaaagattt cagtgtgaaa tggtaaacat ccaattgaca ggatttagat tttgcttagt    120
ttttctgctt tttaatgttt ctatccccca tctcagtgtt ttctttatcc atcccagtga    180
tgccttattt gaaactgggc ttancntgca aaaagaatga agttggattt aggaactgtt    240
atatcattga gtggtgttga gagtgaagtt tcactancag ggaagtttcc ttgagcctaa    300
aataaaaaag aaaaaattna naaagaatca gttttttttaa attaaaaaaa aaaaa        355
```

<210> SEQ ID NO 90
<211> LENGTH: 191
<212> TYPE: DNA
<213> ORGANISM: mammalian

<400> SEQUENCE: 90

```
tttccccttt accagtctgt cctcactgcc tcgccctacc atcctgtcac cagtgggacc     60
tctttaaaac aagcagccaa ccattctttg atgtatccca ttcgctccat gttaacatcc    120
aaaaccagcc tggatttcat acatggactt ctgattaaaa gtggcaggtt gtgcatgtta    180
aaaaaaaaaa a                                                         191
```

<210> SEQ ID NO 91
<211> LENGTH: 336
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 91

```
tcagtaaggg gcaaacagag gatcactgac tcaagatgtg gttttaatta atanaaatgg     60
```

| | |
|---|---|
| aggctgagtg cantggctca cacctgtgat cccagcactt tgggaggcca aggcangagg | 120 |
| actgcttgaa cccaggagtt caagaccagc ctggggaaca tgttgaaacc ctgtctcttg | 180 |
| aaaaaataca aaattagct aggtgtggtg gtgcacagcc tgtagtccca gatacttggg | 240 |
| aggctgaggt ggggaggatca cttgagcctg ggaggtanaa gcttgcatnc gagctatgat | 300 |
| cacaccactg cactccagcc ctgtctcaaa naaaaa | 336 |

<210> SEQ ID NO 92
<211> LENGTH: 467
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 92

| | |
|---|---|
| gaagagctaa ctatcctaaa tatatatgca cccaatacag ggagcaccca gattcataaa | 60 |
| gcaagtcctn agagacctac aaagagactt agactcccac acantaataa tgggagactt | 120 |
| taacacccca ctgtcaacat tagacagatc aacgagacag aaagttaaca aggatacccca | 180 |
| ggaattgaac tcagctctgc accaagngga cctaatagac atctacagaa ctctccaccc | 240 |
| caaatcaaca gaatatacat tttttcagc accacaccac acntattcca aaattgacca | 300 |
| catanttgga agtaaagctc tcctcagcaa atgtaaaaga acagaaatta taacaaactg | 360 |
| tctctcagac ccagtgcatc aaactagaac tcgggattaa gaactcctca aaccgctcac | 420 |
| tcntggaact gacacctggt ctgatgacnc tggggacata caaaaga | 467 |

<210> SEQ ID NO 93
<211> LENGTH: 441
<212> TYPE: DNA
<213> ORGANISM: mammalian

<400> SEQUENCE: 93

| | |
|---|---|
| tcctttaatt taaaaagag ttttaaataa ttatctatgt cgcctgtatt tcccttttga | 60 |
| gtgctgcaca acatgttaac atattagtgt aaaagcagat gaaacaacca cgtgttctaa | 120 |
| agtctaggga ttgtgctata atccctattt agttcaaaat taaccagaat tcttccatgt | 180 |
| gaaatggacc aaaactcatat tattgttatg taaatacaga gttttaatgc agtatgacat | 240 |
| cccacagggg aaaagaatgt ctgtagtggg tgactgttat caaatatttt atagaataca | 300 |
| atgaacggtg aacagactgg gtaacttgtt tgagttccca tgacagattt gagacttgtc | 360 |
| aataagcaaa tcattttgt atttaaattt ttgactgatt tgaaaaacat cattaaatat | 420 |
| ctttaaaagt aaaaaaaaaa a | 441 |

<210> SEQ ID NO 94
<211> LENGTH: 395
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 94

| | |
|---|---|
| tctctgtgac cngacatgag aaggttgcca atgggctgtt gggcgaccaa ggccttcccg | 60 |
| gagtcttcgt cctctatgag ctctcgccca tgatggtgaa gctgacggag aagcacaggt | 120 |
| ccttcaccca cttcctgaca ggtgtgtgcg ccatcattgg gggcatgttc acagtggctg | 180 |

```
gactcatcga ttcgctcatc taccactcag cacgagccat ccagaagaaa attgatctag      240
ggaagacaac gtagtcaccc tcggtgcttc ctctgtctcc tctttctccc tggcctgtgg      300
ttgtccccca gcctctgcca ccctccacct cctcggtcaa gccccagccc caggttgata      360
aatctattga ttgattgtga tagtaaaaaa aaaaa                                  395

<210> SEQ ID NO 95
<211> LENGTH: 350
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 95
atttcgaaaa aatccaaatt tcagcaaaat tatatnggtt gttttcagta cctctgaagg       60
tgctatatca agaattctca tgctactctt tgagaaaaca gattgcgttt ttacctagaa      120
aatcaactgc aaggcatttt tataacctta ccccaagtaa aaaaaataca ttgaaatata      180
ctaataaatg cagactacat tacttgaaaa atggtaatac agaatgccct tttaatattt      240 gaaatatga attttggta gaataatgt aaaataaagc ttctggtaag ccttaggcag         300
ttaaatttac atcagtgtaa agtaggatga aaatctgtaa aaaaaaaaa                  350

<210> SEQ ID NO 96
<211> LENGTH: 251
<212> TYPE: DNA
<213> ORGANISM: mammalian

<400> SEQUENCE: 96
cctcatgtcc tcacctgttt accccatgt cccacgtcct caccacctgc ttctttgttt       60
gattaccagt aaatagtatg ggttcccaga gctcagggcc ttcgcagcct ccatactagc      120
gttggctccc tggacccacc gtatgtactc ttaacttgtc ttgtctcatt ccttttgact      180
ctgtcggact tcatagccac cacgacctgg tgttgagtct tgatcacccc aacaaacagt      240
aaaaaaaaaa a                                                            251

<210> SEQ ID NO 97
<211> LENGTH: 478
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 97
cctgaaaact cttttgcatt aagggatcat tgcaagagca gcgtgactga cattatgaag       60
gcctgtactg aagacagcaa gctgttagta cagaccagat gctttcttgg caggctcgtt      120
gtacctcttg gaaaacctca atgcaagata gtgtttcagt gctggcatat tttggaattc      180
tgcacattca tggagtgcaa taatacttgt atagctttcc ccacctccca caaaatcacc      240
cagttaatgt gtgtgtgtgt gttttttta nggtaaacat tactacttgt aacttttttt      300
cttantcata tttgaaaaag tanaaaattg agttacaatt tgattttttt tccaaagatg      360
tcttgttaaa tctgttgggc ttttatatga atatttgttt ttntagttaa aaattgacct      420
ttgggaatcc agttgaagtc ccaaancttaa aaagagttat caacatctta tttggcct       478
```

<210> SEQ ID NO 98
<211> LENGTH: 479
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 98
tcagaacgcg tcagtaaaca aaacagattt gaatttccct tccttcatgg aacttaagtt     60
ctagtggtgg gaggaggaca gaaaacagta ataactaga ttttgaattg tgttagcaga    120
tgataactga tgtgggaact tagcaggtag aaggcaacac aaggtcaaag aagccgggga    180
ttccaccttg actagggagc tcagggcagg cctcacttga gaaagcacca cttgcatgaa    240
ggaggtggga aaagccttca cctggggaa gagccttcca ggcagaggga acagccaatg    300
ccaaggccct aatgccttgg ccacttgcct ggtatgtcca agaacaagg agacctgtgc    360
cagcggctgc agctgagtga gccagggatg tangaatgtg tanagggtgg ttctgggagg    420
tgcagcagga gaaaagtgct caaagtcact agtggtcctc tggattggtt cngggcctt     479

<210> SEQ ID NO 99
<211> LENGTH: 486
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 99
ccgcaaagct ccttagngac ttctaatctt atttggtaaa acaataaaac aaaacagaac     60
ataaccttgt atcccatcta tcccagatgg agaagttctt gaaaattgtc cagcccactt    120
ctgcatttct actttcaata tactttccga gtatattgtc tcatatattt tgaaggagag    180
agtaaagtct gtatgtccta aatagtggtt cccaccgaac cagttaaaaa aatttggagg    240
acgtgacatg tgtttgccaa catttaaatt tttccaagta agagtattat angtagagaa    300
agtgaggaaa atcgagagag agatagagag accgagagac acgaaaatca ncaaccagcc    360
cctattgcca tgatttctta anaggaaagt tttatgttna aaaaaaatta gtggggaca     420
taccttagaa tgaagggcng atcttcnata cagaaaatgt gtgcaaaacc tnatgacttg    480
ntnttt                                                                486

<210> SEQ ID NO 100
<211> LENGTH: 479
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 100
ctctaagtac ttcccttacc cactcagtgt ggtgatggca cctccctgaa tctcctgaca     60
aatgcgaaca ggaactccta ttcatcagag ccaacttgat aactganaag attcctctct    120
catttatcag cctttgatta tcttttttgtg tctcttacta tttgcgctta gcaagaaaaa    180
taaagaggtt tgaacaatta agaagtaaca aagagctcat agttcacaaa gagcaagtca    240
aaggatgtct ggaatatttg aacatacaac tgcctttggc atgaggtggc ctacatacat    300
tctcaggggc aggataggct tggagagctg atcaagctgc ccgggaaanc tgaagcaaag    360

```
gccgggnggt ggaatnaatg tcncttcaac tgagactttta aaccttgggc tttanctggg      420
cgcagtanct acncctgtaa tccancactt tnggaggtaa gtcnggaaat ccttncgga        479
```

<210> SEQ ID NO 101
<211> LENGTH: 408
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 101

```
ttttctntgg cnncggtcta angttggtaa gcaccttaat ggattggagg gtgtgccaca       60
ggatgaattc cctacctgan ccacttcttg gtgactcagc tttccatgct gtgaaatggg      120
gagaaatgga aaaattgcct ttgctgaggg atatgtggag aatttccatt tttgctctaa     180
gaaaaccaga ggaaacgtcc ccttgagaat tatgtgtgcc ttcagtctcc aacccttct     240 ctccactccc attttctccc ctgttttata aagcttcctg gcaagtcatt gtggctcacg     300
cctgtaatcc cagcactttg ggaggctgag gcaggaggat cccttgagga taagagttga    360
agatcagtct ggtcaacata gtgagattct atctctaaaa aaaaaaaa                  408
```

<210> SEQ ID NO 102
<211> LENGTH: 326
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 102

```
gggcttgtnt tgtagtccca tagctagcag atggctggag ccaagactga ggctcgttct      60
tcaatgctga gccagggctc cttccgctgc accacaagaa cgctagacca ctcgccacca    120
gccttctcat tccctcttcc tccattctaa tcatttctag ctggctggcc tccacagagc    180
ataggaaaac agccagggcc gggcacggtg gctcatgcct gtaatctcac actctgggag    240
gccgagccgg gtggataacc tgaggtcagg aattcgagac cagcctggcc aacatggtaa    300
aaccccatct ctactaaaaa aaaaaa                                          326
```

<210> SEQ ID NO 103
<211> LENGTH: 470
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 103

```
gctctnnttt cttcttgccc gtgatgggaa gcccttggag gattttaagc aaaaatgtgc      60
cacgattcat cgctggtggg tctgtggaag atggattggg ataaggtggg gagtaggctg    120
gtgggtggtt cttgcatagt ccttcatgaa atagtcgtca accttagtgg tagtaaagat    180
tttcattctt tccaatgtgt ttcacatttt ctaggaactg catgttttgg ggacatgata    240
caattgagga aaataagtat tctttttccga taaagtaatg taaggcctca ttaattaaat    300
aaacgcttta tgagagcaaa aagacttgga aagaattaac ctttgctgg gcttggtggc    360 tcacgcctgt aatcccagca ctttgggagg ccaaggcgga tggatcacct gaggtcagga    420
```

```
gtcaagacag cctgccacca tggagaacct ggctctctaa aaaaaaaaaa            470

<210> SEQ ID NO 104
<211> LENGTH: 454
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 104
tggttccctc nggccgtggt gctggcaaaa atgtgtgatt ctctgctgct gggtcagaag     60
gccaagagtt cagatgcctt gtcccanctg tgcccttgac tttcacaatg acctgtcanc    120
agttatttaa cccaggtcaa gccgagtggc aaaatgccga acaccagggt ctttatagat    180
cttantcctn tgcagtaaag cggggaaatg cctccatatg aagttttacg tacatcgtgt    240
ctccttacac ttnttatcct ttcccagngt catgcctttg gggtaaaaat tatttgtgag    300
agttcaatta anaattattg ntgtcagtct gctgtgggct catgcctgta atcccagcac    360
tttgggaggc caangtggga gggatcactt gagtgcagga gttaagacta gccagggcaa    420
catagtgaga tcctgtctct cctaaaaaaa aaaa                                454

<210> SEQ ID NO 105
<211> LENGTH: 240
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 105
gggttnatta ctcccgatat agcaacaaag cctgggcaac ctttgttcct ggattctatt     60
tctcctaaaa aatcttttaa gactcgaaaa caaaagtctt cttcaaaggc tgaatacaat    120
ttaactgcat gcaaatgcct cctttgcaag aggaaatata gttcacaaat aatgcttaaa    180
agacatatgc aaattgtnca caagataact ctttctggaa caaactctaa aaaaaaaaaa    240

<210> SEQ ID NO 106
<211> LENGTH: 240
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 106
gggtactttg gaattgtccc atattaatca gagatggcaa agaaaaagt tctcatatta      60 ccaggttgat tttgtgtctc atttcaaatt ttaatttaaa attatggntt tcatttttgt    120
ttaccttaaa gngangctta aaagtggcat gtanttagga cacttaggtt tgttgaaaga    180
attttcgaca tttgnataaa agaatttgcg ataaatntat ccaggngctc accaaagaaa    240

<210> SEQ ID NO 107
<211> LENGTH: 419
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
```

<400> SEQUENCE: 107

```
gtgaaccttc aaacatcgct aagcatttga tctggccatg tatatggtag ctgtgtttta    60
atttgagaat cttgagggta gagccacaaa tttcaattct tacatttcca tttgcaaagt   120
gactagagaa aaagaaatca gcttaaatga ggtattaagt aatgtttaga gtcgtaggta   180
ttaactanaa tataaatcct tagaaattgt ctttatacct tcaaaaatta tactatgcat   240
ttatcataga aatgtgatta caaagaagtc tgactaccat gtctttaaac atatggcatc   300
tctcaacttt tcttccttat ggggctacat ttgttcattt ccagcagtag cataaactta   360
cgggggacat ggtagacttg ctctaaataa aattttaaa tgtttactaa aaaaaaaa    419
```

<210> SEQ ID NO 108
<211> LENGTH: 509
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 108

```
tgcagnggct ccaatacttn cattttgctc cccattgtga ttctcatcct ggctttgagt    60
tttgcttccc tttgtgtcct gtggtggatc ctccctccag gcagactggc ctgcttgctc   120
tctggaacat gttgtttgtt tctaccactg tacttttgct tcctctcatt ccccacagtg   180
gaccgtnntt ttttcatcat tgcttgtcca aatcccattt gtcctttaaa gggaanaaaa   240
gccnttgttg atgaagtgct ttctgggggc agagcacttt catgtatcat cttactgagt   300
cactacaatc ctcactctgt gaggtgatga tatattagcc ccattacaca agaggagaag   360
gggctcagaa aagttcttaa gctcacctga agtcacacag ctaaaagtgg caaagatggg   420
gctttggatt tttaatccaa gtcagtcttg acagaaaagc ccatggcctg ataccatatc   480
acaagttggc tctcttacat tctccttcc                                      509
```

<210> SEQ ID NO 109
<211> LENGTH: 505
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 109

```
gcngnttgct aggcncgtga gcatanattt agagtccagn tgtggggtgg tggngagatg    60
cagccaaccc agngacggcc tatacccngc accacttagt tgnatactca gantccaggt   120
gtggccttat agctgtgacc ctcgctgaat ctgccagtta gcatctagag ctcatcatag   180
cctggacaca ttccnnttca gtacgagagg agatttcaga gtctgtgttt caaaattaac   240
acttcaactg ctccaagaca ggagccaatg ccagtcttct ctggacattc atgagaagac   300
atgaaaaatg gccacaccct ggctccatcc tgaatgcttg tctctgaggc caaggcgcaa   360
tctgcaagtg gcacngtgtt cccgcgagct ttaggttggg aaaagttgct tttgnttctc   420
tctttctctt cctacttgtc tcatgtggna gggacctgga aggaacttg ctgacaggat   480
ttaaacagna aatccttnca naatg                                          505
```

<210> SEQ ID NO 110
<211> LENGTH: 461

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 110
taccaatgag ggttggttta ttatcaaacc tgaatagctg tggtttctcc agtanatatt      60
ntcttctact gaacatggag ccattattaa nagttgngtg ttttttatta tgtacatttg     120 tatattttt ngcttgtttg angtnctatt tttctaatan nttnctttta gttncttaaa      180
gntgngatac tatatttaga ttctgatgct ancntgcaaa tcaggtnggt ctcctgctgg     240
gtctctcctg ctttaattnt actttaagga cangtgtant nagtcagtcc accaccnttc    300
aaaaaatgtg aaactgccct gcctcccctt tttgctgaca acactgtgtn cattgaccac    360
ttcctaccat nctttatgct gnaaaatcaa accctttggg gggacnttat ctcatgcttc    420
tgcgattcca aanaactcta tggctaccaa aaaaaaaaa a                         461

<210> SEQ ID NO 111
<211> LENGTH: 200
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 111
gcnggtngag tntaaatgat ggatattgac cagacctgct tggacggaga ccgccatatt     60
atctgttctc ttcgttccaa aacagncttc acttgtctca gaatttgatg gacacatact    120
gtgatgagca ggagcttcag atgcactctt tacacattnt gttgaaataa acctctacat    180
ttgtnaaana aaaaaaaaaa                                                200

<210> SEQ ID NO 112
<211> LENGTH: 452
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 112
ctgcncggta gacattntag atggccggtg agagctcttt gaaaatgaaa acattctgct     60
atttgaatgc aaagtgttct tctttgcctg tgatgtttcc taatctgtga actcatactg    120
gacctcgaag ctgtctatta acaaaaatag caaagtggct gggcanggng gctcatgcct    180
gtantcctag cactttgana ngcttnnggg cggnggatca cttgaggcca ggagttcnat    240
accagcctgg ccaatatgtg aaaccccatc tctactaaaa atacaaaaat taccccggtg    300
tggtggngtc tgcctgtaag tcccaactac ttgggaggct gangcacacg aatcatttga    360
gctcaggagg cagaggttgn agtgagctna natggcnccc tgcactccac ctgngngaca    420
canngaggct ctgtctgaaa aanaaaaaaa aa                                 452

<210> SEQ ID NO 113
<211> LENGTH: 195
<212> TYPE: DNA
<213> ORGANISM: mammalian
<220> FEATURE:
<221> NAME/KEY: misc_feature
```

-continued

```
<222> LOCATION: ()..()
<223> OTHER INFORMATION: "n" is an unknown nucleotide

<400> SEQUENCE: 113
gtataaatga nggatattcg accnanacct gcttggacgg anaccgccnt attatctgnt    60
ctnttcgttc acaaaacanc cttcacttgt ctnagaattt gatggacaca tactgtgatg   120
agcaggagct tcagatgcac tctttacaca ttatgttgaa ataaacctct acatttgtga   180
aanaaaaaaa aaaaa                                                    195

<210> SEQ ID NO 114
<211> LENGTH: 508
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 114
gtatacttgt tnatnacatn ttcgtttcct gagcaataac gattatgaaa agtttaacnn    60
caatcccnaa ttaattngag cctgctgaag gagtttgacc accatttgct gnccgctgca   120
caagcctgca agctgncagn tgccttcagt gcctatacnc cgatcttcat gctcacagca   180
tgcgaatatc cngtggcaca gtgtttattg tcctgcagnn gttcaaatga ctgtcctcca   240
nanttgaaac acttncatnt gtgtgaancc aaagaagcct ttgagattgg cctnctcanc   300
aagagagatg atgagcctgt nactggaaaa caggatcttc acagctntgt caangctgnt   360
ttcggtctca ccacngtgcn cagaangntn catggggaga cagggactgt ccctgcagca   420
agtcaagcct ttggaatgaa gcaatgggga agctgncaat ttagccttnt tcanaagtnn   480
gacagagaac tttgtttaag attttgtt                                      508

<210> SEQ ID NO 115
<211> LENGTH: 470
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 115
cgtgtttcgt tgtaatccgc acagacattt ccaaggnaaa ttctaaacag tcacccttcc    60
cttttgcatt cccccaaatc ttaagtgtat acataaaacc ctgggtacat attgttgtgg   120
taatagaagg gaattggtta aacagtacac ttgtttatgg aactttctgt ggccacctac   180
gaaagacaag ttaacanant tgtcatggag gctgttgttg ccagccaggg ccgctgcatt   240
ttgacaacat ttccaccctg gccactcagc acatttcatg gaggtcatgt cttttcactg   300
atactttttt gatagttttt ataacaaa atccttattc tatttataac ttaagatgat   360
aaggcactat aaattaatga cctaaaataa tatatttgtc tgttatcttt tgctatttct   420
acttcacttt aatttttagc tgtaaattgg taatggatct tacactntct                470

<210> SEQ ID NO 116
<211> LENGTH: 473
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
```

<400> SEQUENCE: 116

```
ttaanttatt gtcttgcctg tttgctaaca gttttatttc cgaggtaaaa tttgtctgat      60
tttttctca ttactcattt ttattaccca gatggcagtg aattggaata actatatttg     120
gaaatatgat ctctaaacta gcagtctctg aacattatct aagaggagta gaaatcttta    180
ctgtggttgc agatantaaa tgctattaaa agaaagagcg tcttgtaata cttggagcnt    240
tgacaacagc agcagataag gaattttcct gaattttat ttcctgctag tgtggggaca     300
ggagtggtgg cttggatgtc aggggagagt tcgggtttgt tggtctcatt ttctgtctta    360
tgtggctgag gaagcggttg tctgtatgtt tttgatgcag tcatatgtcg tagttntgga    420
cgttctcttg cagggagggc accgctngtc aatgagtgga accctcgatt tac           473
```

<210> SEQ ID NO 117
<211> LENGTH: 423
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 117

```
tgccanaggt canntttga ggaaagccga aatgagaccc agataagaac cagactgtga      60
aggatcttgc acttgatatg aaaagagttt tgccttttc ctgagggcat cagaaagtca    120
ttaaggtggg tgtggtggct tacgcctgta atcccagcac tttgggaggc caaggccagt    180
ggatcacccg aggtgaggan ttntnaccag cctaatcaac atggcgaacc ctatctctac    240
taaaaataca aaagtagct tgggccgtgg tggcgccgtg cttgtagtgc cagctgttca     300
ggaggccgag gcaggagaat tgcttgaacc tggaatgtag aggttgcaag tgagccgaga    360
tcacacccgc tgcactccca actgggcgac agancgagac tccgtctcaa aaaaaaaaa     420
aaa                                                                  423
```

<210> SEQ ID NO 118
<211> LENGTH: 502
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 118

```
gtctgttttc cagggccccc aagcaaggtt atggagatnt gccctgcaca aggggtaag     60
tagggctgaa atccagcccc actatctgcc ccaaagaaga ggctcctttc tctaattttc   120
ttaaaggtta gctagcccag aaatagcagt ggtggcatgg agttggagca agtggacag    180
atttggcata tactttngtg gcagaatgga caggacttaa ttaattagag tgaaggttag    240
agagagaaag atgtcataaa tgaataccag gtttctgctg gaaccagtg aacagttgga    300
aatgccattt gtangagata ggatagatgg aaagatttga gggtaaagag tgtaagtttt   360
cctttagaa gaatcaacta ctctgagata ataacctaac catcccagag ggatgatttg    420
catcttcttt gctgagagga cacctcatcc tcttccnttc ctgggttana acttccccaa   480
aagngttggg gattgagggt ga                                             502
```

<210> SEQ ID NO 119
<211> LENGTH: 275

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 119
nacctttctg gggacgctgg ccccagtgca ggccaacatc ccaccccta cctcctatgg      60 gaccttgcaa gtcatcccac aggctgcact gtcaggaaga ggaccctgtc ccccagcact    120
gggcttcacc tagaacttca gtgggggcca agggtgctga gaaccagca atgaccagga     180 agatacagtc actaacttca tctgtccccg tgcccttcc caggtcctgc ctccacaggt     240
ttaacccaga acaataaacc tggctttgtc atcaa                               275

<210> SEQ ID NO 120
<211> LENGTH: 450
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 120
aagactgtgt tgtcttttct accaagagta ttaacactac taagtctttc accttaactt     60
atgactcagg atttattcac gtcctgccca ctctaggctc acaggaataa aatcaagtgc    120
tagacacact ggctgctact aaggcactag cctctgtagc tggtggtggc agcgtggggt    180
gccgcccagc gtgctgggtc ctggcagtgc ctctgctgtg cttgcacatt gagcccttc    240 tcagtcagtg gagtatcaag ttgggccatc tgtctactga cctggccttc atgtaagcag    300
ctgtgggctg cgggcagaca ggagctcaga gatgcagcat gaggcgctta gaaaaacctg    360
gccatttgct gcctctaatt ccctttttgct ttgccatatt gggcttgtat tacctccttg   420
aaanataaaa gaatacattt tcaaaaaaaa                                     450

<210> SEQ ID NO 121
<211> LENGTH: 319
<212> TYPE: DNA
<213> ORGANISM: mammalian

<400> SEQUENCE: 121
tttagttgcc tgcctgtggc tggtaaggta atgtcatgat tcatcctctc ttcagtgaga     60
ctgagcctga tgtgttaaca aataggtgaa gaaagtcttg tgctgtattc ctaatcaaaa    120
gacttaatat attgaagtaa cacttttttta gtaagcaaga tacctttta tttcaattca    180 cagaatggaa ttttttttgtt tcatgtctca gatttatttt gtatttcttt tttaacactc   240
tacatttccc ttgttttta actcatgcac atgtgctctt tgtacagttt taaaaagtgt    300
aataaaatct gacatgtca                                                 319

<210> SEQ ID NO 122
<211> LENGTH: 449
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 122
aaatagactt tttgcaatta ataatgtatc atatatacat tactctgtca ttagacattc     60
```

```
ttctacaata anagttttga catgtattgc caaatatcct cctaangttt atacagatta      120
cactatttaa tcatagttac attttcctaa agacttagtt ttggccaggt gcagtggctc      180
atgcctgtaa tctcagcact ttgggaggcc aaggcggntg gatctgctga ggacgggaat      240
tcaagaccag cctggccaac atggcaggaa accgtgtctc tactaaaaat acanaaaatt      300
agcatgngcg tggnggtggg tgcctgtaat ctcagctact cgggaggctg aggcaggaaa      360
atcgcttgaa cccgggagat ggaggttgca atgagccaan gtcacaccat tgccttcann      420
ctgggcaaca agagtgaaaa tccatctca                                        449

<210> SEQ ID NO 123
<211> LENGTH: 289
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 123
agtgagactg agcctgatgt gttaacaaat aggtgaagaa agtcttgtgc tgtattccta       60
atcaaaagac ttaatatatt gaagtaacac ttttttagta agcaagatac cttttattt      120 caattnncag aatggaattt ttttgtttca tgtctcagat ttattttgta tttctttttt      180
aacactctac atttcccttg tttttnnctc atgcacatgt gctctttgta cagttttaaa      240
aagtgtaata aaatctgaca tgtcaatgtg gctagtttta ttttttcttg                289

<210> SEQ ID NO 124
<211> LENGTH: 289
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 124
agtgagactg agcctgatgt gttaacaaat aggtgaagaa agtcttgtgc tgtattccta       60
atcaaaagac ttaatatatt gaagtaacac ttttttagta agcaagatac cttttattt      120 caattnncag aatggaattt ttttgtttca tgtctcagat ttattttgta tttctttttt      180
aacactctac atttcccttg tttttnnctc atgcacatgt gctctttgta cagttttaaa      240
aagtgtaata aaatctgaca tgtcaatgtg gctagtttta ttttttcttg                289

<210> SEQ ID NO 125
<211> LENGTH: 273
<212> TYPE: DNA
<213> ORGANISM: mammalian

<400> SEQUENCE: 125
acagtaagtc atgatccaga aataaaagaa cacacagctc tctattcaga catgtgggct       60
tgtggacatg aagctggaga aacataaggt gataaagaaa atcctgatgg aattggtaaa      120
agagcctaag gcccacacaa atcagagtgt tggctgagtg tggtggctca cgcctgtaat      180
cccggcactc tgggaggccg aggcaggtgg atcaccttga gatcgggagt ttgagaccag      240
cctggccaac atggtgaaac cctgtctcta gta                                   273

<210> SEQ ID NO 126
<211> LENGTH: 440
```

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 126
ccccttcggc cctagcaaaa nttttcctg naccctggtg ccaaaaagat ggctggtgta      60
agggaccctg tgatacgtgc atgaggtgtg aactgactct gttgattatc cggactgtct    120
cgagtgccat gccagcttca tgattccatg ctgtacttta cgcatgtgcc gcactctgag    180
taggcatttt gtgaaatttg ttattccttt tatgttgagg aacttccact tgaaatgctt    240
gtatccttgg atgcctccct tagctctcct gctgtaagct tctcctttca gaacagacaa    300
atagccttgt ctctattgtc aaaaggtagg ctcttttatt gttgtcatac ttttcttggc    360
ttgagaatac tggggctggg caagatggct caatgcctat aatcgcagca ctttgggagg    420
ccgcagtggg cagatacctc                                                440

<210> SEQ ID NO 127
<211> LENGTH: 435
<212> TYPE: DNA
<213> ORGANISM: mammalian

<400> SEQUENCE: 127
cttgggcccc gcttattttt ctctgccccc tggcttataa tgaacaattt ggtacgaact     60
actgacctcc ttctaaaaca ctgagtgacc cttaaaaaaa ttcaaccta gttcccaatg    120
cccttgtgta tatacaaata atcattgcct tcgtttacta tttcctcaaa tccttaaaaa    180
tagaaagaat caaatatact tgccaaaaaa tttagccaat tgttaaaaaa tcataagagg    240
accaaatgag atagtacatg gaaagtcttt agaaaagct caaaaatagg taagaatgaa    300
aaaaactatt gggcatcatt gtaatttatt attgttggat atcctgttgt taggattaaa    360
gtaaaaacat caaacattac aaagagacaa gttccctgca gactctttag ttcagtcagt    420
tgtactgata atttg                                                     435

<210> SEQ ID NO 128
<211> LENGTH: 428
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 128
ttcgaaccac ctctccttcg ggaaagtgag agccaggctc agggcccga atgtcaccct      60
gcatgggaca gggtgaaata aacactgagg aaagagaccc ttagaattga agtctgaggc    120
acatccccac tgtcaccta gcctgtgcag tttcaatgtg accagcctga atgacntgag    180
agaagccgag ggaaggcata agggcatcc attattcagg ctcacctggt gatggtacca    240
tcagcagaat ctttcaccaa cggtgggtcc cagtatactc gagcagtcaa tttctctggc    300
tctgccatct tctcacgtga gtggggacag cggatcttgg ggggatctat gtctgccaag    360
atgaaaaatc aagtgctgac tcgtgggccc cttgctttcc ctggagggaa tccactgaag    420
caatgcnc                                                             428

<210> SEQ ID NO 129
<211> LENGTH: 270
```

<212> TYPE: DNA
<213> ORGANISM: mammalian

<400> SEQUENCE: 129

```
cgaagataga aaggtttct cacattggct ttggaagtca agcactcagt tcaggctgag      60
agaatattct ctcttagttc ctgctctctg gagtggagta gttcagactc aacagaaaaa     120
gctttgctgg gccaggcgca gtggctcaca cctctaatta gaacactttg ggaggccaag    180
gcgggcagat cacctgaggt caggagtttg agaccagcct ggccaacatg gcgaaacccc    240
atctctacta gaaatacaaa aaattagcca                                     270
```

<210> SEQ ID NO 130
<211> LENGTH: 190
<212> TYPE: DNA
<213> ORGANISM: mammalian

<400> SEQUENCE: 130

```
atttaaactg aatctaatca caagaaaaca atcagatata tccagactga gagatattca      60
atatgacatt ataaaaacta agattcttca atatgtcaac atcatgaaca ccacaaaatg    120
gcagaaaaat tgttctagat taatggagac taaagagata taacacaagt gcaactcatg    180
gtacctgaat                                                             190
```

<210> SEQ ID NO 131
<211> LENGTH: 239
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 131

```
aggaaaaact tttgtcgcaa ctccctctca gcaaatagcc ttttatcgaa aaactagaga      60
aactctcatc aatgacttct cttcccattt taatacaata ttaattcaac aagaatctat    120
cataccagaa cctccctaaa aagactaaaa gcaccccccaa aacaattatt cctgaaaacn    180
attnaaaaca atactagata atggataatg aaatgctgaa tggaatacac tcagatgca      239
```

<210> SEQ ID NO 132
<211> LENGTH: 265
<212> TYPE: DNA
<213> ORGANISM: mammalian

<400> SEQUENCE: 132

```
acccagatct aaagcaagtc cttagtgacc tacaaagaga tttagactcc cacacaataa      60
taatgggaga ctttaacacc ccactgtcaa cattagacag atcaacaaga cagaaagtta    120
acaaggatat ccaggaattg aactcagctc tgcactgaag tggacctaat agacatctac    180
agaactctcc accccaaatc aacagaatat acattctttt cagcaccaca ccacacctat    240
tccaaaattg aacacatagg tggaa                                           265
```

<210> SEQ ID NO 133
<211> LENGTH: 410
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 133

```
tgctccaaga caatgagaac ttcaagacaa tagtggagtt tgagtgccgg ggccttgaac      60
cagttgattt ccagccgcag gctgggtttg ctgctgaagg tgtggagtca gggacagcct     120
tcagtgacat taatctgcag gagaaggact ggactgacta tgatgaaagg cccangantt     180
ctgtgggaat ctatgaggtc acccaccagt ttgtgaagtg ctgatccctc ttccttccag     240
tttgccttta aaactgagaa aaggacaaag tctcttaagc agcanancca cagaagctcg     300
ttcttttgac cttggctcct ggtggctntt accaaacctt tcacaatctg cattgctgga     360
ctttattaca gcttnccaag ccccatcaat aaacccttg tcaccctgc                  410
```

<210> SEQ ID NO 134
<211> LENGTH: 231
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 134

```
agtatttatt accccccct atgccctcat tttttaaaa aaggaaaaaa aaagaaact        60 gggttccagt cttaattcat tttccgtgcc aggttctatt tcgtgtgtgt gtgagtgtgt    120
tctgttttgt gttttgtttt ttgttgttgt tttcagttgt tnggttttct tttctttccc    180
ccctcccggt cccatacttc acagcactnc tggtgcggga agaagcagan c             231
```

<210> SEQ ID NO 135
<211> LENGTH: 223
<212> TYPE: DNA
<213> ORGANISM: mammalian

<400> SEQUENCE: 135

```
aacactgtta atgctgtaag tgaaagttca ctgtcgtctg tatactaaat ttattggtgt     60
ttctaactta aaagtaagac tgcagattat ccccaccag ccttagtcca ggggtgtggc    120
tctgtccggg tgcagtatgc agtcatgtgg aaccttgctt tctagtcctg ggaaaaaaaa   180
gatgtctcta attctggctt caataaacac cgaatccaga ctg                      223
```

<210> SEQ ID NO 136
<211> LENGTH: 216
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 136

```
nataagttct cntgttctat agtactgtag atgactatag ttaacaatac tatattatgt    60
agtttaaaat acctaggagt agtttgaatg ttcccaacac aaagaaataa taaatgtttg   120
agatgataga tatgctaatt accctgatct gatcaccatc tacatgtact gaaacatccc   180
cgtatagcca tgaatatgta taatctttgt caattt                              216
```

<210> SEQ ID NO 137
<211> LENGTH: 442
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 137

```
ggtaggtggg tttgcggttc aggactgctt ctggaaggga ctgcctgtac ttctgtacca    60
ccgttgccct ttacactttg ctcagggcgg ggtgggggaa gcattcaaac aaaacaagga   120
agggaactgt ctggcaaagc ataagtggat gcatccagag ctcagtcccc tttaatcttt   180
tgtctctggg cgttctgctg cttcctcata ccggggacat ggcattccag gtcagcttgg   240
atgtggtctt agaggcaggg agtgcctacc cagtcctgcc tcaggagcag ggtgagtagc   300
taaatacaga cttaggcttt tttttccccc cttttaagat gctngctcct ctcccttttc   360
tttttaccac cctaccttta ttgttaagtg ggttacaaag tgacccatat tatgactttg   420
ctgtaaataa agacagacaa aa                                            442
```

<210> SEQ ID NO 138
<211> LENGTH: 426
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 138

```
ggtagtattt agagaagacc aatagacaat aaaaaatgat aaagggata ttaccactga     60
ccctacagaa atacaaacta ctatcagaga atactataaa cacctctatg caaataaatt   120
agaaaatcta gaagaaatga ataaattcct gcacgcatac accctaccaa gactaaacca   180
ggaagaantt naatctctga atagaccaat aagctctgaa attgaggcag taattaatag   240
cctacaccaa aaaaagccc aggaccaaat gggattcaca gctgaatcta ccagaaatac   300
agaggagctg gtccctcctt cagaaattat ttccaacctt ttgaaaaggg aagggactcc   360
tccttactct tttattgagc cngcatcatc ccaatnccca acctggaaga gacacagcca   420
tatcat                                                              426
```

<210> SEQ ID NO 139
<211> LENGTH: 340
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 139

```
nttcaactat acctagggct acagtaacca aaacagcatg gtactggtac aaaaacagac     60
acatagacca gaatagagag cccagaaata aagctgcaca cctacaacta tctgatctcc   120
aacaaagctg acaaaaacaa acaatgggga aaagacttcc tattcagtaa atgatgctgg   180
ggatancttg gatagccata tgcggaagat tgaactggga tcctttcctt ataccatctg   240
caaaattact caagatgaat taaaagactt aatgtgacct caaattataa aatctgggaa   300
gacacctagg gcaatccctt ctcgacacag aaacccagca                         340
```

<210> SEQ ID NO 140
<211> LENGTH: 339
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 140

| | | |
|---|---|---|
| ttntaaacca gtacgtagac tggttccta gtgctttctt tgtctggaag tctccagagt | 60 |
| accaagagca tactccatac cctgcgtggt ggagaaaatc tgcttggtca gaggagctcc | 120 |
| aaattgtaga tggtttaaaa atattttagc ctggatgagc cccatcagca gcactcacac | 180 |
| acctaccctg ttccacataa attcttgctg tgccgtagtt cacactttaa gcattctgtt | 240 |
| ccttccctca ttgacctgtt taacttttca gtacactaga tatgggccat gtcaagctgt | 300 |
| aattcattct ttgntctgaa aacaaccttt tggcaactc | 339 |

<210> SEQ ID NO 141
<211> LENGTH: 369
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 141

| | | |
|---|---|---|
| ctatntgtgc ataggcat gtacatcgca gtgcttttat tttgcaaatg tccaattatc | 60 |
| aggtcacatt tttataacac ttgtgtatgt tgtatgtgct gcttcagaac ccaagcatat | 120 |
| ttctcttagt taggggccgc cttgttgccc aaatgaagaa aattagcagg gaagtgcagt | 180 |
| atgttgtcca ttgaatgtta catacatgta atgtctcaaa tacattataa ttggaagttg | 240 |
| taatctgagt gagccctttg agcatgtaat aaatatcttt tagaacattt tangtatcat | 300 |
| tttaaatgtg attttaatcc ttataaaaac atttaattta ttttgacata ccttttggng | 360 |
| aatcctaag | 369 |

<210> SEQ ID NO 142
<211> LENGTH: 218
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 142

| | | |
|---|---|---|
| ttttnggctc ctatcagtag ttccatctgt ggggctcgca gtaatataag cgacctgttc | 60 |
| tgggacacag cactgggccc gctggggttt tagtagggca gccccttccc tgcaggagtg | 120 |
| aggcatggtg acagcagtcc cctatgtgcc cccaagtcat ctgagcattg gtgtgcatta | 180 |
| aggtactcaa tcttccaaca ataaatacca taagtgca | 218 |

<210> SEQ ID NO 143
<211> LENGTH: 353
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 143

| | | |
|---|---|---|
| cttttccgct ccacattcct tttagcttga ccagtctaat ttaaaatgtg tttgttggag | 60 |
| gtcattaacg ntacttgtac aatgctgtca ctgtgtgaca tccatatgaa ttttggtata | 120 |
| tatcaatcaa tcaatcaatc aatcacattg cattcaatca atcagctgtg attgattgat | 180 |
| tatgcttana aatactatac tatagtaact agatgcagtg tgaattttt ccattaacaa | 240 |

```
acaaacaaac aagtcagtgg cttaaatgtg attatggtcc tgcaaggtga ttcttgctaa      300
aatatctaaa cttttgtttt gttttaactg aatcattttt taacttaaaa agc            353

<210> SEQ ID NO 144
<211> LENGTH: 313
<212> TYPE: DNA
<213> ORGANISM: mammalian

<400> SEQUENCE: 144
tagcttcaag aagaatgatt attmattcgt cagaacagtc cacagtttct gatcataatt       60
ctaatgattt acttcctcag gaatgcaata tggataaaac ataccatg gaattgctac       120 caaaggagaa gtttgtatcc agaccaccca caccaaaatg tgttattgat attacaaatg      180
acactaattt agaaaaggtg gctcaggaaa actcaagtac ctttggcctt cagacacttc      240
agaaaatgga tcctaatgtt agtgattcaa acactctat tgcaaatgca aaattcttgg      300
aaacagcaaa aaa                                                         313

<210> SEQ ID NO 145
<211> LENGTH: 364
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 145
tcgccaggaa gataaaaaac atgaagaagc agagaagcgg aagtctgttg acactcagct       60
tcaagaanat atgattattc attcgtcaga acagtccaca gtttctgatc ataattctaa      120
tgatttactt cctcaggaat gcaatatgga taaaacacat accatggaat tgctaccaaa      180
ggagaagttt gtatccagac cacccacacc aaaatgtgtt attgatatta caaatgacac      240
taatttagaa aaggtggctc aggaaaactc aagtaccttt ggccttcaga cacttcagaa      300
aatggatcct aatgttagtg attcaaaaca ctctattgca aatgcaaaat tcttggaaac      360
agca                                                                   364

<210> SEQ ID NO 146
<211> LENGTH: 451
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 146
ncaggaccca ctcttattgg ccaggcaggg cgctcccaca gagctttgag taacttcttg       60
gntgtgcagt ctgcaggcaa tgttggcatt gtaaattcct cccttgcagc ctccttcatg      120
tggtgagggg atcacttcag ctgcctgctg tggacaaaga acatcanatt acagcatcac      180
gagtgctatt gttgcctgng gnggtctccc tgtccaagcg ggaccgnttt gcagagacca      240
gaggcatatc gcggcttgag ctgaanatgc atttgttgca gcttaggttg aattatttt      300 cgtttgctct ttcttctaca ccgcgcctga tggatagtga acctattcat caaanaagtg      360
cactgctctt ctgnctattg naccgactta acctcttcca cccagtccgc atctgtgtgt      420
anatcaataa cgntgngtgc tttgantgcc a                                     451
```

```
<210> SEQ ID NO 147
<211> LENGTH: 434
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 147
accccgcntt tattggcagg cttctagagt cccaaggctt ttgtggggag gagaatggac        60
aaatttgatt taaggatcaa ctttcaactg caaaatcaaa gaagtataaa aattgtagaa       120
tgaatttaca acttggattt acaaaattaa tttgacaata aagtcattgt agcaatagac       180
acgggatcct ttaataaagt caagaaactc aagtttctaa acctgatgtt gagcttcacc       240
cctattccct atatcactgg tgggttggta tgtcatgttt tctccaccct ctggaccacg       300
acattgttgt ggattcttcc atggaaaagc cctaactgtt attactgtgc ttgttatgtt       360
gtctcatgca acaacattcc tatatttatg gaaatgccag acaagttttg tctgtttggg       420
tataaataaa cctt                                                         434

<210> SEQ ID NO 148
<211> LENGTH: 460
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 148
nccttaggcc ntctcanant tggcagaatc gcaacttcta agatactact agatttcgac        60
ctagtaatac taaatccaaa aaggatgtta aacttgaatt ttttggtttt gaagatcatg       120
agacaggagg tgatgaagga ggttctggaa gttctaatta caaaattaag tattttggct       180
ttgatgatct cagtgaaagc tgaagatgat gaagatgatg actgtcaagt agaaagaaag       240
acaagcaaaa aaagaactaa aacagctcca tcaccctcct tgcagcctcc cccagaaagc       300
aatgataatt cccaggacag tcaggtctgg tactaacaat gcagaggact tgcctggtgt       360
gcctgaaagt gtgaagaagc ccataaataa acaaggagag aaatcaaagg aaaatccaga       420
aagattttta gtggcccaac ggtacccaca aagctgatat                             460

<210> SEQ ID NO 149
<211> LENGTH: 286
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 149
cttgntngac cgaactgttt ctttccttgg aattttcttg gccaaatgca ttcaagacaa        60
tagacttgtg gacttaccta tttctaaacc tttttttaaa cttatgtgta tgggtgacat       120
taaaagcaat atgagtaaac tgatttatga gtcacgaggt gatagagact tacacntgta       180
cttgaaagtc agtctgaagc ttctacagaa gaaggtcatg attcactctc ggtaggaagc       240
tttgaagagg attcaaaatc agaatttatt cttgatcccc ctaaac                      286

<210> SEQ ID NO 150
<211> LENGTH: 335
```

-continued

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 150
ncatgcttat tctcaggttt ttcttagaaa ggatatngtg tcaggagatg aagatgtatt      60
cttttcttgc attggtgacc tgtagtttac actgtgtaaa tgcaaaaaaa aagccctata     120
gtgagtcgta ttaaatcgaa ttcccgcggc cgccatggcg gccggagca tgcgacgtcg      180 ggcccaattc gccctatagt gagtcgtatt aaatcgaatt cccgcggccg ccatggcggc    240
cgggagcatg cnacgtcggg cccaattcgc ctatagtga gtcgtattac aattcactgg     300
ccgtcgtttt acaacgtcgt gactgggaaa accct                               335

<210> SEQ ID NO 151
<211> LENGTH: 418
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 151
cccttngggc ccgggnncat ttnacaagag actaactatc ctaanatatt tgcacccaat      60
acaggagcac caagattcat aaagcaagtc ctgagtgacc tacaaagaga cttagactcc     120
cacacattaa taatgggaga ctttaacacc ccactgtcaa cattagacag atcaatgaga     180
cagaaagtca acaaggatac ccaggaattg aactcagctc tgcaccaagc ggacctaata    240
gacatctaca gaactctcca ccccaaaaaa aagccctata gtgagtcgta ttaaatcgaa     300
ttcccgcggc cgccatggcg gccgggagca tgcgacgtcg ggcccaattc gccctatagt    360
gagtcgtatt acaattcact ggccgtcgtt ttacaacgtc gtgactggga accccctg      418

<210> SEQ ID NO 152
<211> LENGTH: 289
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 152
ccccnttcgn ttnnctttgg cncgggacgg gttggtagtg gcagacgatg aggtgtgagg      60
ggcagaggaa taagaaattt antggttttt attcagactt tattatttgg gcatgagcca    120
ttggtgatta actcaatctc cagccccttt gccctccctg aaggttgggg aggcaggaag    180
tccatccctc tgatcatgcc ttggtctcca ttccccaaac cccatcctga agctacctag    240
ggcccccaat accgagtcat ttcattagag aaggacattc attnctcca                289

<210> SEQ ID NO 153
<211> LENGTH: 266
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 153
```

```
ngnttccctc tgggcccggg ncatttaaca aggaanacta acctaatata tatgcaccca        60
atacaggagc acccagattc ataaagcaag tccttagaga cctagaaaga gacttagact       120
cccacacatt aataatggga gactttaaca ccccactgtc aacattagac agatcaacga       180
gacagaaagt caacaaggat acccaggaat tgaactcagc tctgcaccaa gcagacctaa       240
tagacatcta cagaactctc caccccc                                           266
```

<210> SEQ ID NO 154
<211> LENGTH: 409
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 154

```
gcccgggncc ntntaacaag gagccntaac tatcctaaat atatatgcac ccaatatagg        60
agcacccaga ttcataaagc aagtcctgag tgacctacaa agagacttag actcccacac       120
aataataata agagattttta acaacccact gtcaacatta gacagataaa tgaaacagaa      180
agttaacaag ggtacacagg aattgaactc agctctgcac ttaagcggat ctaatagaca       240
tctacagaac tctccacccc aaatccaaca gaatatacat tcttctcagc accacaacac       300
acctattcca aaattgacca catacttgga agtaaatctc tactcagcaa atgtaaaaga      360
aaagaaatca taacaaactg tctctcagac cacagtgcaa tcaaactag                   409
```

<210> SEQ ID NO 155
<211> LENGTH: 339
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 155

```
cccttgtacc cagatccttt nccagtgcac ccccttttccc caagcgcctc cttctcctct       60 gtgtccctg tattggggtg ctactacctg gttccccatc tcctacttac ctaggaacca        120
cctccagagt tggcagaagt tgggagacat aagggcggac aggcacaaag tggagtagag       180
tgaaaagaca caggctttac agttaaaagc cctgtgttta ggccaggtgc ggtggctcac       240
gcctgtaatc ccagcaattt gggaggctga ggtggacaga tcacaaggtc aggagatcga       300
gaccatcctg gctaacacgg tgaaacccca tctctacca                             339
```

<210> SEQ ID NO 156
<211> LENGTH: 325
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 156

```
cnttcctgta cgcnaacctg gaaatactct tctcaacatt agccttggca aggaatttgt        60
ggctaagtcc tcaaaagcag ttggcaacta aagaaaaat tgaccaatga gacctaatta       120
gagagcttct ggacagcaag agaaactatc aagggagtaa acagacaacc tacagaatgg       180
gagaaaatat tcacaaacta tgcatccaac aaggtctaat gtccaaaatc ttaaggaact       240
```

| | |
|---|---|
| taaatcaact agcagataac cccattataa agggacaaag gacatgaaca gacactttct | 300 |
| caaaagaaga catacaaggt agcca | 325 |

<210> SEQ ID NO 157
<211> LENGTH: 351
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 157

| | |
|---|---|
| acccattctg tgggtcaaag caagtcatga ggccatctca gtttcaagga gaaaggaaat | 60 |
| aagctctacc tcttgaggtg aggaatcaca ataatttat ttctatttca gtctaccgtt | 120 |
| gacctatcct ttaaaactgc attccttaaa aaaacagtta ataatacgg gaactttact | 180 |
| gttctcaagt attttgtgta aagattgaaa gctacnggaa gcattgagca cttgatatac | 240 |
| ttttgttttg aaattcccat tttaaccgtg tgcagttcag tggttttag tatgttcacg | 300 |
| tgattgtgca aacatcatta ctatctaatt ttagaacatt atcaccccaa a | 351 |

<210> SEQ ID NO 158
<211> LENGTH: 440
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 158

| | |
|---|---|
| tgtacccaca ccaggnttcc agtgaaacag tgggctangg gactgggccg cccacagaca | 60 |
| ctgaggaggg tgtataaaga gtcagcggct gaggccctga caagcctgtg cttgcgctgc | 120 |
| gggcatttat tcagtataga tttaatgaca aaggtcttga gtcaacacac ttgtggggaa | 180 |
| ttcacatggt cgtgcttgcg cccaccccca cccccgcta gtcttgcatg cagatgattt | 240 |
| aggccaggtt ccatggtcta agtaaactaa cttacttaga tgagtttctt tacatcccct | 300 |
| tgttacctaa cctaaagttt caggcaccag ataagacaat ctggcttgcc ttcagccaaa | 360 |
| tcttttccg aagcttttgt aaaaccttcc agccttccaa gaaggttaca tctttctaca | 420 |
| attttttccac cccctgactg | 440 |

<210> SEQ ID NO 159
<211> LENGTH: 281
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 159

| | |
|---|---|
| aatatctgca ttattagtat tttctttaa attggatcac ttttttct acctangtaa | 60 |
| atatatctta aaaggaaact atattactgg cttaaatgga aagctattat cacttgttat | 120 |
| gcagggaagg tgaccataaa aataatcaca atggagggcc ntggcacagn ggcttatgcc | 180 |
| tgtaatccca gcactttggg aggtcgagac aggcagatca cctgangttg ggagntcgag | 240 |
| accagccctg accaacatgg agaaactcca attctaccan a | 281 |

```
<210> SEQ ID NO 160
<211> LENGTH: 260
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 160
tggcaaaaat gtgtgattct ctgctgctgg gtcagaaggc aagagttca dgatgccttgt      60 cccagctgtg cccttgactt tcacaatgac ctgtcagcag ttatttaacc caggtcaagc     120
cgagtggcaa aatgccgaac accagggtct ttatagatct taatacctct gcagtaaagc     180
gggggaaatg cctccatatg aagttttncg tacanctgtc tccttacact ttcttatccn     240
tttnccagtg nccatgcctt                                                 260

<210> SEQ ID NO 161
<211> LENGTH: 249
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 161
aagtgtcaac cttgcagcag gatttggaca ctctgggagc caaactggat gtggaagctc      60
caaaggtaca gaaaaagaac tccaaaatgt tgacttttac ctctgtcctg ggaatcaccc     120
tgacgctagc tgtcgagata cttatcagtt tttctgccct gatnggacat ttgtaacttt     180
tatncaccta ctntgggga tcaaccagat cttcattcta tactcgtgct ccttgcccta     240
attatgtcc                                                             249

<210> SEQ ID NO 162
<211> LENGTH: 410
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 162
gggagctccc ncgtcctcag gaccttgact cggctataat gagaagaatg cctacaagat      60
ttcatatcaa ccagcctgct ttaaaacaga gagaagcaat cctgaaactc atcttgaaaa     120
atgaaaatgt ggataggcat gtagacctgc tagaagttgc ccaggaaact gatgggtttt     180
cagggaagtg acctaaaaga gatgtgtcga gatgctgcct cctctgtgtt agagaatatg     240
ttaattctac atcagaagaa agccatgacg aaagatgaaa ttccggcctg ttcaacagca     300
gggacctgca tcggggcaat tgaaaagatg aagaaatcaa aggatgcagc atttcagaat     360
gttttaccac atgtttgttt agattaagaa gtaagatctt ttgtncagtc                410

<210> SEQ ID NO 163
<211> LENGTH: 428
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 163
```

```
gtnnnttnta gatggccngt gagagctctt tgaaaatgaa acattctgc tatttgaatg      60 caaagtgttc ttctttgcct gtgatgtttc ctaatctgtg aactcatact ggacctcgaa    120
gctgtctatt aacaaaaaat ggcaaagtgg ctgggcatgg tggctcatgc ctgtagtcct    180
agcactttga gaggctgaag ggggcnggat cactttgaga ccaggagttc gatgccagcc    240
tggccaatat gtgaaactcc atctctacta ataatacaaa aattagccag gtgtggtggc    300
atctgcttgt agtcccagct actcaggagg ctgaggcaca gaatcattt gagctcagga     360 ggcagaggtt gcagtgagct gagatggcac cactgcactc cagcctgggt gacagaggga    420
ggctctgt                                                             428
```

<210> SEQ ID NO 164
<211> LENGTH: 303
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 164

```
agaatctaat ggaatgaatt agttctgtag atgacaattt cttcacccat ttatgagacc     60
taaatctttt ccataacact catgtattca gtataacaac atactaactg aaagagggac    120
ctgattgttt aaagtttgat tgcagacact gggnancata actcattatg tttcagataa    180
ggtaactcct agatatcaaa ctaatttgtt ggggnagaga ttttacangt catgccatta    240
caagattttc tctgatatta tatgtgcagg tcagttncaa gatgaaatca tgttttttta    300
aca                                                                  303
```

<210> SEQ ID NO 165
<211> LENGTH: 411
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 165

```
agtgatttaa tacgactcac tatagggctt ttttttttt caggcntgcn cagcatccct      60
gtgctggagt ttattttaaa aancancncc ccagttatca cagtttcttt tttngttcac    120
cattttccat aacnttntaa cctacacaaa atttgggggg agatcctctn tttggagact    180
gacncatttg cagaggggtc atgaataatg attccaaagc tcctatttac cttctgaatc    240
aggcaaagaa tangngacan tntaanaatg aattttgttt ccggcagtnt cattaatncn    300
ncattggaat cnttnccggg gcnggggggt ggaaattaan nccccaana aaantttttt    360 agccccgacc cccnanccac ttaaatcccc actggttcca accaaaagaa c             411
```

<210> SEQ ID NO 166
<211> LENGTH: 404
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 166

```
gcggataaca atttccacag gacgactcca agtgagggcg gccaagtcct cgctgagcag     60
```

```
agagggagcc gttcatgtca gagactcact gccagaaaag ccttacccat tttggttttc      120
actattgaga ccgcaactgc ttgcactgat cattttggtt ccgtgagcag ttggtgattt      180
tagttggtct ggtgttcggg ctaagaatat tttattgtgg acttaattac aaccctgcct      240
gtaatgattc aatgctgnat tatgatattg ctgnaaacaa aattcattct tatattggca      300
cttattcttt gnctgattca naagttaata ggagctttgg aatcattatt catgacccct      360
ttgcaatgtg tcagctccaa naaagntttc ccccaatttg ngac                      404

<210> SEQ ID NO 167
<211> LENGTH: 403
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 167
gtgattagcg gataacaatt tcacacagga cgactccaag ggtacccagt catagttgtg       60
ggggctatat acttttatga gtttgatctt taggagctct aactactagg tcctcacagt      120
aagtatcaga tgannnagtc ctcttgtgct tcttggtagg aggagggaa aaaactatta       180 taaaataagc cagaggtggg aggatcactt gagcccagaa gtttgagacc agcctggaca      240
acatagtgag atcctatctt tacaaacaat tacaaaaaaa ttaagccatg catggtggcg      300
catgctggtg gtcccagctc tcangttgaa taggagcntc gcttgggccc angaggcaag      360
gctgcagtga ccatgattat atactgcctt cagctgggtg aca                       403

<210> SEQ ID NO 168
<211> LENGTH: 290
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 168
ccagactctt tgtgatgtag cttttaggag gcactcaggt gncacggcta nactgcagct       60
atgagacaga tctggcttcn atccaanagt tgncatgcac ttgctgtgtg accttgggca      120
agtcacttca cttctctgag ccccgtgttc ctcatctgta caatgnggct tacgatacta      180
ctacctcata gggttntcct ggggatccag tatgangaag tgcnccaggg gcttggcatg      240
gtgcccggca cggcaaaaag tgctcaataa atgttttgt cntaacgnga                  290

<210> SEQ ID NO 169
<211> LENGTH: 473
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 169
tccacgactc tctacnnatg ataactcaat tcaaatgtgt tagcctaaag ctctggaact       60
ggtattccaa ccagctgacc gaactcactg accagtacag gcatggttat ttcaacatta      120
atagcatgtc aactgactc ctatttgtaa atgttatcaa tctaagcaat ccagctcatc       180
agtctactag tttgcttctt tccnagagat gtcaagtcct caagaatttg atggcttctt      240
```

```
ctgcagctat aaccacaagg aacctacaca ttgtaactca ngtccactgc tggctcatga      300
aatgtgtaaa gtagaaccct ccttcccgag aataagaca ggacaataaa aggtggcgtt      360

tttgtacttt acctggattc cattggctgg ttttaccact cctatcagat tgtagtgtaa      420

ttgtgtgatc gcanaccatt anttttccca gtgatgattt aataaaatta tga            473

<210> SEQ ID NO 170
<211> LENGTH: 386
<212> TYPE: DNA
<213> ORGANISM: mammalian

<400> SEQUENCE: 170
cacgaccgta atacccagcc catgtttggt gctctgctga gtgggctgcg agaagcggga       60
agaattgcag accagttttt ggggccatg tatacgctgc ctcgccaggc cacaccaggt      120
gttcctgcac agcagtcccc aagcatgtga gacagatgca ttctaaggga agaggcccat      180
gtgcctgttt ctgccatgta aggaaggctc ttctagcaat actagatccc actgagaaaa      240

tccaccctgg catctgggct cctgatcagc ttgatggagc tcctgatttg acaaaggagc      300

ttgcctcctt tgaatgacct agagcacagg gaggaacttg tccattagtt tggaattgtg      360

ttcttcgtaa agactgaggc aagcaa                                          386

<210> SEQ ID NO 171
<211> LENGTH: 233
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 171

tcaccacaca ctagccttga tatttgtggc tcccgctctc tcactccccc agttcctttc       60
agacatcttt agtttaaagg tgagctgaaa ttaagaagtt ggaaatccta accangtgtg      120
gtgggattcg cctgtaatcc cagctacttg ggagactgag atganaggat cacattgagc      180
ccangagttt gaggccngcc tgggcaacat ataccctccc ctgacatctn tga            233

<210> SEQ ID NO 172
<211> LENGTH: 215
<212> TYPE: DNA
<213> ORGANISM: mammalian

<400> SEQUENCE: 172

tcgcctaggg aaaagagagt taacggatac aaattacagc tagaaagatg ggaagagtga       60
attccagtgt tctaaagcag ggtaggtgac tacagttaat gattatttat tgtctactta      120

ttgtatatta ttgtatattt tcaaatattg tatattttca agaggattc tgaatgttcc       180 caacacaaca aaataataaa tatttgaggt gatga                                215

<210> SEQ ID NO 173
<211> LENGTH: 267
<212> TYPE: DNA
<213> ORGANISM: mammalian

<400> SEQUENCE: 173

tcgcctaggc tgacctgtta tggaccccca aattctgaga gttcctgcaa caagaatact       60
gctgttgaca ctccagtgga aatcccagca gccttgttag tgcacttgaa agtgggagaa      120

tgctgaccct gatgacttgt actgattcct gagccttaac actgtgctct ttccttctgt      180
```

| | |
|---|---|
| atataccatg gtcttacttt ccaactctgt acagatttat ttatggagga gctaggtcca | 240 |
| taaatgttgt aataaatatt cctttga | 267 |

<210> SEQ ID NO 174
<211> LENGTH: 423
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 174

| | |
|---|---|
| ggatagtgac cgtgacttnc taacgcataa tattctgtga tacagccttc cgtacatgtg | 60 |
| tgaagtcctg cataactttc gaactttgtt aaatgttggc actaggagtc atcagatcta | 120 |
| ggcttcatca ttttccagtg agaagcagag acccaagggg cctgttactt gtgcttggtc | 180 |
| aggggactgt ctgtcatgcc tggaggctct tcggcacact tccccatctt tcccttctgc | 240 |
| acttgtggct ttcaagcacc tctgttcata gagcgtctct gaaattgagt ctcggtcatg | 300 |
| acttatcccg aagtagagca atgtgtttcc tctcattgta gtttcaggac tttgtcagta | 360 |
| caaagctctg ccctaggctt gttactttat actcatatcc tgaaaagatg tgatttcatc | 420 |
| tat | 423 |

<210> SEQ ID NO 175
<211> LENGTH: 503
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 175

| | |
|---|---|
| tcccntatat gcgccaagnc tgttttggct aatccccata cattaatttt agatattctc | 60 |
| tattttatgg atagcatttn ccttgtaccc tttaaaaaag acatgtgaaa tgattgacaa | 120 |
| attaaagcac aatgaaaata agatataaat gaaatcagaa gtaagttagc tttaaaaaaa | 180 |
| aaaaaanagt nggggcana nancctgttn tttgctccan agncnggcct tntttctttt | 240 |
| taangacctn cancaccttt ntngaccaaa gatacoctaa ngaccnttaa atngatntgg | 300 |
| ancangtcnt tcantctccc tgccctntca gttggctcat aggctctggc agctaagggc | 360 |
| cctgtntccc taagagggtt gtttctcggg nctaatgaca caangannag cacgggggnt | 420 |
| aatttggncc ggngatgggg gggggtcaan cgtcccnccc accttncacg gggngngngg | 480 |
| ggggctcccc cctaannntta ncg | 503 |

<210> SEQ ID NO 176
<211> LENGTH: 203
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 176

| | |
|---|---|
| nttttggctc ctgggttgac aattnggtgg aaacagctnt attgctacta tntaaaaaaa | 60 |
| atcagcaaat ctttcccttt aagctatgtt aaattcaaac tattcctggc tattcctgtt | 120 |
| ntgtcaaaga attatatttt tcaaaatatg tntatttgtt tgatgggtcc caggaaacac | 180 |

```
taataaaaac cacagagacc agc                                          203

<210> SEQ ID NO 177
<211> LENGTH: 444
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 177
gctccctgct gccctcagga taaagtctgg gacccctcag catggcttgt gagactcatg     60
gngtccttgt ccctgctcac ctctctggtc tcatcacttg ccttcttgca ttctgggtcc    120
cagcctcctg tatccagaga tgcagtggct ctccattgcc actctgattc ctcctttctt    180
ttggtcacag agaaagggta ctttctctgt caaancnnna cttacacttg acttcctcca    240
aggagctnan ggctatactc tnttctcccg accccaccc tggcatacta cacagatcac     300
tctgggctca cttgcctgcc taatggtcat ctccccagta gactgtaagc tccttgaggc    360
caaggattgt gttggaattt tgtattaac agtgcctgnc ttggngctgc acctagaaag     420
cactcaataa ntgnttgtta atga                                          444

<210> SEQ ID NO 178
<211> LENGTH: 364
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 178
catacttgaa atccaaggag tctgtgaccg atgcaattct acagacagac cagattctca     60
cagaaaagga aaaggagatt gaagtggaat gtgtaaaagc tgaatctgca caggcttcag    120
caaaaatggt ggaggaaatg caaataaagt atcagcagat gatggaagag aaagagaaga    180
gttatcaaga acatgtgaaa caattgactt gagaagatgg agagggagag ggcccagttg    240
ntggaagagc aagagaagac cctcactagt aaacttcagg aacaggcccg agtactaaag    300
gagagatgcc aaggtgaaag tacccaactt caaaatgaga tacaaaagct acagacgacc    360
ctga                                                               364

<210> SEQ ID NO 179
<211> LENGTH: 438
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 179
ccagaatcta aaatgctgc gtatagtgga accttatgtg acctggggat ttccaaatct     60
gaagtctgtc cgagaactca ttttgaaacg tggacnagcc aaggtcaana atangaccat    120
ccctctgaca gacaatacag tgattganga gcacctgggg aagtttggcc gtcatttgct    180
tggaagacct cattcatgaa attgccttcc cagggaagca tttccaggag atctcatggt    240
tcttgtgccc tttccacctc tcagtggccc gtcatgctac caaaaataga gtgggcttcc    300
tcaaggagat gggcacacct ggctatcggg gtgaactgca tnantcacct catccgtcan    360
```

```
ctnaactaaa cccaggtgag gcagggctga aaactgncct tgggctgact tttgataggc    420
catgccttgc cactntac                                                 438
```

<210> SEQ ID NO 180
<211> LENGTH: 356
<212> TYPE: DNA
<213> ORGANISM: mammalian

<400> SEQUENCE: 180

```
acaatttcac acaggataca acgaggaaaa gacattagca aaagacttga ctaagaattt    60
ttacacaaga gaatatccac acggtggctc acacctgtaa tcccagcact tgggaggct    120 gaggtgggca gataacctga ggtcaggagt ttgagaccag cctggtcaac atggtaaaac   180
tccatctcta ctaaaaatac aaaaactaac ttgggcatgg tggcaggcac ctgtaatccc   240
agctactcag gaggcttgag gcaggagaat cacttgaacc cgggaggcag aggttgcagt   300
gagctgagat tgtgccactg cgctccagtc tggatgacag agcaaaactc catctc       356
```

<210> SEQ ID NO 181
<211> LENGTH: 191
<212> TYPE: DNA
<213> ORGANISM: mammalian

<400> SEQUENCE: 181

```
gaagctgtgt gctctgggta tttcccattc tggattttc aaatccttt gttaattttt     60 gaccatggtg agttcaggcg ttgttattat gttgcttatt atgaatacag tgaggatgac   120
taggtgtaaa tgaatgtaag gtaacagcta gatctgcctg aggtggagag agactgggtg   180
tgtattttgg a                                                       191
```

<210> SEQ ID NO 182
<211> LENGTH: 450
<212> TYPE: DNA
<213> ORGANISM: mammalian

<400> SEQUENCE: 182

```
taccaatcaa tctcggttta atcaccaaaa gtgcagagca ggcaaaatgc agctgtttat    60
caatctcaaa agctttggga cagtgtcata gttgaaagat gagacttaag aaaacagttt   120
cttaaacttc ttaaaactta agaaacattg tttcataaaa caatattgag tgggcattct   180
tctgcacagt gtgatgctcc aaccctggcc ctagtctcag tagaccatgc ttgctcgagt   240
gtgcatcgga gagaagccat gggtaccttc cccattagag gctacttcct tctagtaaca   300
ggaagggaag ttccagcatg aggtaagtta tccagggtag aaggtccttt gaggggcttg   360
gttgaattga gagcatcatc tctagatgat gctgttcctg ctgcagatct ctaggatgga   420
gagaattctc tctttagtca gagaagttat                                   450
```

<210> SEQ ID NO 183
<211> LENGTH: 302
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 183

```
tgtttatcac actgctggat gtcaatgacc ccccctcag tttggaaaga gcgttcagaa     60
gaagacgatg gtgctaggga ccccagtgaa aattgaggcc atagacgagg atgcagagga   120
```

```
acccaacaac ctggtggatt attccatcac ccatgcagag cccgccaacg tgttcgacat    180
caattcccac acgggggaga tctggctcaa gaattccatc cgctccctgg atgccctgca    240
caacatcaca cctggaaggg actgnctatg gtccctagag gtgcaggcca aggaccgggg    300
ct                                                                   302
```

<210> SEQ ID NO 184
<211> LENGTH: 228
<212> TYPE: DNA
<213> ORGANISM: mammalian

<400> SEQUENCE: 184

```
tgttggtcct ttcttcctta agtgccaagt gctgagctaa aggaggataa cttttggg     60 aagtcatgct gagggtggta gtgtgaccct gcctgaaaaa agggtctctt accctcccag   120
ccctggctca actctgaaga aggatcttgc tacagaagga gcccttgggc tcccttctct   180
ttgatagcag ttataatgcc cttgttccca ataaaactgg gcagatgg                228
```

<210> SEQ ID NO 185
<211> LENGTH: 443
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 185

```
ggcttcctca gggganggc acacctggct atcggggtga acgcatcaat cagctcatcc     60
gtcaactgan ctaaacccan gtgaggcagg gctgaaaact gcccttgggc tgactttga   120 taggccatgc cttgccactt tacaagttct ttttgcattt actagtattt aagagtaacc   180
ttgagattgg gaggaataaa ggaggcttgg tacaaataga tgganacctg ctgggatcag   240
ngaatgcctg attacgacat ggggctatgc ataagcctaa gagttatagg cttaaagatg   300
tngagtaact aaaaactgta ttgctggccg ggcgcggtgg ctcacncctg taatcccanc   360
actttgggag gccanggcgg gcagaccatg aggtcangag attgagacca tcctggccaa   420
catggngaaa ccctgttcta cta                                            443
```

<210> SEQ ID NO 186
<211> LENGTH: 203
<212> TYPE: DNA
<213> ORGANISM: mammalian

<400> SEQUENCE: 186

```
gctcctacta caaccgggta cacatcctgg ggggagcctc gaccacacct ctttggtcag     60
atgttcgtcc gcctgcagct tctgagagct gtgcgtgagg tgctccatac tggcctggct   120
atgctgggtc tccctccact gagccacatt taaggccaca gaggctccaa tacctgggaa   180
tgttcacaaa gtcatcaact gga                                            203
```

<210> SEQ ID NO 187
<211> LENGTH: 302
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 187

```
tgtttatcac actgctggat gtcaatgacc ccccctcag tttggaaaga gcgttcagaa    60
gaagacgatg gtgctaggga ccccagtgaa aattgaggcc atagacgagg atgcagagga   120
acccaacaac ctggtggatt attccatcac ccatgcagag cccgccaacg tgttcgacat   180
caattcccac acgggggaga tctggctcaa gaattccatc cgctccctgg atgccctgca   240
caacatcaca cctggaaggg actgnctatg gtccctagag gtgcaggcca aggaccgggg   300
ct                                                                 302
```

<210> SEQ ID NO 188
<211> LENGTH: 131
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 188

```
tctcgttccc gctcaagatc aagacacagg cataggacta gaagcaggag taggacaagg    60
agtaggagtc gagatagaaa gaagagaatt gaaaagccga gaagatttan cagaagttta   120
agccggactc c                                                       131
```

<210> SEQ ID NO 189
<211> LENGTH: 274
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 189

```
gattagcgga taacaatttc acacaggacg actccaagca aagatcttcc ctgagattct    60
cctgtgcctc ctgttggctc tctttgcatc tggcctcatc caccgagtct gtgtcaccac   120
ctgcttcatc ttntncatgg ttggtctgta ctacatcaac aagatctcct ccaccctgta   180
ccaggcagca gctccagtcc tcacaccagc caaggtcaca ggcaagagca agaagagaaa   240
ctgaccctga atgttcaata aagttgattc tttg                              274
```

<210> SEQ ID NO 190
<211> LENGTH: 157
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 190

```
attagcggat aacaatttca cacaggatgg attggtcttc tagtggaata atgccctagt    60
ttctctgaga tgatgtaagt ggcatgatgt tacctaaggc ttaggcttag cttgatttct   120
gggcccantg tttgtgttnt taagatgcca cctgttg                           157
```

<210> SEQ ID NO 191
<211> LENGTH: 403
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 191

| acaatttcac acaggaacgc tagtgtgtat ctatcatgta tgcaatactt tcccccttt | 60 |
| tgctttgcta accaaagagc atatatttta ctgtcagttg tctcaactct tgaatccatg | 120 |
| tggcngtttt ctctgtcctg ctgcttcttt tggcctcctc gttttccttc tcttttcga | 180 |
| caatggtaga catgaatgag atatttaaag ttcattggaa atcttcttcc ctacagcagt | 240 |
| aagcaaaaat tagcaaagag ataggtctaa atggcctctc agcttggtat gtgaaaatga | 300 |
| gatcacatac tttttaaatc caaatacaaa agcatagtct ctgcaagatt ttgttctttg | 360 |
| aatttcttga tattgnattg attattgana ctgncatcat gaa | 403 |

<210> SEQ ID NO 192
<211> LENGTH: 296
<212> TYPE: DNA
<213> ORGANISM: mammalian

<400> SEQUENCE: 192

| ctgaaaatgc agtcaaggct gctggaaagt acagacaaca aggcagaaat tatattgttg | 60 |
| aagatggaga tattatcttc ttcaaattta acacacctca acaaccgaag aagaaataaa | 120 |
| atttagttat tgctcagata aacatacaac ttccaaaagg catctgattt ttaaaaaatt | 180 |
| aaaatttctg aaaccaatg cgacaaataa agttggggag atgggaatct ttgacaaaca | 240 |
| aattattttt atttgtttta aaattaaaat actgtgtccc cccccccccc taaaaa | 296 |

<210> SEQ ID NO 193
<211> LENGTH: 420
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 193

| aggcatctgg tgcccatagc agantctcaa aaggcaggag aangggacga cgatgaggaa | 60 |
| aaccttcctg agggagagat ccctcctccc caagacccca gtgaagaatg ggtggattac | 120 |
| gtggactctt tggggcgttc ccggcgctgt atgagaaagg atttgccaga tctgcttgga | 180 |
| gatggataaa aatcttcagg ggagacttt tattagtcct gctaatgaaa aaaccctatt | 240 |
| atctgaagat atgaagaaaa gaacttcagc gccagcaatg ggaggaagaa gaaagagagg | 300 |
| ccctgaagag gcccatgggg cccgtacatt atgaagacat tcgggaaaat gaggcccggc | 360 |
| aactnggtgt tgggtatttt gcctttgccc gagacaagag ttgagaacaa gccgatgaaa | 420 |

<210> SEQ ID NO 194
<211> LENGTH: 327
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 194

| tgattttttt agtanccgga tcctgtggac agggtgcagc tctaccagtt cctgtttctt | 60 |
| ctgagccaga ccctcttcag ggaagggacc aattaattt aaaactcact tgaagcacag | 120 |
| ctggtcatgg ggcttggtat aaagttccta tttccaccct gatacttcca attcctggaa | 180 |
| ccccagccca ctcccccatc cctcctccct atcaaactag tataatgatt tgaatcggt | 240 |

```
acagtgtgtt taactgtaac taagttcaac agactattat tatctttgta ataaattaac    300
ctagcaataa aaattattct gtttcga                                        327

<210> SEQ ID NO 195
<211> LENGTH: 336
<212> TYPE: DNA
<213> ORGANISM: mammalian

<400> SEQUENCE: 195
agtgattagc ggataacaat ttcacacagg atgatgctac ctctgctgct gcactcacag     60
ccacacttga tacacgatga caccttgctt gtttggaaac atctaaacat ctagtagatg    120
acttgcaggc tgttggctac cagtttcctg tctgaggtgt atatgttaac ttcgtgatca    180
gtttgtatgt ttgggactct tgtcctatgt aaagttaagg tgggccgggt gcagtggctc    240
acgcctgtaa tcctaacact tgggaggccg aggcgggtgg atcacctgat ggtgaaacct    300
catctctact gaaaatacaa aaattagctg agtggc                              336

<210> SEQ ID NO 196
<211> LENGTH: 368
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 196
cgcctagcgg ataacaattt cacacaggat tttggctccc cccaaaaata caaaccaaca     60
gaaacttgtt atgcactcat caaaatgtac taatgggtac tctgaactca ttaccattga    120
catctgcatn ntnttntnca gggaaaaaat ctcatcttct tttccagtac aaaatagttn    180
gtgaaangat gagggcattt tatctgcttg ctgtgaccan cgtgngtaca cataaacctt    240
aacaangact acaagnatat tccacanagg acactcattt gcngnnatca ncctaantna    300
tanacaatta cnaacttcnn aagcnaggng tcttggctan tancgccaca tttagcagct    360 ccacatcn                                                             368

<210> SEQ ID NO 197
<211> LENGTH: 386
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 197
acgactcact ataggncttt ttttttttcn cataaaaaca agttttaatt tgattgaaaa     60
taaaataaca gtcgtctctg acagnggaga aactatgctc aaangattac tttgaaatan    120
anttttnnnt tatcgtactt tnggattnga catttcatac tgactctcag atagcacata    180
atagagaatc ctccgtcttc taaattngnc ttttctgaa atctgtacaa gtcctttgat    240
aacactatat tattgaaagt ctctggagtg aaacactata cactaattta cagtnataaa    300
tacaaaaaat tggacacggg gggaaaaaaa gttctgattg cctgcnagct gggttctcat    360
cccatggntg ccagtttgnc cagttg                                         386

<210> SEQ ID NO 198
<211> LENGTH: 303
```

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 198
aacaatttcc acaggatttt ggctcctcat tagttatgca aatttctgca gccagcttga      60
atttctcctc agaaaatagg acttcctttc tatcacattg tcaggctgca aattttttt     120 ngtttnatgc ttnngttccc ttattaaact gaatgccttt aacagcacgc aagcacctct    180
tgaatgcttt nttgcttaga aatttcttcc accagatacc ctaaatcatt gctcttaagt    240
tcaaagttcc acagatctct gggncagggg gtaaaatgct gcgaggtttg tttgctggaa    300
cgt                                                                   303

<210> SEQ ID NO 199
<211> LENGTH: 267
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 199
ttagcggata acaatttcca caggacgact ccaaggaaaa gaaatcatta tatcagaaag     60
aaacctgaac ttgtaagttt atcgcagcac tattcatttc ttatttgttt atttattttt   120
attttaaaag gttagttctt gagtcagtat gacntgacta tgtaccgagg acacaatctg   180
aagagttcct gagaaagtgt atctgcagaa gttagactgc actttggttt tatacatttt   240
agaaagggag gaggttttat acatttt                                        267

<210> SEQ ID NO 200
<211> LENGTH: 197
<212> TYPE: DNA
<213> ORGANISM: mammalian

<400> SEQUENCE: 200
tggtcgtctg tatactaaat ttattgggtg tttctaactt aaaagtaaga ctgcagatta     60
tcccccacca gccttagtcc aggggtgtgg ctctgtccgg gtgcagtatg cagtcatgtg    120
gaaccttgct ttctagtcct gggaaaaaaa gatgtctcta attactggct tcaataaaca    180
cgaatccaga ctgctta                                                   197

<210> SEQ ID NO 201
<211> LENGTH: 498
<212> TYPE: DNA
<213> ORGANISM: mammalian

<400> SEQUENCE: 201
ggtcgtctac tttaaggtgc attcaacacc acatttctag cataaagaac aaatttgact     60
tactcgtgat ggagtgttct gccgtgtttt caggctagca catttcggtg atcattactt    120
aggtggattc ttttaatcta aaacaactca gttttagaat catgtgttta attcatgccc    180
aagaaccata tcttgtctca aggtacaagt gtagtttcgg ttcagtgaaa ctcaggaaaa    240
aacattgaag cagctttagt gtttttaaaa taccatgctg agtgactcat tatctttgat    300
cacacttgct tgaaatttgc acagagaagt aggttgcagc agcttgcctt agaaagattt    360
ctgagctcta acttatttg tgacctgttg gctaaaattt gacatttata tgccttactt    420
```

```
tgcagtttct tgatcctctg tgaagtcttg agaaagagta ctattgctat ccctcgtaac    480
aggaagaact tgtgctta                                                  498
```

<210> SEQ ID NO 202
<211> LENGTH: 442
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 202

```
atggtcgtct aacagaanta aaatgctgta aatatttgta acaacatntt tttttaacaa     60
ggccaaaaaa gaaaaaaagg tttttgggaa caaatgaact tataaagtgg ttttatataa    120
aacatcaatt gtcttgtata ttttggataa gcagcagtac cagctttcat ttgtaacagt    180
ctgtggcatt ggaaaaaaag gagtctgtga ttgttgaagt gaattatgtt ataaatgcaa    240
agagaagata aaatattaaa aaacatattt tctaaatgcg tagtgcatgg ttaattcaag    300
cttctgtaca ctacagtata ttccattttc gttcagtttg tatatttgct gactattact    360
tgatatctct aatctctttt cctaacaaat atagcattgt agcatgcctt ttaataaatg    420
tcatgacatc tgtactctct ta                                             442
```

<210> SEQ ID NO 203
<211> LENGTH: 411
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 203

```
ttagcggata acaatttcac acaggagttg caccatgttg gctaggttgg tcttgaaccc     60
ctaacctcag gtgatccacc ctccttgacc tcccaaagtg ctgggattac aggcatgagc    120
cacagtcccn ngcccaatac ttaacatctt tgcatgataa aaacctgaac aagttaggta    180
taaaaggaag atgtctcaac acattaaagg ccctatatga ccggcccaga gctgaaatct    240
taacaccgaa gagttgaagg cttttctct aagatcagga acaagacatg gatgccattt     300
tttctccttc tgttcagtgt tgtactggaa gtcatagcaa gagcatttag gcaagagaaa    360
taaagacatc taagtaggaa aagaagaaaa acttgcctct ctgattatct t             411
```

<210> SEQ ID NO 204
<211> LENGTH: 490
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 204

```
tagaagtgan gagatggcca cagttagaaa tcgtatgtct gantgacccg ggctgcttcc     60
gagaaattga tgagctaata aaaaggaaa ctaaaggcaa aggttctttg gaagtactca     120
atctgaaaga tgtanaagaa ggagatgaga aatttgaatg acacccatca atctcttcac    180
ctctaaaaca ctaaagtgtt tccgtttccg acggcacatg tttcatgtct gtggtctgcc    240
aaatacttgc ttaaactatt tgacattttc tatctttgtg ttaacagtgg acacagcaag    300
```

```
gctttcctac ataagtataa taatgtggga atgatttggt tttaattata aactggggtc    360
taaatcctaa aagcaaaatt gaaactccaa gatgcaaagt ccagagtggc attttgctac    420
tctgtctcat gccttgatag ctttccaaat gaaagtncttt gaggcagctc ttgtggggtg    480
aaaagtattt                                                           490
```

```
<210> SEQ ID NO 205
<211> LENGTH: 448
<212> TYPE: DNA
<213> ORGANISM: mammalian

<400> SEQUENCE: 205
cactggcatt accgcttgac caggagccct caagcggccc ttatgcaggt gtgacagagg     60
gctcacctct tgccttctag gtcacttctc acaatgttcc ttcagcacct gaccctatac    120
ttgccggtta ttcttaggtt atattagtag tgcaacaagg agtaatatta aaagctaatg    180
attaatagtg tttatactaa tgattgataa ttgtccatga tcatctctat atctaatttg    240
tgttgtgact attcttattc tattttcttt attatactga aacagtttgt gccttcagtc    300
tcttgcctca gcacctgggt aatcctttgc ccacacattt ccgggtggct ctgctctcct    360
cttgccattc tctttctaca cacctgctcc aagttctgac tcccactccc tcagcccacc    420
ccagtgccca caaccctcct atctctct                                       448
```

```
<210> SEQ ID NO 206
<211> LENGTH: 466
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 206
ttttcgctcc aggtanncac tctaaacnta agaaagctc ttctgtccgg ttactttatg     60
cagattgctc ggnatgttga tggatcaggt aactacttaa tgctgacaca taagcaggtt    120
gctcagctgc atcccctgtc tggttactca atcaccaaga agatgccaga gtgggtcctc    180
ttccataaat tcagcatttc tgagaacaac tacatcagga ttacctcaga aatctctcct    240
gaactattta tgcagctggt accacaatac tatttcagta atctgcctcc tagtgaaagt    300
aaggacattc tacagcaagt agtggatcac ctatcccctg tgtcaacaat gaataaggaa    360
cagcaaatgt gtgagacgtg ccctgaaact gaacagagat gcactctcca gtgactcccc    420
agcaaacaca aggtgcagca gggtcccaaa ggtagctgga tggctg                   466
```

```
<210> SEQ ID NO 207
<211> LENGTH: 341
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 207
gggcattntt gaagacaaac gatgtagtac aattgaaaga acattaaaca ntagaacaaa     60
gggcaagcct ctcaacctgg ccctgccact aattaattgt gaccttanna caaggaggag    120
cactgaagtc aaataaaaca ttcctttcag taaagcacag agcttgagga ngtgcttgag    180
gaagactgaa attctctgtc caggagggta aactatatta ttagtaaata ccacaaattt    240
```

```
atcagtccat acaatttcta attagtgttt ctgttctttta gggaggcatg ggtagaacaa    300
atatattaac ttattttttta gactacagac atgctttaat t                       341
```

<210> SEQ ID NO 208
<211> LENGTH: 405
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 208

```
gcggataaca atttcacaca ggacgactcc aagtactaca aagccatcga gggcaagtac     60
tgcttcacca tgtaataata acataaatgc agctacagct gtggctctac gggaaccccg    120
aaagttaagt tatgcntgaa gtgtgccaga agcccctaa agagccatct tcagttcttg    180
tgcagccact acgggaactt cgctccaatg tggtgtctcc caccaaaaat gaagacaatg    240
gagctcctga gaactccgtt gagaaaccac atgagaagcc agaagcaagg ggctagtaag    300
ggattatttc tggcttncga ggcaatataa tccccagggg agcagcaggg aaaattaggg    360
aacanaacnc cagttaacct aaggctttcc ttagggagtg ctcnc                    405
```

<210> SEQ ID NO 209
<211> LENGTH: 295
<212> TYPE: DNA
<213> ORGANISM: mammalian

<400> SEQUENCE: 209

```
tgaaattcgc tgaaatactt aatgtggaat aggataatat acttccaatg ccctcaaggc     60 tgtgaccta cagccatttt acatagcaca tcattcctcc tatagggatg aacttttttcc    120 tggcacgaaa agtagccgat ctggttgaag ctttgcttat tgtaacaggc ttttatttcc    180
aggtaatatg tcttggaaga cttaattctg attagagata tagatattac tggaaactaa    240 ttgtttttttt tctattgcct ctgctttatc aaagaagtaa aacatttaaa tcgta         295
```

<210> SEQ ID NO 210
<211> LENGTH: 405
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 210

```
ggataacaat ttcacacagg atggattggt cctttacatg ccagctttgc ttgtgaatcc     60 ttgcttttttt cctctcatca gccttaagtt taggcgtttg ntgttctcca gggatgtaga   120
cagttnnntt cacaagtcac agttcttccc atanatgagg ccctnntgac ctctgcngga   180
ctttaanaat ctatgcanat atttccgagt nagtggcctn gnttaaattc ttcctgngtg    240
tttctttatt ccttaaattg gttggtggga naganganga tgcttggga acccnnnngg    300 nntccttagc gcnnaggatt gcttttaacn aattanncta aaaagncnna cttttcannn    360
cccncnntta cntanacaaa anagccccctt tnggnggccg cattn                  405
```

<210> SEQ ID NO 211
<211> LENGTH: 412
<212> TYPE: DNA
<213> ORGANISM: mammalian

```
<220> FEATURE:
<221> NAME/KEY: misc_feature
<222> LOCATION: ()..()
<223> OTHER INFORMATION: "n" is an unknown nucleotide

<400> SEQUENCE: 211
gcggataaca atttcacaca ggatggtaaa gggcatattt ctgaaagcac agatgggaag      60
acgggatttg ttccgtgtcc aggtgattat ggtacctcta tgcgcctggc cggcacntgg    120
ggacagaggc catgaaaatg aatacagcac agcctttgcc tccaagaaac nttaagacct    180
agtagaaatg gcaggctttt aaaacaggtt gttgggatct gatttggtga gtgcaatgac    240
agagatactc acagcacaaa atggggaatg agggcgggca ttgggacaca catagcctta    300
aggggcccaa aggcttttag aactgtattc cctattaaaa catgatttgc acagagcaca    360
ttctttgctt tggagacctc agaactcctt actataggcc gggcatggtt at            412

<210> SEQ ID NO 212
<211> LENGTH: 305
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 212
cggataacaa tttcacacag gaccaaaccc ancaggcgcc ctggcaccgg ggaggcgagt      60
agttgnactc tgcttgtaca gtccttgagc ccagtttaca gatctggaga gcaggaggcc    120
attnttnngg acaanggctg gaggatggag taggacccag gngctctgcc atcctaggca    180
tcattcaagg tcttttatga acactctaca natgtcctcc tgnaantagc anccgagagc    240
ggcnctcagc tcctttctct nctntntttn gtctgatngc cacacacnta tctgctcctg    300
tggcc                                                                 305

<210> SEQ ID NO 213
<211> LENGTH: 439
<212> TYPE: DNA
<213> ORGANISM: mammalian

<400> SEQUENCE: 213
gatacgaaaa atccaattca gcaaaattat atggttgttt tcagtacctc tgaaggtgct      60
atatcaagaa ttctcatgct actctttgag aaaacagatt gcgttttttac ctagaaaatc    120
aactgcaagg catttttata accttacccc aagtaaaaaa aatacattga aatatactta    180
ataaatgcag actacattac ttgaaaaatg gtaatacaga atgccacttt taatatttga    240
aaatatgaat ttttggtaag aaataatgta aaataaagct tctggtaagg ccttaggcag    300
ttaaatttac atcagtgtaa agtaggatga aaatctgtaa aaaataaaaa caaaaaaaca    360
aacaaaaacc tacaccaaaa aaaccctaac atccaccaat gcatacatat tgatctttgt    420
gctgggaaaa tctaaagca                                                  439

<210> SEQ ID NO 214
<211> LENGTH: 393
<212> TYPE: DNA
<213> ORGANISM: mammalian

<400> SEQUENCE: 214
gtcataaaca aaacagattt gatttttttc ctttatggaa cttaagttct agtggtggga      60
ggaggacaga aaacagtaaa taactagatt ttgaattgtg ttagcagatg ataactgatg    120
```

```
tgggaactta gcaggtagaa ggcaacacaa ggtcaaagaa gccggggatt ccaccttgac    180
tagggagctc agggcaggcc tcactgagaa agcaccactt gcatgaagga ggtgggaaaa    240
gccttcacct gggggaagag ccttccaggc agagggaaca gccaatgcca aggccctaat    300
gccttggcca ctgcctggta tgtccaaaga acaaggagac ctgtgccagc ggctgcagct    360
gagtgagcca gggatgtagg aatgtgtaga ggg                                 393

<210> SEQ ID NO 215
<211> LENGTH: 408
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 215
agcggataac aatttcacac aggactgcta ggtagacaag attagatggc aggtaagagc     60
tctttgaaaa tgaaaacatt ctgctatttg aatgcaaagt gttcttcttt gcctgtgatg    120
tttcctaatc tgtgaaatca tacntggacc tcgaagcntg tgtgttaaaa aaaaatagca    180
aagtggcttg ggcatggtgg ctcatgcctg taatcctagc actttgagag gctgaggggg    240
gtggatcact tgaggccagg agttcgatac cagcctggcc aatatgtgaa acgccatctc    300
tactaaaaat acaaaaattt gccaggtgtg gtggcgtcta cctgtagtcc cagctcctcg    360
ggaggctgag gcacaagaat catttgaact caggaggcag aggttgca                 408

<210> SEQ ID NO 216
<211> LENGTH: 308
<212> TYPE: DNA
<213> ORGANISM: mammalian

<400> SEQUENCE: 216
tagcggataa caatttcaca caggactgct aggtagaagg aaacaagcat ttatcctaat     60
tttcttgtat agactgtacc tcagggtatt caaatattga taaggaaaaa gtaattcttc    120
atgaaataat tctagctaac aagtagaatt ataataccat catttgcaac cctaatgaaa    180
caataggtcc gagtgttatc aatggctgct aaaagcattg catgaaaagc cagtgggaaa    240
ttttgtaatg gatgaatcta gctggcccca ttgatatatc ttaatgttac aaaaagggag    300
atgactct                                                            308

<210> SEQ ID NO 217
<211> LENGTH: 404
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 217
tagtgattag cggataacaa tttcacacag gagctagcag acaagctggt tttgtaggtg     60 cagattttt ggacaatatt tcaagaaact catgagagtg tgttttacag gtatgtaggt    120
ttgtgtgtgt gcacatgtgt gcatgtgtgt cnttaatttg gcatcattat gcacttgtcc    180
acactccata atactaggtt atagtcaaaa tttggctttg gcttatgtgt tcctgtggct    240
taattatgtt ccacttgata catattattt gcttacacag aacagacttt tgctgtgtag    300
gccagctttg ggaggcaaag ctgccaatct gaatctttct cctcacaaag acttcactgg    360
```

| | |
|---|---:|
| atagaaacca caaagcaatg tttaaacaag caaagtgtgc taaa | 404 |

<210> SEQ ID NO 218
<211> LENGTH: 368
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 218

| | |
|---|---:|
| taacctggta gtttatcatt ctcgcatcca aagggtactc aatattggta acatcctctc | 60 |
| ctgataagca aaacngtcct gccatctgta ttcattgtga ataacaacat tgtcatctac | 120 |
| acagcctctt aagctgaaaa ttttgatatc tgctaactct tttactaccg tataattaaa | 180 |
| cattcattta ttcacacatt tctcnaagct ttgaccatct aaacagatac tggcttatgt | 240 |
| gttangaant ataagaaagt ccttgacctc anggagttta tagnttaatt gganagattg | 300 |
| acagtntatt tccagaaant taaattatat ccatgtgatt ggccgcncat ggctatgcct | 360 |
| tatccacc | 368 |

<210> SEQ ID NO 219
<211> LENGTH: 426
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 219

| | |
|---|---:|
| taggcattat agaggcnnag agactctttg aaaatgaaaa cattctgcta ttggaatgca | 60 |
| aagtgttctt ctttgcctgt gatgtttcct aatctgtgaa atcatactgg acctcgaagc | 120 |
| tgtctattaa aaaaaatagc taagtggctg ggcatggtgg ctcatgcctg taatcctagc | 180 |
| actttgagag gctgaggggg ttggatcact tgaggccagg agttcgatac cagcctggcc | 240 |
| aatatgcgaa accctgcctc ttctaaaagt acaaaaatta gcccggtgtg gtgacatctg | 300 |
| cctgtagtcc caactactcg ggaggctgag gcacaagaat catttgagct caggaggcag | 360 |
| agtttgcagt gagctgggat ggcgccactg cactccagcc tgagtgacag agtgaggctc | 420 |
| tgtctg | 426 |

<210> SEQ ID NO 220
<211> LENGTH: 307
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 220

| | |
|---|---:|
| tgtagttaat ctcaagagaa tttggggctt ccaagttgtt cgggccaagg acctgagacc | 60 |
| tgaagggttg actttaccca tttggtggg agtgttgagc atctgtcccc ctttagatct | 120 |
| ctgaagccac aaataggatg cttgggaaga ctcctagctg tccttttcc tctccacaca | 180 |
| gtgctcaagg ccagcttata gtcatatata tcacccagac ataaaggaaa agacacattt | 240 |
| tttaggaaat gttttaata aagaaaatt acaaaaaaaa aaanncntn tagngagtcc | 300 |
| naattaa | 307 |

<210> SEQ ID NO 221
<211> LENGTH: 409
<212> TYPE: DNA
<213> ORGANISM: mammalian

<400> SEQUENCE: 221

| | | | | | |
|---|---|---|---|---|---|
| agaaggaaca | atggtcgtgc | caaaagggcc | gcggcccgtg | cagcctattc | gctgcactaa | 60 |
| ctgtgcccga | tgcgtgccca | aggacaaggc | cattaagaaa | ttcgtcattc | gaaacatagt | 120 |
| ggaggccgca | gcagtcaggg | acatttctga | agcgagcgtc | ttcgatgcct | atgtgcttcc | 180 |
| caagctgtat | gtgaagctac | attactgtgt | gagttgtgca | attcacagca | aagtagtcag | 240 |
| gaatcgatct | cgtgaagccc | gcaaggaccg | aacaccccca | cccgatttta | gacctgcggg | 300 |
| tgctgcccca | cgtcccccac | caaagcccat | gtaaggagct | gagttcttaa | agactgaaga | 360 |
| caggctattc | tctggagaaa | aataaaatgg | aaattgtcaa | aaaaaaaaa | | 409 |

<210> SEQ ID NO 222
<211> LENGTH: 333
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 222

| | | | | | |
|---|---|---|---|---|---|
| ctntgggtaa | tcnccctggc | cttggctgcc | ctccttgttg | tggacaggga | agtgccagtg | 60 |
| gcagcaggaa | agctccctt | ctcaagaatg | cccatctgtg | aacacatggt | agagtctcca | 120 |
| acctgttccc | agatgtccaa | cctggtctgc | ggcactgatg | ggctcacata | tacgaatgaa | 180 |
| tgccagctct | gcttggcccg | gataaaaacc | aaacaggaca | tccagatcat | gaaagatggc | 240 |
| aaatgctgat | cccacaggag | cacctcaagc | catgaagtgt | cagctggaga | acagtggtgg | 300 |
| gcatggagag | gatatgacat | gaaaaaaaaa | aaa | | | 333 |

<210> SEQ ID NO 223
<211> LENGTH: 232
<212> TYPE: DNA
<213> ORGANISM: mammalian

<400> SEQUENCE: 223

| | | | | | |
|---|---|---|---|---|---|
| cccttgccag | ctgttagcct | tagagtgatt | gcagtgaaca | ctgtttacac | accgtgaatc | 60 |
| cattcccatc | agtccattcc | agttggcacc | agcctgaacc | atttggtacc | tggtgttaac | 120 |
| tggagtcctg | tttacaaggt | gggagtcgggg | cttgctgact | tctcttcatt | tgaggtcaca | 180 |
| tttttccccc | gtggggaaat | aaactgactt | tggactgctt | caaaaaaaaa | aa | 232 |

<210> SEQ ID NO 224
<211> LENGTH: 463
<212> TYPE: DNA
<213> ORGANISM: mammalian

<400> SEQUENCE: 224

| | | | | | |
|---|---|---|---|---|---|
| tcttgttttc | ttcctcctcc | ttaagcctct | gctcctcgtc | ctgtttgtcc | ttcatttgtt | 60 |
| tctctgctgc | ctttgttacg | ccccacgtct | cgttgccaaa | ctcctcagcg | tatgcctcat | 120 |
| cgttggtgat | gaggaagttg | tcaaagatgg | tgccagactt | gacctgccag | aggtccaggc | 180 |
| ccagcacgcc | aaagttatca | taggcataga | tacatgggat | cggagaaata | tcgggtttg | 240 |
| tcaatttctg | ggtggatcca | agtgcccttg | taatctgggt | tgtcgatctg | ccggggcttc | 300 |

```
cactcaccct tgtactcagg gttctgaatc actgggggtt cccactctcc gtccatctct    360
tcatcccagt cctcgggctt cttagcatca gggtcaggga tatgctcggg cttgtcccag    420
tcctcaggct tggagtcgtc ctgtgtgaaa ttgttatccg cta                      463
```

<210> SEQ ID NO 225
<211> LENGTH: 388
<212> TYPE: DNA
<213> ORGANISM: mammalian

<400> SEQUENCE: 225

```
cgtcccctga cgagttctat gtatgtccct gggaagctgc atgatgtgga acacgtgctc     60
atcgatgtgg gaactgggta ctatgtagag aagacagctg aggatgccaa ggacttcttc    120
aagaggaaga tagattttct aaccaagcag atggagaaaa tccaaccagc tcttcaggag    180
aagcacgcca tgaaacaggc cgtcatggaa atgatgagtc agaagattca gcagctcaca    240
gccctggggg cagctcaggc tacttgctaa ggcctgagag tttttgcaga aatggggcag    300
agggacaccc tttgggcgtg gcttcctggt gatgggaagg gtcttgtgtt taatgccaat    360
aaatgtgcca gctgggcaaa aaaaaaaa                                       388
```

<210> SEQ ID NO 226
<211> LENGTH: 494
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 226

```
ctccttcctg tctaccttaa tcatgaaacc gaatnntngg ggtngtattc tccccaccct     60
canctcctcc tgttctcacn agggatgtga gggaactgaa cnctggtgcc nngctangng    120
gtangggcct ctccctcact gnnngactgn agctggnctc ctgtatacct ganggtccn    180 tctntntagg gnctcctgta nggcttatga ctgtgaatcc ttgatgtcat gattntatgt    240
gacnattcct aggagtccct gccctagag tntgagcagg gctggacccc aanccctcc    300 ctcttccatg gagagaagag tgatctggct tctcctcgga cctgtgngaa tatcattcta    360
ttaatggntc ccgagacgtt ntttggtgaa ggangnccat ccctgggcat tatctgctat    420
gctgannagc tcctctctgg ncntgctnng gggctgnatt tgatatattt ntataannct    480
tncnccaaaa aaaa                                                      494
```

<210> SEQ ID NO 227
<211> LENGTH: 287
<212> TYPE: DNA
<213> ORGANISM: mammalian

<400> SEQUENCE: 227

```
gaatattgta agtcagccct gggacccgag gatttctggg accccgcagt tgggaggagg     60
aagtagtcca gccttccagg tggcgtgaga ggcaatgact cgttacctgc cgcccatcac    120
cttggaggcc ttccctggcc ttgagtagaa aagtcgggga tcgggcaag agaggctgag    180 tacggatggg aaactattgt gcacaagtct ttccagagga gtttcttaat gagatatttg    240
tatttatttc cagaccaata aatttgtaac tttgcaaaaa aaaaaaa                  287
```

<210> SEQ ID NO 228
<211> LENGTH: 300

```
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 228
caatggtaaa cctcgagaca acaaacaagc agggggtgttt gaaccaacca tagttaaagt      60
taagagtttg aaatttgcaa cagaagctgc aatcaccatt cttcgaattg atgatcttat     120
taaattacat ccagaaagta aagatgataa acatggaagt tatgaagatg ctgttcactc     180
tggagccctt aatgattgat ctgatgttcc ttttatttat aacaatgtta aatgcaattg     240
tcttgtaccn tgagttgagt attacacatt aaagtaaagt acaagctgca aaaaaaaaa      300

<210> SEQ ID NO 229
<211> LENGTH: 306
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 229
gctttggagt tctgcctgga gtggttcaac agtctctggt gcaagtctaa taagagatca      60
ggcntatata tctgcctttg cataatatta tggtgcccct attgatatat ggtaagggtg     120
tactagggga ttaggatgat tgtaagagaa tgagaaagat gaccaaaagg ttggtggtag     180
ggaggctttt tcttatttcc aaatacttga gaaattacct tttggtttac aaatctatga     240
tcaacttatt ccattaaata gatacattaa aaaaattaaa aactgattct tctgcaaaaa     300
aaaaaa                                                                306

<210> SEQ ID NO 230
<211> LENGTH: 317
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 230
gagcttgtgc tcaggagtcc agcncgtcca gcctcggggt gtaggtttct gaggtgtgcc      60
attggggcct cagccttctc tggtgacaga ggctcagctg tggccaccaa cacacaacca     120
cacacacaca accacacaca caatgggggg caaccacatc cagtacaagc ttttacaaat     180
gttattagtg tccttttta tttctaatgc cttgtcctct taaaagntat tttatttgtt     240
attattattt gttcttgact gntaattgtg aatggtaatg caataaagtg cctttgttag     300
atggcaaaaa aaaaaaa                                                    317

<210> SEQ ID NO 231
<211> LENGTH: 279
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 231
cggntnantt nctgngggac ccaacnaaac gcaccnnngc tntnattnag gtacactgca      60
```

| | |
|---|---|
| tcagcacaga atttactccc ggangcacgg aggtgaaaag ggagtgccct ttaggatcca | 120 |
| ggttgacncc tttaagcaca atgaaaatgg agaatacaca gatcatntac actcagctag | 180 |
| ctgccaaatc anagttttta agcctaaagg tgcagacang aaacanaaaa cttgaccgag | 240 |
| agaatatgga gaagagaaca gctcatgaaa aaaaaaaaa | 279 |

<210> SEQ ID NO 232
<211> LENGTH: 485
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 232

| | |
|---|---|
| tctgacaang tagnagnagg acatctgtgn cccagattnc cttctacngt ggccgactta | 60 |
| ccttgtgatt ttatgcaccc tntangaccc cttcatnngt ctncacaaca ccaacagcaa | 120 |
| atggggcagg ttttacagca gcagaatata caacaaggat caattaattc accctccacc | 180 |
| caaactttca tgcagactaa tgagcgaagg caggtaggcc ctccttcatt tgttcctgat | 240 |
| tcaccatcaa tccctgttgg aagcccaaat ttttcttctg tgaagcaggg acatggaaat | 300 |
| ctttctggga ccagcttcca gcagtcccca gtgaggcctt cttttacacc tgctttacca | 360 |
| gcagcacctc cagtagctaa tagcagtctc ccatgtggcc aagattctac tataacccat | 420 |
| ggacacagtt atccgggata ncccaatcgt cattcagttg tatttgatat atccagagga | 480 |
| aaaag | 485 |

<210> SEQ ID NO 233
<211> LENGTH: 449
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 233

| | |
|---|---|
| caccctcttc tgaacacctg ctgcctgggc ttcatagcat tcgcctactc cgtgaagtct | 60 |
| agggacagga agatggttgg cgacgtgacc ggggcccagg cctatgcctc caccgccaag | 120 |
| tgcctgaaca tctgggccct gatttggggc atcttcatga ccattctgct catcatcatc | 180 |
| ccagtgttgg tcngtccagg cccagcgata gatcaggagg catcattgag gccaggagct | 240 |
| ctgcccgtga cctgtatccc actgtactct atcttccatt cctcgccctg ccccagagg | 300 |
| ccaggagctn tgcccttgac ctgtattcca cttactcccc ttccattcct cgccctgtcc | 360 |
| ccacagcccg agtcctgcat cagccctta tcctacacgc ttttctacan tggcattaat | 420 |
| aaagtgatat gtttctggaa aaaaaaaaa | 449 |

<210> SEQ ID NO 234
<211> LENGTH: 480
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 234

| | |
|---|---|
| gcctaccaag gatgtgcatg agtgtggcct tctcctctga caaccggcag attgtctctg | 60 |

```
gatctcgaga taaaaccatc aagctatgga atacccgggg tgtgtgcaaa tacactgtcc    120
aggatgagag ccactcagag tgggtgtctt gtgtccgctt ctcgcccaac agcagcaacc    180
ctatcatcgt ctcctgtggc tgggacaagc ttggtcaagg tatggaacct ggctaacttg    240
caagctgaag accaaccaca ttggccacac aggctatctg aacacggtga ctgtctctcc    300
agatggatcc ctctgtgctt ctggaggcaa ggatggccag gccatgttat gggatctcaa    360
cgaaggcaaa cacctttaca cgctagatgg tggggacatc atcaacgccc tgtgcttcag    420
ccctaccgnt ctgctgtgtg ctgcacagcc ccacataaga ttgggattag aggaaagatc    480
```

<210> SEQ ID NO 235
<211> LENGTH: 241
<212> TYPE: DNA
<213> ORGANISM: mammalian

<400> SEQUENCE: 235

```
tttcttctcc cttgcctttg actcttggac tagtgcagag gctttaagta gtttaaaatg     60
ggcttttgct tttctaggtc attaacgttt tttatttagt ttctttagcc aatagtggct    120
gagtttcgca cttgattttc aatatttat agtaagaaat gacaaactgc tttgtttcat     180
ttcataaaca aactctgcat ttagataact attaaaggtt gttaagacga aaaaaaaaa    240 a                                                                   241
```

<210> SEQ ID NO 236
<211> LENGTH: 345
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 236

```
ttcagttcaa ataattaagg ctcttctnga ctgcagtgac ttccccacac attgaaattc     60
atgagggtac tatcctgcag acagtgagaa catgttacaa tatctatttg ccagcaaaa    120 atctcatcaa tcaaaccctg ccaaggctac ccttactcag atgctgaacg tcattttcac    180
ccgcatggaa aaccaagtgt tgcaggaggc cagagaactg gaaaaaccaa tccagtcaaa    240
accccagtcc cctgtgatcc aagctgcagc aggtatcccc aaagttcgtt cgtttgaagc    300
acagtcaggc acaaagcaaa ccaacaactc ccgaaaaaaa aaaaa                    345
```

<210> SEQ ID NO 237
<211> LENGTH: 487
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 237

```
ctccgnatcg gtcgnaaatg gcanaggtgg angagacact gaagcgactg canagccaga     60
agggagtgca gggaatcatc gtcntgaaca cagaaggcnt tcccatnang agcaccatgg    120
acaaccccac caccacccan tatgccaacc tcatgcacag cttcatcctg aaggcacgga    180
gcaccgtncg tgacatcaga ccnccagaac gatctcacct tccttctgaa ttcgctccaa    240
gaaaaaatga attattggtt gcaccaaata aanactattt cctgatngtg attcagaatc    300
caaccgaata agccnctctc ttggctccct gtgtcattcc ttaatttaat gccccccaan    360
```

```
aatgttaatg tcaatcatgt cagtggacta ncacatggca gtcgnttgga ccnactcccc      420
caatccantg accgtgtgtg gctgcggttt tttccccacc acggaaccct gtgtgnccac      480
cttccca                                                                487
```

<210> SEQ ID NO 238
<211> LENGTH: 211
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 238

```
aatgacccat agtgtgagaa cttccaacaa gcctcaaagt cccttgagac tccccaatac       60
ctaataaggc atgcgaaatg ttctcatgaa ctaccccaca acacgcctaa aactcaaaac      120
acccaaaaat atctcctcca atgtcctgan acatgaaccc aaaaagagac ccacaataaa      180
ctcgtgactt gtcccctcga aaaaaaaaa a                                      211
```

<210> SEQ ID NO 239
<211> LENGTH: 367
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 239

```
ctttggaaag cccagggca cntgtggcnc cgggttcaca ttggccaagt tatcatgtcc        60
atccgcacca agctgcagaa caaggagcat gtgattgagg ccctgcgcag ggccaagttc      120
aagtttcctg gccgcagaag atccacatct caaagaagtg gggcttcacc aagttcaatg     180
ctgatgaatt tgaagacatg gnggntgaaa agcggctcat cccagatggc tgtggggtca     240
agtacatccc cagtcgtggc cctctggaca agtggcgggg ccctgcgctc atgagggctt     300
ccaatgtgct gccccctct taatactcac naataaaatt ctacttcctg tccgaaaaaa      360
aaaaaaa                                                                367
```

<210> SEQ ID NO 240
<211> LENGTH: 451
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
<400> SEQUENCE: 240

```
natgaccagc acactggact ccgaggtggt tcagacattn cagaggggag cagtggccat       60
catcctcccg ccaggagctt nttcgttcct gcgcatatag actgtacgtt atgaanaata     120
cccanganga ctttgtgact gncacttgct gcttttttctg cgcttcagta acaagtgttg    180
gcaaactata ttttctcctg gcccctgcct gctggagatc ancatgcctg tcctttcagt    240
ctgatccatc catctctctc ttgcctgagg ggaaagagag atgggccacn gcagagaaca    300
gaactggagg cagtccatcn agggaaatgg cgactgtgcg gccataccnn gcgaaacgna    360
nggantgcta tncnagangc ntttatcang gtgtggnccn tgcacancnt gtntcacncg    420
tttantaaag ccttatnnnc nttaaaanaa a                                    451
```

<210> SEQ ID NO 241
<211> LENGTH: 361
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 241

| | | |
|---|---|---|
| catctccctc cctttcttc tctctgtggt ggagaaccca gctgcagagt aggcagctgc | 60 |
| ctccaggatg anttacttga aatttgcctt gagtgtgtta cctcctttcc aagctcctcg | 120 |
| tgataatgca gacttcctgg agtacaaaca caggatttgt aattccttac tgtaacgnag | 180 |
| tttacagcca gggcatgatg ctttggtgtg gccancactc tgaaactgag aaatgttcan | 240 |
| aatgtactgg aaagatgatc anctattttc aacataactt gaaggcatat gctggcccat | 300 |
| aaacaccctg taggttcttg atatttataa taaaacttgg tgttttgtaa aaaaaaaaa | 360 |
| a | 361 |

<210> SEQ ID NO 242
<211> LENGTH: 429
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 242

| | | |
|---|---|---|
| tccttcnact ttcagtagca ctcgttttac atatgcttat aaaagaagtg atgtatcagt | 60 |
| aatgtatcaa taatcccagc ccagtcaaag caccgccacc tgtaggcttc tgtctcatgg | 120 |
| taattactgg gcctggcctc tgtaagcctg tgtatgttat caatactgtt tcttcctgtg | 180 |
| agttccatta tttctatctc ttatgggcaa agcattgtgg gtaattggtg cttggctaac | 240 |
| attgcatggt cggatagaga agtccagctt gtgagtctct ccccaaagca gccccacagt | 300 |
| ggagcctttg gcttggaagt ccatgggcca ccctgttctt gtccatggag gactccgagg | 360 |
| ggttccaagt atactcttaa gacccctctg tttaaaaata tatattctat gtatgcgtaa | 420 |
| aaaaaaaaa | 429 |

<210> SEQ ID NO 243
<211> LENGTH: 482
<212> TYPE: DNA
<213> ORGANISM: mammalian

<400> SEQUENCE: 243

| | | |
|---|---|---|
| atgatgtaga tgacactgat gattctcacc agtctgatga gtctcaccat tctgatgaat | 60 |
| ctgatgaact ggtcactgat tttcccacgg acctgccagc aaccgaagtt ttcactccag | 120 |
| ttgtccccac agtagacaca tatgatggcc gaggtgatag tgtggtttat ggactgaggt | 180 |
| caaaatctaa gaagtttcgc agacctgaca tccagtaccc tgatgctaca gacgaggaca | 240 |
| tcacctcaca catggaaagc gaggagttga atggtgcata caggccatc cccgttgccc | 300 |
| aggacctgaa cgcgccttct gattgggaca gcccgtggga aggacagtta tgaaacgagt | 360 |
| cagctggatg accagagtgc tgaaaccca agccacaagc agtccagatt atataagcgg | 420 |
| aaagctaatg atgaagcatg acattccgat gtgattgata gtcaggactt tcaaagtcac | 480 |
| cg | 482 |

<210> SEQ ID NO 244
<211> LENGTH: 241
<212> TYPE: DNA
<213> ORGANISM: mammalian

<400> SEQUENCE: 244

```
cttgaactcc tggccccagt gagtgtaatg tctcccatgc caaagtactt ttatcttaaa      60
ttgcttattt ttttgtttat tttttaact gactctgttt acaaaattaa cctttatct      120
agtgacagct agattgtatc acatttgtca tctatggaca actgattttt agttgtttaa      180
tatggtaagt ttattattgt ttttccttat ttaagaaaca ggatctgagt aaaaaaaaaa      240
a                                                                     241
```

<210> SEQ ID NO 245
<211> LENGTH: 334
<212> TYPE: DNA
<213> ORGANISM: mammalian

<400> SEQUENCE: 245

```
agattgaaaa acgagacaaa tatagccgga gacgtcctta taatgatgat gcagatatcg      60
actacattaa tgaaaggaat gccaaattca acaagaaagc tgaaagattc tatgggaaat     120
acacagctga aattaaacag aatttggaaa aggaacagct gtctaatcc cttcaagaac     180
tgtttataga agcttgagaa tggggtaaaa atttctgcta gcaaaatcaa gttcttttg     240
aaatttatc agtaatccag aatttagtag tccatgcctt ctcactcagc atttagaaat     300
aaaaatgtgg tttcttaaac gtaaaaaaaa aaaa                                 334
```

<210> SEQ ID NO 246
<211> LENGTH: 286
<212> TYPE: DNA
<213> ORGANISM: mammalian

<400> SEQUENCE: 246

```
ttgacctaaa cttccaggca ggattcttaa tgaaaaaaga ggtacaggat gaggagaaaa      60
acaagaaatt tggcctttct gtgggccatc acttgggcaa gtccatccca actgacaacc     120
agatcaaagc tagaaaatga gattccttag cctggatttc cttctaacat gttatcaaat     180
ctgggtatct ttccaggctt ccctgacttg ctttagtttt taagatttgt gttttttcttt     240
ttccacaagg aataaatgag agggaatcga ctgtaaaaaa aaaaaa                    286
```

<210> SEQ ID NO 247
<211> LENGTH: 481
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 247

```
tgantagttg acggctagcg gggagctagt tccgccgcat agttatagtg ttgatgtgtg      60
aacgctgacc tgtcctgtgt gctaagagct atgcagctta gctgaggcgc ctagattact     120
agatgtgctg tatcacgggg aatgaggtgg gggtgcttat ttttaatga actaatcana     180
gcctcttgag aaattgttac tcattgaact ggagcatcaa gacatctcat ggaagtggat     240
acggagtgat tgtgtgtcca tgcttttcac tctgaggaca tttaatcgga gaacctnctg     300
gggaatttg tgggagacac ttgggaacaa aacagacacc ctgggaatgc agtttgcaag     360
```

```
gcacaagatg ctgccaccag tgtccnttga ccaccctggt gtgactgctg acttgccagc    420
gtggtacctc catgctgcag gctccatcta atgagacacc aacncactgn cactgttaca    480
a                                                                    481

<210> SEQ ID NO 248
<211> LENGTH: 266
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 248
nccctgcccc ccccaacacg tgcttatgta acccgtggaa agcggcccct gctgcccctc     60
cacacacaca tacacactca ctgatctaca gccctgttc ggcgtcagag tccccactag    120
acccagtgga aggggttaga gaccaagtag gggccagttt ccaattcacc ctgtcaggga    180
gtgagnngga tctgacgttc cttgtgactt aagggtccgg cttgggaatt aaagtttgtt    240
tctggccttt agcctaaaaa aaaaaa                                         266

<210> SEQ ID NO 249
<211> LENGTH: 490
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 249
tctcttcccg cctctgatga gcagttgaaa tctggaactg cctctgttgt gtgcctgctg     60
aataacttct atcccagaga ggccaaagta cagtggaagg tggataacgc cctccaatcg    120
ggtaactccc aggagagtgt cacagagcag gacagcaagg acagcaccta cagcctcagc    180
ancaccctnn cncttgagca aagcagacta cgagaaacac aaagtctacg cctgcgaagt    240
cacccatcag ggcctgagct cgcccgtcac aaagagcttc aacagggag agtgttagag    300 ggagaagtgc ccccacctgc tcctcagttc cagcctgacc cctcccatc ctttggcctc    360 tgacccttt ttcacagggg acctaccct attgcggcct tcagctcatn tttacctnac    420
cccctctctc ttggtttaat tatgctaatg ttggaggaaa tgaataatna ngtgatcttt    480 naaaaaaaaa                                                           490

<210> SEQ ID NO 250
<211> LENGTH: 491
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 250
tcacctctgt cttcatcttc ccgccatctg atgagcagtt gaaatctggg aactgcctct     60
gttgtgtgcc tgctgaataa cttctatccc agagaggcca agtacagtg gaaggtggat    120 aacgccctcc aatcgggtaa ctcccaggag agtgtcacag agcaggacag caaggacagc    180
acctacagcc tcagcagcac cctgacgcnt gagcaaagca gactacgaga aacacaaagt    240
ctacgcctgc gaagtcaccc atcagggcct gagctcgccc gtcacaaaga gcttcaacag    300
```

```
gggagagtgt tagagggaga agtgccccca cctgctcctc agttccagcc tgacccctc    360 ccatcctttg gcctctgacc cttttccac aggggaccta ccctattgc ggtcctccag     420 ctcatcttta cctacccct cctctccttg cttaatttgc taatgttgga ggagatgaat    480
aataaagtga c                                                        491
```

```
<210> SEQ ID NO 251
<211> LENGTH: 484
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 251
ccctctgtct tcatcttccc gccatctgat gagcagttga aatctgggaa ctgcctctgt   60
tgtgtgcctg ctgaataact tctatcccag agaggccaaa gtacagtgga aggtggataa   120
cgccctccaa tcgggtaact cccaggagag tgtcacagag caggacagca aggacagcac   180
ctacagcctc agcagcaccc tgacgcttga gcaaagcaga ctacgagaaa cacaaantct   240
acgcctgcga agtcacccat cagggcctga gctcgcccgt cacaaagagc ttcaacaggg   300
gagagtgtta gagggagaag tgcccccacc tgctcctcag ttccagcctg accccctccc   360
atcctttggc ctctgacccct ttttccacag gggacctacc cctattgcgg tcctccagct   420
catctttacc tcacccccct cctcctcctt ggctttaatt atgctaatgt tggaggagat   480
gaaa                                                                484
```

```
<210> SEQ ID NO 252
<211> LENGTH: 262
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 252
gcagtttnta ttaaananta gtgtgaaatg aatgaaatag aagaaggtaa aaataaggaa   60
caagcaataa acagttcaga gaacataatg gacatcaatg aggaaccagg aacaactgaa   120
ggtgaagaaa tcctgagtca agtagcactg aagaaatgga ggtcagaagt gtggtggctg   180
atactgacca aaaggcttta ggaagtgaag ttcaggatgc ttctaaagtc actactcana   240
tagataaaga gaaaaaaaaa aa                                            262
```

```
<210> SEQ ID NO 253
<211> LENGTH: 359
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 253
tctcaaggac ttcaaactct actcccctaa tagcttttg atgacttcta gcaagcctcg    60
ctaacctcgc cttaccccc actattaacc tactgggaga actctctgtg ctagtaacca    120
cgttctcctg atcaaatatc actctcctac ttacaggact caacatacta gtcacagccc    180
tatactccct ctacatattt accacaacac aatggggctc actcacccac cacattaaca    240
```

```
acataaaacc ctcattcaca cgagaaaaca ccctcatgtt catacaccta tcccccattc    300
tcctcctatc cctcaacccc gacatcatta ccgggttttc ctcttanaaa aaaaaaaaa    359
```

<210> SEQ ID NO 254
<211> LENGTH: 210
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 254

```
catagnccca tcaccctcct taacctctac ttctacctac gcctaatcta ctccacctca    60
atcacactac tccccatatc taacaacgta aaaataaaat gacagtttga acatacaaaa   120
cccaccccat tcctccccac actcatcgcc cttaccacgc tactcctacc tatctcccct   180
tttatactaa taatcttaga aaaaaaaaaa                                    210
```

<210> SEQ ID NO 255
<211> LENGTH: 257
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 255

```
gtcgcancag gggcantagg gtggggttnc cctgggaagc agctggctag tggcttatta    60
cttgtgactg gacctctggt cctcaatcga gttcctctac gaagaacaca ccagaaattt   120
gtcattgcca cttcaaccaa aatcgatatc agcaatgtaa aaatcccaaa acatcttact   180
gatgcttact tcaagaagaa gaacttgtgg aagcccagac accaggaagg tgagacttcg   240
acacagaaaa aaaaaaa                                                  257
```

<210> SEQ ID NO 256
<211> LENGTH: 392
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 256

```
tgcgctccag gcatgcttag gtgccttcng aaagccccag ggcactgtgg ccagggttca    60
cattggccaa gttatcatgt ccatccgcac caagctgcag aacaaggagc atgtgattga   120
ggccctgcgc agggccaagt tcaagtttcc tggccgccag aagatccaca tctcaaagaa   180
gtggggcttc accaagttca atgcttgntn aatttgaaga catggtggnt tgaaaagcgg   240
ctcatcccan atggctgtgg ggtcaagtac atcccagtc ntggccctct ggacaaagtg    300
gcgggccctg cactcatgag ggcttccaat gtgcttgccc cctcttaat actcaccaat   360 aaattctact ttcctgtcca gaaaaaaaaa aa                                 392
```

<210> SEQ ID NO 257
<211> LENGTH: 500
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 257

```
ttgctttatg aaactgcnct cctgtcttct ggcttcagtc tggaagatcc ccagacacat      60
gctaacagga tctacaggat gatcaaactt ggtctgggta ttgatgaaga tgaccctact     120
gctgatgata ccagtgctgc tgtaactgaa gaaatgccac cccttgaagg agatgacgac     180
acatcacgca tggaanaant agactaatct ctggcttgag ggatgactta cctgttcagt     240
actctacaat tcctctgata atatattttc aaggatgttt ttctttattt ttgttaatat     300
taaaaagtct gtatggcatg acaactactt taaggggaag ataagatttc tgtctactaa     360
gtgatgctgt gataccttag gcactaaagc agagctagta atgcttttg agtttcatgt      420 tggtttattt tcacagattg gggtaacgtc actgtaaacg tatgtacatg atgtacttgt     480
gtgggctaag tgttanctgc                                                  500
```

<210> SEQ ID NO 258
<211> LENGTH: 375
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 258

```
accatnaatc ctntctcang gacttcaaac tctactccca ctaatacgct ttttgatcga      60
cttctagcaa gcctcgctaa cctcgcctta cccccacta ttaacctact gggagaactc      120
tctgtgctag taaccacgtt ctcctgatca aatatcactc tcctacttac aggactcaac     180
atactagtca cagccctata ctccctctac atatttacca caacacaatg gggctcactc     240
acccaccaca ttaacaacat aaaaccctca ttcacacgag aaaacaccct catgttcata     300
cacctatccc ccattctcct cctatccctc aaccccgaca tcattaccgg gtttttcctct    360 tacaaaaaaa aaaaa                                                       375
```

<210> SEQ ID NO 259
<211> LENGTH: 376
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 259

```
ttcatcttat cctaaccaaa tgagaataat gacatattga aaacagcctc tagcttcagg      60
ctgggcacgg tggctcacag ctataatctc agcactttgg gaggctgagg tgggagaatt     120
gcctgagccc aggagttcaa gaccagcttg tgcaatatag ggagactccg gctctacaaa     180
aaagagtttt tcaaaattag ccaggcngaa gtggcacaca tctgtggtcc caggtgctca     240
ggaagctgag gtgggaggat cacttgagcc caattcaaag ctgcagtgag ctngtaattg     300
catcacttgc actccaacct gggcaacaga gtaatgacct tgtcttaaaa aaaaataaaa     360
acataaaaaa aaaaaa                                                      376
```

<210> SEQ ID NO 260
<211> LENGTH: 194
<212> TYPE: DNA
<213> ORGANISM: mammalian

```
<220> FEATURE:
<221> NAME/KEY: misc_feature
<222> LOCATION: ()..()
<223> OTHER INFORMATION: "n" is an unknown nucleotide

<400> SEQUENCE: 260
gttngcgggt gaggaacgcg gccaacagga cgggctatgt accgtccaac tacgtggagc    60
ggaagaacag cctgaagaag ggctccctcg tgaagaacct gaaggacaca ctaggtgagt   120
gtttcaccct cgagagagga agccttgtgc atttcaaggg acacatgttc gtctttctag   180
ttagtttgct gttt                                                    194

<210> SEQ ID NO 261
<211> LENGTH: 406
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 261
tgatttaata cgactcacta tagggctttt tttttttgan cgaagggaaa attcccgntt    60
tttatttttg taaangtatc catatatagn catcgacatg acagatgagg aancccatga   120 agttcccac tagtcanata tncattttca cttcatcana agcacctgat atctacngct    180
aatttataat tanatnctgt ttcaatgaan ccaaaangan ccctacaagt tcctataanc   240
aaaagcttcc aangtactag acagtcagt aattaangca tcatttcana ggattatggc   300
tgttccttaa gaagtgcaag ttcaanncctg tcaacaccag aggtaatcat tttatattaa   360
tttatccgna taccattaaa atctttatct gagtatacat atgaaa                 406

<210> SEQ ID NO 262
<211> LENGTH: 391
<212> TYPE: DNA
<213> ORGANISM: mammalian

<400> SEQUENCE: 262
attagcggat aacaatttca cacaggatgg attggtccga agggccacgt gatctcccag    60
atagcacagg aggcaggcca tgacctcatg gacatcttcc tctgcgatgt tgacatccgc   120
ctctctgtga agctcctcaa gtgaccaccc tctactgacc ctcccagggc attccagctc   180
aagctgctgg caggaactga ccagttctgt ccttggctgg ggaccctcca ggcactggtg   240
agagacatga acactgactg gccactagct tggcctggcc ctgttgagtc tgcacagtcc   300
ctgcccagct gtgtcttctg ttggaagaag gaacctgcct tagctcagtt tccaggtggt   360
tcctctgcct ggcaccacag ctacaaggtg t                                 391

<210> SEQ ID NO 263
<211> LENGTH: 307
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 263
aagaacaggc aggaggtaaa aagatgatgg gaaggtgtgg tagactaagg gcccggttat    60
tgggtgaaat ttgagattgt aggccaactg tattttcaag cttctgaact taggcaaaat   120
attcatcgca aagtctctag ctgtcatatt tttctcaccc aaattacgtt tccacgagat   180
```

| | |
|---|---|
| tatttatata tagttggtct atctctgcag tccttgaagg tgaagttgtg tgttactagg | 240 |
| cttgtgtttt gggatgtcan cagtggcctg aagtgagttg tgcaataaat gttaagttga | 300 |
| aacctca | 307 |

<210> SEQ ID NO 264
<211> LENGTH: 192
<212> TYPE: DNA
<213> ORGANISM: mammalian

<400> SEQUENCE: 264

| | |
|---|---|
| tcgagggccc tctctcagtt ctgggaggat gactccagtc cctgcacgcc ctggcacacc | 60 |
| cttcacggtt gctacccagg cggccaagct ccagaccgtg ccagacccag gtgccccagt | 120 |
| gcctttgtct atattctgct cccagcctgc caggcccagg aggaaataaa catgccccag | 180 |
| ttgctgatct ca | 192 |

<210> SEQ ID NO 265
<211> LENGTH: 243
<212> TYPE: DNA
<213> ORGANISM: mammalian

<400> SEQUENCE: 265

| | |
|---|---|
| tctgttggag atgaccagga aattcacatc tatgattgtc caatttaaac atcaaagtct | 60 |
| ccaggcttat gctgcaaaga gaatgtacgg attgatcatg acattcctta ccttcttagg | 120 |
| cttgtttaaa agaaatatag catttattgt agcaaagact taaattttgt agatacaata | 180 |
| tgaatctttt catgttttat tggaaatgct gttcatactt taacataaag ctttcttaat | 240 |
| gca | 243 |

<210> SEQ ID NO 266
<211> LENGTH: 400
<212> TYPE: DNA
<213> ORGANISM: mammalian

<400> SEQUENCE: 266

| | |
|---|---|
| gataacaatt tcacacagga tacaacgagg ggacgtaacg gaggcaggtt ggagccgctg | 60 |
| ccgtcgccat gacccgcggt aaccagcgtg agctcgcccg ccagaagaat atgaaaaagc | 120 |
| agagcgactc ggttaaggga aagcgccgag atgacgggct ttctgctgcc gcccgcaagc | 180 |
| agaggggctc ggagatcatg cagcagaagc agaaaaaggc aaacgagaag aaggaggaac | 240 |
| ccaagtagct tttgtggctt tcgtgtccaa ccctcttgcc cttcgcctgt gtgcctggag | 300 |
| ccagtcccac cacgctcgcg tttcctcctg tagtgctcac aggtcccagc accgatggca | 360 |
| ttcccttgc cctgagtctg accgggtccc ttttgtgctt | 400 |

<210> SEQ ID NO 267
<211> LENGTH: 394
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 267

| | |
|---|---|
| gtgatttaat acgactcact atagggcttt ttttttttgc tgggtnccaa atttctttat | 60 |
| ttgaaggaan ggtncaaatc aaanaactta agnggatgtt tnggtncaac tnatanaaaa | 120 |
| ggtaanggaa nccccancat gcatgcnctt gccttggnga ccaggnaagc cnccccacgg | 180 |

```
ntatggggaa attaccccga ggcttacctt ncattatcac tggtttccca gggngggctn      240
gccaaanana tattccccca acccanattc gggccgctcc catcttgccc aagttgncca      300
cgcggccccc ccaattcttt tgancgcctt nccccctgct catncnggaa gngngcccca      360
nggnanccnc accaannggg gnncattttn nccc                                  394
```

<210> SEQ ID NO 268
<211> LENGTH: 343
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 268

```
ggtccttata ccgatgtcnc ctctgccttt tgtttttcag cttcagagaa gaccaatata       60
atcccaggga cctgggtctc tgggagagga aggaagaggg agggagcaaa gagattgggg      120
tatgtcccct gtagtacact cttacctctt acttcctaga ctttgatttc tccggcagcc      180
cagatgttca gttctcttgg cccctctcta cccttactg ggatctggtt ttcattttcc       240
ggtccttttg ccatacacag ttacagagat cagtcaaatc cataccacca cttgagatct      300
catttattgc cacagatgca caaataaat aacccaaaat cgc                         343
```

<210> SEQ ID NO 269
<211> LENGTH: 279
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 269

```
caatgcccgg ggataaccag cgttatcaac cagaagctaa aggatgatga ggttgctcag       60
ctcaagaaaa gtgcagatac cctgtgggac atccagaagg acctaaaaga cctgtgacta      120
gtgagctcta ggntgtagaa atttaaaaac tacaatgtga ttaactcgag cctttagttt      180
tcatccatgt acatggatca cagtttgctt tgatcttctt caatatgtga atttgggctc      240
acagaatcaa agcctatgct tggtttaatg cttgcaatc                             279
```

<210> SEQ ID NO 270
<211> LENGTH: 209
<212> TYPE: DNA
<213> ORGANISM: mammalian

<400> SEQUENCE: 270

```
tgaagatatt tgtcttcaga attaaaactg cccttaattt taatataccct ttcaatcggc      60 cactggccat ttttttctaa gtattcaatt aagtgggaat tttctggaag atggttagct      120
atgaattaat agagtttgct taatcatttg taattcaaac atgctatatt ttttaaaatc      180
aatgtgaaaa catagactta tttttaaat                                        209
```

<210> SEQ ID NO 271
<211> LENGTH: 319
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 271

```
gtnntncagg acnctctctt tgcttcaagc aagcgaaaac tagaggaggt gctctctact    60
gaggggctg  aagaaaatgg caacagcgac aagaagaaga aggccaagcg agactagcag   120
tcatccagac cctgcccacc tagattgttt tttgagccct ccggacctga gactgagttt   180
tgtcttttc  ctttagcctt agcagtgggt atgaggtgtg caggggagc  ttgggtggct   240
tcactccgcc cattccaaag agggctctcc ctccgcactg cagccgggag cctntgctgt   300
tttgntgggn ggagggaag                                                319
```

<210> SEQ ID NO 272
<211> LENGTH: 296
<212> TYPE: DNA
<213> ORGANISM: mammalian

<400> SEQUENCE: 272

```
caaagccagg cagaccgtcc tcctgccctg ctgggatggc tgtcctggct gtgcttgtgg    60
ctatggctgt ggttcgtggg atgttcagct ggaaaccacc tgccactgcc agtgcagtgt   120
ggtggactgg accctgcccg ctgctgccac ctgacctgac aggaggagg  ctgagaactc   180
agttttgtga ccatgacagt aatgaaacca gggtcccaac caagaaatct actcaaacgt   240
cccacttcat ttgttccatt cctgattctt gggtaataaa gacaaacttt gcaaaa       296
```

<210> SEQ ID NO 273
<211> LENGTH: 316
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 273

```
ttcagatttc ttgctttggt ttgcatttc  ctagtataat tntagcaagt tgacctcaga    60
gttcctgtat cagggagatt gtctgattct ctaataaaag acacattgct gaccttggcc   120
ttgccctttg tacacaagtt cccagggtga gcagcttttg gatttaatat gaacatgtac   180
agcgtgcata gggactcttg ccttaaggag tgtaaacttg atctgcattt gctgatttgt   240
ttttaaaaaa acaagaaatg catgtttcaa ataaaattct ctattgtaaa taaaattttt   300
tctttggatc ttggca                                                   316
```

<210> SEQ ID NO 274
<211> LENGTH: 211
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 274

```
tagtataatt ctagcaagtt gacctcagag ttcctgtatc agggagattg tctgattctc    60
taataaaaga cacattgctg accttggcct tgccctttgt cacaagttcc cagggtgagc   120
agcttttgga tttaatatga acatgtacag cgtgcatagg gactcttgcc ttaaggagt   180
gtaacttgat ctgcatttgc tgatttgttt t                                  211
```

<210> SEQ ID NO 275
<211> LENGTH: 484

<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 275

```
ccctctgtct tcatcttccc gccatctgat gagcagttga aatctgggaa ctgcctctgt      60
tgtgtgcctg ctgaataact tctatcccag agaggccaaa gtacagtgga aggtggataa     120
cgccctccaa tcgggtaact cccaggagag tgtcacagag caggacagca aggacagcac     180
ctacagcctc agcagcaccc tgacgcttga gcaaagcaga ctacgagaaa cacaaantct     240
acgcctgcga agtcacccat cagggcctga gctcgcccgt cacaaagagc ttcaacaggg     300
gagagtgtta gagggagaag tgcccccacc tgctcctcag ttccagcctg accccctccc     360
atcctttggc ctctgaccct ttttccacag gggacctacc cctattgcgg tcctccagct     420
catctttacc tcaccccct cctcctcctt ggctttaatt atgctaatgt tggaggagat     480
gaaa                                                                  484
```

<210> SEQ ID NO 276
<211> LENGTH: 415
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 276

```
taanttatgg atccagattg ttctgagaga cgaagatact tgctgctgat agaggtgaaa      60
acgagattga tccgtctggg gttttacggt gtgcactggg tgctgcacag acttgtcaag     120
gtttgctacg tcctctgggc atctgcaaaa ggccctgctc tctggagtgt tgtatatagt     180
gtagcaaaag agtatttata catcccacca atcaaaacac agcttttatt acctcatgcg     240
aactcataca accaatagaa tttcaacatg ttctgtagct taaaagtgct cacttactac     300
cttttgaaca atactcccct ggaagttggc nctttcntat cttttttgcat cttnggaatt     360
aacctntttg nttcccttca taaaangaan ggncattgga atcttttaaa aaaaa          415
```

<210> SEQ ID NO 277
<211> LENGTH: 389
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 277

```
ctgcccggta ctattttagg gggcccgnta gaaaataatg aggtcctttg aggagagatc      60
ttctaaaatc cacattagtg atactgaatt attgagagtg acaaactttt ttatcttcac     120
ccataataaa cttttttat cttcactttg ttagcaaatc caaagaaatg tggaattttt     180
agtttagcag attcaaaatg tagaaaacag tttaccttca tatgacatat ttatatgcac     240
tatttaagct ttgaggtgta gcccatttaa attcttcttt tgagatttcc aaatacatta     300
tatccatctc acaatccccc ccacgtctcc aaatttttgc atgggtttac cattgnccca     360
ttctgaccct cattctttct tttctaagt                                        389
```

<210> SEQ ID NO 278
<211> LENGTH: 302
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 278

| | | | | | |
|---|---|---|---|---|---|
| cttttttccct | gcgcngtgga | cctgagaact | ccgccgtgtg | ttcaacgact | gccgtgacat | 60 |
| cattcagcgc | atgcacccttc | gtcagtacga | gctgctctaa | gaagggaacc | cccaaattta | 120 |
| attaaagcct | taagcacaat | taattaaaag | tgaaacgtaa | ttgtacaagc | agttaatcac | 180 |
| ccaccattan | ggcatgatta | acaaagcacc | tttcccttcc | cccgagtgat | tttgcgaaac | 240 |
| cccctttttcc | cttcagcttg | ctttagatgt | tcccaaattt | agaaagctta | aggcgggcct | 300 |
| ac | | | | | | 302 |

<210> SEQ ID NO 279
<211> LENGTH: 340
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 279

| | | | | | |
|---|---|---|---|---|---|
| aggaacacga | cgacctacaa | taaaaagtac | cagtactatt | ccaataaaca | ctgcagaggg | 60 |
| agcacccctc | gttgctgagt | cccctcttcc | ctggaaacct | tccacccagt | gctgaatttc | 120 |
| cctctctcat | accctcccctc | cctacccctaa | ccaagttcct | tggccatgca | gaaagcatcc | 180 |
| ctcacccatc | ctagaggcca | ggcaggagcc | cttctatacc | cacccagaat | gagacatcca | 240 |
| gcagatttcc | agccttctac | tgntnctcct | ccacctcact | tccgtgctta | accaaagaag | 300 |
| ctgtctccgg | gggggtctct | ttcttgaata | aagcatttag | | | 340 |

<210> SEQ ID NO 280
<211> LENGTH: 434
<212> TYPE: DNA
<213> ORGANISM: mammalian

<400> SEQUENCE: 280

| | | | | | |
|---|---|---|---|---|---|
| cagaaatgct | acccagcatc | ttaaaccagc | ttggtgcgga | tagtctgact | agtttaagga | 60 |
| gactggccga | agctctgccc | aaacaatctg | tggatggaaa | agcaccactt | gctactggag | 120 |
| aggatgatga | tgatgaagtt | ccagatcttg | tggagaattt | tgatgaggct | tccaagaatg | 180 |
| aggcaaactg | aattgagtca | acttctgaag | ataaaacctg | aagaagttac | tgggagctgc | 240 |
| tattttatat | tatgactgct | ttttaagaaa | tttttgttta | tggatctgat | aaaatctaga | 300 |
| tctctaatat | ttttaagccc | aagcccccttg | gacactgcag | ctcttttcag | tttttgctta | 360 |
| tacacaattc | attctttgca | gctaattaag | ccgaagaagc | ctgggaatca | agtttgaaac | 420 |
| aaagattaat | aaag | | | | | 434 |

<210> SEQ ID NO 281
<211> LENGTH: 461
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 281

```
atctgctcat tatttcagag gggaaaccta gcaaactaag agtgataagg ggccctacta      60
cactggcttt tttaggctta gagacagaaa ctttagcatt ggcccagtag gtggcttcta     120
gctctaaatg tttgccccgc catcccttc cacagtatcc ttcttccctc ctncctgtc       180
tctggctgtc tcgagcagtc tataagagtg catctccagc ctatgaaaca gcttgggtct    240
ttggccataa gaagtaaaga tttgaagaca gaaggaagaa cctcagggag taagcttcta    300
gccccttca gctttctaca cccttctgcc ctctctccat tgcctgcacc ccaccccagc     360
cactcaactc ctgcttgntt ttccttnggc catgggangg ttaccagtaa aatccttgct    420
aggntgatgt gggcccncat tcctttaata accattgtga c                        461
```

<210> SEQ ID NO 282
<211> LENGTH: 213
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 282

```
catccgcatc gaacattggg gtttctncaa aatggtgtgt gtcatacntt cttttgggag     60
gggggttngt tttcttctgt ttattttctg agactcctac aggagccaaa tttgtaattt    120
agagacactt aattttgtta atcctgtctg ggacacttaa gtaacatcta aagcattatt    180
gctttagaat gttcaaataa aatttcctga cca                                 213
```

<210> SEQ ID NO 283
<211> LENGTH: 422
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 283

```
gcacctccnt acctgtcagc ctgagtatgg gcaatggcgt tttagtttgc aaaaccagac     60
acatagaggc caggtttccc ccgctcaaca ctaggccact gtgcctgcca ctgctgtctg    120
caaatgcagg ttcctggggc tctgggtggt ttgtccaatg gctaagcttt ccccaggaat    180
gggtaacntg gaaaaatgta ggaattacat atgattccat caatgacagt tttcctatta    240
aaacataact tgttaaagca tagagcttag ttcaagagta aacatttcta aaaaagaggt    300
agaagcccct acctactgac tggcatcaca aacactgccc tgaaatgcca actcatttca    360
aatactgctc tagacaactg ggccctgcat ctgctgcaag gaacatccct tactttccca    420
tc                                                                   422
```

<210> SEQ ID NO 284
<211> LENGTH: 447
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 284

```
gctcttgnnc gccactggcg gtcctgaaaa acagatgact tgggcaaagg tggaaatgaa     60
```

```
gaaagtacaa agacaggaaa cgctggaagt cgtttggctt gtggtgtaat tgggatcgcc    120
caataaacat tcccttggat gtagtctgag gccccttact catctgttat cctgctagcn    180
tgtagaaatg tatcctgata aacattaaac acttgtaatc ttaaaagtgt aattgtgtga    240 cttttttcaga gttgctttaa agtacctgta gtgagaaact gatttatgat cacttggaag    300
atttgtatag ttttataaaa ctcagttaaa atgtctgttt caatgacctg tattttgcca    360
gacttaaatc acagatgggt attaaacttg tcagaatttc tttgtcattc aagcctgtga    420
ataaaaaccc tgttggactt attatga                                        447
```

<210> SEQ ID NO 285
<211> LENGTH: 479
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 285

```
cccncctcnn cgttnggggg agacngaana accttctccg ctgacctggt tgtggggctg    60
tgcactgggc agatcaagac tggtgcccct tgccgatctg agcgcttggc caagtacaac    120
cagctcctca gaattgaaga ggagctgggc agcaaggcta agtttgccgg caggaacttc    180
agaaacccct tggccaagta agctgtgggc aggcaagccc ttcggtcacc tgttggctac    240
acagacccct cccctcgtgt cagctcaggc agctcgaggc ccccgaccaa cacttgcagg    300
ggtccctgct agttaagcgc cccaccgccg tggagttcgt accgcttcct tagaacttct    360
acagaagcca agctccctgg agccctgttg gcagctctag cttttgcagtc gtgtaattgg    420 ccaagtcatt gttttttcgct cgcttccacc aagtgttaga gtatgtagcc tcgtgtatc    479
```

<210> SEQ ID NO 286
<211> LENGTH: 459
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 286

```
tncnccctccc attttttgaac atcccaagac tttccggaca gaacgtcctg tcaactcagc    60
tgccctctcc cccaactatg accatgtggt cctgggcggt ggtcaggaag ccatggatgt    120
aacccaacct ccaccaggat tggcaagttt gaggccaggt tcttccatttt ggcccttgaa    180 gaagagtttg gaagagtcaa gggtcacttt ggacctatca acagtgttgc cttccatcct    240
gatggcaaga gctacagcag cggcggcgaa gatggttacn gtccgtatcc attacttcga    300
cccacagtac ttcgaatttg agtttgaggc ttaagaagct ggatctcctg ccgggcgtgg    360
tggctcatgc ctgtaatccc accactttt tttttaaggca ggcggatcac ctgaggtcag    420
gagtttaaga ccagcctgac caacatggag aaacctcgt                           459
```

<210> SEQ ID NO 287
<211> LENGTH: 457
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 287

```
cctaccaatg tttggggatg aanncgggtt tgctcccaac atcctggaga ataaagaagg    60
cctggagctg ctgaagaccg ctattgggaa agctggctac actgataagg tggtcatcgg   120
catggacgta gcggcctccg agttcttcag gtctgggaag tatgacctgg acttcaagtc   180
tcccgatgac cccagcaggt acatctcgcc tgaccagctt ggcatgacct gtacaagtcc   240
ttcatcaagg actacccagt ggtgtctatc gaagatccct ttgaccagga tgactgggga   300
gcttggcaga agttcacagc cagtgcagga atccaggtag tggggatgga tctcacagtg   360
accaacccaa agaggatcgc caaggccgtg aacgagaagt cctgcaactg cctcctgctc   420
aaagtcaacc agattgctcc gtgaccgagt ctcttcc                             457
```

<210> SEQ ID NO 288
<211> LENGTH: 492
<212> TYPE: DNA
<213> ORGANISM: mammalian

<400> SEQUENCE: 288

```
gctccgtgac gagtctcttc aggcgtgcaa gctggcccag gccaatggtt ggggcgtcat    60
ggtgtctcat cgttcggggg agactgaaga taccttcatc gctgacctgg ttgtggggct   120
gtgcactggg cagatcaaga ctggtgcccc ttgccgatct gagcgcttgg ccaagtacaa   180
ccagctcctc agaattgaag aggagcttgg gcagcaaggc taagtttgcc ggcaggaact   240
tcagaaaccc cttggccaag taagctgtgg gcaggcaagc ccttcggtca cctgttggct   300
acacagaccc ctcccctcgt gtcagctcag gcagctcgag gcccccgacc aacacttgca   360
ggggtccctg ctagttagcc gccccaccgc cgtggagttc gtaccgcttc ttagaacttc   420
tacagaagcc aagctccctg agccctgtt ggcagctcta gctttgcagt cgtgtattgc   480
ccaagtcatt ga                                                       492
```

<210> SEQ ID NO 289
<211> LENGTH: 409
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 289

```
tnaggcngcc tgacttncgc tggctccaca gctctagggg cctgctcctc taatcacagt    60
gggttttgtg aggctctgtg gcccagagca gacctgcata tctgagcaaa aatagcaaaa   120
gcctctctca gcccactggc ctgaatctac actggaagcc aacttgctgg cacccccgct   180
ccccaaccct tcttgcctgg gtaggagagg ctaaagatca ccctaaattt actcatctct   240
ctagtgctgc ctcacattgg gcctcagcag ctccccagca ccaattcaca ggtcacccct   300
ctcttcttgc actgtcccca aacttgctgt caattccgag atctagtctc cccctacgct   360
ctgccaggaa ttctttcaga cctcactagc acaagcccgg ttgtccttg                409
```

<210> SEQ ID NO 290
<211> LENGTH: 347
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 290

```
aaaataatgt ctgatcctgt tcctaagttc caaactatag ccaacactct gatgctgctc    60
tttttcttgt aggaccaacc gtcccagttt gcctgggact ttctcatttt tacagagtcc   120
caaatcctag gaaactggag caactggtac aactggtcac ctactcttgc ccctctgtaa   180
atcaagccaa ctgtgaccat ccaatgtgcc atcttacagg gaaaagttat aaccacttat   240
tccctataa  cntaatgcta atgattgtac ttagtacatt tttatacttt tatgatattt   300
tactgattgg aaatgtcatc ctttattaaa aataaacatg gttttcc                 347
```

<210> SEQ ID NO 291
<211> LENGTH: 340
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 291

```
cccttgtacc cagnagcant tttacaacac ccttacctgc ccgctccaca gcctcagact    60
tgttggagaa cctacaactt tctacatcag cccatcccct acttacacaa cactctttcc   120
tgcgagttcc agcacatcag gcctcactga ggaatctacc accttccaca ccagtccaag   180
cttcacttct acaattgtgt ctacttgaaa gcctggaaac cttagcacca gggttgtgcc   240
aggaaggaca aatttggaat ggaaaacaat gcgtctgtcc ccaaggctac gttggttacc   300
aagtgcttgt cccctctgga atccttccct gtagaaaccc                         340
```

<210> SEQ ID NO 292
<211> LENGTH: 424
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 292

```
tccnacctca ngtttccagg ggcctcactc ttcagagtgg cagagatgaa ctaaatgagg    60
agctcatnca ggaagaaagc tctgaagacg aaggagaata tgaagaggtt agaaaagatc   120
aggattctgt tggtgaaatg aaggatgaag gggaagagac attaaattat cctgatacta   180
ccattgactt gtctcnnntt tcaccccaa aggtccatcc agaaattggc ttcaaaanag    240
gatcttctaa ttctagtgac agtaaatcac agacccggag acattttgca gcccaaggaa   300
agaangggaa atgaaaanaa anacgncccc nttngtngcg ccnnattnaa cccctagtg    360
aactncccgg ccnncntccg gtccnnccct tttggggaga gccccaccc nttgggatgc    420
ctan                                                                424
```

<210> SEQ ID NO 293
<211> LENGTH: 401
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 293

```
gtacttttaa ttaaatnccc agtatttaaa aagacaaagt atttttgtcc atttgagatt    60
```

```
ctgcactcca tgaaaagttc acttggacgc tggggccaaa agctgttgat tttcttaagt    120
tgacggttgt caatatatcg aactgttccc aagttagtca agtatgtctc aacactagca    180
tgatataaaa ntggnacact gcagctgaat gaaaaaggaa tcaaaaccac tttgtacata    240
agttaaatcc tattggattt gtnccgtcct cccatttggt ctccggacna ttaaatgcta    300
catggggtaa ggtctggcct aaatagggta gcttaaaact tatggtnaaa nngcntgcnn    360
ccagttttgt cnattaaagg ttttatcccc ttttttaacc c                        401
```

<210> SEQ ID NO 294
<211> LENGTH: 400
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 294

```
taggtattat tgtgacancg gccagtcttt tttcttgacg ccccagattc cccagccacg     60
ttagcctaca gaagtataat tcagagaatc caagagtttt gtaatctcca tcagtcaaaa    120
gaagagaacc tcatcagttc ctgaagcgag agaatgttca ggaccaagca gttaccgagc    180
gaggcactca cttgggcagc acatccagcc agaccganca gctnccggga tggggtgggg    240
tcacagcaaa agggaccaga tgctggtgtg ggcccgaagc cacttttctc agagacactt    300
ttaatcattg agtatttgta ccttttcttt agaacatata ttaaaggggc attctctaca    360
aatgtggccg ttttaagaaa taaaacccccc tcaaatcccc                          400
```

<210> SEQ ID NO 295
<211> LENGTH: 411
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 295

```
nattttcata gaggcccgag gatgtcaatg acaatgcacc acagtacatc agagcctgtt     60
tattacccag aaatcatgga aaattctcct aaagatgtat ctgtggtcca gatcgaggca    120
tttgatccag attcgagctc taatgacaag ctcatgtaca aaattcaagt ggaaatccac    180
aggattnttt ttcaatacat cctaaaccag gtctcatcac acttacgtca aggaaagcta    240
gaccgagaac agcaagatga acacatatta gagggtactg tgacagacaa tgggtagtcc    300
ccccaatcaa ccattgcaag agtcattggt gaaaatcctt gatgaaatga caacaaacct    360
cagtttctgc aaaagtctac aaatcagact ccttgacggg aaaagcccga c             411
```

<210> SEQ ID NO 296
<211> LENGTH: 416
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 296

```
ctttcctatg ccncaccttt tggacttata tgatgagtgc tcgatccaag aatgttngtt     60
ggcgccttga ttactttttg ttgtcccact ctctgttacc tgcattgtgt gacagcaaga    120
```

| | |
|---|---|
| tccgttccaa ggccctcggc agtgatcact gtcctatcac cctataccta gcactgtgac | 180 |
| accnntccct aaatcacttt gagcctgggg aaataacccc ctcactacca ttccttcttt | 240 |
| aaacactctt cagagaaatc tgcattctat tctcatgtat aaaactnagg aatcctccac | 300 |
| cagggctcct gtggatagaa gttcttttaa agcccaagat ttttatttta angggttttt | 360 |
| ggtttttttna aaaaaaatt gaacaaagac tctatgactt ggttcgaata tcccat | 416 |

<210> SEQ ID NO 297
<211> LENGTH: 439
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 297

| | |
|---|---|
| cttggccctg ctgagctcta ctgcctgcag gatgggagta cactgggcaa catgaccacc | 60 |
| atggttagcc ctgtggaatt ggtggccatg gagtccggcc taacctcggc aattcaggct | 120 |
| gttgaaagca cctcagagga tgggcagacc atcattgaga ttgatccagc ccccngaccn | 180 |
| tttaagctga agatcctgat gntaaagcag tcatcttgga gacagagctg aggactgang | 240 |
| agaaagttgt gggcttgaga atggaagaac acccagcatc naagttcaca atgtgggaga | 300 |
| nttggggggtc cttaaaagga attaacctgg ngggatcttc agggccccgg agttnttgtt | 360 |
| ttgattttgg aaattttttan ntattttggt ttattttttca cnatnnnccc actcatttcc | 420 |
| cccatnggac ccctttttg | 439 |

<210> SEQ ID NO 298
<211> LENGTH: 213
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 298

| | |
|---|---|
| tcgcctagcg gagactagaa nccgtagcat gattttttaaa taacctgtct ttgttttttga | 60 |
| tgttaaacag taaatgccag taangaccan gaaccagtga ttatatacac tatactggag | 120 |
| ggatttcatt tttaattcat ctttatgaag atttagaact cattccttgn gtttaaaggg | 180 |
| aatgtttaat tgagaaataa acatttgtgt aca | 213 |

<210> SEQ ID NO 299
<211> LENGTH: 937
<212> TYPE: DNA
<213> ORGANISM: mammalian

<400> SEQUENCE: 299

| | |
|---|---|
| gttcttgcct ggtgtcggtg gttagtttct gcgacttgtg ttgggactgc tgataggaag | 60 |
| atgtcttcag gaaatgctaa aattgggcac cctgccccca acttcaaagc cacagctgtt | 120 |
| atgccagatg gtcagtttaa agatatcagc ctgtctgact acaaaggaaa atatgttgtg | 180 |
| ttcttctttt accctcttga cttcaccttt gtgtgcccca cggagatcat tgctttcagt | 240 |
| gatagggcag aagaatttaa gaaactcaac tgccaagtga ttggtgcttc tgtggattct | 300 |
| cacttctgtc atctagcatg ggtcaataca cctaagaaac aaggaggact gggacccatg | 360 |
| aacattcctt tggtatcaga cccgaagcgc accattgctc aggattatgg ggtcttaaag | 420 |

-continued

```
gctgatgaag gcatctcgtt caggggcctt tttatcattg atgataaggg tattcttcgg      480
cagatcactg taaatgacct ccctgttggc cgctctgtgg atgagacttt gagactagtt      540
caggccttcc agttcactga caaacatggg aagtgtgcc cagctggctg aaacctggc        600 agtgatacca tcaagcctga tgtccaaaag agcaaagaat atttctccaa gcagaagtga     660
gcgctgggct gttttagtgc caggctgcgg tgggcagcca tgagaacaaa acctcttctg      720
tatttttttt ttccattagt aaaacacaag acttcagatt cagccgaatt gtggtgtctt     780
acaaggcagg cctttcctac aggggtggaa gagaccagcc tttcttcctt tggtaggaat     840
ggcctgagtt ggcgttgtgg gcaggctact ggtttgtatg atgtattagt agagcaaccc     900
attaatcttt tgtagtttgt attaaacttg aactgag                              937

<210> SEQ ID NO 300
<211> LENGTH: 204
<212> TYPE: DNA
<213> ORGANISM: mammalian

<400> SEQUENCE: 300
gaagaggaag cagctatgaa ggccaaaaca gagtagcaga ggtatccgtg ttggctggat       60
tttgaaaatc caggaattat gttataacgt gcctgtatta aaaggatgt ggtatgagga      120 tccatttcat aaagtatgat ttgcccaaac ctgtaccatt tccgtatttc tgctgtagaa     180
gtagaaataa attttcttaa ataa                                            204

<210> SEQ ID NO 301
<211> LENGTH: 430
<212> TYPE: DNA
<213> ORGANISM: mammalian

<400> SEQUENCE: 301
gggcagtgag gctgttcgca gagctgcgga agatgaatgc cagaggactt ggatctgagc       60
taaaggacag tattccagtt actgaacttt cagcaagtgg acctttttgaa agtcatgatc     120 ttcttcggaa aggttttttct tgtgtgaaaa atgaactttt gcctagtcat cccccttgaat    180 tatcagaaaa aaatttccag ctcaaccaag ataaaatgaa ttttccaca cttgagaaac      240 attcagggtc tatttgctcc gctaaaatta cagatggaat tcaaggcagt gcagcaggtt     300
cagcgtcttc catttctttc aagctcaaat cttttcactgg atgttttgag gggtaatgat     360
gagactattg gatttgagga tatccttaat gatccatcac aaagcgaagt catgggagag     420
ccacactcga                                                            430

<210> SEQ ID NO 302
<211> LENGTH: 551
<212> TYPE: DNA
<213> ORGANISM: mammalian

<400> SEQUENCE: 302
ggcacgaggc tccagacccg cacgccgcgc gcacagagct ctcagcgccg ctcccagcca       60
cagcctcccg cgcctcgctc agctccaaca tggcaaaaat ctccagccct acagagactg     120
agcggtgcat cgagtccctg attgctgtct tccagaagta tgctggaaag gatggttata     180
actacactct ctccaagaca gagttcctaa gcttcatgaa tacagaacta gctgccttca     240
caaagaacca gaaggaccct ggtgtccttg accgcatgat gaagaaactg gacaccaaca     300
gtgatggtca gctagatttc tcagaatttc ttaatctgat tggtggccta gctatggctt     360
gccatgactc cttcctcaag gctgtccctt cccagaagcg gacctgagga ccccttggcc     420
```

```
ctggccttca aacccacccc ctttccttcc agcctttctg tcatcatctc cacagcccac    480
ccatcccctg agcacactaa ccacctcatg caggcccac ctgccaatag taataaagca    540
atgtcacttt t                                                         551
```

<210> SEQ ID NO 303
<211> LENGTH: 403
<212> TYPE: DNA
<213> ORGANISM: mammalian

<400> SEQUENCE: 303

```
tccgactact tcagagttag atggaaggtg ctggatggat gctttggagt tggctttgaa     60
atgttctagt cttcttaaac gtacaatgat cagagaagga aaggaacatg acctgagcgt    120
ttcatcagat agcgcacatg tgactttcta tggcttacta cgtgctaaca atctccacag    180
tggtgataac ttccagttaa atgatagtga aattgaacga caacatttta aggaccaaga    240
tatgtattct gataaatctg ataaagaaaa tgatcaagaa catgatgagt ctgataatga    300
ggtgatgggg aaaagtgaag aaagtgacac agatacatca gaaagacaag atgactcata    360
tatcgaacct gagcctgttg agcctttaag gagactccta cct                     403
```

<210> SEQ ID NO 304
<211> LENGTH: 243
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 304

```
ctttctccct gntgttgctg ttggttccct ctcagattca gtaactattt tnanggatcc     60
cggcctgtga ttaatattna taanaccatc acagtaactc ctaacagaat tgacctccgc    120
cagaaaacag cgtgtggggc gcctagtcgg gatatgcctc caggttaaat cctgttttga    180
atatactgct aaccccgctg ttataatcc ttcaatatna attgtgggca cacttgaagc    240
tga                                                                  243
```

<210> SEQ ID NO 305
<211> LENGTH: 210
<212> TYPE: DNA
<213> ORGANISM: mammalian

<400> SEQUENCE: 305

```
agcactttgt tcactgtcct gtgtcagagc actgagctcc acccttttct gagagttatt     60
acagccagaa agtgtgggct gaagatggtt ggtttcatgt ttttgtatta tgtatctttt    120
tgtatggtaa agactatatt ttgtacttaa ccagatatat ttttacccca gatggggata    180
ttctttgtaa aaaatgaaaa taaagttttt                                    210
```

<210> SEQ ID NO 306
<211> LENGTH: 339
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 306

```
ctgccggtat tctncagatc ctagctnggn cttgatagcc cttaatatat gtttgtatta     60
```

-continued

| | |
|---|---|
| tgntattttt caactaaatc gcagttggaa aaaaacatat tnaatattat gcccttggat | 120 |
| ctgttactgc atcactagca cttgtgatgc aatanaacac ttcgcctgta ctgaangggc | 180 |
| caanagtaaa tgccttgntt tgttttttg ttttgttctg ttntgatttt tgttaaacat | 240 |
| gtctatagag ttggnagnta atgcttgaat ttgtcanata ccccttccaa aattatactt | 300 |
| gtatttaaaa aatnaangga tctacctaat ttctattga | 339 |

<210> SEQ ID NO 307
<211> LENGTH: 459
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 307

| | |
|---|---|
| tttgccntcc caaantttcc aggntaacna caaggagata gaaaggttaa aacaactgat | 60 |
| cgacaaagaa acaaatgacc ggaaatgcct ggaagatgaa aacgcgagat tacaaagggt | 120 |
| ccagtatgac ctgcagaaag caaacagtag tgcgacggag acaataaaca aactgaaggt | 180 |
| tcaggagcaa gaacttgaca cgcctgatga tcgactatga aagggtttcc caggagagga | 240 |
| ctgtgaagga ccaggatatc acgcggttcc agaactctct gaaagagctt gcagcttgca | 300 |
| gaagcagaag gtggaagagg agcttgaatc ggctgaagag gaccgcgtca gaagactcct | 360 |
| gcaagaggaa gaagctggag gaagagctgg aaggcatgag gaggtcgctt gaaggagcaa | 420 |
| gcctcaaaat cccacctgac ccagcagctt ggagcaggc | 459 |

<210> SEQ ID NO 308
<211> LENGTH: 481
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 308

| | |
|---|---|
| cccttggac cctaccctgt tttcattaca gtnacttcca aaacgaacaa ggacaccagc | 60 |
| aaattcccca gccctctggt agtttatgca aatattcgcc aaggagcctc cccaattctc | 120 |
| agggccagtg tcacagccct gattgaatca gtgaatggaa aaacagttac cttggaacta | 180 |
| cttggataat ggagcaggtg cttgatgcta cttaaggatg acggtgtcta ctcaaggtat | 240 |
| ttcacaactt atgacacgaa tggtagatac agtgtaaaag tgcgggctct gggaggagtt | 300 |
| aacgcagcca gacggagagt gatacccag cagagtggag cactgtacat acctggctgg | 360 |
| attgagaatg atgaaataca atggaatcca ccaagacctg aaattaataa ggatgatgtt | 420 |
| caacacaagc aagtgtgttt cagcagaaca tcctcgggag gctatttgtg gntntgatgt | 480 |
| a | 481 |

<210> SEQ ID NO 309
<211> LENGTH: 344
<212> TYPE: DNA
<213> ORGANISM: mammalian

<400> SEQUENCE: 309

| | |
|---|---|
| atgaagccaa cacacttgtc cttggtttta agaaagattg gttgcaagca gatatgaggg | 60 |
| atgtggatat gtatataaac ttatttcatg atgcttttga catacaatat ggagtagtgg | 120 |

| | |
|---|---|
| ttattcgcct aaaagaaggt ctggatatat ctcatcttca aggacaagaa gaattattgt | 180 |
| catcacaaga gaaatctcct ggcaccaagg atgtggtagt aagtgtggaa tatagtaaaa | 240 |
| agtccgattt agatacttcc aaaccactca gtgaaaaacc aattacacac aaagttgagg | 300 |
| aagaggatgg caagactgca actcaaccac tgttgaaaaa aaaa | 344 |

<210> SEQ ID NO 310
<211> LENGTH: 357
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 310

| | |
|---|---|
| tgaccagcgg ataacaattt cacacaggac gactccaagg aaagctttgc atttaaacca | 60 |
| gaaaatatct cagaagaaaa tgcaacccac atatttattg ccattaaann gnatagataa | 120 |
| aagcaatttg acnttttaa gtatccaaca ttgcacaagt aactttgttt atccctcaag | 180 |
| caaatcctcg atgacattga tcctactcct actcctactc ctactcctga taaagtcat | 240 |
| aattctggag ttaatatttc tacgctggta ttgtctgtga ttgggtctgn nngtcnttgt | 300 |
| taacttctat ttnaactacc accattngaa ccttaacgaa anaanaaaat cttcaag | 357 |

<210> SEQ ID NO 311
<211> LENGTH: 373
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 311

| | |
|---|---|
| agcggataac aatttcacac aggagaccat tgcatgccct caactcttgc ttggcagggg | 60 |
| taccagagac tgaaagacac ggcacaaatc tcaatattca tctcccacat caccttttcnt | 120 |
| gggaactgga nagggngaaa gtcctcaaac tctgggaaca ggcganaagg aacagggatt | 180 |
| taantnccecg gccacaggnn catgggaagc ttgaggnagn aagggggaan ccagggaccc | 240 |
| anntnaagga nngggtggga gnntttttncc taanttgggg ggacaccca gnntgnaaag | 300 |
| ctactaagna naaggggntg angggntnaa ggctnccctg agaggataa nctgagananan | 360 |
| anntntaact tct | 373 |

<210> SEQ ID NO 312
<211> LENGTH: 377
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 312

| | |
|---|---|
| tagtgnntag cggataacaa tttcacacag gagaccattg cagtacattg agctccatag | 60 |
| agacagcgcc ggggcaagtg agagccggac gggcactggg cgactctgtg cctcgctgag | 120 |
| gaaaataac taacntnnnc aaaggagatc ctaagaagcc gagaggcaaa atgtcatcat | 180 |
| atgcattttt tgngcaaact tgtcgggagg agcataagaa gaancaccca gatgcttcaa | 240 |
| gtcaacttct nagagttttc taanaagtgc tcaaaagagg tggaagacca tgtctgctaa | 300 |

```
agagaaagga aaatttgaag atatngnaaa agcggacnag ggccgttatg aaananaaan    360
gaaacctata ttcctnc                                                  377
```

<210> SEQ ID NO 313
<211> LENGTH: 387
<212> TYPE: DNA
<213> ORGANISM: mammalian

<400> SEQUENCE: 313

```
agcggataac aatttcacac aggaatggtc gtctcggaga tgcagccaag aaagccatca    60
gtaaattgac aaccaggaca gtaaagaagg gtgacaagga aactgaccca gactttgatc   120
attgtgcagt ctgcatagag agctataagc agaatgatgt cgtccgaatt ctcccctgca   180
agcatgtttt ccacaaatcc tgcgtggatc cctggcttag tgaacattgt acctgtccta   240
tgtgcaaact taatatattg aaggccctgg gaattgtgcc gaatttgcca tgtactgata   300
acgtagcatt cgatatggaa gggctcacca gaacccaagc tgttaacccg aagatcagcc   360
ctcggcgacc tcgccggcga caactcc                                       387
```

<210> SEQ ID NO 314
<211> LENGTH: 289
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 314

```
gacaaaagga ccgnaggccc aagggcaata ataaggtgga atttgcaggt cagcccagga    60
attggcagag gaagtaggtg tctgataacc cttttgtggag aatgagattc cccccacctg   120
tgtgagaaaa ataaacagct ctggagtctt gttcctgact ccagaggaac gagagcattc   180
caggaaagag agattccctg gaaaattgaa aatgtgaatc ctaggggaa attggggatt    240 gtgtctttcc ctgttgaaaa tgtttggatg ggaataaata tcttcagga              289
```

<210> SEQ ID NO 315
<211> LENGTH: 389
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 315

```
tactggaata ttctaaaact cttgttcaca tgctattatg acttataaag cagcaacagc    60
tgaggcgcac caggacacag cttccatttc tttaacgtct gttcccttaa catcgctgaa   120
atgatttact gttgaagaga tgccttgcgg tgtggccagc tgtgaggaga aagcagcttg   180
cagtgttagg acattagtcc accttcagct gcagggtctc tggccgggtc tgactcagaa   240
accttggtac tcgccccttg gccacagtgc ccagacccat gtaacccact ggctcctgca   300
ttaacccaga ataccctcgc ttctatctgt gcactttagc ttgngaactt acccactgna   360
ntccctanat aaagcgntta tnaacagga                                     389
```

<210> SEQ ID NO 316
<211> LENGTH: 439
<212> TYPE: DNA
<213> ORGANISM: mammalian

```
<220> FEATURE:
<221> NAME/KEY: misc_feature
<222> LOCATION: ()..()
<223> OTHER INFORMATION: "n" is an unknown nucleotide

<400> SEQUENCE: 316
gctcccacgg ttgntntctg gaggnctcct aaacaccatt attcttcttc acgcttctca      60
nagccctaag gaagagagtg attcctcagc tcaattgtga actgctcctg ccactntgcc     120
ttcctcgtgn aaaaaaacca gactttacat catgggtgac cactcccgca gagttgtaca     180
gaacctccct tggggccaca ggatggctgg attctgtccc ctcatataca aggaggttat     240
tgggacagca tttctcccta gaacaagagt gtatatttca gaaagctatg gatgacttnc     300
catggtcatc agatcactta ggcangaatg ctattctcct gatagatgtg tggaanggat     360
tcaattcatt ttgaccccaa gntctaggcn ctggattaaa aatgccaacc ccaaacgtta     420
acttttaata aaaaaaaa                                                  439

<210> SEQ ID NO 317
<211> LENGTH: 354
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 317
tggtgggctt tccctcatg tcattggagg catctttggg aagaacaacg ccagcccctt       60
tgatgcaccc tgtcgcacca agaacatcgc ccgggagatt ccaccccagc cctggtacaa     120
gtctacntgt catccacatg actgttggag gcttcctgcc tttcaggtat cctcccttta     180
ttccatggct attactgtca ggttcctgac ctcaattttt cctgtcccta ctcatccagt     240
accctaaccc aacccgttga tccctggttc agtggtacca ttcagagatc attaaatggt     300
tcctcctatc cccaagcagg actgagcttg aatgatatga gagtgtctac ttat          354

<210> SEQ ID NO 318
<211> LENGTH: 393
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 318
gntgnnnttn nnnttttttg tagcacggtt aacgtcctta aaacccgccg gactttctgt      60
aagaagtgtg gcaagcacca accccataaa gtgacacagt acaagaaggg caaggattct    120
ctgtacgccc agggaaagcg gcgttatgac aggaagcana gtggctatgg tgggcaaact    180
aagccgattt tccggaaaaa ggctaaaact acaaanaaga ttgtgctaag gcttgagtgc    240
tgttgagccc aactgcagat ctaagagaat gctggctatt aaaagatgca agcattttga    300
actgggagga gataagaaga gaaagggcca agtgatccag ttctaagtgt catcttttat    360
tatgaagaca ataaaatctt gagtttatgt tcg                                 393

<210> SEQ ID NO 319
<211> LENGTH: 991
<212> TYPE: DNA
<213> ORGANISM: mammalian

<400> SEQUENCE: 319
```

```
ctggattccc gtcgtaactt aaagggaaat tttcacaatg tccggagccc ttgatgtcct    60
gcaaatgaag gaggaggatg tccttaagtt ccttgcagca ggaacccact taggtggcac   120
caatcttgac ttccagatgg aacagtacat ctataaaagg aaaagtgatg gcatctatat   180
cataaatctc aagaggacct gggagaagct tctgctggca gctcgtgcaa ttgttgccat   240
tgaaaaccct gctgatgtca gtgttatatc ctccaggaat actggccaga gggctgtgct   300
gaagtttgct gctgccactg gagccactcc aattgctggc cgcttcactc ctggaacctt   360
cactaaccag atccaggcag ccttccggga gccacggctt cttgtggtta ctgaccccag   420
ggctgaccac cagcctctca cggaggcatc ttatgttaac ctacctacca ttgcgctgtg   480
taacacagat tctcctctgc gctatgtgga cattgccatc ccatgcaaca acaagggagc   540
tcactcagtg ggtttgatgt ggtggatgct ggctcgggaa gttctgcgca tgcgtggcac   600
catttcccgt gaacacccat gggaggtcat gcctgatctg tacttctaca gagatcctga   660
agagattgaa aaagaagagc aggctgctgc tgagaaggca gtgaccaagg aggaatttca   720
gggtgaatgg actgctcccg ctcctgagtt cactgctact cagcctgagg ttgcagactg   780
gtctgaaggt gtacaggtgc cctctgtgcc tattcagcaa ttccctactg aagactggag   840
cgctcagcct gccacggaag actggtctgc agctcccact gctcaggcca ctgaatgggt   900
aggagcaacc actgactggt cttaagctgt tcttgcatag gctcttaagc agcatggaaa   960
aatggttgat ggaaaataaa catcagtttc t                                  991

<210> SEQ ID NO 320
<211> LENGTH: 810
<212> TYPE: DNA
<213> ORGANISM: mammalian

<400> SEQUENCE: 320
gctgcaccgc gctcgctccg agtttcaggc tcgtgctaag ctagcgccgt cgtcgtctcc    60
cttcagtcgc catcatgatt atctaccggg acctcatcag ccacgatgag atgttctccg   120
acatctacaa gatccgggag atcgcggacg ggttgtgcct ggaggtggag gggaagatgg   180
tcagtaggac agaaggtaac attgatgact cgctcattgg tggaaatgcc tccgctgaag   240
gccccgaggg cgaaggtacc gaaagcacag taatcactgg tgtcgatatt gtcatgaacc   300
atcacctgca ggaaacaagt ttcacaaaag aagcctacaa gaagtacatc aaagattaca   360
tgaaatcaat caagggaaa cttgaagaac agagaccaga aagagtaaaa ccttttatga   420 cagggctgc agaacaaatc aagcacatcc ttgctaattt caaaaactac cagttctta   480 ttggtgaaaa catgaatcca gatggcatgg ttgctctatt ggactaccgt gaggatggtg   540
tgaccccata tatgattttc tttaaggatg gtttagaaat ggaaaatgt aacaaatgt   600 ggcaattatt ttggatctat cacctgtcat cataactggc ttctgcttgt catccacaca   660
acaccaggac ttaagacaaa tgggactgat gtcatcttga gctcttcatt tattttgact   720
gtgatttatt tggagtggag gcattgtttt taagaaaaac atgtcatgta ggttgtctaa   780
aaataaaatg catttaaact catttgagag                                   810

<210> SEQ ID NO 321
<211> LENGTH: 280
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide
```

<400> SEQUENCE: 321

```
gactcactat agggcttttt tttttttnggn ggcaatcaca gtctttaatc attaatngtc     60
atatttctga ttngttagca agtgccagct ttgtaggctg gttgaagtac agaactcaga    120
ggaanaaaaa aataaaattt tagcttttnt ggganagnag cccnttttg ggacnataa     180 aacactttt tggtttcctt tnaacttgga aactttttaa aacattangg gggtnggga     240 ggggttgggc nattttttta atntnggggn canggngagn                          280
```

<210> SEQ ID NO 322
<211> LENGTH: 373
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 322

```
gcggataaca atttcacaca ggatcgatac aggactgttc tggggccagc ttcccttaac     60
tctgtagcct ggcagtctga cccaaagttg ccctcaccca aaggtctgg ctcttccctc    120 cctcantttt actttcccttt cccccataag ttggaggata aatgggtat caatgctaat    180 atttccaggg agaacatgaa accagaggtt tctttcttc tctgtaatct gctatgaaag    240 aaataacaa atgaaaataa atgtgtacta cactttgaaa tattttaact aaagccttta    300
ttctatacaa ctgtgaaata cagattttac ccttttggca ttgcgaaaaa aaaaaaagcc    360
ctatagnggt cgt                                                       373
```

<210> SEQ ID NO 323
<211> LENGTH: 400
<212> TYPE: DNA
<213> ORGANISM: mammalian

<400> SEQUENCE: 323

```
attagcggat aacaatttca cacaggatcg atacaggatg cttgccaaaa gaggtggata     60
tgtctgggtt gaaactcaag caactgtcat atataacacc aagaattctc aaccacagtg    120
cattgtatgt gtgaattacg ttgtgagtgg tattattcag cacgacttga ttttctccct    180
tcaacaaaca gaatgtgtcc ttaaaccggt tgaatcttca gatatgaaaa tgactcagct    240
attcaccaaa gttgaatcag aagatacaag taagcctctt tgacaaactt aagaaggaac    300
ctgatgcttt aactttgctg gccccagccg ctggagacac aatcatatct ttagattttg    360
gcagcaacga cacagaaact gatgaccaca cttgaggaag                          400
```

<210> SEQ ID NO 324
<211> LENGTH: 405
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 324

```
gatttaatac gactcactat agggcttttt tttttttcgg ancaatgaat ttttaatttt     60
ctcancacaa aaananata atngaggnga taaatgngct aattncactg attngatcat    120
tatncatcat atncntatat ttaaatatca cacttgtncc ccataaatat gtncaacact    180
tacgtgtcat ttaaaaataa ngataaaatt atatcaagat tcaagcgcct ntngtagcgg    240
```

```
cttcccacag tcttcacatt ngganggatt ttctccactg nggtttttt gttggtcttt      300 acggtatgac cggtatacaa gcttctttcc caatcctcac atttgaatgg ttttttcgga     360
atggagtctn tatgattcaa aaacttgagg ccggctaaag ctttt                     405
```

<210> SEQ ID NO 325
<211> LENGTH: 391
<212> TYPE: DNA
<213> ORGANISM: mammalian

<400> SEQUENCE: 325

```
cgctccagcc cagccctcag cctggcatgc cccctggatc aggccattgg cctcctcgtg      60
gccatcttcc caagtactcc ggcagggagg gtgacaagca caccctgagc aagaaggagc     120
tgaaggagct gatccagaag gagctcacca ttggctcgaa gctgcaggat gctgaaattg     180
caaggctgat ggaagacttg gaccggaaca aggaccagga ggtgaacttc caggagtatg     240
tcaccttcct gggggccttg gctttgatct acaatgaagc cctcaaggc ttgaaaataa      300 atagggaaga tggagacacc ctctgggggt cctctctgag tcaaatccag tggtgggtaa     360
ttgtacaata aatttttttt ggtcaaattt a                                   391
```

<210> SEQ ID NO 326
<211> LENGTH: 300
<212> TYPE: DNA
<213> ORGANISM: mammalian

<400> SEQUENCE: 326

```
catgttggca gaaaattgaa catgactcca gaagaagctg aaaggtggat tgtaaatttg      60
attagaaatg caagactgga tgccaagatt gattctaaat taggtcatgt ggttatgggt     120
aacaatgcag tctcacccta tcattwaagt gattgaaaag accaaaagcc tttcctttag     180
aagccagatg ttggccatga atattgagaa gaaacttaat cagaatagca ggtcagaggc     240
tcctaacttg ggcaactcaa gattctggct tctactgaag aaccayaaag aaaagatgaa     300
```

<210> SEQ ID NO 327
<211> LENGTH: 372
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 327

```
aatacgactc actatagggc ttttttttt ttaagttgta atctttgccg ttgtcactga      60
ncctcaaaag caattgtttt cccaaatcat tttaagccct ccccagtcaa tcttttccct    120
ctcatcanta acttacaagg accctatttg aaaaacaacg cttattcatt ccttttctta   180
taccccacac attccgttct aggaaatngg caaccaccca acacagcccg ggttctccct    240
ccttganatg tgaatttaaa caaanggatt ttcgtctccn ttcttcaagc ttanaggatg    300
ancacgcgtt tactacaacg cttaattcct tctagcagca tttctcttct ataactactt    360
gcnctgcttt tt                                                        372
```

<210> SEQ ID NO 328
<211> LENGTH: 408
<212> TYPE: DNA
<213> ORGANISM: mammalian
<220> FEATURE:
<221> NAME/KEY: misc_feature

```
<222> LOCATION: ()..()
<223> OTHER INFORMATION: "n" is an unknown nucleotide

<400> SEQUENCE: 328
tgattagcgg ataacaattt cacacaggat ccatgactcc acctccatca tcacctcaac      60
ccaaaaaggc ataattaaac tttacttcct ctctttcttc ttcccactca tcctaaccct     120
actcctaatc acataaccta ttcccccgag caatctcaat tacaatatat acaccaacaa     180
acaatgttca accagtaact actactaatc aacgcccata atcatacaaa gccccgcac      240 caataggatc ctcccgaatc aaccctgacc cctctccttc ataaattatt cagcttccta     300
cactattaaa gtttaccaca accaccaccc catcatactc tttcacccac agcaccaatc     360
ctaccttcat cgntacccca ctaaaacact cccaagactt aacccctg                  408

<210> SEQ ID NO 329
<211> LENGTH: 426
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 329
agcggataac aatttcacac aggacgactc caagtgagaa agatggaaaa atattttgtt      60
tctgatgcta gtccatacac tttccaagtc ccacaaaact ttcacaaaaa tgtatataag     120
ctaaatatta gaaacnggat aacaaacntt gttttattta tagatgtaaa aaccaaacaa     180
gtcaatatga aagcttttaa tctcttaata ccattaagct ttccagtaag agcatcacat     240
aatgctctac tgttccagaa accaaatagt aaaaaaaaaa aagccctata gngagtcgta     300
ttaaatcgaa tttccccgcg gccgccatgg cggccggnag catgcnacgt cggnccccaat    360 tcncccctata gtgagtcgta ttacaattca ctggccgtcg ttttacaacg tcgtgctgga    420 aacccn                                                                426

<210> SEQ ID NO 330
<211> LENGTH: 282
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 330
ttcctgtcat tccattccaa aaattatgtg gaagtggata ggagaactgc agctgtcaat      60
agcctagggc tgaattttg tcanataaat aaaataaatc attcatcctt ttttttgatt     120
ataaaatttt ctaaaatgta ttttagactt cctgtagggg gcgatatact aaatgtatat     180
agtacattta tactaaatgt attcctgtag ggggctgata tactaaatgt attttanact     240
tcctgtaggg ggcgataaaa taaaatgcta aacaactggg ta                        282

<210> SEQ ID NO 331
<211> LENGTH: 1008
<212> TYPE: DNA
<213> ORGANISM: mammalian

<400> SEQUENCE: 331
atgtccacag aaggaggatt tggtggtact agcagcagtg atgcccagca aagcctacag      60
tcgttctggc ctcgggtcat ggaagaaatc cggaatttaa cagtgaaaga cttccgagtg    120
```

-continued

```
caggaactcc cactggctcg tattaagaag attatgaaac tggatgaaga tgtgaagatg      180
atcagtgcag aagcgcctgt actctttgcc aaggcagccc agattttat cacagagttg       240 actcttcgag cctggattca cacagaaaat aacaagcgcc ggactctaca gagaaatgat      300
atcgccatgg caattacaaa atttgatcag tttgattttc tcatcgatat tgttccaaga      360
gatgaactga aacctccaaa gcgtcaggag gaggtgcgcc agtctgtaac tcctgccgag      420
ccagtccagt actatttcac gctggctcag caacccaccg ctgtccaagt ccatggacag      480
cagcaaggcc agcaaacaac cagctccacg aacaccatcc agcctgggca gatcttcatc      540
gcacagcctc agcagggcca gaccacacct gtgacaatgc aagttggaga aagtcagcag      600
gtgcagattg tccaggctca gccacagggt caagcccaac aggcccataa tggcactgga      660
caaaccatgc aggtgatgca gcagatcatc actaacacag agagatcca gcagatcccg       720 gtgcagctga atgccggcca gctgcagtat atccgcttag cccagcctgt atcaggcact      780
caagttgtgc aggacagat ccagacactt gccaccaatg ctcaacgat tacacagaca        840 gaggtccagc aaggacagca gcagttcagc cagttcacag atggacagca gctctaccag      900
atccagcaag tcaccatgcc tgcgggccag gacctcgccc agcccatgtt catccagtca      960
gccaaccagc cctccgacgg caaggccccc caggtgaccg gcgactga                  1008
```

<210> SEQ ID NO 332
<211> LENGTH: 298
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 332

```
agtgatttaa tacgactcac tatagggctt ttttttttta gggttnggct ttttattgac       60
acaaacacac aaaggcagct gnggtaatgg ggnggnggg tacacaaaag canaaatcgc       120
acttcacaca tttaggcctc atttanacaa tgaggaggct gagcctgtcc ctccacctcc      180
cattgcaang gttgggcaa tanccctccc taatcctagc tcagngagta nagggagtga      240
cctccctacc caggaagtcc ccattttggt tgcaanggnc tcctgtgtga aattgtta       298
```

<210> SEQ ID NO 333
<211> LENGTH: 286
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 333

```
cccgggcatc agccccgagg aatgcgcctc tcggaagtgc tgcttctcca acttcatctt       60
tgaagtgccc tggtgcttct tcccgaagtc tgtggaagac tgccattact aagagaggct      120
ggttccagag gatgcatctg gctcaccggg tgttccgaac caaagaagaa acttcgcntt      180
atnagcttca tatttcatga aatcctgggt tttcttaacc atcttttcct cattttcaat      240
ggtttaacat ataatttctt taaataaaac tcttaaaatc tgctaa                   286
```

<210> SEQ ID NO 334
<211> LENGTH: 442
<212> TYPE: DNA
<213> ORGANISM: mammalian

```
<220> FEATURE:
<221> NAME/KEY: misc_feature
<222> LOCATION: ()..()
<223> OTHER INFORMATION: "n" is an unknown nucleotide

<400> SEQUENCE: 334
ggtccaaggt ggattcaaac gaactgtggc tgcaccatct gtcttcatct tcccgccatc      60
tgatgagcag ttgaaatctg gaactgcctc tgttgtgtgc ctgctgaata acttctatcc     120
cagagaggcc aaagtacagt ggaaggtgga taacgccctc caatcgggta actcccagga     180
gagtgtcaca gagcaggaca gcaaggacag cacctacagc ctcagcagca ccctgacgct     240
tgagcaaagc agactacgag aaacacaaag tctacgcctg cgaagtcacc catcagggcc     300
tgagctcgcc cgtcacaaag agcttcaaca ggggagagtg ttagagggag aagtgccccc     360
acctgctcct cagttccagc ctgacccct nccatccttt ggcctctgac ccttttcca      420 caggggacct accctattg cg                                              442

<210> SEQ ID NO 335
<211> LENGTH: 353
<212> TYPE: DNA
<213> ORGANISM: mammalian
<220> FEATURE:
<221> NAME/KEY: misc_feature
<222> LOCATION: ()..()
<223> OTHER INFORMATION: "n" is an unknown nucleotide

<400> SEQUENCE: 335
gagcnggcgc agtgattata ggctttcgct ctaagattaa aaatgcccta gcccacttct      60
taccacaagg cacacctaca cccttatcc ccatactagt tattatcgaa accatcagcc     120
tactcattca accatagcc ctggccgtac gcctaaccgc taacattact gcaggccacc     180
tactcatgca cctaattgga agcgcaccct agcaatatca accattaacc ttccctctac     240
acttatcatc ttcacaattc tgattctact gactatccta gaaatcgctg tcgcttaatc     300
caagcctacg ttttcacact tctagtaagc ctctacctgc acgacaacac ata            353

<210> SEQ ID NO 336
<211> LENGTH: 396
<212> TYPE: DNA
<213> ORGANISM: mammalian

<400> SEQUENCE: 336
cttcggtttt agtcattcct atctcaatct taatggtgat tcttctctgt tgaactgaag      60
tttgtgagag tagttttcct ttgctacttg aatagcaata aaagcgtgtt aactttttga     120
ttgatgaaag aagtacaaaa agcctttagc cttgaggtgc cttctgaaat taaccaaatt     180
tcatccatat atcctctttt ataaacttat agaatgtcaa actttgcctt caactgtttt     240
tatttctagt ctcttccact ttaaaacaaa atgaacactg cttgtcttct tccattgacc     300
atttagtgtt gagtactgta tgtgtttgt taattctata aaggtatctg ttagatatta     360
aaggtgagaa ttagggcagg ttaatcaaaa aaaaaa                              396

<210> SEQ ID NO 337
<211> LENGTH: 279
<212> TYPE: DNA
<213> ORGANISM: mammalian

<400> SEQUENCE: 337
gtattgaaca aaagacggaa ggtgctgaga aaaacagca gatgggctcg agaatacaga      60
gagaaaattg agacggagct aagagatatc tcgcaatgat gtactgtctc ttttggaaaa     120
```

```
gttcttgatc cccaatgctt cacaagcaga gagcaaagtc ttctatttga aaatgaaagg      180
agattctacc gttacttggc tgaggttgcc gctggtgatg acaagaaagg gattgtcgat      240
cagtcacaac aagcatacca agaagctttt gaaatcagc                            279

<210> SEQ ID NO 338
<211> LENGTH: 749
<212> TYPE: DNA
<213> ORGANISM: mammalian

<400> SEQUENCE: 338
agccaacaga gattgttgat ttgcctctta agcaagagat tcattgcagc tcagcatggc       60
tcagaccagc tcatacttca tgctgatctc ctgcctgatg tttctgtctc agagccaagg      120
ccaagaggcc cagacagagt tgccccaggc ccggatcagc tgcccagaag gcaccaatgc      180
ctatcgctcc tactgctact actttaatga agaccgtgag acctgggttg atgcagatct      240
ctattgccag aacatgaatt cgggcaacct ggtgtctgtg ctcacccagg ccgagggtgc      300
ctttgtggcc tcactgatta aggagagtgg cactgatgac ttcaatgtct ggattggcct      360
ccatgacccc aaaaagaacc gccgctggca ctggagcagt gggtccctgg tctcctacaa      420
gtcctggggc attggagccc caagcagtgt taatcctggc tactgtgtga gcctgacctc      480
aagcacagga ttccagaaat ggaaggatgt gccttgtgaa gacaagttct cctttgtctg      540
caagttcaaa aactagaggc agctggaaaa tacatgtcta gaactgatcc agcaattaca      600
acggagtcaa aaattaaacc ggaccatctc tccaactcaa ctcaacctgg acactctctt      660
ctctgctgag tttgccttgt taatcttcaa tagtttttacc taccccagtc tttggaacct      720
taaataataa aaataaacat gtttccact                                       749
```

NUCLEIC ACID MARKERS FOR USE IN DETERMINING PREDISPOSITION TO NEOPLASM AND/OR ADENOMA

CROSS-REFERENCE TO RELATED APPLICATIONS

This application is a continuation application based on PCT Patent Application No. PCT/AU02/01258, filed Sep. 13, 2002, which claims priority to U.S. provisional application 60/322,288, filed Sep. 14, 2001, which is incorporated herein in its entirety.

FIELD OF THE INVENTION

The present invention relates generally to novel nucleic acid molecules, the levels and/or patterns of expression of which are indicative of the onset, predisposition to the onset and/or progression of a neoplasm and to derivatives, homologues or analogues of said molecules. More particularly, the present invention is directed to novel nucleic acid molecules, the levels of expression of which are indicative of the onset and/or progression of a gastrointestinal tract neoplasm, such as an adenoma, and to derivatives, homologues or analogues of said molecules. The present invention is further directed to isolated proteins encoded thereby and to derivatives, homologues, analogues, chemical equivalents and mimetics thereof. The molecules of the present invention are useful in a range of prophylactic, therapeutic and/or diagnostic applications including, but not limited to, those relating to the diagnosis and/or treatment of colorectal neoplasms such as colorectal adenomas. In a related aspect, the present invention is directed to a method of screening a subject for the onset, predisposition to the onset and/or progression of a neoplasm by screening for modulation in the level of expression of one or more nucleic acid molecule markers.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Adenomas are benign tumours of epithelial origin which are derived from glandular tissue or exhibit clearly defined glandular structures. Some adenomas show recognisable tissue elements, such as fibrous tissue (fibroadenomas), while others, such as bronchial adenomas, produce active compounds giving rise to clinical syndromes. Tumours in certain organs, including the pituitary gland, are often classified by their histological staining affinities, for example eosinophil, basophil and chromophobe adenomas.

Adenomas may become carcinogenic and are then termed adenocarcinomas. Accordingly, adenocarcinomas are defined as malignant epithelial tumours arising from glandular structures, which are constituent parts of most organs of the body. This term is also applied to tumours showing a glandular growth pattern. These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both muconous and cystadenocarcinoma. In general, the overall incidence of carcinoma within an adenoma is approximately 5%. However, this is related to size and although it is rare in adenomas of less than 1 centimeter, it is estimated at 40 to 50% villous lesions which are greater than 4 centimeters. Adenomas with higher degrees of dysplasia have a higher incidence of carcinoma. Once a sporadic adenoma has developed, the chance of a new adenoma occurring is approximately 30% within 26 months.

Colorectal adenomas represent a class of adenomas which are exhibiting an increasing incidence, particularly in more affluent countries. The causes of adenoma, and its shift to adenocarcinoma, are still the subject of intensive research. To date it has been speculated that in addition to genetic predisposition, environmental factors (such as diet) play a role in the development of this condition. Most studies indicate that the relevant environmental factors relate to high dietary fat, low fibre and high refined carbohydrates.

Colonic adenomas are localised proliferations of dysplastic epithelium which are initially flat, but with increased growth from the mucosal forming adenomas. They are classified by their gross appearance as either sessile (flat) or penduculated (having a stalk). While small adenomas (less than 0.5 millimeters) exhibit a smooth tan surface, penduculated adenomas have a head with a cobblestone or lobulated red-brown surface. Sessile adenomas exhibit a more delicate villous surface. Penduculated adenomas are more likely to be tubular or tubulovillous while sessile lesions are more likely to be villous. Sessile adenomas are most common in the cecum and rectum while overall penduculated adenomas are equally split between the sigmoid-rectum and the remainder of the colon.

The etiology of adenoma of the colon, and in particular the dysplasia-adenoma-carcinoma sequence is thought to occur in the setting of increasing loss of heterozygosity in genes involved in DNA replication accuracy, tumour suppression and oncogene activation. A hereditary predisposition to cancer is found in 1% of colorectal carcinoma patients and in 5-10% of patients with Hereditary Non-Adenomatosis Polyposis. It is thought that for each lesion the loss of heterozygosity must occur in multiple genes. Currently there are a number of mechanisms proposed to account for the known environment, dietary and genetic predispositions to colorectal cancer. Although no consensus has yet been reached, loss of heterozygosity appears to be a common feature.

Adenomas are generally asymptomatic, therefore rendering difficult their early diagnosis and treatment. It is technically impossible to predict the presence or absence of carcinoma based on the gross appearance of adenomas, although larger adenomas are thought to exhibit a higher incidence of concurrent malignancy than smaller adenomas. Sessile adenomas exhibit a higher incidence of malignancy than penduculated adenomas of the same size. Some adenomas result in the production of microscopic stool blood loss. However, since stool blood can also be indicative of non-adenomatous conditions and obstructive symptoms are generally not observed in the absence of malignant change, the accurate diagnosis of adenoma is rendered difficult without the application of highly invasive procedures such as biopsy analysis. Accordingly, there is an on-going need to elucidate not only the causes of adenoma and its shift to malignancy but to develop more informative diagnostic protocols, in particular protocols which will enable the rapid, routine and accurate diagnosis of adenoma at an early stage, such as the pre-malignant stage.

To date, research has focused on the identification of gene mutations which lead to the development of adenoma. In work leading up to the present invention, however, the inventors have surprisingly determined that changes in the level of expression of unmutated genes which are also expressed in healthy individuals are indicative of adenoma development. The inventors have further determined that in relation to colorectal adenomas, diagnosis can be made based on screening for the expression of mRNA gene transcripts corresponding to any one or more of the panel of genes disclosed herein. In this regard, the inventors have still further determined that some of the genes identified herein as being expressed in healthy individuals at significantly lower levels than that observed in individuals who have developed an adenoma do not correlate with any known gene sequences. Accordingly, the inventors have identified a panel of genes which, in addition to facilitating the diagnosis of adenoma development, further facilitate the development of prophylactic and therapeutic protocols directed to modulation of their expression and functional activity and thereby the development of therapeutic and/or prophylactic protocols for treating patients at risk of or who have developed adenomas.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 3.0, presented herein after the bibliography. Each nucleotide sequence is identified in the sequence listing by the numeric indicator <201> followed by the sequence identifier (eg. <210>1, <210>2, etc). The length, type of sequence (DNA, etc) and source organism for each nucleotide sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

A summary of the sequences detailed in this specification is provided prior to the examples.

One aspect of the present invention provides a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 1-2, SEQ ID NOs: 4-6, SEQ ID NOs: 8-32, SEQ ID NOs: 35-37 or SEQ ID NO: 59 or a functional derivative, variant or homologue of said nucleic acid molecule; or
(ii) nucleic acid molecules comprising a nucleotide sequence capable of hybridising any one or more of the sequences of
   (i) under low stringency conditions at 42° C. or a functional derivative, variant or homologue of said nucleic acid molecule
in a biological sample from said individual wherein an increase in the level of expression of said nucleic acid molecule relative to the normal level of expression of said nucleic acid molecule in an individual is indicative of the onset or predisposition to the onset of a neoplasm.

In another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NO: 38, SEQ ID NOs: 40-43, SEQ ID NOs: 45-49, SEQ ID NOs: 58-60, SEQ ID NO: 62, SEQ ID NOs: 64-66, SEQ ID NOs: 68-72 or SEQ ID NOs: 337-338 or a functional derivative, variant or homologue of said nucleic acid molecule; or
(ii) nucleic acid molecules comprising a nucleotide sequence capable of hybridising any one or more of the sequences of
   (i) under low stringency conditions at 42° C. or a functional derivative, variant or homologue of said nucleic acid molecule
in a biological sample from said individual wherein an increase in the level of expression of said nucleic acid molecule relative to the normal level of expression of said nucleic acid molecule in an individual is indicative of the onset or predisposition to the onset of a neoplasm.

In yet another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 73-219 or a functional derivative, variant or homologue of said nucleic acid molecule; or
(ii) nucleic acid molecules comprising a nucleotide sequence capable of hybridising any one or more of the sequences of
   (i) under low stringency conditions at 42° C. or a functional derivative, variant or homologue of said nucleic acid molecule
in a biological sample from said individual wherein an increase in the level of expression of said nucleic acid molecule relative to the normal level of expression of said nucleic acid molecule in an individual is indicative of the onset or predisposition to the onset of a neoplasm.

In still another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 220-336 or a functional derivative, variant or homologue of said nucleic acid molecule; or
(ii) nucleic acid molecules comprising a nucleotide sequence capable of hybridising any one or more of the sequences of
   (i) under low stringency conditions at 42° C. or a functional derivative, variant or homologue of said nucleic acid molecule
in a biological sample from said individual wherein an increase in the level of expression of said nucleic acid molecule relative to the normal level of expression of said nucleic acid molecule in an individual is indicative of the onset or predisposition to the onset of a neoplasm.

Another aspect of the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NOs: 1-2, SEQ ID NOs: 4-6, SEQ ID NOs: 8-32, SEQ ID NOs: 35-37 or SEQ ID NO: 59 or a functional derivative, variant or homologue of said nucleic acid molecule; or
(ii) nucleic acid molecules comprising a nucleotide sequence capable of hybridising any two or more of the sequences of
   (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In another aspect, the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NO: 38, SEQ ID NOs: 40-43, SEQ ID NOs: 45-49, SEQ ID NOs: 51-56, SEQ ID NOs: 58-60, SEQ ID NO: 62, SEQ ID NOs: 64-66, SEQ ID NOs: 68-72 or SEQ ID NOs: 337-338 or a functional derivative, variant or homologue of said nucleic acid molecule; or
(ii) nucleic acid molecules comprising a nucleotide sequence capable of hybridising any two or more of the sequences of
   (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In yet another aspect the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NOs: 73-219 or a functional derivative, variant or homologue of said nucleic acid molecule; or
(ii) nucleic acid molecules comprising a nucleotide sequence capable of hybridising any two or more of the sequences of
   (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In still another aspect the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NOs: 220-336 or a functional derivative, variant or homologue of said nucleic acid molecule; or
(ii) nucleic acid molecules comprising a nucleotide sequence capable of hybridising any two or more of the sequences of
   (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In a preferred embodiment, the present invention provides a method for determining the onset or predisposition to the onset of a neoplasm in an individual, said method comprising detecting the co-expression of any three:
(i) nucleic acid molecules comprising a nucleotide sequence substantially as set forth in any one of SEQ ID NO: 7, SEQ ID NO: 14, SEQ ID NO: 16, SEQ ID NO: 24, SEQ ID NO: 65, SEQ ID NO: 19, SEQ ID NO: 1, SEQ ID NO: 53, SEQ ID NO: 72, SEQ ID NO: 11 or SEQ ID NO: 26 or a functional derivative, variant or homologue of said nucleic acid molecule; or
(ii) nucleic acid molecules comprising a nucleotide sequence capable of hybridising any three of the sequences of (i) under low stringency conditions at 42° C. or a functional derivative, variant or homologue of said nucleic acid molecule,
in one or more biological samples from said individual wherein the co-expression of said nucleic acid molecules is indicative of the onset or predisposition to the onset of a neoplasm.

In another preferred embodiment the present invention provides a method for determining the onset or the predisposition to the onset of a neoplasm in an individual, said method comprising detecting the co-expression of any four:
(i) nucleic acid molecules comprising a nucleotide sequence substantially as set forth in any one of SEQ ID NOs: 4-6, SEQ ID NO: 9, SEQ ID NO: 13, SEQ ID NO: 15, SEQ ID NOs: 21-22, SEQ ID NOs: 27-29, SEQ ID NOs: 30-31, SEQ ID NO: 36, SEQ ID NOs: 37-38, SEQ ID NO: 40, SEQ ID NO: 43, SEQ ID NOs: 48-49, SEQ ID NO: 52, SEQ ID NO: 56, SEQ ID NO: 59, SEQ ID NO: 64, SEQ ID NOs: 68-69, SEQ ID NO: 71 or SEQ ID NO: 337 or a functional derivative, variant or homologue of said nucleic acid molecule; or
(ii) nucleic acid molecules comprising a nucleotide sequence capable of hybridising any two or more of the sequences of
   (i) under low stringency conditions at 42° C. or a functional derivative, variant or homologue of said nucleic acid molecule,
in one or more biological samples from said individual wherein the co-expression of said nucleic acid molecules is indicative of the onset or predisposition to the onset of a neoplasm.

Another aspect of the present invention provides a method of monitoring for the onset or progression of a neoplasm in an individual, said method comprising measuring the level of expression of one or more adenoma markers and/or adenoma markers, as hereinbefore defined, in a biological sample from said individual wherein the level of said adenoma marker and/or adenoma marker relative to the normal level of said adenoma marker and/or adenoma marker is indicative of the onset of progression of a neoplasm.

In yet another aspect there is provided a method of monitoring for the onset or progression of a neoplasm in an individual, said method comprising detecting the co-expression of any two or more adenoma markers and/or adenoma markers, as hereinbefore defined, in a biological sample from said individual wherein the expression profile of said adenoma markers and/or adenoma markers relative to normal expression profiles is indicative of the onset or progression of a neoplasm.

Another aspect of the present invention provides a method of classifying an adenoma, said method comprising identifying the expression pattern of one or more adenoma markers and/or adenoma markers and/or the expression levels of one or more adenoma markers and/or adenoma markers of said adenoma and correlating said adenoma marker expression results with the morphological and/or phenotypic features of said adenoma.

The present invention should also be understood to extend to the determination of an adenoma's classification status based on the known expression levels and/or expression profiles of the adenoma markers and/or adenoma markers expressed by said adenoma, and as previously identified above.

Another aspect of the present invention provides a diagnostic kit for assaying biological samples comprising an agent for detecting one or more adenoma markers and/or adenoma markers and reagents useful for facilitating the detection by said agent.

A related aspect of the present invention contemplates an isolated nucleic acid molecule or derivative, homologue or analogue thereof comprising a nucleotide sequence substantially as set forth in any one or more of SEQ ID NO: 1 or SEQ ID NO: 6 or SEQ ID NOs: 8-10 or derivative or homologue thereof, or capable of hybridising to any one or more of SEQ ID NO: 1 or SEQ ID NO: 6 or SEQ ID NOs: 8-10 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NO: 4 or SEQ ID NO: 5 or derivative or homologue thereof, or capable of hybridising to any one or more of SEQ ID NO: 4 or SEQ ID NO: 5 under low stringency conditions at 42° C.

Still yet another aspect of the present invention contemplates an isolated nucleic acid molecule or derivative, homologue or analogue thereof comprising a nucleotide sequence substantially as set forth in any one or more of SEQ ID NO: 7 or derivative or homologue thereof, or capable of hybridising to any one or more of SEQ ID NO: 7 under low stringency conditions at 42° C.

Yet still another aspect of the present invention contemplates an isolated nucleic acid molecule or derivative, homologue or analogue thereof comprising a nucleotide sequence substantially as set forth in any one or more of SEQ ID NOs: 11-13 or SEQ ID NOs: 15-16 or derivative or homologue thereof, or capable of hybridising to any one or more of SEQ ID NOs: 11-13 or SEQ ID NOs: 15-16 under low stringency conditions at 42° C.

A further aspect of the present invention contemplates an isolated nucleic acid molecule or derivative, homologue or analogue thereof comprising a nucleotide sequence substantially as set forth in any one or more of SEQ ID NO: 14 or derivative or homologue thereof, or capable of hybridising to any one or more of SEQ ID NO: 14 under low stringency conditions at 42° C.

Another further aspect of the present invention contemplates an isolated nucleic acid molecule or derivative, homologue or analogue thereof comprising a nucleotide sequence substantially as set forth in any one or more of SEQ ID NOs: 17-19 or SEQ ID NOs: 22-23 or derivative or homologue thereof, or capable of hybridising to any one or more of SEQ ID NOs: 17-19 or SEQ ID NOs: 22-23 under low stringency conditions at 42° C.

Yet another further aspect of the present invention contemplates an isolated nucleic acid molecule or derivative, homologue or analogue thereof comprising a nucleotide sequence substantially as set forth in any one or more of SEQ ID NO: 20 or derivative or homologue thereof, or capable of hybridising to any one or more of SEQ ID NO: 20 under low stringency conditions at 42° C.

Still yet another further aspect of the present invention contemplates an isolated nucleic acid molecule or derivative, homologue or analogue thereof comprising a nucleotide sequence substantially as set forth in any one or more of SEQ ID NO: 21 or derivative or homologue thereof, or capable of hybridising to any one or more of SEQ ID NO: 21 under low stringency conditions at 42° C.

Yet still another further aspect of the present invention contemplates an isolated nucleic acid molecule or derivative, homologue or analogue thereof comprising a nucleotide sequence substantially as set forth in any one or more of SEQ ID NOs: 24-26, SEQ ID NO: 31 or SEQ ID NOs: 35-37 or derivative or homologue thereof, or capable of hybridising to any one or more of SEQ ID NOs: 24-26, SEQ ID NO: 31 or SEQ ID NOs: 35-37 under low stringency conditions at 42° C.

Another aspect of the present invention contemplates an isolated nucleic acid molecule or derivative, homologue or analogue thereof comprising a nucleotide sequence substantially as set forth in any one or more of SEQ ID NO: 27, SEQ ID NO: 28 or SEQ ID NO: 29 or derivative or homologue thereof, or capable of hybridising to any one or more of SEQ ID NO: 27, SEQ ID NO: 28 or SEQ ID NO: 29 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NO: 30 or derivative or homologue thereof, or capable of hybridising to any one or more of SEQ ID NO: 30 under low stringency conditions at 42° C.

Still another aspect of the present invention contemplates an isolated nucleic acid molecule or derivative, homologue or analogue thereof comprising a nucleotide sequence substantially as set forth in any one or more of SEQ ID NO: 59 or derivative or homologue thereof, or capable of hybridising to any one or more of SEQ ID NO: 59 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NOs: 73-145 or derivative or homologue thereof, or capable of hybridising to any one or more of SEQ ID NOs: 73-145 under low stringency conditions at 42° C.

A further aspect of the present invention contemplates an isolated nucleic acid molecule or derivative, homologue or analogue thereof comprising a nucleotide sequence substantially as set forth in any one or more of SEQ ID NOs: 146-219 or SEQ ID NO: 336 or derivative or homologue thereof, or capable of hybridising to any one or more of SEQ ID NOs: 146-219 or SEQ ID NO: 336 under low stringency conditions at 42° C.

Yet another aspect of the present invention is directed to an isolated protein selected from the list consisting of:

(i) a protein encoded by a nucleotide sequence or derivative, homologue or analogue thereof comprising a nucleotide sequence substantially as set forth in any one or more of SEQ ID NO: 1, SEQ ID NO: 6 or SEQ ID NOs: 8-10 or a derivative, homologue, analogue, chemical equivalent or mimetic or said protein.

(ii) a protein encoded by a nucleotide sequence or derivative, homologue or analogue thereof comprising a nucleotide sequence substantially as set forth in any one or more of SEQ ID NO: 4 or SEQ ID NO: 5 or a derivative, homologue, analogue, chemical equivalent or mimetic or said protein.

(iii) a protein encoded by a nucleotide sequence or derivative, homologue or analogue thereof comprising a nucleotide sequence substantially as set forth in SEQ ID NO: 7 or a derivative, homologue, analogue, chemical equivalent or mimetic or said protein.

(iv) a protein encoded by a nucleotide sequence or derivative, homologue or analogue thereof comprising a nucleotide sequence substantially as set forth in any one or more of SEQ ID NOs: 11-13 or SEQ ID NOs: 15-16 or a derivative, homologue, analogue, chemical equivalent or mimetic or said protein.

(v) a protein encoded by a nucleotide sequence or derivative, homologue or analogue thereof comprising a nucleotide sequence substantially as set forth in SEQ ID NO: 14 or a derivative, homologue, analogue, chemical equivalent or mimetic or said protein.

(vi) a protein encoded by a nucleotide sequence or derivative, homologue or analogue thereof comprising a nucleotide sequence substantially as set forth in any one or more of SEQ ID NOs: 17-19 or SEQ ID NOs: 22-23 or a derivative, homologue, analogue, chemical equivalent or mimetic or said protein.

(vii) a protein encoded by a nucleotide sequence or derivative, homologue or analogue thereof comprising a nucleotide sequence substantially as set forth in SEQ ID NO: 20 or a derivative, homologue, analogue, chemical equivalent or mimetic or said protein.

(viii) a protein encoded by a nucleotide sequence or derivative, homologue or analogue thereof comprising a nucleotide sequence substantially as set forth in SEQ ID NO: 21 or a derivative, homologue, analogue, chemical equivalent or mimetic or said protein.

(ix) a protein encoded by a nucleotide sequence or derivative, homologue or analogue thereof comprising a nucleotide sequence substantially as set forth in any one or more of SEQ ID NOs: 24-26, SEQ ID NO: 31 or SEQ ID NOs: 35-37 or a derivative, homologue, analogue, chemical equivalent or mimetic or said protein.

(x) a protein encoded by a nucleotide sequence or derivative, homologue or analogue thereof comprising a nucleotide sequence substantially as set forth in any one or more of SEQ ID NO: 27 or SEQ ID NO: 28 or SEQ ID NO: 29 or a derivative, homologue, analogue, chemical equivalent or mimetic or said protein.

(xi) a protein encoded by a nucleotide sequence or derivative, homologue or analogue thereof comprising a nucleotide sequence capable of hybridising to any one or more of the nucleotide sequences as set forth in SEQ ID NO: 30 or a derivative, homologue or analogue thereof under low stringency conditions or a derivative, homologue, analogue, chemical equivalent or mimetic of said protein.

(xii) a protein encoded by a nucleotide sequence or derivative, homologue or analogue thereof comprising a nucleotide sequence capable of hybridising to any one or more of the nucleotide sequences as set forth in SEQ ID NO: 59 or a derivative, homologue or analogue thereof under low stringency conditions or a derivative, homologue, analogue, chemical equivalent or mimetic of said protein.

(xiii) a protein encoded by a nucleotide sequence or derivative, homologue or analogue thereof comprising a nucleotide sequence capable of hybridising to any one or more of the nucleotide sequences as set forth in any one or more of SEQ ID NOs: 73-145 or a derivative, homologue or analogue thereof under low stringency conditions or a derivative, homologue, analogue, chemical equivalent or mimetic of said protein.

(xiv) a protein encoded by a nucleotide sequence or derivative, homologue or analogue thereof comprising a nucleotide sequence capable of hybridising to any one or more of the nucleotide sequences as set forth in any one or more of SEQ ID NOs: 146-219 or SEQ ID NO: 336 or a derivative, homologue or analogue thereof under low stringency conditions or a derivative, homologue, analogue, chemical equivalent or mimetic of said protein.

The present invention contemplates a method for the treatment and/or prophylaxis of a condition characterised by aberrant, unwanted or otherwise inappropriate cell growth in a subject, said method comprising administering to said subject an effective amount of an agent for a time and under conditions sufficient to modulate adenoma marker expression and/or adenoma marker functional activity.

Another aspect of the present invention contemplates the use of an agent as hereinbefore defined in the manufacture of a medicament for the treatment of a condition in a manual, which condition is characterised by the aberrant, unwanted or otherwise inappropriate cell growth wherein said agent modulates adenoma marker functional activity or adenoma marker expression.

In yet another further aspect, the present invention contemplates a pharmaceutical composition comprising a modulatory agent as hereinbefore defined and one or more pharmaceutically acceptable carriers and/or diluents. Said modulatory agents are referred to as the active ingredients.

Yet another aspect of the present invention relates to modulatory agents, as hereinbefore defined, when used in the method of the present invention.

Still another aspect of the present invention is directed to antibodies to adenoma markers or adenoma markers including catalytic antibodies.

BRIEF DESCRIPTION OF THE DRAWINGS

FIG. 2 is a graphical representation of a close up of the graph depicted in FIG. 1, highlighting missed tissues using markers 8-2d and 11-10a;

DETAILED DESCRIPTION OF THE INVENTION

Figure 1:
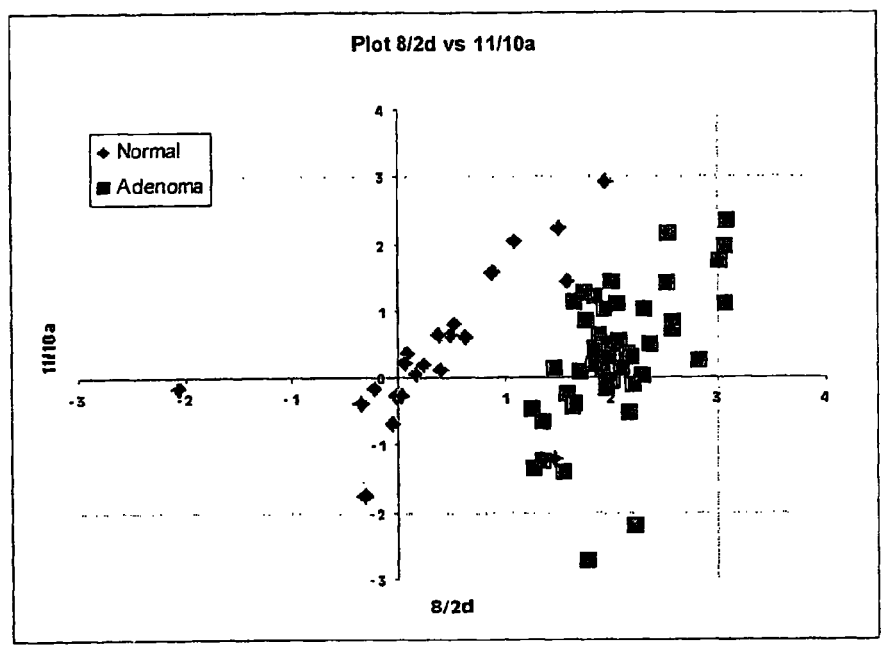
FIG. 1 is a graphical representation of the plot of 8-2d vs 11-10a demonstrating two dimensional cluster analysis.

The present invention is predicated, in part, on the identification of genetic molecules which have been determined to be expressed at either higher levels or in unique co-expression profiles in individuals who have developed an adenoma than in unaffected individuals. The inventors have still further determined that a proportion of these genetic molecules represent novel genetic molecules. The identification of this population of genetic molecules has now permitted the development of diagnostic methodology based thereon and, further, the identification and rational design of a range of products for use in therapy, prophylaxis, diagnosis and antibody generation.

Accordingly, one aspect of the present invention provides a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 1-2, SEQ ID NOs: 4-6, SEQ ID NOs: 8-32, SEQ ID NOs: 35-37 or SEQ ID NO: 59 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

In another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NO: 38, SEQ ID NOs: 40-43, SEQ ID NOs: 45-49, SEQ ID NOs: 58-60, SEQ ID NO: 62, SEQ ID NOs: 64-66, SEQ ID NOs: 68-72 or SEQ ID NOs: 337-338 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

In yet another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 73-219 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

In still another aspect of the present invention there is provided a method for determining the onset or a predisposition to the onset of a neoplasm in an individual, said method comprising measuring the level of expression of one or more:
(i) nucleic acid molecules comprising a nucleotide sequence substantially as set forth in any one of SEQ ID NOs: 220-336 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

Reference to "neoplasm" should be understood as a reference to a lesion, tumour or other encapsulated or unencapsulated mass or other form of growth which comprises neoplastic cells. A "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. The neoplastic cell may be a benign cell or a malignant cell. In a preferred embodiment, the subject neoplasm is an adenoma. Without limiting the present invention to any one theory or mode of action, an adenoma is generally a benign tumour of epithelial origin which is either derived from glandular tissue or exhibits clearly defined glandular structures. It can comprise a malignant cell population within the adenoma, such as occurs in the shift of a benign adenoma to a malignant adenocarcinoma. Some adenomas exhibit recognisable tissue elements, such a fibrous tissue, while others produce active compounds giving rise to clinical syndrome. Preferably, said adenoma is a gastrointestinal tract adenoma and even more preferably a colorectal adenoma such as a tubular adenoma, tubulovillous adenoma or villous adenoma. Still more preferably, said adenoma is a tubular adenoma, tubulovillous adenoma or villous adenoma greater than 10 mm in diameter.

As detailed hereinbefore, it has been determined that modulation in the level of expression or pattern of expression of the nucleic acid molecules detailed above correlates with the development of, or a predisposition to the development of an adenoma, in particular a colorectal adenoma. For ease of reference, these nucleic acid molecules are sometimes herein collectively referred to as "adenoma markers". The expression products of the adenoma marker nucleic acid molecules are herein collectively referred to in non-italicised text as "adenoma markers".

Reference to "expression" should be understood as a reference to the transcription and/or translation of a nucleic acid molecule. In this regard, the present invention is exemplified with respect to screening for adenoma markers taking the form of mRNA transcripts. Without limiting the present invention in any way, the up-regulation of gene transcription leading to increased mRNA synthesis will also correlate with translation of these mRNA transcripts to produce an expression product. Accordingly, the present invention also extends to adenoma diagnostic methodology which is directed to screening for elevated levels or patterns of expression of the adenoma marker expression products as an indicator of the development of, or predisposition to the development of, an adenoma. Although the preferred method is to screen for mRNA transcripts and/or the corresponding expression product, it should be understood that the present invention is not limited in this regard and extends to screening for any other form of adenoma marker or its protein expression product such as, for example, a primary RNA transcript. It is well within the skills of the person of skill in the art to determine the most appropriate screening target for any given situation.

Reference to "nucleic acid molecule" should be understood as a reference to both deoxyribonucleic acid molecules and ribonucleic acid molecules. Without limiting the present invention to any one theory or mode of action, the nucleotide sequences disclosed herein are cDNA sequences which correspond to partial or whole mRNA gene transcripts, the concentrations of any one or more of which are elevated greater than 2-fold in individuals exhibiting gastrointestinal tract adenoma development, as compared to unaffected individuals. The present invention therefore extends to both directly screening for mRNA levels in a biological sample or screening for the complimentary cDNA which has been reverse-transcribed from an mRNA population of interest. It is well within the skill of the person of skill in the art to design methodology directed to screening for either DNA or RNA. As detailed above, the method of the present invention also extends to screening for the protein expression product translated from the subject mRNA.

Reference to "biological sample" should be understood as a reference to any sample of biological material derived from an individual such, but not limited to, mucus, stool, urine, blood, serum, biopsy specimens and fluid which has been introduced into the body of an individual and subsequently removed such as, for example, the saline solution extracted from the lung following lung lavage or the solution retrieved from an enema wash. The biological sample which is tested according to the method of the present invention may be tested directly or may require some form of treatment prior to testing. For example, a biopsy sample may require homogenisation prior to testing. To the extent that the neoplasm of interest is a gastrointestinal tract adenoma, the biological sample is preferably a stool sample or any other biological sample of gastrointestinal origin. Where the sample comprises cellular material, it may be necessary to extract or otherwise expose the nucleic acid material present in the cellular material in order to facilitate interaction of a probe with the test sample.

Without limiting the present invention to any one theory or mode of action, it has been determined that, based on a single marker analysis, the adenoma markers detailed herein exhibit an upregulation in levels of expression in individuals with adenoma versus those without. The level of upregulation varied from 2 fold to upwards of 200 fold.

Accordingly, in a preferred embodiment the present invention provides a method for determining the onset or the predisposition to the onset of a neoplasm in an individual, said method comprising measuring the level of expression of one or more:
(i) nucleic acid molecule comprising a nucleotide sequence substantially as set forth in any one of SEQ ID NOs: 2 or 30 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

Without limiting the present invention to any one theory or mode of action, it has been determined that these adenoma markers are expressed in excess of 100 fold. Further, it has been determined that the nucleic acid molecule defined by SEQ ID NO: 2 corresponds to the gene Claudin 2 and expresses the protein product detailed in SEQ ID NO: 3.

In another embodiment, the present invention provides a method for determining the onset or the predisposition to the onset of a neoplasm in an individual, said method comprising measuring the level of expression of one or more:
(i) nucleic acid molecules comprising a nucleotide sequence substantially as set forth in any one of SEQ ID NO: 7, SEQ ID NO: 14, SEQ ID NOs: 20-21, SEQ ID NOs: 27-29, SEQ ID NO: 38, SEQ ID NO: 43, SEQ ID NO: 49, SEQ ID NOs: 60-62 or SEQ ID NO: 66 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

Without limiting the present invention to any one theory or mode of action, it has been determined that these adenoma markers are expressed at levels of between 10-100 fold above normal levels. Further, it has been determined that a number of the subject nucleic acid molecules correspond to known genes as follows:

SEQ ID NO: 43 corresponds to the gene encoding gastric intrinsic factor and expresses the protein product detailed in SEQ ID NO: 44.

SEQ ID NO: 49 corresponds to defensin α-6 (paneth cell specific) and expresses the protein product detailed in SEQ ID NO: 50.

SEQ ID NO: 66 corresponds to the gene encoding solute carrier family 12, member 2 and expresses the protein product detailed in SEQ ID NO: 67.

SEQ ID NO: 38 corresponds to the gene encoding regenerating protein IV and expresses the protein product detailed in SEQ ID NO: 39.

SEQ ID NO: 60 corresponds to the gene encoding GW112 protein and expresses the protein product detailed in SEQ ID NO: 61.

SEQ ID NO: 62 corresponds to the gene encoding S100 calcium binding protein P and expresses the protein product detailed in SEQ ID NO: 63.

In yet another embodiment, the present invention provides a method for determining the onset or predisposition to the onset of a neoplasm in an individual, said method comprising measuring the level of expression of one or more:
(i) nucleic acid molecules comprising a nucleotide sequence substantially as set forth in any one of SEQ ID NO: 5, SEQ ID NO: 9, SEQ ID NO: 17, SEQ ID NO: 32, SEQ ID NO: 38, SEQ ID NO: 53, SEQ ID NO: 56, SEQ ID NO: 64 or SEQ ID NO: 68 or a functional derivative, variant or homologue of said nucleic acid molecule; or
(ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

Without limiting the present invention to any one theory or mode of action, it has been determined that these adenoma markers are expressed at levels between 4.5-10.5 fold above normal levels. Further, it has been determined that the nucleic acid molecule defined by SEQ ID NO: 56 corresponds to the gene transforming growth factor β and expresses the protein product detailed in SEQ ID NO: 57. It has also been determined that the nucleic acid molecule defined by SEQ ID NO: 32 corresponds to the gene encoding transposon L1.1 and expresses the protein product detained in SEQ ID NOs: 33 and 34.

In still another embodiment, the present invention provides a method for determining the onset or the predisposition to the onset of a neoplasm in an individual, said method comprising measuring the level of expression of one or more:

(i) nucleic acid molecules comprising a nucleotide sequence substantially as set forth in any one of SEQ ID NO: 4, SEQ ID NO: 8, SEQ ID NO: 12, SEQ ID NOs: 18-19, SEQ ID NO: 31, SEQ ID NOs: 35-36, SEQ ID NOs: 40-41, SEQ ID NOs: 45-46 or SEQ ID NOs: 51-52, SEQ ID NOs: 54-55, SEQ ID NO: 59, SEQ ID NO: 65, SEQ ID NO: 72 or SEQ ID NOs: 337-338 or a functional derivative, variant or homologue of said nucleic acid molecule; or (ii) nucleic acid molecules comprising a nucleotide sequence capable of hybridising any one or more of the sequences of (i) under low stringency conditions at 42° C. or a functional derivative, variant or homologue of said nucleic acid molecule in a biological sample from said individual wherein an increase in the level of expression of said nucleic acid molecule relative to the normal level of expression of said nucleic acid molecule in an individual is indicative of the onset or predisposition to the onset of a neoplasm.

Without limiting the present invention to any one theory or mode of action, it has been determined that these adenoma markers are expressed in excess of 1.5-4 fold.

In another most preferred embodiment, the subject nucleotide sequence is SEQ ID NO: 2, SEQ ID NO: 7, SEQ ID NO: 14, SEQ ID NOs: 20-21, SEQ ID NOs: 27-29, SEQ ID NO: 30, SEQ ID NO: 32, SEQ ID NO: 38, SEQ ID NO: 43, SEQ ID NO: 49, SEQ ID NO: 53, SEQ ID NO: 56, SEQ ID NO: 60, SEQ ID NO: 62 or SEQ ID NO: 66.

In yet another most preferred embodiment the subject nucleotide sequence is SEQ ID NO: 2, SEQ ID NO: 5, SEQ ID NO: 7, SEQ ID NO: 9, SEQ ID NO: 14, SEQ ID NO: 17, SEQ ID NO: 20, SEQ ID NOs: 27-29, SEQ ID NO: 38, SEQ ID NO: 43, SEQ ID NO: 49, SEQ ID NO: 53, SEQ ID NO: 56, SEQ ID NO: 60, SEQ ID NO: 62, SEQ ID NO: 64, SEQ ID NO: 66 or SEQ ID NO: 68.

In still yet another preferred embodiment, the subject nucleotide sequence is SEQ ID NO: 2, SEQ ID NO: 7, SEQ ID NO: 14, SEQ ID NO: 17, SEQ ID NO: 20, SEQ ID NOs: 27-29, SEQ ID NO: 38, SEQ ID NO: 43, SEQ ID NO: 49, SEQ ID NO: 53, SEQ ID NO: 56, SEQ ID NO: 60, SEQ ID NO: 62 or SEQ ID NO: 66.

Most preferably, the subject nucleotide sequence is SEQ ID NO: 2, SEQ ID NO: 7, SEQ ID NO: 14, SEQ ID NO: 43 or SEQ ID NO: 62.

The method of the present invention is predicated on the correlation of levels of adenoma markers and/or adenoma markers in individuals with normal levels of said markers. The "normal level" is either the level of adenoma marker or adenoma marker in a corresponding biological sample of an individual who has not developed an adenoma nor is predisposed to the development of an adenoma or is the level in a non-adenomous tissue which is derived from the patient who is the subject of testing. This latter method of analysis is a relative form of analysis in terms of the normal and test levels being determined from non-adenomatous and test tissues, respectively, derived from a single individual. However, the method of the present invention should also be understood to encompass non-relative analyses means such as the analysis of test results relative to a standard result which reflects individual or collective results obtained from healthy individuals, other than the patient in issue. Said "normal level" may be a discrete level or a range of levels. Individuals exhibiting adenoma marker and/or adenoma marker levels higher than the normal range are generally regarded as having undergone the onset of adenoma development or may be predisposed to the onset of adenoma development.

It should be understood that the "individual" who is the subject of testing may be any human or nonhuman manual. Examples of non-human mammals includes primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). Preferably the mammal is a human.

In addition to modulation of the level of expression of any one or more adenoma markers relative to the levels of expression which are normally observed, the inventors have also surprisingly determined that irrespective of the actual level of expression of any given adenoma marker, the expression, per se, of some adenoma markers in combination with other adenoma markers in an individual is indicative of the development of or a predisposition to the development of an adenoma. For example, there can occur similar expression profiles within tissues of the same type, such expression profiles being differentiable from the expression profiles in other tissue types. It should be understood that the level of expression itself is not the unique identifier and may equate to more, less or equal to that which is expressed by healthy individuals. Of relevance is the occurrence of any level of expression in combination with other specified markers. The identification of these profile analyses is consistent with current biological understanding that in some situations it is the co-expression of more than one gene which actually causes the development of a given condition. This is certainly consistent with what is known of the complexity of the genomic network. The identification of the diagnostic profiles disclosed herein provides a highly sophisticated means of accurately diagnosing the existence of or predisposition to the development of an adenoma in an individual.

Accordingly, another aspect of the present invention provides a method for determining the onset or predisposition to the onset of a neoplasm in an individual, said method comprising detecting the co-expression of any two or more:

(i) nucleic acid molecules comprising a nucleotide sequence substantially as set forth in any one of SEQ ID NOs: 1-2, SEQ ID NOs: 4-6, SEQ ID NOs: 8-32, SEQ ID NOs: 35-37 or SEQ ID NO: 59 or a functional derivative, variant or homologue of said nucleic acid molecule; or (ii) nucleic acid molecules comprising a nucleotide sequence capable of hybridising any two or more of the sequences of (i) under low stringency conditions at 42° C. or a functional derivative, variant or homologue of said nucleic acid molecule in one or more biological samples from said individual wherein the co-expression of said nucleic acid molecules is indicative of the onset or predisposition to the onset of a neoplasm.

In another aspect, the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NO: 38, SEQ ID NOs: 40-43, SEQ ID NOs: 45-49, SEQ ID NOs: 51-56, SEQ ID NOs: 58-60, SEQ ID NO: 62, SEQ ID NOs: 64-66, SEQ ID NOs: 68-72 or SEQ ID NOs: 337-338 or a functional derivative, variant or homologue of said nucleic acid molecule; or
(ii) nucleic acid molecules comprising a nucleotide sequence capable of hybridising any two or more of the sequences of (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In yet another aspect the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NOs: 73-219 or a functional derivative, variant or homologue of said nucleic acid molecule; or
(ii) nucleic acid molecules comprising a nucleotide sequence capable of hybridising any two or more of the sequences of (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

In still another aspect the present invention provides a method for determining the onset or predisposition to the onset of a neoplasm in an individual, said method comprising detecting the co-expression of any two or more:
(i) nucleic acid molecules comprising a nucleotide sequence substantially as set forth in any one of SEQ ID NOs: 220-336 or a functional derivative, variant or homologue of said nucleic acid molecule; or
(ii) nucleic acid molecules comprising a nucleotide sequence capable of hybridising any two or more of the sequences of (i) under low stringency conditions at 42° C. or a functional derivative, variant or homologue of said nucleic acid molecule
in one or more biological samples from said individual wherein the co-expression of said nucleic acid molecules is indicative of the onset or predisposition to the onset of a neoplasm.

Reference to "co-expression" should be understood as a reference to the simultaneous expression of the subject adenoma marker or its expression product. In this regard the onset of co-expression may be simultaneous or it may be staggered. By "staggered" is meant that changes in the gene expression level of one gene occurs at a different time point (ie. either earlier or later) than the change in expression level of other gene or genes. Accordingly, "co-expression" is defined as the subject genes being simultaneously expressed for at least part of the time frame during which each gene is expressed, even if the subject expression is not commenced and concluded simultaneously. The method of the present invention is directed to detecting these periods of co-expression. It should be understood that although it is preferred that the co-expressed nucleic acid molecules are detectable in the one biological sample, for example a stool sample, they may only be detectable in two separate but simultaneously harvested tissue samples. For example, one adenoma marker may be detectable in a stool sample and the other in a blood sample. It should be understood that such tissue specific expression, which is nevertheless characterised by a period of simultaneous expression, is an example of co-expression within the meaning defined herein.

In a preferred embodiment, the present invention provides a method for determining the onset or predisposition to the onset of a neoplasm in an individual, said method comprising detecting the co-expression of any three:
(i) nucleic acid molecules comprising a nucleotide sequence substantially as set forth in any one of SEQ ID NO: 7, SEQ ID NO: 14, SEQ ID NO: 16, SEQ ID NO: 24, SEQ ID NO: 65, SEQ ID NO: 19, SEQ ID NO: 1, SEQ ID NO: 53, SEQ ID NO: 72, SEQ ID NO: 11 or SEQ ID NO: 26 or a functional derivative, variant or homologue of said nucleic acid molecule; or
(ii) nucleic acid molecules comprising a nucleotide sequence capable of hybridising any three of the sequences of (i) under low stringency conditions at 42° C. or a functional derivative, variant or homologue of said nucleic acid molecule,
in one or more biological samples from said individual wherein the co-expression of said nucleic acid molecules is indicative of the onset or predisposition to the onset of a neoplasm.

Preferably, the subject nucleotide sequences are co-expressed as a profile of three, which profile is selected from the list of:
(i) SEQ ID NO:7 and SEQ ID NO: 72 and SEQ ID NO: 11;
(ii) SEQ ID NO: 7 and SEQ ID NO: 72 and SEQ ID NO: 26;
(iii) SEQ ID NO: 7 and SEQ ID NO: 14 and SEQ ID NO: 16;
(iv) SEQ ID NO: 7 and SEQ ID NO: 14 and SEQ ID NO: 1;
(v) SEQ ID NO: 7 and SEQ ID NO: 14 and SEQ ID NO: 24; or
(vi) SEQ ID NO: 7 and SEQ ID NO: 14 and SEQ ID NO: 16.

Still more preferably, the subject nucleotide sequences are co-expressed as a profile of three, which profile is selected from the list of:
(i) SEQ ID NO:7 and SEQ ID NO: 56 and SEQ ID NO: 11;
(ii) SEQ ID NO:7 and SEQ ID NO: 64 and SEQ ID NO: 11;
(iii) SEQ ID NO: 7 and SEQ ID NO: 72 and SEQ ID NO: 11;
(iv) SEQ ID NO:7 and SEQ ID NO: 9 and SEQ ID NO: 11; or
(v) SEQ ID NO:7 and SEQ ID NO: 14 and SEQ ID NO: 11.

In another preferred embodiment the present invention provides a method for determining the onset or the predisposition to the onset of a neoplasm in an individual, said method comprising detecting the co-expression of any four:
(i) nucleic acid molecules comprising a nucleotide sequence substantially as set forth in any one of SEQ ID NOs: 4-6, SEQ ID NO: 9, SEQ ID NO: 13, SEQ ID NO: 15, SEQ ID NOs: 21-22, SEQ ID NOs: 27-29, SEQ ID NOs: 30-31, SEQ ID NO: 36, SEQ ID NOs: 37-38, SEQ ID NO: 40, SEQ ID NO: 43, SEQ ID NOs: 48-49, SEQ ID NO: 52, SEQ ID NO: 56, SEQ ID NO: 59, SEQ ID NO: 64, SEQ ID NOs: 68-69, SEQ ID NO: 71 or SEQ ID NO: 337 or a functional derivative, variant or homologue of said nucleic acid molecule; or
(ii) nucleic acid molecules comprising a nucleotide sequence capable of hybridising any two or more of the sequences of (i) under low stringency conditions at 42° C. or a functional derivative, variant or homologue of said nucleic acid molecule, in one or more biological samples from said individual wherein the co-expression of said nucleic acid molecules is indicative of the onset or predisposition to the onset of a neoplasm.

Still more preferably, the subject nucleotide sequences are co-expressed as a profile of four, which profile is selected from the list of:
(i) SEQ ID NO: 7 and SEQ ID NO: 14 and SEQ ID NO: 24 and SEQ ID NO: 65;
(ii) SEQ ID NO: 7 and SEQ ID NO: 14 and SEQ ID NO: 24 and SEQ ID NO: 19;
(iii) SEQ ID NO: 7 and SEQ ID NO: 14 and SEQ ID NO: 53 and SEQ ID NO: 1;
(iv) SEQ ID NO: 7 and SEQ ID NO: 14 and SEQ ID NO: 16 and SEQ ID NO: 19;
(v) SEQ ID NO: 7 and SEQ ID NO: 14 and SEQ ID NO: 16 and SEQ ID NO: 46; or
(vi) SEQ ID NO: 7 and SEQ ID NO: 14 and SEQ ID NO: 65 and SEQ ID NO: 1.

In another most preferred embodiment, the subject nucleotide sequences are co-expressed as a profile of four, which profile is selected from the list of:
(i) SEQ ID NO: 30 and SEQ ID NO: 7 and SEQ ID NO: 14 and SEQ ID NO: 1;
(ii) SEQ ID NO: 7 and SEQ ID NO: 43 and SEQ ID NO: 14 and SEQ ID NO: 24;
(iii) SEQ ID NO: 7 and SEQ ID NO: 43 and SEQ ID NO: 59 and SEQ ID NO: 1;
(iv) SEQ ID NO: 7 and SEQ ID NO: 14 and SEQ ID NO: 49 and SEQ ID NO: 24;
(v) SEQ ID NO: 7 and SEQ ID NO: 14 and SEQ ID NO: 49 and SEQ ID NO: 16;
(vi) SEQ ID NO: 7 and SEQ ID NO: 14 and SEQ ID NO: 49 and SEQ ID NO: 1;
(vii) SEQ ID NO: 7 and SEQ ID NO: 14 and SEQ ID NO: 21 and SEQ ID NO: 16;
(viii) SEQ ID NO: 7 and SEQ ID NO: 14 and SEQ ID NO: 21 and SEQ ID NO: 1;
(ix) SEQ ID NO: 7 and SEQ ID NO: 14 and SEQ ID NOs: 27-29 and SEQ ID NO: 24;
(x) SEQ ID NO: 7 and SEQ ID NO: 14 and SEQ ID NOs: 27-29 and SEQ ID NO: 16;
(xi) SEQ ID NO: 7 and SEQ ID NO: 14 and SEQ ID NOs: 27-29 and SEQ ID NO: 1;
(xii) SEQ ID NO: 7 and SEQ ID NO: 14 and SEQ ID NO: 56 and SEQ ID NO: 1;
(xiii) SEQ ID NO: 7 and SEQ ID NO: 14 and SEQ ID NO: 9 and SEQ ID NO: 24;
(xiv) SEQ ID NO: 7 and SEQ ID NO: 14 and SEQ ID NO: 9 and SEQ ID NO: 37;
(xv) SEQ ID NO: 7 and SEQ ID NO: 14 and SEQ ID NO: 9 and SEQ ID NO: 16;
(xvi) SEQ ID NO: 7 and SEQ ID NO: 14 and SEQ ID NO: 9 and SEQ ID NO: 1;
(xvii) SEQ ID NO: 7 and SEQ ID NO: 14 and SEQ ID NO: 24 and SEQ ID NO: 16;
(xviii) SEQ ID NO: 7 and SEQ ID NO: 14 and SEQ ID NO: 24 and SEQ ID NO: 46;
(xix) SEQ ID NO: 7 and SEQ ID NO: 14 and SEQ ID NO: 24 and SEQ ID NO: 1; or
(xx) SEQ ID NO: 7 and SEQ ID NO: 14 and SEQ ID NO: 24 and SEQ ID NO: 337.

In yet another most preferred embodiment, the subject nucleotide sequences are co-expressed as a profile of four, which profile is selected from the list of:
(i) SEQ ID NO: 7 and SEQ ID NO: 14 and SEQ ID NO: 5 and SEQ ID NO: 1;
(ii) SEQ ID NO: 7 and SEQ ID NO: 14 and SEQ ID NO: 65 and SEQ ID NO: 16;
(iii) SEQ ID NO: 7 and SEQ ID NO: 14 and SEQ ID NO: 65 and SEQ ID NO: 1;
(iv) SEQ ID NO: 7 and SEQ ID NO: 14 and SEQ ID NO: 53 and SEQ ID NO: 37;
(v) SEQ ID NO: 7 and SEQ ID NO: 14 and SEQ ID NO: 53 and SEQ ID NO: 48;
(vi) SEQ ID NO: 7 and SEQ ID NO: 14 and SEQ ID NO: 68 and SEQ ID NO: 1;
(vii) SEQ ID NO: 7 and SEQ ID NO: 14 and SEQ ID NO: 31 and SEQ ID NO: 1;
(viii) SEQ ID NO: 7 and SEQ ID NO: 14 and SEQ ID NO: 69 and SEQ ID NO: 16;
(ix) SEQ ID NO: 7 and SEQ ID NO: 14 and SEQ ID NO: 69 and SEQ ID NO: 1;
(x) SEQ ID NO: 7 and SEQ ID NO: 14 and SEQ ID NO: 52 and SEQ ID NO: 1:
(xi) SEQ ID NO: 7 and SEQ ID NO: 14 and SEQ ID NO: 16 and SEQ ID NO: 337;
(xii) SEQ ID NO: 7 and SEQ ID NO: 14 and SEQ ID NO: 16 and SEQ ID NO: 71;
(xiii) SEQ ID NO: 7 and SEQ ID NO: 14 and SEQ ID NO: 36 and SEQ ID NO: 1;
(xiv) SEQ ID NO: 7 and SEQ ID NO: 14 and SEQ ID NO: 19 and SEQ ID NO: 1;
(xv) SEQ ID NO: 7 and SEQ ID NO: 14 and SEQ ID NO: 40 and SEQ ID NO: 1;
(xvi) SEQ ID NO: 7 and SEQ ID NO: 14 and SEQ ID NO: 22 and SEQ ID NO: 1;
(xvii) SEQ ID NO: 7 and SEQ ID NO: 14 and SEQ ID NO: 46 and SEQ ID NO: 1;
(xviii) SEQ ID NO: 7 and SEQ ID NOs: 27-29 and SEQ ID NO: 24 and SEQ ID NO: 4;
(xix) SEQ ID NO: 7 and SEQ ID NOs: 27-29 and SEQ ID NO: 65 and SEQ ID NO: 11; or
(xx) SEQ ID NO: 7 and SEQ ID NO: 38 and SEQ ID NO: 64 and SEQ ID NO: 13.

In still another most preferred embodiment, the subject nucleotide sequences are co-expressed as a profile of four, which profile is selected from the list of:
(i) SEQ ID NO: 7 and SEQ ID NO:9 and SEQ ID NO: 68 and SEQ ID NO: 11;
(ii) SEQ ID NO: 7 and SEQ ID NO: 24 and SEQ ID NO: 69 and SEQ ID NO: 11;
(iii) SEQ ID NO: 7 and SEQ ID NO: 64 and SEQ ID NO: 53 and SEQ ID NO: 11;
(iv) SEQ ID NO: 7 and SEQ ID NO: 64 and SEQ ID NO: 68 and SEQ ID NO: 11;
(v) SEQ ID NO: 7 and SEQ ID NO: 64 and SEQ ID NO: 69 and SEQ ID NO: 13;
(vi) SEQ ID NO: 7 and SEQ ID NO: 64 and SEQ ID NO: 36 and SEQ ID NO: 13;
(vii) SEQ ID NO: 7 and SEQ ID NO: 64 and SEQ ID NO: 11 and SEQ ID NO: 337;
(viii) SEQ ID NO: 7 and SEQ ID NO: 53 and SEQ ID NO: 72 and SEQ ID NO: 11;
(ix) SEQ ID NO: 7 and SEQ ID NO: 72 and SEQ ID NO: 26 and SEQ ID NO: 46;
(x) SEQ ID NO:7 and SEQ ID NO: 72 and SEQ ID NO: 36 and SEQ ID NO: 11;
(xi) SEQ ID NO: 7 and SEQ ID NO: 72 and SEQ ID NO: 46 and SEQ ID NO: 11;
(xii) SEQ ID NO: 7 and SEQ ID NO: 69 and SEQ ID NO: 46 and SEQ ID NO:11;
(xiii) SEQ ID NO: 43 and SEQ ID NO: 7 and SEQ ID NO: 14 and SEQ ID NO: 24;

(xiv) SEQ ID NO: 43 and SEQ ID NO: 7 and SEQ ID NO: 14 and SEQ ID NO: 16;
(xv) SEQ ID NO: 43 and SEQ ID NO: 7 and SEQ ID NO: 14 and SEQ ID NO: 1;
(xvi) SEQ ID NO: 43 and SEQ ID NO: 7 and SEQ ID NOs: 27-29 and SEQ ID NO: 24;
(xvii) SEQ ID NO: 43 and SEQ ID NO: 7 and SEQ ID NO: 36 and SEQ ID NO: 11;
(xviii) SEQ ID NO: 43 and SEQ ID NO: 7 and SEQ ID NO: 59 and SEQ ID NO: 1;
(xix) SEQ ID NO: 7 and SEQ ID NO: 14 and SEQ ID NO: 49 and SEQ ID NO: 24; or
(xx) SEQ ID NO: 7 and SEQ ID NO: 14 and SEQ ID NO: 49 and SEQ ID NO: 22.

In yet still another most preferred embodiment, the subject nucleotide sequences are co-expressed as a profile of four, which profile is selected from the list of:
(i) SEQ ID NO: 7 and SEQ ID NO: 14 and SEQ ID NO: 49 and SEQ ID NO: 1;
(ii) SEQ ID NO: 7 and SEQ ID NO: 14 and SEQ ID NO: 56 and SEQ ID NO: 1;
(iii) SEQ ID NO: 7 and SEQ ID NO: 14 and SEQ ID NO: 56 and SEQ ID NO: 1;
(iv) SEQ ID NO: 7 and SEQ ID NO: 14 and SEQ ID NO: 9 and SEQ ID NO: 1;
(v) SEQ ID NO: 7 and SEQ ID NO: 14 and SEQ ID NO: 24 and SEQ ID NO: 19;
(vi) SEQ ID NO: 7 and SEQ ID NO: 14 and SEQ ID NO: 65 and SEQ ID NO: 37;
(vii) SEQ ID NO: 7 and SEQ ID NO: 14 and SEQ ID NO: 53 and SEQ ID NO: 48;
(viii) SEQ ID NO: 7 and SEQ ID NO: 14 and SEQ ID NO: 53 and SEQ ID NO: 1;
(ix) SEQ ID NO: 7 and SEQ ID NO: 14 and SEQ ID NO: 72 and SEQ ID NO: 1;
(x) SEQ ID NO: 7 and SEQ ID NO: 14 and SEQ ID NO: 69 and SEQ ID NO: 16;
(xi) SEQ ID NO: 7 and SEQ ID NO: 14 and SEQ ID NO: 16 and SEQ ID NO: 19;
(xii) SEQ ID NO: 7 and SEQ ID NO: 14 and SEQ ID NO: 19 and SEQ ID NO: 1;
(xiii) SEQ ID NO: 7 and SEQ ID NO: 14 and SEQ ID NO: 1 and SEQ ID NO: 71;
(xiv) SEQ ID NO: 7 and SEQ ID NO: 49 and SEQ ID NO: 64 and SEQ ID NO: 11;
(xv) SEQ ID NO: 7 and SEQ ID NO: 38 and SEQ ID NO: 56 and SEQ ID NO: 13;
(xvi) SEQ ID NO: 7 and SEQ ID NO: 38 and SEQ ID NO: 56 and SEQ ID NO: 13;
(xvii) SEQ ID NO: 7 and SEQ ID NO: 56 and SEQ ID NO: 64 and SEQ ID NO: 11;
(xviii) SEQ ID NO: 7 and SEQ ID NO: 56 and SEQ ID NO: 53 and SEQ ID NO: 6;
(xix) SEQ ID NO: 7 and SEQ ID NO: 9 and SEQ ID NO: 64 and SEQ ID NO: 16; or
(xx) SEQ ID NO: 7 and SEQ ID NO: 9 and SEQ ID NO: 64 and SEQ ID NO: 13.

In still yet another most preferred embodiment, the subject nucleotide sequences are co-expressed as a profile of four, which profile is selected from the list of:
(i) SEQ ID NO: 7 and SEQ ID NO: 9 and SEQ ID NO: 68 and SEQ ID NO: 11;
(ii) SEQ ID NO: 7 and SEQ ID NO: 24 and SEQ ID NO: 72 and SEQ ID NO: 13;
(iii) SEQ ID NO: 7 and SEQ ID NO: 24 and SEQ ID NO: 72 and SEQ ID NO: 46;
(iv) SEQ ID NO: 7 and SEQ ID NO: 24 and SEQ ID NO: 72 and SEQ ID NO: 71;
(v) SEQ ID NO: 7 and SEQ ID NO: 64 and SEQ ID NO: 72 and SEQ ID NO: 16;
(vi) SEQ ID NO: 7 and SEQ ID NO: 64 and SEQ ID NO: 68 and SEQ ID NO: 11;
(vii) SEQ ID NO: 7 and SEQ ID NO: 64 and SEQ ID NO: 69 and SEQ ID NO: 11;
(viii) SEQ ID NO: 7 and SEQ ID NO: 64 and SEQ ID NO: 19 and SEQ ID NO: 11;
(ix) SEQ ID NO: 7 and SEQ ID NO: 64 and SEQ ID NO: 13 SEQ ID NO: 11:
(x) SEQ ID NO: 7 and SEQ ID NO: 53 and SEQ ID NO: 72 and SEQ ID NO: 11;
(xi) SEQ ID NO: 7 and SEQ ID NO: 53 and SEQ ID NO: 15 and SEQ ID NO: 11;
(xii) SEQ ID NO: 7 and SEQ ID NO: 72 and SEQ ID NO: 68 and SEQ ID NO: 11;
(xiii) SEQ ID NO: 7 and SEQ ID NO: 72 and SEQ ID NO: 69 and SEQ ID NO: 1;
(xiv) SEQ ID NO: 7 and SEQ ID NO: 72 and SEQ ID NO: 36 and SEQ ID NO: 11;
(xv) SEQ ID NO: 7 and SEQ ID NO: 72 and SEQ ID NO: 19 and SEQ ID NO: 11;
(xvi) SEQ ID NO: 7 and SEQ ID NO: 72 and SEQ ID NO: 46 and SEQ ID NO: 11;
(xvii) SEQ ID NO: 7 and SEQ ID NO: 72 and SEQ ID NO: 46 and SEQ ID NO: 1;
(xviii) SEQ ID NO: 7 and SEQ ID NO: 68 and SEQ ID NO: 16 and SEQ ID NO: 36; or
(xix) SEQ ID NO:7 and SEQ ID NO: 68 and SEQ ID NO: 36 and SEQ ID NO: 11.

In yet still another preferred embodiment, the subject nucleotide sequences are co-expressed as a profile of five.

In a further preferred embodiment, the subject nucleotide sequences are co-expressed as a profile of six.

In still yet a further preferred embodiment, the subject nucleotide sequences are co-expressed as a profile of more than 6.

In accordance with these preferred embodiments, the subject neoplasm is preferably an adenoma and even more preferably a colorectal adenoma.

As detailed hereinbefore, it should be understood that although the present invention is exemplified with respect to the detection of nucleic acid molecules, it also encompasses methods of detection based on screening for the expression product of the subject adenoma markers or derivatives thereof. The present invention should also be understood to mean methods of screening based on identifying either protein product and nucleic acid material in one or more biological samples. However, it should be understood that some of the adenoma markers may correlate to genes or gene fragments which do not encode a protein expression product. Accordingly, to the extent that this occurs it would not be possible to screen for an expression product and the subject marker must be assessed on the basis of nucleic acid expression profiles.

Without limiting the present invention in any way, the following expression products are exemplified herein:
(i) SEQ ID NO: 2 corresponds to the claudin 2 gene and encodes the expression product detailed in SEQ ID NO: 3;
(ii) SEQ ID NO: 32 corresponds to the transposon L1.1 gene and encodes the expression product detailed in SEQ ID NOs: 33 and 34;
(iii) SEQ ID NO: 38 corresponds to the regenerating protein IV gene and encodes the expression product detailed in SEQ ID NO: 39;

(iv) SEQ ID NO: 43 corresponds to the gastric intrinsic factor gene and encodes the expression product detailed in SEQ ID NO: 44;
(v) SEQ ID NO: 49 corresponds to the defensin α6 gene (paneth cell specific) and encodes the expression product detailed in SEQ ID NO: 50;
(vi) SEQ ID NO: 56 corresponds to the TGF β1 gene and encodes the expression product detailed in SEQ ID NO: 57;
(vii) SEQ ID NO: 60 corresponds to the GW112 gene and encodes the expression product detailed in SEQ ID NO: 61
(viii) SEQ ID NO: 62 corresponds to the S100P gene and encodes the expression product detailed in SEQ ID NO: 63;
(ix) SEQ ID NO: 66 corresponds to the SLC12A1 gene and encodes the expression product detailed in SEQ ID NO: 67.

Further details in relation to each of these genes and proteins are provided in Example 6.

"Derivatives" should be understood to have the same meaning as hereinafter provided. Reference to a "functional derivative" should be understood as a reference to a derivative which, in accordance with the teachings provided herein, is indicative of the development of a neoplasm, in particular adenoma. In particular, however, the subject derivative may be a partially degraded or denatured molecule. For example, the mRNA which is screened for in stool samples in accordance with the exemplification provided herein is likely to lack the polyA tail which generally characterises a mRNA transcript. In another example, proteinaceous adenoma markers may be fragmented, denatured (for example due to breakdown of disulphide bonds) or may be otherwise degraded. This is likely to be the case, for example, where the biological sample which is the subject of screening comprises proteinases, such as are sometimes found in urine.

Reference herein to adenoma markers or adenoma markers (either collectively or in terms of specific SEQ ID NOs) should be read as including reference to all forms of these molecules and to functional derivatives, variants or homologues thereof, in the context of the diagnostic aspects of the present invention. Accordingly, reference to adenoma markers should be understood to include reference to isoforms which arise from alternative splicing of the adenoma marker mRNA or mutants or polymorphic variants of the adenoma markers. In this regard, for example, it is particularly significant to note that the markers exemplified herein have been derived from individual tissue. However, some genes are known to exhibit allelic variation between individuals. Accordingly, the present invention should be understood to extend to such variants which, in terms of the concept of the present diagnostic applications, achieve the same outcome despite the fact that minor genetic variants between the actual nucleic acid sequences may exist between individuals. Accordingly, the present invention should be understood to extend to all mRNA, cDNA and peptide isoforms which arise from alternative splicing or any other mutation or polymorphic variation.

Reference to the "onset" of a neoplasm, preferably adenoma development, should be understood as a reference to one or more cells of that individual exhibiting abnormal growth characteristic. In this regard, the adenoma may be well developed in that a mass of proliferating cells has developed. Alternatively, the adenoma may be at a very early stage in that only relatively few abnormal cell divisions have occurred at the time of diagnosis. The present invention also extends to the assessment of an individual's predisposition to the development of a neoplasm, such as an adenoma. Without limiting the present invention in any way, increased levels of or expression profiles of adenoma markers or adenoma markers in an individual who has not undergone the onset of adenoma development may be indicative of that individual's predisposition to developing an adenoma, such as the imminent development of an adenoma.

Although the preferred method is to detect the expression of adenoma markers and/or adenoma markers for the purpose of diagnosing adenoma development or predisposition thereto, the detection of a decrease in the levels of or down-regulation of expression profiles said markers may be desired under certain circumstances, for example, to monitor the effectiveness of therapeutic or prophylactic treatment directed to modulating a neoplastic condition, such as adenoma development. For example, where elevated levels of adenoma markers and/or adenoma markers indicated that an individual had developed a condition characterised by adenoma development, screening for a decrease in the levels of these markers subsequently to the onset of a therapeutic regime may be utilised to indicate reversal or other form of improvement of the subject individual's condition.

The method of the present invention is useful as a one off test or as an on-going monitor of those individuals thought to be at risk of adenoma development or as a monitor of the effectiveness of therapeutic or prophylactic treatment regimes directed to inhibiting or otherwise slowing adenoma development. In these situations, mapping the modulation of adenoma marker and/or adenoma marker levels or expression profiles in any one or more classes of biological samples is a valuable indicator of the status of an individual or the effectiveness of a therapeutic or prophylactic regime which is currently in use. Accordingly, the method of the present invention should be understood to extend to monitoring for increases or decreases in marker levels or expression profiles in an individual relative to their normal level (as hereinbefore defined) or relative to one or more earlier marker levels or expression profiles determined from a biological sample of said individual.

Accordingly, another aspect of the present invention provides a method of monitoring for the onset or progression of a neoplasm in an individual, said method comprising measuring the level of expression of one or more adenoma markers and/or adenoma markers, as hereinbefore defined, in a biological sample from said individual wherein the level of said adenoma marker and/or adenoma marker relative to the normal level of said adenoma marker and/or adenoma marker is indicative of the onset of progression or a neoplasm.

In yet another aspect there is provided a method of monitoring for the onset or progression of a neoplasm in an individual, said method comprising detecting the co-expression of any two or more adenoma markers and/or adenoma markers, as hereinbefore defined, in a biological sample from said individual wherein the expression profile of said adenoma markers and/or adenoma markers relative to normal expression profiles is indicative of the onset or progression of a neoplasm.

Preferably said neoplasm is an adenoma. Even more preferably said adenoma is a gastrointestinal tract adenoma. Most preferably said gastrointestinal tract adenoma is a colorectal adenoma.

In still another aspect, the present invention extends to the classification of adenomas obtained by biopsy based on the expression profile and/or expression levels of one or more of the adenoma markers and/or adenoma markers defined herein.

Without limiting the present invention to any one theory or mode of action, adenomas may develop through progressive stages of size, appearance and dysplasia (cellular disorganization), into colorectal cancer (Young, G. P., Rozen, P. and Levin, B. Chapter 3: Ed. Rozen, P., Young, G. P., Levin, P., Spann, S. J. Martin Dunitz 2002). The process is by a series of steps, each of which constitutes a change in the biology that is driven by accumulation of genetic mutations. Unless inherited, the mutations occur by chance and in random order. Once acquired the process is not inevitable, as more chance mutations must occur.

Progression of adenoma development is characterised by any one or more of the following:

a) An increase in size: 1 cm or over is definitely at-risk and some consider >5 mm as significant.
b) An increase in the villous component.
   The usual histology is "tubular". Adenomas can develop a villous appearance in some areas. If <25%, the adenoma remains a tubular adenoma (TA).
   25-50% is a tubulovillous adenoma (TVA).
   >50% change is a villous adenoma (VA). Regardless of size, villous change is important and risk increases as the degree of villous change increases.
c) An increase in the degree of dysplasia. All adenomas show dysplasia by definition, as this is the histologic hallmark of neoplasia. Adenomas are usually classified as a low (LGD) or high (HGD) grade dysplasia. High-grade means increased risk.
d) Multiplicity. While not strictly a marker of progression for the individual adenoma, multiplicity does denote increased risk of progression.

The risk of a polyp developing into cancer is summarized in the following table:

| Type of polyp | Risk increase |
| --- | --- |
| Adenoma: Multiple (i.e. >2 of any size) | 8-fold |
| Adenoma: >9 mm, or villous change, or HGD | 4-fold |
| Adenoma: <10 mm, tubular and single | No identified increased risk |
| Hyperplastic | No identified increased risk |

Many adenomas never progress, but remain single, tubular and less than 1 cm in size. Overall, it is estimated that about 5-10% of adenomas will progress to cancer. The process is generally slow and takes about 10 years. The adenoma "dwell-time" takes 5-10 years and a cancer may take 5 years before death ensues. Most adenomas are asymptomatic, as are cancers in the early phases.

Accordingly, the present invention now provides a means of classifying adenomas other than by the currently accepted techniques which are based on gross histological morphology. The currently used methods lack precision in relation to disease classification and prognosis. The identification of adenoma markers and adenoma markers together with identification of their expression uplift levels and expression profile can now be correlated to disease stage and/or cancer invasiveness. This provides a means of more effectively classifying staging and predicting disease progression.

Accordingly, another aspect of the present invention provides a method of classifying an adenoma, said method comprising identifying the expression pattern of one or more adenoma markers and/or adenoma markers and/or the expression levels of one or more adenoma markers and/or adenoma markers of said adenoma and correlating said adenoma marker expression results with the morphological and/or phenotypic features of said adenoma.

The present invention should also be understood to extend to the determination of an adenoma's classification status based on the known expression levels and/or expression profiles of the adenoma markers and/or adenoma markers expressed by said adenoma, and as previously identified above.

Means of screening for adenoma markers or adenoma markers in a biological sample can be achieved by any suitable method, which would be well known to the person of skill in the art, such as but not limited to:

(i) In vivo detection of adenomas.
   Molecular Imaging may be used following administration of imaging probes or reagents capable of disclosing altered expression of the markers in the intestinal tissues.
   Molecular imaging (Moore, A., Basilion, J., Chiocca, e., and Weissleder, R., Measuring Transferrin Receptor Gene Expression by NMR Imaging. BBA, 1402:239-249, 1988; Weissleder, R., Moore, A., Ph. D., Mahmnood-Bhorade, U., Benveniste, H., Chiocca, E. A., Basilion, J. P. High resolution in vivo imaging of transgene expression, Nature Medicine, 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy. Historically, detection of malignant tumor cells in a background of normal or hyperplastic benign tissue is often based on differences in physical properties between tissues, which are frequently minimal, resulting in low contrast resolution. Application of expression profiling will define the differences in "molecular properties" between cancer and normal tissues that arise as a result of malignant transformation. Definition of "molecular signatures" for adenomas will enable development of more sensitive and informative imaging methods that exploit these genetic differences. Additionally, identification of imaging marker genes, expression profiles or gene products for adenomas that can be correlated to disease stage and/or cancer invasiveness may eventually lead to non-invasive staging and prognosis of disease.

(ii) Detection of up-regulation of mRNA expression in the cells by Fluorescent In Situ Hybridization (FISH), or in extracts from the cells by technologies such as Quantitative Reverse Transcriptase Polymerase Chain Reaction (QRT-PCR) or Flow cytometric qualification of competitive RT-PCR products (Wedemeyer, N., Potter, T., Wetzlich, S. and Gohde, W. Flow Cytometric Quantification of Competitive Reverse Transcriptase-PCR products, Clinical Chemistry 48:9 1398-1405, 2002).

(iii) Assessment of expression profiles of mRNA from cellular extracts, for example by array technologies (Alon, A., Barkai, N. Notterman, D. A., Gish, K., Ybarra, S., Mach, D. and Levine, A. J. Broad patterns of gene expression revealed by clustering analysis of tumor and normal colon tissues probed by oligonucleotide arrays. Proc. Natl. Acad. Sci. USA: 96, 6745-6750, June 1999).

(iv) Measurement of altered marker protein levels in cell extracts, for example by immunoassay.

(v) The use of aptamers in screening for nucleic acid molecules or expression products (vi) Determining altered expression of protein markers on the cell surface, for example by immunohistochemistry.

(vii) Determining altered protein expression based on any suitable functional test, enzymatic test or immunological test in addition to those detailed in points (iv) and (vi) above.

A person of ordinary skill in the art could determine, as a matter of routine procedure, the appropriateness of applying a given method to a particular type of biological sample.

Another aspect of the present invention provides a diagnostic kit for assaying biological samples comprising an agent for detecting one or more adenoma markers and/or adenoma markers and reagents useful for facilitating the detection by the agent in the first compartment. Further means may also be included, for example, to receive a biological sample. The agent may be any suitable detecting molecule.

As detailed hereinbefore, the inventors have determined that a proportion of the adenoma markers represent novel genetic molecules. The identification of this population of genes has now permitted the rational design of a range of products and methods for use in diagnosis, therapy, prophylaxis and antibody generation.

Accordingly, a related aspect of the present invention contemplates an isolated nucleic acid molecule or derivative, homologue or analogue thereof comprising a nucleotide sequence substantially as set forth in any one or more of SEQ ID NO: 1 or SEQ ID NO: 6 or SEQ ID NOs: 8-10 or derivative or homologue thereof, or capable of hybridising to any one or more of SEQ ID NO: 1 or SEQ ID NO: 6 or SEQ ID NOs: 8-10 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NO: 4 or SEQ ID NO: 5 or derivative or homologue thereof, or capable of hybridising to any one or more of SEQ ID NO: 4 or SEQ ID NO: 5 under low stringency conditions at 42° C.

Still yet another aspect of the present invention contemplates an isolated nucleic acid molecule or derivative, homologue or analogue thereof comprising a nucleotide sequence substantially as set forth in any one or more of SEQ ID NO: 7 or derivative or homologue thereof, or capable of hybridising to any one or more of SEQ ID NO: 7 under low stringency conditions at 42° C.

Yet still another aspect of the present invention contemplates an isolated nucleic acid molecule or derivative, homologue or analogue thereof comprising a nucleotide sequence substantially as set forth in any one or more of SEQ ID NOs: 11-13 or SEQ ID NOs: 15-16 or derivative or homologue thereof, or capable of hybridising to any one or more of SEQ ID NOs: 11-13 or SEQ ID NOs: 15-16 under low stringency conditions at 42° C.

A further aspect of the present invention contemplates an isolated nucleic acid molecule or derivative, homologue or analogue thereof comprising a nucleotide sequence substantially as set forth in any one or more of SEQ ID NO: 14 or derivative or homologue thereof, or capable of hybridising to any one or more of SEQ ID NO: 14 under low stringency conditions at 42° C.

Another further aspect of the present invention contemplates an isolated nucleic acid molecule or derivative, homologue or analogue thereof comprising a nucleotide sequence substantially as set forth in any one or more of SEQ ID NOs: 17-19 or SEQ ID NOs: 22-23 or derivative or homologue thereof, or capable of hybridising to any one or more of SEQ ID NOs: 17-19 or SEQ ID NOs: 22-23 under low stringency conditions at 42° C.

Yet another further aspect of the present invention contemplates an isolated nucleic acid molecule or derivative, homologue or analogue thereof comprising a nucleotide sequence substantially as set forth in any one or more of SEQ ID NO: 20 or derivative or homologue thereof, or capable of hybridising to any one or more of SEQ ID NO: 20 under low stringency conditions at 42° C.

Still yet another further aspect of the present invention contemplates an isolated nucleic acid molecule or derivative, homologue or analogue thereof comprising a nucleotide sequence substantially as set forth in any one or more of SEQ ID NO: 21 or derivative or homologue thereof, or capable of hybridising to any one or more of SEQ ID NO: 21 under low stringency conditions at 42° C.

Yet still another further aspect of the present invention contemplates an isolated nucleic acid molecule or derivative, homologue or analogue thereof comprising a nucleotide sequence substantially as set forth in any one or more of SEQ ID NOs: 24-26, SEQ ID NO: 31 or SEQ ID NOs: 35-37 or derivative or homologue thereof, or capable of hybridising to any one or more of SEQ ID NOs: 24-26, SEQ ID NO: 31 or SEQ ID NOs: 35-37 under low stringency conditions at 42° C.

Another aspect of the present invention contemplates an isolated nucleic acid molecule or derivative, homologue or analogue thereof comprising a nucleotide sequence substantially as set forth in any one or more of SEQ ID NO: 27, SEQ ID NO: 28 or SEQ ID NO: 29 or derivative or homologue thereof, or capable of hybridising to any one or more of SEQ ID NO: 27, SEQ ID NO: 28 or SEQ ID NO: 29 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NO: 30 or derivative or homologue thereof, or capable of hybridising to any one or more of SEQ ID NO: 30 under low stringency conditions at 42° C.

Still another aspect of the present invention contemplates an isolated nucleic acid molecule or derivative, homologue or analogue thereof comprising a nucleotide sequence substantially as set forth in any one or more of SEQ ID NO: 59 or derivative or homologue thereof, or capable of hybridising to any one or more of SEQ ID NO: 59 under low stringency conditions at 42° C.

Yet another aspect of the present invention contemplates an isolated nucleic acid molecule or derivative, homologue or analogue thereof comprising a nucleotide sequence substantially as set forth in any one or more of SEQ ID NOs: 73-145 or derivative or homologue thereof, or capable of hybridising to any one or more of SEQ ID NOs: 73-145 under low stringency conditions at 42° C.

A further aspect of the present invention contemplates an isolated nucleic acid molecule or derivative, homologue or analogue thereof comprising a nucleotide sequence substantially as set forth in any one or more of SEQ ID NOs: 146-219 or SEQ ID NO: 336 or derivative or homologue thereof, or capable of hybridising to any one or more of SEQ ID NOs: 146-219 or SEQ ID NO: 336 under low stringency conditions at 42° C.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. In general, washing is carried out at $T_m = 69.3 + 0.41$ (G+C) % [19]=−12° C. However, the $T_m$ of a duplex DNA decreases by 1° C. with every increase of 1% in the number of mismatched based pairs (Bonner et al (1973) *J. Mol. Biol.* 81:123).

Without limiting the present invention to any one theory or mode of action, the nucleic acid molecules according to these aspects of the present invention are cDNA sequences which correspond to partial mRNA gene transcripts, the concentrations of which are elevated more than 2-fold in the tissues of individuals exhibiting gastrointestinal tract adenoma development, as compared to unaffected individuals or tissues. These mRNA transcript sequences do not correlate with any known gene sequences and therefore reflect the identification of a novel population of genes which, inter alia, are useful as diagnostic markers of adenoma development. More particularly, these genes are thought to form a novel group of genes which are indicative of the onset of or a predisposition to the onset of adenoma development when expressed at either higher levels or in unique co-expression profiles in individuals who have developed an adenoma than in unaffected individuals. The nucleic acid molecules according to this aspect of the present invention are herein collectively referred to as "novel adenoma markers". The expression product of the adenoma marker nucleic acid molecules are herein referred to non-italicised text as "novel adenoma markers". It should be understood that these molecules form a subgroup of the "adenoma markers" and "adenoma markers" as defined in relation to the diagnostic aspects of the present invention. For ease of reference, the two groups of markers are distinguishable by the presence or absence of the prefix "novel".

More particularly, the present invention contemplates a nucleic acid molecule or a derivative, homologue or analogue thereof comprising a sequence of nucleotides substantially as set forth in any one or more of SEQ ID NO: 1 or SEQ ID NO: 6 or SEQ ID NOs: 8-10.

In another embodiment, the present invention contemplates a nucleic acid molecule or a derivative, homologue or analogue thereof comprising a sequence of nucleotides substantially as set forth in any one or more of SEQ ID NO: 4 or SEQ ID NO: 5.

In yet another embodiment, the present invention contemplates a nucleic acid molecule or a derivative, homologue or analogue thereof comprising a sequence of nucleotides substantially as set forth in SEQ ID NO: 7.

In yet another embodiment, the present invention contemplates a nucleic acid molecule or a derivative, homologue or analogue thereof comprising a sequence of nucleotides substantially as set forth in any one or more of SEQ ID NOs: 11-13 or SEQ ID NOs: 15-16.

In still another embodiment, the present invention contemplates a nucleic acid molecule or a derivative, homologue or analogue thereof comprising a sequence of nucleotides substantially as set forth in SEQ ID NO: 14.

In yet still another embodiment, the present invention contemplates a nucleic acid molecule or a derivative, homologue or analogue thereof comprising a sequence of nucleotides substantially as set forth in any one or more of SEQ ID NOs: 17-19 or SEQ ID NOs: 22-23.

In still yet another embodiment, the present invention contemplates a nucleic acid molecule or a derivative, homologue or analogue thereof comprising a sequence of nucleotides substantially as set forth in SEQ ID NO: 20.

In a further embodiment, the present invention contemplates a nucleic acid molecule or a derivative, homologue or analogue thereof comprising a sequence of nucleotides substantially as set forth in SEQ ID NO: 21.

In a still further embodiment, the present invention contemplates a nucleic acid molecule or a derivative, homologue or analogue thereof comprising a sequence of nucleotides substantially as set forth in any one or more of SEQ ID NOs: 24-26, SEQ ID NO: 31 or SEQ ID NOs: 35-37.

In a yet further embodiment the present invention contemplates a nucleic acid molecule or a derivative, homologue or analogue thereof comprising a sequence of nucleotides substantially as set forth in any one or more of SEQ ID NO: 27, SEQ ID NO: 28 or SEQ ID NO: 29.

In a yet still further embodiment, the present invention contemplates a nucleic acid molecule or a derivative, homologue or analogue thereof comprising a sequence of nucleotides substantially as set forth in any one or more of SEQ ID NO: 30.

In yet another embodiment, the present invention contemplates a nucleic acid molecule or a derivative, homologue or analogue thereof comprising a sequence of nucleotides substantially as set forth in any one or more of SEQ ID NO: 59.

In still another embodiment, the present invention contemplates a nucleic acid molecule or a derivative, homologue or analogue thereof comprising a sequence of nucleotides substantially as set forth in any one or more of SEQ ID NOs: 73-145.

In a further embodiment, the present invention contemplates a nucleic acid molecule or a derivative, homologue or analogue thereof comprising a sequence of nucleotides substantially as set forth in any one or more of SEQ ID NOs: 146-219 or SEQ ID NO: 336.

The novel adenoma marker nucleic acid molecules of the present invention are preferably cDNA sequences of deoxyribonucleic acids or mRNA sequences of ribonucleic acids. However, the novel nucleic acid molecules of the present invention should be understood to extend to any form of deoxyribonucleic acid or ribonucleic acid molecule such as genomic sequences (which will comprise exons and introns and may also comprise promoter or other regulatory regions) or primary RNA transcript sequences.

Accordingly, another aspect of the present invention contemplates a genomic nucleic acid molecule or derivative, homologue or analogue thereof capable of hybridising to any one or more of SEQ ID NO: 1 or SEQ ID NO: 6 or SEQ ID NOs: 8-16 under low stringency conditions at 42° C.

Yet another aspect of the present invention contemplates a genomic nucleic acid molecule or derivative, homologue or analogue thereof capable of hybridising to any one or more of SEQ ID NO: 4 or SEQ ID NO: 5 under low stringency conditions at 42° C.

Still yet another aspect of the present invention contemplates a genomic nucleic acid molecule or derivative, homologue or analogue thereof capable of hybridising to SEQ ID NO: 7 under low stringency conditions at 42° C.

Yet still another aspect of the present invention contemplates a genomic nucleic acid molecule or derivative, homologue or analogue thereof capable of hybridising to any one or more of SEQ ID NOs: 11-13 or SEQ ID NOs: 15-16 under low stringency conditions at 42° C.

A further aspect of the present invention contemplates a genomic nucleic acid molecule or derivative, homologue or analogue thereof capable of hybridising to SEQ ID NO: 14 under low stringency conditions at 42° C.

Another further aspect of the present invention contemplates a genomic nucleic acid molecule or derivative, homologue or analogue thereof capable of hybridising to any one or more of SEQ ID NOs: 17-19 or SEQ ID NOs: 22-23 under low stringency conditions at 42° C.

Yet another further aspect of the present invention contemplates a genomic nucleic acid molecule or derivative, homologue or analogue thereof capable of hybridising to SEQ ID NO: 20 under low stringency conditions at 42° C.

Still yet another aspect of the present invention contemplates a genomic nucleic acid molecule or derivative, homologue or analogue thereof capable of hybridising to SEQ ID NO: 21 under low stringency conditions at 42° C.

Yet still another aspect of the present invention contemplates a genomic nucleic acid molecule or derivative, homologue or analogue thereof capable of hybridising to any one or more of SEQ ID NOs: 24-26, SEQ ID NO: 31 or SEQ ID NOs: 35-37 under low stringency conditions at 42° C.

Another aspect of the present invention contemplates a genomic nucleic acid molecule or derivative, homologue or analogue thereof capable of hybridising to any one or more of SEQ ID NOs: 27-29 under low stringency conditions at 42° C.

Yet another aspect of the present invention contemplates a genomic nucleic acid molecule or derivative, homologue or analogue thereof capable of hybridising to SEQ ID NO: 30 under low stringency conditions at 42° C.

Still another aspect of the present invention contemplates a genomic nucleic acid molecule or derivative, homologue or analogue thereof capable of hybridising to SEQ ID NO: 59 under low stringency conditions at 42° C.

Yet another aspect of the present invention contemplates a genomic nucleic acid molecule or derivative, homologue or analogue thereof capable of hybridising to any one or more of SEQ ID NOs: 73-145 under low stringency conditions at 42° C.

A further aspect of the present invention contemplates a genomic nucleic acid molecule or derivative, homologue or analogue thereof capable of hybridising to any one or more of SEQ ID NOs: 146-219 or SEQ ID NO: 336 under low stringency conditions at 42° C.

Reference herein to "novel adenoma markers" and "novel adenoma markers" should be understood as a reference to all forms of these molecules and to derivatives, homologues, analogues, chemical equivalents and mimetics thereof including, for example, any peptide or cDNA isoforms which arise from alternative splicing of novel adenoma marker mRNA or mutants or polymorphic variants of novel adenoma markers or novel adenoma markers.

The molecules disclosed herein have been isolated from the human. However, it should be understood that the protein and/or nucleic acid molecules may also be isolated from any other animal or non-animal source. For example, other animal and non-animal sources include, but are not limited to, primates, livestock animals (e.g. sheep, pigs, cows, goats, horses, donkeys), laboratory test animals (e.g. mice, hampsters, rabbits, rats, guinea pigs), domestic companion animals (e.g. dogs and cats), birds (e.g. chicken, geese, ducks and other poultry birds, game birds, emus, ostriches), captive wild or tamed animals (e.g. foxes, kangaroos, dingoes), reptiles or fish.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40-50%, even still more preferably at least about 60-70%, yet even still more preferably 80-90% or greater of subject nucleic acid molecule relative to other components as determined by molecular weight, encoding activity, nucleotide sequence, base composition or other convenient means. The nucleic acid molecule of the present invention may also be considered, in a preferred embodiment, to be biologically pure.

In a particularly preferred embodiment, the nucleotide sequence corresponding to a novel adenoma marker is a cDNA sequence comprising a sequence of nucleotides substantially as set forth in any one or more of SEQ ID NO: 1 or SEQ ID NO: 6 or SEQ ID NOs: 8-10 or is a derivative, homologue or analogue thereof including a cDNA sequence comprising a sequence of nucleotides having similarity to anyone or more of SEQ ID NO: 1 or SEQ ID NO: 6 or SEQ ID NOs: 8-10.

In another particularly preferred embodiment, the nucleotide sequence corresponding to a novel adenoma marker is a cDNA sequence comprising a sequence of nucleotides substantially as set forth in any one or more of SEQ ID NO: 4 or SEQ ID NO: 5 or is a derivative, homologue or analogue thereof including a cDNA sequence comprising a sequence of nucleotides having similarity to anyone or more of SEQ ID NO: 4 or SEQ ID NO: 5.

In yet another particularly preferred embodiment, the nucleotide sequence corresponding to a novel adenoma marker is a cDNA sequence comprising a sequence of nucleotides substantially as set forth in SEQ ID NO: 7 or is a derivative, homologue or analogue thereof including a cDNA sequence comprising a sequence of nucleotides having similarity to SEQ ID NO: 7.

In still another particularly preferred embodiment, the nucleotide sequence corresponding to a novel adenoma marker is a cDNA sequence comprising a sequence of nucleotides substantially as set forth in any one or more of SEQ ID NOs: 11-13 or SEQ ID NOs: 15-16 or is a derivative, homologue or analogue thereof including a cDNA sequence comprising a sequence of nucleotides having similarity to anyone or more of SEQ ID NOs: 11-13 or SEQ ID NOs: 15-16.

In yet still another particularly preferred embodiment, the nucleotide sequence corresponding to a novel adenoma marker is a cDNA sequence comprising a sequence of nucleotides substantially as set forth in SEQ ID NO: 14 or is a derivative, homologue or analogue thereof including a cDNA sequence comprising a sequence of nucleotides having similarity to SEQ ID NO: 14.

In still yet another particularly preferred embodiment, the nucleotide sequence corresponding to a novel adenoma marker is a cDNA sequence comprising a sequence of nucleotides substantially as set forth in any one or more of SEQ ID NOs: 17-19 or SEQ ID NOs: 22-23 or is a derivative, homologue or analogue thereof including a cDNA sequence comprising a sequence of nucleotides having similarity to anyone or more of SEQ ID NOs: 17-19 or SEQ ID NOs: 22-23.

In a further particularly preferred embodiment, the nucleotide sequence corresponding to a novel adenoma marker is a cDNA sequence comprising a sequence of nucleotides substantially as set forth in SEQ ID NO: 20 or is a derivative, homologue or analogue thereof including a cDNA sequence comprising a sequence of nucleotides having similarity to SEQ ID NO: 20.

In a still further particularly preferred embodiment, the nucleotide sequence corresponding to a novel adenoma marker is a cDNA sequence comprising a sequence of nucleotides substantially as set forth in SEQ ID NO: 21 or is a derivative, homologue or analogue thereof including a cDNA sequence comprising a sequence of nucleotides having similarity to SEQ ID NO: 21.

In a yet further particularly preferred embodiment, the nucleotide sequence corresponding to a novel adenoma marker is a cDNA sequence comprising a sequence of nucleotides substantially as set forth in any one or more of SEQ ID NOs: 24-26 or SEQ ID NO: 31 or SEQ ID NOs: 35-37 or is a derivative, homologue or analogue thereof including a cDNA sequence comprising a sequence of nucleotides having similarity to anyone or more of SEQ ID NOs: 24-26 or SEQ ID NO: 31 or SEQ ID NOs: 35-37.

In a still yet further particularly preferred embodiment, the nucleotide sequence corresponding to a novel adenoma marker is a cDNA sequence comprising a sequence of nucleotides substantially as set forth in any one or more of SEQ ID NOs: 27-29 or is a derivative, homologue or analogue thereof including a cDNA sequence comprising a sequence of nucleotides having similarity to anyone or more of SEQ ID NOs: 27-29.

In another embodiment, the nucleotide sequence corresponding to a novel adenoma marker is a cDNA sequence comprising a sequence of nucleotides substantially as set forth in SEQ ID NO: 30 or is a derivative, homologue or analogue thereof including a cDNA sequence comprising a sequence of nucleotides having similarity to SEQ ID NO: 30.

In yet another embodiment, the nucleotide sequence corresponding to a novel adenoma marker is a cDNA sequence comprising a sequence of nucleotides substantially as set forth in SEQ ID NO: 59 or is a derivative, homologue or analogue thereof including a cDNA sequence comprising a sequence of nucleotides having similarity to SEQ ID NO: 59.

In still another embodiment, the nucleotide sequence corresponding to a novel adenoma marker is a cDNA sequence comprising a sequence of nucleotides substantially as set forth in any one or more of SEQ ID NOs: 73-145 or is a derivative, homologue or analogue thereof including a cDNA sequence comprising a sequence of nucleotides having similarity to anyone or more of SEQ ID NOs: 73-145.

In a further embodiment, the nucleotide sequence corresponding to a novel adenoma marker is a cDNA sequence comprising a sequence of nucleotides substantially as set forth in any one or more of SEQ ID NOs: 146-219 or SEQ ID NO: 336 or is a derivative, homologue or analogue thereof including a cDNA sequence comprising a sequence of nucleotides having similarity to anyone or more of SEQ ID NOs: 146-219 or SEQ ID NO: 336.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. The percentage similarity may be greater than 50% such as at least 70% or at least 80% or at least 90% or at least 95% or higher.

To determine the percent identity of two amino acid sequences or of two nucleic acids, the sequences may be aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e. % identity=# of identical positions/total # of overlapping positions×100). Preferably, the two sequences are the same length. The determination of percent identity or homology between two sequences can be accomplished using a mathematical algorithm. A suitable, mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to the nucleic acid molecules of the invention. BLAST protein searches can be performed with XBLAST program, score=50, wordlength=3 to obtain amino acid sequences homologous to the protein molecules of the invention. To obtain gapped alignments for comparison purposes, Gapped BLAST can be utilized as described in Altschul et al. (1997). When utilizing BLAST and Gapped BLAST programs, the default parameters of the respective programs (e.g., XBLAST and NBLAST) can be used. See http://wxvv.ncbi.nlm.nih-.gov. Another example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, only exact matches are counted.

The nucleic acid molecule may be ligated to an expression vector capable of expression in a prokaryotic cell (e.g. *E. coli*) or a eukaryotic cell (e.g. yeast cells, fungal cells, insect cells, mammalian cells or plant cells). The nucleic acid molecule may be ligated or fused or otherwise associated with a nucleic acid molecule encoding another entity such as, for example, a signal peptide, epitope tag, fluorescent tag, dimerisation motif, inhibitory motif, activation motif or regulatory motif.

The present invention extends to the expression product of the nucleic acid molecules hereinbefore defined.

Accordingly, yet another aspect of the present invention is directed to an isolated protein selected from the list consisting of:

(i) a protein encoded by a nucleotide sequence or derivative, homologue or analogue thereof comprising a nucleotide sequence substantially as set forth in any one or more of SEQ ID NO: 1, SEQ ID NO: 6 or SEQ ID NOs: 8-10 or a derivative homologue, analogue, chemical equivalent or mimetic or said protein.

(ii) a protein encoded by a nucleotide sequence or derivative, homologue or analogue thereof comprising a nucleotide sequence substantially as set forth in any one or more of SEQ ID NO: 4 or SEQ ID NO: 5 or a derivative, homologue, analogue, chemical equivalent or mimetic or said protein.

(iii) a protein encoded by a nucleotide sequence or derivative, homologue or analogue thereof comprising a nucleotide sequence substantially as set forth in SEQ ID NO: 7 or a derivative, homologue, analogue, chemical equivalent or mimetic or said protein.

(iv) a protein encoded by a nucleotide sequence or derivative, homologue or analogue thereof comprising a nucleotide sequence substantially as set forth in any one or more of SEQ ID NOs: 11-13 or SEQ ID NOs: 15-16 or a derivative, homologue, analogue, chemical equivalent or mimetic or said protein.

(v) a protein encoded by a nucleotide sequence or derivative, homologue or analogue thereof comprising a nucleotide sequence substantially as set forth in SEQ ID NO: 14 or a derivative, homologue, analogue, chemical equivalent or mimetic or said protein.

(vi) a protein encoded by a nucleotide sequence or derivative, homologue or analogue thereof comprising a nucleotide sequence substantially as set forth in any one or more of SEQ ID NOs: 17-19 or SEQ ID NOs: 22-23 or a derivative, homologue, analogue, chemical equivalent or mimetic or said protein.

(vii) a protein encoded by a nucleotide sequence or derivative, homologue or analogue thereof comprising a nucleotide sequence substantially as set forth in SEQ ID NO: 20 or a derivative, homologue, analogue, chemical equivalent or mimetic or said protein.

(viii) a protein encoded by a nucleotide sequence or derivative, homologue or analogue thereof comprising a nucleotide sequence substantially as set forth in SEQ ID NO: 21 or a derivative, homologue, analogue, chemical equivalent or mimetic or said protein.

(ix) a protein encoded by a nucleotide sequence or derivative, homologue or analogue thereof comprising a nucleotide sequence substantially as set forth in any one or more of SEQ ID NOs: 24-26, SEQ ID NO: 31 or SEQ ID NOs: 35-37 or a derivative, homologue, analogue, chemical equivalent or mimetic or said protein.

(x) a protein encoded by a nucleotide sequence or derivative, homologue or analogue thereof comprising a nucleotide sequence substantially as set forth in any one or more of SEQ ID NO: 27 or SEQ ID NO: 28 or SEQ ID NO: 29 or a derivative, homologue, analogue, chemical equivalent or mimetic or said protein.

(xi) a protein encoded by a nucleotide sequence or derivative, homologue or analogue thereof comprising a nucleotide sequence capable of hybridising to any one or more of the nucleotide sequences as set forth in SEQ ID NO: 30 or a derivative, homologue or analogue thereof under low stringency conditions or a derivative, homologue, analogue, chemical equivalent or mimetic of said protein.

(xii) a protein encoded by a nucleotide sequence or derivative, homologue or analogue thereof comprising a nucleotide sequence capable of hybridising to any one or more of the nucleotide sequences as set forth in SEQ ID NO: 59 or a derivative, homologue or analogue thereof under low stringency conditions or a derivative, homologue, analogue, chemical equivalent or mimetic of said protein.

(xiii) a protein encoded by a nucleotide sequence or derivative, homologue or analogue thereof comprising a nucleotide sequence capable of hybridising to any one or more of the nucleotide sequences as set forth in any one or more of SEQ ID NOs: 73-145 or a derivative, homologue or analogue thereof under low stringency conditions or a derivative, homologue, analogue, chemical equivalent or mimetic of said protein.

(xiv) a protein encoded by a nucleotide sequence or derivative, homologue or analogue thereof comprising a nucleotide sequence capable of hybridising to any one or more of the nucleotide sequences as set forth in any one or more of SEQ ID NOs: 146-219 or SEQ ID NO: 336 or a derivative, homologue or analogue thereof under low stringency conditions or a derivative, homologue, analogue, chemical equivalent or mimetic of said protein.

The term "protein" should be understood to encompass peptides, polypeptides and proteins. The protein may be glycosylated or unglycosylated and/or may contain a range of other molecules fused, linked, bound or otherwise associated to the protein such as amino acids, lipids, carbohydrates or other peptides, polypeptides or proteins. Reference herein to a "protein" includes a protein comprising a sequence of amino acids as well as a protein associated with other molecules such as amino acids, lipids, carbohydrates or other peptides, polypeptides or proteins.

The protein of the present invention is preferably in isolated form. By "isolated" is meant a protein having undergone at least one purification step and this is conveniently defined, for example, by a composition comprising at least about 10% subject protein, preferably at least about 20%, more preferably at least about 30%, still more preferably at least about 40-50%, even still more preferably at least about 60-70%, yet even still more preferably 80-90% or greater of subject protein relative to other components as determined by molecular weight, amino acid sequence or other convenient means. The protein of the present invention may also be considered, in a preferred embodiment, to be biologically pure.

The adenoma marker proteins of the present invention may be in multimeric form meaning that two or more molecules are associated together. Where the same protein molecules are associated together, the complex is a homomultimer. An example of a homomultimer is a homodimer. Where at least one adenoma marker protein is associated with at least one non-adenoma marker protein, then the complex is a heteromultimer such as a heterodimer.

The ability to produce recombinant proteins permits the large scale production of adenoma markers for commercial use. The adenoma markers may need to be produced as part of a large peptide, adenomaeptide or protein which may be used as is or may first need to be processed in order to remove the extraneous proteinaceous sequences. Such processing includes digestion with proteases, peptidases and amidases or a range of chemical, electrochemical, sonic or mechanical disruption techniques.

Notwithstanding that the present invention encompasses recombinant proteins, chemical synthetic techniques are also preferred in the synthesis of the subject proteins.

Adenoma marker proteins according to the present invention are conveniently synthesised based on molecules isolated from the human. Isolation of the human molecules may be accomplished by any suitable means such as by chromotographic separation, for example using CM-cellulose ion exchange chromatography followed by Sephadex (e.g. G-50 column) filtration. Many other techniques are available including HPLC, PAGE amongst others.

The subject proteins may be synthesised by solid phase synthesis using F-moc chemistry as described by Carpino et al. (1991). Proteins and fragments thereof may also be synthesised by alternative chemistries including, but not limited to, t-Boc chemistry as described in Stewart et al. (1985) or by classical methods of liquid phase peptide synthesis.

Derivatives of the nucleic acid and protein molecules defined herein include fragments, parts, portions, mutants, variants and mimetics from natural, synthetic or recombinant sources including fusion proteins. Parts or fragments include, for example, active regions of the adenoma markers. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place.

An example of substitutional amino acid variants are conservative amino acid substitutions. Conservative amino acid substitutions typically include substitutions within the following groups: glycine and alanine; valine, isoleucine and leucine; aspartic acid and glutaric acid; asparagine and glutamine; serine and threonine; lysine and arginine; and phenylalanine and tyrosine. Additions to amino acid sequences include fusions with other peptides, polypeptides or proteins.

Homologues should be understood as a reference to nucleic acid or protein molecules isolated from or otherwise corresponding to molecules found in species other than the human.

Chemical and functional equivalents of the subject nucleic acid or protein molecules should be understood as molecules exhibiting any one or more of the functional activities of these molecules and may be derived from any source such as being chemically synthesized or identified via screening processes such as natural product screening.

The derivatives include fragments having particular epitopes or parts of the entire protein fused to peptides, polypeptides or other proteinaceous or non-proteinaceous molecules.

Analogues contemplated herein include, but are not limited to, modification to side chains, incorporating of unnatural amino acids and/or their derivatives during peptide, adenomaeptide or protein synthesis and the use of crosslinkers and other methods which impose conformational constraints on the proteinaceous molecules or their analogues.

Derivatives of nucleic acid sequences may similarly be derived from single or multiple nucleotide substitutions, deletions and/or additions including fusion with other nucleic acid molecules. The derivatives of the nucleic acid molecules of the present invention include oligonucleotides, PCR primers, antisense molecules, molecules suitable for use in cosuppression and fusion of nucleic acid molecules. Derivatives of nucleic acid sequences also include degenerate variants.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in the following Table 1 below:

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |

| Non-conventional amino acid | Code |
|---|---|
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

A further aspect of the present invention relates to the use of the invention in relation to the treatment and/or prophylaxis of disease conditions. Without limiting the present invention to any one theory or mode of action, the inventors have determined that increased levels of any one or more the adenoma markers (both novel and those which have been previously characterised but not recognised as being an adenoma marker) disclosed herein is associated with the onset or a predisposition to the onset of a neoplasm, in particular an adenoma. Accordingly, modulation of the expression and/or functional activity of these adenoma markers provides a mechanism for treating conditions characterised by aberrant, unwanted or otherwise inappropriate cell growth. Although the preferred method is to down-regulate uncontrolled cellular proliferation in an individual, by down-regulating the expression and/or functional activity of one or more of the adenoma markers disclosed herein, up-regulation of cell growth may also be desirable in certain circumstances such as to promote wound healing and angiogenesis or other human processes.

The present invention therefore contemplates a method for the treatment and/or prophylaxis of a condition characterised by aberrant, unwanted or otherwise inappropriate cell growth in a subject, said method comprising administering to said subject an effective amount of an agent for a time and under conditions sufficient to modulate adenoma marker expression and/or adenoma marker functional activity.

Reference to "aberrant, unwanted or otherwise inappropriate" cell growth should be understood as a reference to overactive cell growth, to physiologically normal cell growth which is inappropriate in that it is unwanted or to insufficient cell growth. Preferably said inappropriate cell growth is uncontrolled cell proliferation.

According to this preferred embodiment there is provided a method for the treatment and/or prophylaxis of a condition characterised by uncontrolled cell proliferation in a subject, said method comprising administering to said subject an effective amount of an agent for a time and under conditions sufficient to down-regulate adenoma marker expression and/or adenoma marker functional activity.

Preferably said condition is a neoplastic condition and still more preferably an adenoma.

In a most preferred embodiment there is provided a method for the treatment and/or prophylaxis of an adenoma in a subject said method comprising administering to said subject an effective amount of and agent for a time and under conditions sufficient to down-regulate adenoma starker expression and/or adenoma marker functional activity.

Still more preferably said adenoma is a colorectal adenoma.

The method of the present invention preferably facilitates the subject proliferation being reduced, retarded or otherwise inhibited. Reference to "reduced, retarded or otherwise inhibited" should be understood as a reference to inducing or facilitating the partial or complete inhibition of cell proliferation. Said inhibition may occur either by direct or indirect mechanisms and includes the induction of cellular apoptosis or other cellular mechanisms.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Administration of the agent (including an adenoma marker or functional equivalent, derivative, homologue, analogue or mimetic thereof or an adenoma marker nucleic acid molecule or derivative, equivalent, homologue or analogue thereof) [herein referred to as "modulatory agent"], in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of modulatory agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in a convenient manner such as by the oral, intravenous (where water soluble), intraperitoneal, intramuscular, subcutaneous, intradermal or suppository routes or implanting (e.g. using slow release molecules). The modulatory agent may be administered in the form of pharmaceutically acceptable non-toxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip, patch and implant. Preferably, said route of administration is oral.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

Another aspect of the present invention contemplates the use of an agent as hereinbefore defined in the manufacture of a medicament for the treatment of a condition in a mammal, which condition is characterised by the aberrant, unwanted or otherwise inappropriate cell growth wherein said agent modulates adenoma marker functional activity or adenoma marker expression.

Preferably said condition is a neoplastic condition and even more preferably an adenoma. Still more preferably, said adenoma is a colorectal adenoma.

In yet another further aspect, the present invention contemplates a pharmaceutical composition comprising a modulatory agent as hereinbefore defined and one or more pharmaceutically acceptable carriers and/or diluents. Said modulatory agents are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations. The pharmaceutical composition may also comprise genetic molecules such as a vector capable of transfecting target cells where the vector carries a nucleic acid molecule encoding a modulatory agent. The vector may, for example, be a viral vector.

Yet another aspect of the present invention relates to modulatory agents, as hereinbefore defined, when used in the method of the present invention.

Still another aspect of the present invention is directed to antibodies to adenoma markers or adenoma markers including catalytic antibodies. Such antibodies may be monoclonal or polyclonal and may be selected from naturally occurring antibodies to adenoma markers or may be specifically raised to an adenoma marker. In the case of the latter, the adenoma marker may first need to be associated with a carrier molecule. The antibodies and/or recombinant adenoma marker of the present invention are particularly useful as therapeutic or diagnostic agents. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regime.

For example, an adenoma marker can be used to screen for naturally occurring antibodies to an adenoma marker.

For example, specific antibodies can be used to screen for adenoma marker proteins. The latter would be important, for example, as a means for screening for levels of an adenoma marker in a cell extract or other biological fluid or purifying an adenoma marker made by recombinant means from culture supernatant fluid. Techniques for the assays contemplated herein are known in the art and include, for example, sandwich assays, ELISA and flow cytometry. It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of an adenoma marker.

Both polyclonal and monoclonal antibodies are obtainable by immunization with the protein or peptide derivatives and either type is utilizable for immunoassays. The methods of obtaining both types of sera are well known in the art. Polyclonal sera are less preferred but are relatively easily prepared by injection of a suitable laboratory animal with an effective amount of an adenoma marker, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman (1981).

The present invention is further described by the following non-limiting examples:

TABLE 2

SEQUENCE LISTING SUMMARY

| PCT Sequence ID Number | Adenoma Marker Clone Name | Sequence Description | Additional clone information |
|---|---|---|---|
| 1 | 11-10a | Adenoma marker cDNA sequence | gi|15431275|gb|AC079240.6|*Homo sapiens* BAC clone RP11-808H.523 e−146 |
| 2 | 11-10e; and 11-5b | Claudin 2 cDNA sequence | Genbank Accession Number NM020384 |
| 3 | 11-10e; and 11-5b | Clauding 2 protein sequence | Genbank Accession Number NP065117 |
| 4 | 1-1d | Adenoma marker cDNA sequence | gi|5763746|emb|AL049766.14|HSDJ686N 3 Human DNA sequence fro . . . 373 e−100 |
| 5 | 1-1g | Adenoma marker cDNA sequence | gi|5763746|emb|AL049766.14|HSDJ686N 3 Human DNA sequence from clone RP4-686N3 on chromosome 20q13.2-13.2 Contains the 3' part of the gene for a novel ATP dependent RNA helicase (contains conserved C-terminal helicase domains and DEAD-DEAH boxes), the KIAA1404 gene, a putative novel gene |
| 6 | 12-17a | Adenoma marker cDNA sequence | gi|21629406|gb|AC099845.2|*Homo sapiens* chromosome 18, clon . . . 456 e−126 |
| 7 | 12-2f 8-2d | Adenoma marker cDNA sequencey | gi|18104869|gb|AC023302.9|*Homo sapiens* chromosome 15, clon . . . 593 e−167 |
| 8 | 2-12e clone 8 | Adenoma marker cDNA sequence | gi|18645166|gb|BC023990.1| *Homo sapiens*, annexin A2, clone . . . 141 9e−31 |
| 9 | 2-13a clone 5 | Adenoma marker cDNA sequence | |
| 10 | 2-20b clone 2 | Adenoma marker cDNA sequence | gi|21732430|emb|AL831917.1|HSM803250 *Homo sapiens* mRNA; cDNA DKFZp761F0118 (from clone DKFZp761F0118) |
| 11 | 3-10e clone 6 | Adenoma marker cDNA sequence | gi|15823776|dbj|AB063285.1|*Homo sapiens* HLCS gene for holocarboxylase synthetase, complete cds |
| 12 | 3-12a | Adenoma marker cDNA sequence | gi|11597162|gb|AC013410.5|AC013410 *Homo sapiens* BAC clone RP11-495I2 from 2, complete sequence |
| 13 | 3-16b clone 4 | Adenoma marker cDNA sequence | gi|6382477|gb|AC005881.3|AC005881 citb_79_e_16, complete sequence [*Homo sapiens*] |
| 14 | 4-14b | Adenoma marker cDNA sequence | |
| 15 | 4-17d | Adenoma marker cDNA sequence | gi|18426891|gb|AC000385.2| *Homo sapiens* chromosome 11 clone PAC pDJ392a17, complete sequence i|21732802|emb|AL832255.1|HSM803562 *Homo sapiens* mRNA; cDNA DKFZp667D1717 (from clone DKFZp667D1717) |
| 16 | 4-18e | Adenoma marker cDNA sequence | gi|17985585|gb|AF381996.1|AF381996 *Homo sapiens* haplotype M12 mitochondrion, complete genome |
| 17 | 4-2a | Adenoma marker cDNA sequence | gi|17149447|gb|AC096915.2| *sapiens* chromosome 3 clone RP11-24H1, complete sequence |
| 18 | 5-2f | Adenoma marker cDNA sequence | gi|21359956|ref|NM_024569.2| *Homo sapiens* hypothetical protein FLJ21047 (FLJ21047), mRNA |
| 19 | 5-2g | Adenoma marker cDNA sequence | gi|21749695|dbj|AK091346.1| *Homo sapiens* cDNA FLJ34027 fis, clone FCBBF2003549, highly similar to GAP-associated tyrosine phosphoprotein p62 (Sam68) |
| 20 | 6-12a | Adenoma marker cDNA sequence | |
| 21 | 6-12b | Adenoma marker cDNA sequence | |
| 22 | 6-16c clone 1 | Adenoma marker cDNA sequence | gi|2429080|dbj|D87675.1| *Homo sapiens* DNA for amyloid precursor protein, complete cds |
| 23 | 6-17b | Adenoma marker cDNA sequence | gi|4502264|ref|NM_001675.1| *Homo sapiens* activating transcription factor 4 (tax-responsive enhancer element B67) (ATF4), mRNA |

TABLE 2-continued

SEQUENCE LISTING SUMMARY

| PCT Sequence ID Number | Adenoma Marker Clone Name | Sequence Description | Additional clone information |
|---|---|---|---|
| 24 | 6-18d clone 7 | Adenoma marker cDNA sequence | gi|19335766|emb|AL356738.14| Human DNA sequence from clone RP13-228J13 on chromosome X, complete sequence [*Homo sapiens* |
| 25 | 7-12a | Adenoma marker cDNA sequence | gi|15991856|gb|BC012895.1|BC012895 *Homo sapiens*, clone MGC: 18288 IMAGE: 4179238, mRNA, complete cds |
| 26 | 8-17a | Adenoma marker cDNA sequence | gi|3873300|gb|AC005829.1|AC005829 *Homo sapiens* chromosome 17, clone hRPK.259_G_18, complete sequence |
| 27 | 8-19a | Adenoma marker cDNA sequence transcript 1 | |
| 28 | 8-19a | Adenoma marker cDNA sequence transcript 2 | |
| 29 | 8-19a | Adenoma marker cDNA sequence transcript 3 | |
| 30 | 8-7bi | Adenoma marker cDNA sequence | |
| 31 | 9-4g clone 5 | Adenoma marker cDNA sequence | gi|21700762|ref|NM_144570.1| *Homo sapiens* HN1 like (HNIL), mRNA |
| 32 | 9-8a; and 2-20a-2 | Transposon L1.1 cDNA sequence | Genbank Accession Number M80340 |
| 33 | 9-8a; and 2-20a-2 | Transposon L1.1 CDS 1 protein sequence | Genbank Accession Number AAA51621 |
| 34 | 9-8a; and 2-20a-2 | Transposon L1.1 CDS 2 protein sequence | Genbank Accession Number AAA51622 |
| 35 | 9-8f2 clone 5 | Adenoma marker cDNA sequence | gi|6562085|emb|AL078591.18|HSDJ198I9 Human DNA sequence from clone RP1-198I9 on chromosome 6q12-13. Contains the gene KIAA1411, ESTs, STSs and GSSs, complete sequence |
| 36 | 9-8g | Adenoma marker cDNA sequence | gi|21733549|emb|AL832961.1|HSM804272 *Homo sapiens* mRNA; cDNA DKFZp666O0110 (from clone DKFZp666O0110) |
| 37 | 9-8j2 clone 4 | Adenoma marker cDNA sequence | gi|22002110|gb|AC022080.37| *Homo sapiens* 12 BAC RP11-820K3 (Roswell Park Cancer Institute Human BAC |
| 38 | 11-10b; 3-2c; 12-7c; 9-2d; and 11-2d | Regenerating Protein IV cDNA sequence | Genbank Accession Number NM032044 |
| 39 | 11-10b; 3-2c; 12-7c; 9-2d; and 11-2d | Regenerating Protein IV protein sequence | Genbank Accession Number NP114433 |
| 40 | 11-20e | Adenoma marker cDNA sequence | gi|20539919|ref|XM_168302.1| *Homo sapiens* zinc finger prote . . . 854 0.0 |
| 41 | 3-19e | Adenoma marker cDNA sequence | gi|20539919|ref|XM_168302.1| *Homo sapiens* zinc finger protein 36 (KOX 18) (ZNF36), mRNA |
| 42 | 1-19e | Adenoma marker cDNA sequence | gi|16933566|ref|NM_005370.3| *Homo sapiens* mel transforming . . . 884 0.0 |
| 43 | 1-6aii | Gastric Intrinsic Factor cDNA sequence | Genbank Accession Number NM005142 |
| 44 | 1-6aii | Gastric Intrinsic Factor protein sequence | Genbank Accession Number NP005133 |
| 45 | 2-10b | Adenoma marker cDNA sequence | gi|6633800|ref|NM_007329.1| *Homo sapiens* deleted in maligna . . . 404 e-110 |
| 46 | 2-12f | Adenoma marker cDNA sequence | gi|21166384|ref|NM_138737.1| *Homo sapiens* hephaestin (HEPH) . . . 791 0.0 |
| 47 | 3-13e | Adenoma marker cDNA sequence | |
| 48 | 2-18f clone 5 | Adenoma marker cDNA sequence | gi|5051939|gb|AF143313.1|PTEN2 *Homo sapiens* PTEN (PTEN) gen . . . 569 e-160 |
| 49 | 2-1c | Defensin alpha 6 cDNA sequence | Genbank Accession Number NM001926 |

TABLE 2-continued

SEQUENCE LISTING SUMMARY

| PCT Sequence ID Number | Adenoma Marker Clone Name | Sequence Description | Additional clone information |
|---|---|---|---|
| 50 | 2-1c | Defensin alpha 6 protein sequence | Genbank Accession Number NP001917 |
| 51 | 2-1g | Adenoma marker cDNA sequence | gi|19923767|ref|NM_005682.2| *Homo sapiens* G protein-coupled receptor 56 (GPR56), mRNA |
| 52 | 2-7g clone 4 | Adenoma marker cDNA sequence | Genbank Accession Number NM 022149.1 |
| 53 | 3-12e clone 3 | Adenoma marker cDNA sequence | Accession Number XM 010264.2 |
| 54 | 3-16k | Adenoma marker cDNA sequence | gi|12654696|gb|BC001188.1|BC001188 *Homo sapiens*, transferri . . . 523 e−146 |
| 55 | 3-5c clone 4 | Adenoma marker cDNA sequence | gi|4758719|ref|NM_004529.1| *Homo sapiens* myeloid-lymphoid or mixed-lineage leukemia |
| 56 | 4-11e; and 5-13d | Transforming growth factor beta cDNA sequence | Genbank Accession Number NM000358 |
| 57 | 4-11e; and 5-13d | Transforming growth factor beta protein sequence | Genbank Accession Number NP000349 |
| 58 | 4-16d | Adenoma marker cDNA sequence | gi|17985823|gb|AF382013.1|AF382013 *Homo sapiens* haplotype M*2 mitochondrion, complete genome Length = 16567 |
| 59 | 4-18d | Adenoma marker cDNA sequence | Accession Number XM 015882.1 |
| 60 | 5-14j | GW112 cDNA sequence | Genbank Accession Number NM006418 |
| 61 | 5-14j | GW112 protein sequence | Genbank Accession Number NP006409 |
| 62 | 5-4a | S100 calcium binding protein P cDNA sequence | Genbank Accession Number NM005980 |
| 63 | 5-4a | S100 calcium binding protein P protein sequence | Genbank Accession Number NP005971 |
| 64 | 6-10d | Adenoma marker cDNA sequence | gi|20127471|ref|NM_005239.2| *Homo sapiens* v-ets erythroblastosis virus E26 oncogene homolog |
| 65 | 6-16a | Adenoma marker cDNA sequence | gi|15145625|gb|AC023150.5|*Homo sapiens* BAC clone RP11-709L9 from 4, complete sequence |
| 66 | 7-13b | SLC12A2 cDNA sequence | Genbank Accession Number NM001046 |
| 67 | 7-13b | SLC12A2 protein sequence | Genbank Accession Number NP001037 |
| 68 | 7-13d clone 4 | Adenoma marker cDNA sequence | Accession Number M22146.1 |
| 69 | 8-12b | Adenoma marker cDNA sequence | Accession Number gbU16738.1 |
| 70 | 5-12a | Adenoma marker cDNA sequence | Accession Number gbU16738.1 |
| 71 | 8-16b | Adenoma marker cDNA sequence | |7739724|gb|AF257305.1|AF257305 *Homo sapiens* ASH1 mRNA, complete cds |
| 72 | 9-13c3 | Adenoma marker cDNA sequence | gi|21707883|gb|BC034141.1| *Homo sapiens*, similar to anti TNF-alpha antibody light-chain Fab >gi|21707883|gb|BC034141.1| *Homo sapiens*, similar to anti TNF-alpha antibody light-chain |
| 73 | 3-1d2 | Adenoma marker cDNA sequence | |
| 74 | 3-1 cl 4 | Adenoma marker cDNA sequence | |
| 75 | 3-1 cl 7 | Adenoma marker cDNA sequence | |
| 76 | 4-1 cl 11 | Adenoma marker cDNA sequence | |
| 77 | 4-1 cl 13 | Adenoma marker cDNA sequence | |
| 78 | 4-1 cl 17 | Adenoma marker cDNA sequence | |
| 79 | 6-1a | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 80 | 6-3d | Adenoma marker cDNA sequence | |
| 81 | 2-6a | Adenoma marker cDNA sequence | |
| 82 | 2-7n | Adenoma marker cDNA sequence | |
| 83 | 2-8r | Adenoma marker cDNA sequence | |
| 84 | 6-5d | Adenoma marker cDNA sequence | |
| 85 | 7-16g | Adenoma marker cDNA sequence | |
| 86 | 7-17b2 | Adenoma marker cDNA sequence | |
| 87 | 8-2a | Adenoma marker cDNA sequence | |
| 88 | 8-2c | Adenoma marker cDNA sequence | |
| 89 | 8-12d | Adenoma marker cDNA sequence | |
| 90 | 8-15a | Adenoma marker cDNA sequence | |
| 91 | 9-8h | Adenoma marker cDNA sequence | |
| 92 | 9-8i | Adenoma marker cDNA sequence | |
| 93 | 9-10e | Adenoma marker cDNA sequence | |
| 94 | 9-12a | Adenoma marker cDNA sequence | |
| 95 | 9-14a | Adenoma marker cDNA sequence | |
| 96 | 9-15a | Adenoma marker cDNA sequence | |
| 97 | 9-16h | Adenoma marker cDNA sequence | |
| 98 | 9-17a | Adenoma marker cDNA sequence | |
| 99 | 9-19b | Adenoma marker cDNA sequence | |
| 100 | 9-19c | Adenoma marker cDNA sequence | |
| 101 | 10-7b | Adenoma marker cDNA sequence | |
| 102 | 10-8a | Adenoma marker cDNA sequence | |
| 103 | 10-8c | Adenoma marker cDNA sequence | |
| 104 | 10-11b | Adenoma marker cDNA sequence | |
| 105 | 10-12a | Adenoma marker cDNA sequence | |
| 106 | 10-14j | Adenoma marker cDNA sequence | |
| 107 | 10-16a | Adenoma marker cDNA sequence | |
| 108 | 10-17b | Adenoma marker cDNA sequence | |
| 109 | 10-17c | Adenoma marker cDNA sequence | |
| 110 | 11-12d | Adenoma marker cDNA sequence | |
| 111 | 11-12a | Adenoma marker cDNA sequence | |
| 112 | 11-17a | Adenoma marker cDNA sequence | |
| 113 | 11-17c | Adenoma marker cDNA sequence | |
| 114 | 11-17d | Adenoma marker cDNA sequence | |
| 115 | 11-19i | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 116 | 12-20b | Adenoma marker cDNA sequence | |
| 117 | 12-7a | Adenoma marker cDNA sequence | |
| 118 | 12-7d | Adenoma marker cDNA sequence | |
| 119 | 1-1B-1 | Adenoma marker cDNA sequence | |
| 120 | 1-1H | Adenoma marker cDNA sequence | |
| 121 | 1-11B2 | Adenoma marker cDNA sequence | |
| 122 | 1-14A | Adenoma marker cDNA sequence | |
| 123 | 1-14B | Adenoma marker cDNA sequence | |
| 124 | 1-14E2 | Adenoma marker cDNA sequence | |
| 125 | 1-15D | Adenoma marker cDNA sequence | |
| 126 | 1-16A-3 | Adenoma marker cDNA sequence | |
| 127 | 1-16 | Adenoma marker cDNA sequence | |
| 128 | 1-16A-6 | Adenoma marker cDNA sequence | |
| 129 | 1-20B | Adenoma marker cDNA sequence | |
| 130 | 1-20C | Adenoma marker cDNA sequence | |
| 131 | 2-8A | Adenoma marker cDNA sequence | |
| 132 | 2-8R | Adenoma marker cDNA sequence | |
| 133 | 2-13A-2 | Adenoma marker cDNA sequence | |
| 134 | 2-17A-1 | Adenoma marker cDNA sequence | |
| 135 | 2-17A-5 | Adenoma marker cDNA sequence | |
| 136 | 2-17A-6 | Adenoma marker cDNA sequence | |
| 137 | 2-17F | Adenoma marker cDNA sequence | |
| 138 | 2-17I-2 | Adenoma marker cDNA sequence | |
| 139 | 2-18D-1 | Adenoma marker cDNA sequence | |
| 140 | 2-18D-5 | Adenoma marker cDNA sequence | |
| 141 | 2-18F-1 | Adenoma marker cDNA sequence | |
| 142 | 2-19A | Adenoma marker cDNA sequence | |
| 143 | 2-19C | Adenoma marker cDNA sequence | |
| 144 | 2-20B-1 | Adenoma marker cDNA sequence | |
| 145 | 2-20C | Adenoma marker cDNA sequence | |
| 146 | 2-20D | Adenoma marker cDNA sequence | |
| 147 | 3-3F-6 | Adenoma marker cDNA sequence | |
| 148 | 3-5C-2 | Adenoma marker cDNA sequence | |
| 149 | 3-5C-5 | Adenoma marker cDNA sequence | |
| 150 | 3-5D-2 | Adenoma marker cDNA sequence | |
| 151 | 3-8A-3 | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 152 | 3-8A-5 | Adenoma marker cDNA sequence | |
| 153 | 3-8A-7 | Adenoma marker cDNA sequence | |
| 154 | 3-8E-5 | Adenoma marker cDNA sequence | |
| 155 | 3-10A-5 | Adenoma marker cDNA sequence | |
| 156 | 3-10A-8 | Adenoma marker cDNA sequence | |
| 157 | 3-10B | Adenoma marker cDNA sequence | |
| 158 | 3-11A | Adenoma marker cDNA sequence | |
| 159 | 3-11G | Adenoma marker cDNA sequence | |
| 160 | 3-14E | Adenoma marker cDNA sequence | |
| 161 | 3-16H-6 | Adenoma marker cDNA sequence | |
| 162 | 3-16J-1 | Adenoma marker cDNA sequence | |
| 163 | 4-17C-3 | Adenoma marker cDNA sequence | |
| 164 | 4-18B | Adenoma marker cDNA sequence | |
| 165 | 5-1C-1 | Adenoma marker cDNA sequence | |
| 166 | 5-1C-2 | Adenoma marker cDNA sequence | |
| 167 | 5-1E-4 | Adenoma marker cDNA sequence | |
| 168 | 5-10A | Adenoma marker cDNA sequence | |
| 169 | 5-14M | Adenoma marker cDNA sequence | |
| 170 | 5-14N-1 | Adenoma marker cDNA sequence | |
| 171 | 5-15C | Adenoma marker cDNA sequence | |
| 172 | 5-16A | Adenoma marker cDNA sequence | |
| 173 | 5-16C | Adenoma marker cDNA sequence | |
| 174 | 5-17C | Adenoma marker cDNA sequence | |
| 175 | 5-17D | Adenoma marker cDNA sequence | |
| 176 | 5-19A | Adenoma marker cDNA sequence | |
| 177 | 5-19H | Adenoma marker cDNA sequence | |
| 178 | 5-20D | Adenoma marker cDNA sequence | |
| 179 | 6-3D | Adenoma marker cDNA sequence | |
| 180 | 6-6B2-1 | Adenoma marker cDNA sequence | |
| 181 | 6-14A | Adenoma marker cDNA sequence | |
| 182 | 6-14B | Adenoma marker cDNA sequence | |
| 183 | 6-17H-3 | Adenoma marker cDNA sequence | |
| 184 | 6-18B | Adenoma marker cDNA sequence | |
| 185 | 6-18F | Adenoma marker cDNA sequence | |
| 186 | 6-19AIII | Adenoma marker cDNA sequence | |
| 187 | 6-20E-1 | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 188 | 6-20E-3 | Adenoma marker cDNA sequence | |
| 189 | 7-1D-1 | Adenoma marker cDNA sequence | |
| 190 | 7-7D-1 | Adenoma marker cDNA sequence | |
| 191 | 7-11B2-3 | Adenoma marker cDNA sequence | |
| 192 | 7-12C | Adenoma marker cDNA sequence | |
| 193 | 7-16E | Adenoma marker cDNA sequence | |
| 194 | 7-17D | Adenoma marker cDNA sequence | |
| 195 | 7-18C-2 | Adenoma marker cDNA sequence | |
| 196 | 7-19I-2 | Adenoma marker cDNA sequence | |
| 197 | 7-19I-5 | Adenoma marker cDNA sequence | |
| 198 | 7-19I-6 | Adenoma marker cDNA sequence | |
| 199 | 8-1A-2 | Adenoma marker cDNA sequence | |
| 200 | 8-5A | Adenoma marker cDNA sequence | |
| 201 | 8-5D | Adenoma marker cDNA sequence | |
| 202 | 8-5E | Adenoma marker cDNA sequence | |
| 203 | 8-13E-2 | Adenoma marker cDNA sequence | |
| 204 | 8-16E | Adenoma marker cDNA sequence | |
| 205 | 8-17C | Adenoma marker cDNA sequence | |
| 206 | 8-19D | Adenoma marker cDNA sequence | |
| 207 | 8-20A | Adenoma marker cDNA sequence | |
| 208 | 8-1B-1 | Adenoma marker cDNA sequence | |
| 209 | 9-2B | Adenoma marker cDNA sequence | |
| 210 | 9-7A-1 | Adenoma marker cDNA sequence | |
| 211 | 9-8F2-2 | Adenoma marker cDNA sequence | |
| 212 | 9-12C-5 | Adenoma marker cDNA sequence | |
| 213 | 9-16E-3 | Adenoma marker cDNA sequence | |
| 214 | 9-17A-2+5 | Adenoma marker cDNA sequence | |
| 215 | 9-17B | Adenoma marker cDNA sequence | |
| 216 | 9-17D-2 | Adenoma marker cDNA sequence | |
| 217 | 10-4B-6 | Adenoma marker cDNA sequence | |
| 218 | 12-6D | Adenoma marker cDNA sequence | |
| 219 | 12-17B | Adenoma marker cDNA sequence | |
| 220 | 4-1 cl 2 | Adenoma marker cDNA sequence | |
| 221 | 4-1 cl 8 | Adenoma marker cDNA sequence | |
| 222 | 5-2c | Adenoma marker cDNA sequence | |
| 223 | 1-10a | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 224 | 2-1e | Adenoma marker cDNA sequence | |
| 225 | 2-6f | Adenoma marker cDNA sequence | |
| 226 | 2-6i | Adenoma marker cDNA sequence | |
| 227 | 2-7a | Adenoma marker cDNA sequence | |
| 228 | 2-7b | Adenoma marker cDNA sequence | |
| 229 | 2-7d | Adenoma marker cDNA sequence | |
| 230 | 2-8f | Adenoma marker cDNA sequence | |
| 231 | 5-1a | Adenoma marker cDNA sequence | |
| 232 | 6-2a | Adenoma marker cDNA sequence | |
| 233 | 6-5c | Adenoma marker cDNA sequence | |
| 234 | 6-6d | Adenoma marker cDNA sequence | |
| 235 | 7-5a | Adenoma marker cDNA sequence | |
| 236 | 7-10b | Adenoma marker cDNA sequence | |
| 237 | 7-11d3 | Adenoma marker cDNA sequence | |
| 238 | 7-18a | Adenoma marker cDNA sequence | |
| 239 | 7-20b | Adenoma marker cDNA sequence | |
| 240 | 8-2f | Adenoma marker cDNA sequence | |
| 241 | 9-10c | Adenoma marker cDNA sequence | |
| 242 | 9-14c | Adenoma marker cDNA sequence | |
| 243 | 9-14g | Adenoma marker cDNA sequence | |
| 244 | 9-16a | Adenoma marker cDNA sequence | |
| 245 | 9-16b | Adenoma marker cDNA sequence | |
| 246 | 9-19a | Adenoma marker cDNA sequence | |
| 247 | 9-20a | Adenoma marker cDNA sequence | |
| 248 | 10-10a | Adenoma marker cDNA sequence | |
| 249 | 11-11b | Adenoma marker cDNA sequence | |
| 250 | 5-13E | Adenoma marker cDNA sequence | |
| 251 | 2-13B | Adenoma marker cDNA sequence | |
| 252 | 11-12c | Adenoma marker cDNA sequence | |
| 253 | 11-13a | Adenoma marker cDNA sequence | |
| 254 | 11-13d | Adenoma marker cDNA sequence | |
| 255 | 11-20b | Adenoma marker cDNA sequence | |
| 256 | 11-20d | Adenoma marker cDNA sequence | |
| 257 | 11-5f | Adenoma marker cDNA sequence | |
| 258 | 12-13b | Adenoma marker cDNA sequence | |
| 259 | 12-15a | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 260 | 1-1B-4 | Adenoma marker cDNA sequence | |
| 261 | 1-7F-2 | Adenoma marker cDNA sequence | |
| 262 | 1-7G-2 | Adenoma marker cDNA sequence | |
| 263 | 1-8E | Adenoma marker cDNA sequence | |
| 264 | 1-9B | Adenoma marker cDNA sequence | |
| 265 | 2-5G | Adenoma marker cDNA sequence | |
| 266 | 2-6G-1 | Adenoma marker cDNA sequence | |
| 267 | 2-6G-2 | Adenoma marker cDNA sequence | |
| 268 | 2-7G-6 | Adenoma marker cDNA sequence | |
| 269 | 2-8G-1 | Adenoma marker cDNA sequence | |
| 270 | 2-8G-2 | Adenoma marker cDNA sequence | |
| 271 | 2-8Q | Adenoma marker cDNA sequence | |
| 272 | 2-11A | Adenoma marker cDNA sequence | |
| 273 | 2-12D | Adenoma marker cDNA sequence | |
| 274 | 2-12E-7 | Adenoma marker cDNA sequence | |
| 275 | 2-17H | Adenoma marker cDNA sequence | |
| 276 | 2-17I-5 | Adenoma marker cDNA sequence | |
| 277 | 2-17I-1 | Adenoma marker cDNA sequence | |
| 278 | 2-18C-2 | Adenoma marker cDNA sequence | |
| 279 | 2-18C-5 | Adenoma marker cDNA sequence | |
| 280 | 2-18G | Adenoma marker cDNA sequence | |
| 281 | 3-2C-A | Adenoma marker cDNA sequence | |
| 282 | 3-3A | Adenoma marker cDNA sequence | |
| 283 | 3-3F-5 | Adenoma marker cDNA sequence | |
| 284 | 3-3F-7 | Adenoma marker cDNA sequence | |
| 285 | 3-5C-3 | Adenoma marker cDNA sequence | |
| 286 | 3-19J-1 | Adenoma marker cDNA sequence | |
| 287 | 5-18F-2 | Adenoma marker cDNA sequence | |
| 288 | 5-19I | Adenoma marker cDNA sequence | |
| 289 | 3-5D-6 | Adenoma marker cDNA sequence | |
| 290 | 3-8B | Adenoma marker cDNA sequence | |
| 291 | 3-10A-6 | Adenoma marker cDNA sequence | |
| 292 | 3-16B-3 | Adenoma marker cDNA sequence | |
| 293 | 3-16H-5 | Adenoma marker cDNA sequence | |
| 294 | 3-16HII-5 | Adenoma marker cDNA sequence | |
| 295 | 3-16J-2 | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 296 | 3-18E-1 | Adenoma marker cDNA sequence | |
| 297 | 3-18E-6 | Adenoma marker cDNA sequence | |
| 298 | 4-16E | Adenoma marker cDNA sequence | |
| 299 | 5-2I | Adenoma marker cDNA sequence | |
| 300 | 5-5A | Adenoma marker cDNA sequence | |
| 301 | 5-8B | Adenoma marker cDNA sequence | |
| 302 | 5-14A | Adenoma marker cDNA sequence | |
| 303 | 5-14N-2 | Adenoma marker cDNA sequence | |
| 304 | 5-15C | Adenoma marker cDNA sequence | |
| 305 | 5-16B | Adenoma marker cDNA sequence | |
| 306 | 5-17A | Adenoma marker cDNA sequence | |
| 307 | 5-18F-6 | Adenoma marker cDNA sequence | |
| 308 | 5-18F-7 | Adenoma marker cDNA sequence | |
| 309 | 5-20C-3 | Adenoma marker cDNA sequence | |
| 310 | 6-1F-4 | Adenoma marker cDNA sequence | |
| 311 | 6-3C-2 | Adenoma marker cDNA sequence | |
| 312 | 6-3C-4 | Adenoma marker cDNA sequence | |
| 313 | 6-5E-2 | Adenoma marker cDNA sequence | |
| 314 | 6-10C | Adenoma marker cDNA sequence | |
| 315 | 6-12G | Adenoma marker cDNA sequence | |
| 316 | 6-17B | Adenoma marker cDNA sequence | |
| 317 | 6-20E-2 | Adenoma marker cDNA sequence | |
| 318 | 7-2D | Adenoma marker cDNA sequence | |
| 319 | 7-11A | Adenoma marker cDNA sequence | |
| 320 | 7-11C2 | Adenoma marker cDNA sequence | |
| 321 | 7-13D-2 | Adenoma marker cDNA sequence | |
| 322 | 7-20A-4 | Adenoma marker cDNA sequence | |
| 323 | 7-20D-2 | Adenoma marker cDNA sequence | |
| 324 | 7-20D-3 | Adenoma marker cDNA sequence | |
| 325 | 8-1D | Adenoma marker cDNA sequence | |
| 326 | 8-5F4-1 | Adenoma marker cDNA sequence | |
| 327 | 8-13E-5 | Adenoma marker cDNA sequence | |
| 328 | 8-14C-1 | Adenoma marker cDNA sequence | |
| 329 | 9-1A-1 | Adenoma marker cDNA sequence | |
| 330 | 8-15B2 | Adenoma marker cDNA sequence | |
| 331 | 9-18A-2 | Adenoma marker cDNA sequence | |

TABLE 2-continued

SEQUENCE LISTING SUMMARY

| PCT Sequence ID Number | Adenoma Marker Clone Name | Sequence Description | Additional clone information |
|---|---|---|---|
| 332 | 10-4B-3 | Adenoma marker cDNA sequence | |
| 333 | 10-10D | Adenoma marker cDNA sequence | |
| 334 | 11-12E | Adenoma marker cDNA sequence | |
| 335 | 12-2C | Adenoma marker cDNA sequence | |
| 336 | XS81 | Adenoma marker cDNA sequence | |
| 337 | 2-5a | Adenoma marker cDNA sequence | |
| 338 | HumregA | Adenoma marker cDNA sequence | |

EXAMPLE 1

Adenoma Collection and RNA Isolation a) Samples of adenoma and normal tissue were obtained from patients undergoing colonoscopy. A portion from each lesion was allocated for routine diagnostic pathology analysis and the remainder quick frozen and stored at −70° C.
b) RNA was extracted from frozen tissue using a standard guanidine thiocyanate, acid phenol method. The quality of each RNA preparation was examined by denaturing agarose gel electrophoresis.

Characterization of Novel Genes c) The adenoma cDNA library was prepared in a bacteriophage lambda vector (λSCREEN-1) using commercially available reagents obtained from Novagen. Library screening was performed under standard conditions at 65° C. using 4×SSC hybridization buffer. Filters were washed twice at 65° C. in 2×SSC for 30 minutes each and then at 65° C. in 0.2×SSC for 15 minutes each. Filters were then exposed to X-ray film overnight at −70° C. in the presence of one intensifying screen. Positive plaques were picked, grown up and rescreened under the same conditions until a homogeneous population emerged. The inserts from individual phage were then characterized by restriction enzyme mapping and DNA sequence analysis.

In some cases library screening was performed by PCR screening of pools of library clones using sequence information from the cloned differential display products to design appropriate primers. DNA fragments of the predicted size were identified after gel electrophoresis of the PCR reaction. These bands were excised from the gel, cloned and sequenced.

d) Sequence of the 5' and 3' ends of selected mRNAs was determined by the Rapid Amplification of cDNA Ends (RACE) technique using 5-10 μg of total RNA. The FirstChoice kit made by Ambion was used for these experiments according to the suppliers instructions.

e) Northern blot analysis was performed with 2 μg of poly (A)+ RNA which was electrophoresed on a 1% agarose gel containing 1% formaldehyde. RNA was transferred from the gel to a Hybond N+ membrane (Amersham Pharmacia Biotech) which was then hybridized to selected probes under conditions described for library screening.

EXAMPLE 2

Differential Display Analysis of Colonic Tissue RNA

1. Total RNA (DNAse treated) isolated from up to 32 patient samples was reverse transcribed with one of 12 anchored primers (AP1-12) from the set $T7dT_{12}VN$ to generate one of 12 cDNA samples for each patient sample to be used in subsequent differential display PCR.

where:—T7=the last 17 bp of the T7 primer sequence;

V=the bases A,C or G

N=the bases A,C,G or T

2. An aliquot of each of up to 32 patient cDNA samples was used in subsequent PCR's (Using Applied Biosystems Amplitaq Gold) using the appropriate $T7dT_{12}VN$ primer with one of a series of 20 arbitrary primers comprising the last 16 bp of an M13 primer sequence followed by a 10 bp core annealing sequence.

3. PCR conditions led to 4 cycles of amplification based around core sequence annealing to cDNA template followed by 25 cycles of PCR in which amplicons generated in the first four rounds are exponentially amplified.

4. $\alpha^{32}$P-dATP incorporation into PCR products allowed visualisation after they had been electrophoresed through a large format polyacrylamide gel at 850 volts overnight at 50° C.

5. Gels were then air dried and exposed to X-ray film at room temperature for 24-36 hours. Film images of gels were then examined for bands which were more intense in the adenoma samples as compared to normals. The film was then used as a template to locate the appropriate region on the dried gel and the required bands excised with a scalpel blade.

6. DNA was passively eluted from excised bands in 1×TE solution overnight (TE=10 mMTris-HCl pH7.4, 1 mM EDTA)

7. An aliquot of the eluate was then subjected to further rounds of PCR to generate enough material for cloning and DNA sequence analysis using Big Dye Terminator (Applied Biosystems) chemistry according to manufacturers instructions.

EXAMPLE 3

Real Time PCR Confirmation of Differential Display Clones

1. Sequences isolated from differential display were compared using the BLAST algorithm to sequence databases housed on the National Centre for Biotechnology Information server available on line.

Primer sets were then designed for selected sequences so that accurate measurement of tissue mRNA levels could be determined by quantitative PCR. Total RNA was reverse transcribed into cDNA using an oligo(dT) primer and Superscript II (Invitrogen) enzyme according to standard methods. Each cDNA population was then analyzed by real time PCR using a Corbett Research Rotorgene 2000 and reagents from a SYBR Green PCR Master Mix kit (Applied Biosystems). Cycle thresholds were then computed using Rotorgene 2000 version 4.6 software. The fold elevation in the level of each mRNA was then calculated according to the formula $2^{(Nt-Nc)-(Tt-Tc)}$ where Nt is the cycle threshold for the test gene observed in the normal tissue, Nc is the cycle threshold for the control gene observed in the normal tissue, Tt is the cycle threshold for the test gene in the tumour and Tc is the cycle threshold for the control gene in the tumour. All calculations were performed assuming 100 percent efficiency at each PCR cycle. The control mRNA used to calculate Nc and Tc was β-actin.

EXAMPLE 4 mRNA Expression Analysis for Colorectal Adenomas

Single Marker Analysis (i) Background 67 mRNA sequences were isolated using differential display analysis. The expression level of the Markers was quantified using QRTPCR in 71 tissue samples (21 normal, 20 Tubular Adenoma, 26 Tubulovillous Adenoma, and 4 Villous Adenoma.) This expression data has been tabulated as "fold increase" in expression levels for each adenoma tissue over the mean expression level of Normal tissues, as previously described.

Two analytical approaches have been used to investigate the diagnostic utility of the Markers in Normal and Adenoma Tissues. First, we explored the upregulation for each Marker across the range of tissues in terms of total fold upregulation. Further, cluster analysis was used to assess the utility of the candidate Markers by identifying subsets of the 67 Markers that correctly discriminate between the Normal and Adenoma tissues. For the purposes of this analysis, "Adenoma" tissue includes all histological grades.

(ii) Results

To analyze the Markers individually we rank-ordered each Marker in terms of three criteria: a) average fold upregulation for Adenoma tissues relative to the average Normal expression level, b) the percentage of disease tissues expressing greater than 5-fold upregulation, and c) the percentage of normal tissues expressing greater than 5-fold upregulation.

Average Upregulation

One diagnostic application using these Markers may be to establish a clinically relevant threshold of over-expression for one or more Markers relative to normal colorectal epithelium expression levels. Twenty-eight (28) Markers were determined to yield a five fold or greater average expression for Adenoma tissues relative to the average expression levels of the Normal tissues. A further twenty-six (26) markers were shown to express an average of 2 to 4 fold over the average normal signal. These Markers are listed in Table 3 and Table 4, respectively.

Percent of Disease Tissues Demonstrating Upregulation

To assess the application "Sensitivity" using individual Markers, each Marker clone was ranked according to the percent of Adenoma tissues that would be identified for a given threshold of expression. Twenty-four (24) Markers were shown to express at least five-fold higher in 50% of individual tissues relative to the average Normal expression level. These Markers are listed in Table 5. Using multiple markers from this list in combination yields a higher apparent sensitivity in terms of the number of diseased tissues included and a higher specificity in terms of the percentage of normal tissues excluded.

Percent of Normal Tissues Demonstrating Upregulation

To assess the "Specificity" for individual Markers, we re-evaluated the marker lists identified in Table 3 and Table 5 in light of expression levels also demonstrated for individual Normal Tissues. For this purpose Table 6 and Table 7 combine the sensitivity measures of Tables 3 and 5 with a threshold value of 5-fold over-expression in any individual Normal tissue. The Tables include all such markers that are upregulated greater than 5 fold in less than 20% of Normal tissues. Twenty-five Markers were shown to yield over 5-fold expression in less than 20% of Normal tissues as shown in Table 6. Of these markers in Table 4, twenty-one (21) were also identified as expressing greater than 5-fold in at least 50% of Adenoma tissues while not over-expressing in greater than 20% of Normal tissues. These Markers are listed in Table 7.

EXAMPLE 5 mRNA Expression Analysis for Colorectal Adenomas

Cluster Analysis

Cluster analysis showed that near perfect discrimination (70/71) can be achieved for one set of three markers and six unique sets of four markers.

(i) Methods

This cluster analysis is based on the k-nearest neighbor (KNN) technique described in Li, L., Darden, T., Weinberg, C., Levine, A. and Pedersen, L. (2001) Gene Asssssment and Sample classification for gene expression data using a genetic algorithm/k nearest neighbor method. Combinatorial Chemistry & High Throughput Screening, Vol. 4(8), 727-739. whereby a given Tissue (X) is classified according to the class membership of the k tissues nearest to (X) in n-dimensional space described by expression levels of genes in the Marker set. Tissues were considered unclassified (and "missed") if analysis of the k-nearest neighbors tissues failed to achieve a unanimous result. In this analysis a range of k values was explored (1,2, . . . ,5) and the final results are calculated based k=3. As expected, increasing k values result in lowers numbers of correctly classified tissues.

Successful classification is measured by comparison of the KNN derived tissue class against pathology diagnosis.

The array of expression values for each Marker in each Tissue forms the raw data for cluster analysis.

Diagnostically Useful Marker Sets

A set of markers is determined to be diagnostically useful if that set provides discrimination between tissue classes of interest (e.g. between Normal and Adenoma tissues) across a reasonably large sample of known tissues.

To illustrate this discrimination, it has been shown that the expression levels of two genes, designated clones 8/2d and 11-10a, provide segregation (or classification) between 21 Normal tissues and 50 Adenoma tissues that we have analyzed. Using these two markers, the k-nearest neighbor analysis is able to properly classify 68 out of the total 71 tissues. This classification is demonstrated as follows:

The average level of expression for each marker was calculated relative to the average level of its expression in normal tissue. Each value is then log normalized to give an expression table (Table 8) for the two markers such as:

TABLE 8

| Num | Tissue ID | Type | Log (8/2d Fold ↑) | Log (11/10a Fold ↑) |
|---|---|---|---|---|
| 1 | A1 | Norm | −0.3180 | −1.7505 |
| 2 | A2 | Norm | 0.0797 | 0.3718 |
| 3 | A3 | Norm | 0.6337 | 0.5975 |
| 4 | A4 | Norm | 0.4982 | 0.6487 |
| 5 | A5 | Norm | −0.2363 | −0.0158 |
|  |  |  | ↓ |  |
| 69 | I5 | Adenoma | 1.9401 | 0.4982 |
| 70 | I6 | Adenoma | 1.8498 | 0.4440 |
| 71 | I7 | Adenoma | 2.1840 | 0.3146 |

In this two-marker analysis, each tissue is therefore specified by the (two dimensional) coordinates described by the log values, e.g. Tissue A1: (−0.0318, −1.7505), A2: (0.0797, 0.3718), . . . , I7: (2.1840, 0.3146). Finally the distance is calculated between each tissue to determine which tissues are "nearest" to each other in terms of the chosen markers. For the two dimensional analysis using just the markers 8/2d and 11/10a, this relationship is conveniently visualized in a Cartesian plot of all tissue data points. This plot is shown in FIG. 1.

Visual inspection of this graph clearly shows the relationship between each tissue, and demonstrates the self-clustering between the Normal tissues and Adenoma tissues.

To measure the utility of unique marker sets to provide class discrimination we have chosen the k-nearest neighbor (KNN) metric, where each data point (tissue) is classified according to its k nearest neighbors in the plot space according to the Euclidean distance formula:

$A$ is a point described by the vector, $A = \{\xi_1, \xi_2, \xi_3, \ldots \xi_n\}$, and
$B$ is a point described by the vector, $B = \{\eta_1, \eta_2, \eta_3, \ldots \eta_n\}$, then $$\rho_E(A, B) = \|A - B\| = +\sqrt{\sum_{i=1}^{n} (\xi_i - \eta_i)^2} \quad \text{(positive root only)}$$

To assure a robust clustering analysis we have chosen to use a k value of three (3). In other words, each tissue is calculated to belong to the same class as the three nearest data points in the plot. Next, the calculated tissue class is compared to the known tissue class as defined by histopathology to determine whether the KNN classification is correct for that tissue. If the three nearest tissues do not agree (i.e. one of the neighbors is of a different class to the other two) then the tissue is considered unclassified. Finally, the number of correctly classified tissues is totalled to provide a measure of classification strength for that particular set of markers.

Figure 2:
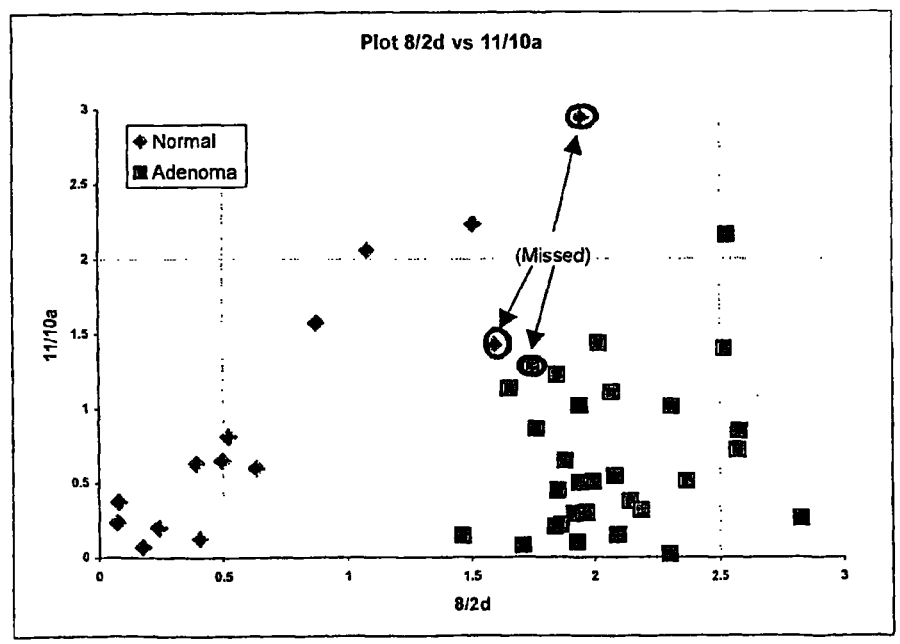

In this plot, only three tissue data points, A7, C5, and H1—two presumed normal tissues and one adenoma, are misclassified using markers 8/2d and 11/10a with this KNN rule yielding a diagnostic accuracy of 96% (68/71). These points are highlighted in FIG. 2.

Using this method, larger marker sets were explored in higher dimensions for clustering potential. By evaluating all possible combinations of three marker sets we have identified one set that is 99% (70/71) accurate. In four dimensions we have identified six unique sets that also achieve 99% accuracy. In all cases, one Normal tissue is missed (A7 in 5 cases, and C5 in 1 case) yielding an apparent sensitivity of 100% (50/50) and specificity of 95% (20/21) for these six sets.

It is instructive to note that this classification technique is not simply a reflection of the average fold upregulation for each marker in adenomas relative to normal tissues. In fact, while the first marker of the pair 8/2d shows relatively large upregulation in Adenomas vs. Normals (ranked $4^{th}$ in the list of 67 markers), tissue 11/10a is not distinguished based on its over-expression alone (ranked $63^{rd}$ of 67 markers). Further, not all highly over-expressed markers demonstrate strong discriminatory power when analyzed by cluster analysis.

Discussion of Tissue Classes

Figure 3:
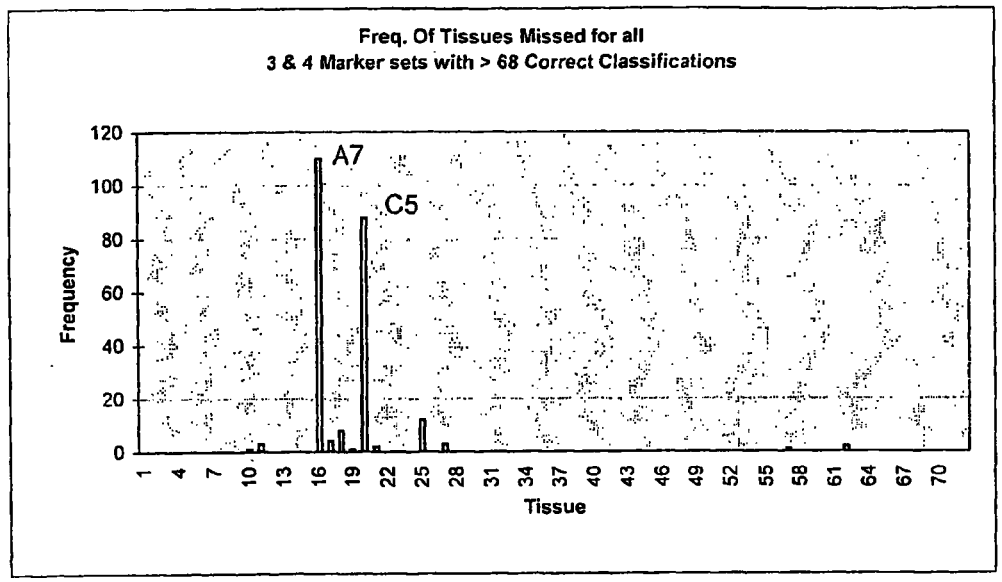
FIG. 3 is a graphical representation of tissues missed by all sets of 3 and 4 markers that provide >=69/71 correct classifications.

All clustering analysis experiments discussed here were performed using the complete set of 71 tissues available. As previously stated, no set of Markers is able to correctly classify all Normal tissues (n=21) and all Adenoma tissues (n=51). In fact, two particular Normal tissues, A7 and C5, are frequently missed using the k=3 nearest neighbor rule. The frequency of tissues missed for all 3 and 4 marker sets that achieve ≥69/71 correct classification is shown in FIG. 3.

This finding demonstrates that, in terms of clustering analysis, these two Tissues yield an expression profile that is more typical of adenoma tissues than for the other healthy tissues in this pool. One hypothesis to support this result is that these two tissues are transcribing an adenoma gene profile that proceeds, or is independent of, the morphological changes evident to the examining pathologist by histological analysis. Current theories of colorectal carcinogenesis suggest that the adenoma-carcinoma cycle is proceeded by field defects, precursors to dysplasia. While field defects have been associated with biochemical changes such as altered enzyme levels involved in proliferation, mucosal tissue sections often show no gross or histopathological changes (Young, G., Rozen, P. and Levin, B., Early Detection and Screening for Colorectal Cancer. (1996.) Saunders, N.Y.). Therefore, it is possible that these tissues are, in fact, not normal but rather represent early adenoma development undetected by previous diagnostic techniques.

(ii) Cluster Results by Vector Size

Sets of 2 Markers

Using a brute-force analysis of all 2,211 possible 2-marker combinations, the highest score achieved was 68/71. This score was achieved with exactly 3 unique sets of Markers: (8/2d-11/10a; 12/2f-11/10a; 12/2f-3/16bC4).

Sets of 3 Markers

Analysis of all 47,905 possible 3 marker combinations yields exactly one set of markers able to identify the near perfect score of (70/71.) (See Table 9.) Exactly 6 and 60 sets of three markers were also able to correctly classify 69/71 and 68/71 tissues, respectively. Subsets yielding 69/71 are shown in Table 11.

Sets of 4 Markers

Analysis of the 766,480 possible four marker combinations yields exactly six unique subsets of markers able to correctly classify (70/71) tissues. (See Table 9.) 108 unique sets of four markers were able to correctly classify (69/71) of the tissues. (See Table 13.)

Sets of 5 or Greater Markers

As the problem space for all possible five marker combinations for 67 Markers approaches 10 million, a brute-force analysis of all combinations is not practical. To analyze sets of Markers greater than five elements, a genetic algorithm was used to search the n-dimensional expression landscape for optimum or near optimum Marker sets.

Using this technique Marker sets of 5, 8, 12 and 15 Markers were explored by cluster analysis. In data collected, a number of near perfect (70/71) solution sets have been identified, however no combination has been identified that is able to perfectly classify all 71 markers.

EXAMPLE 6

Summary of Partially or Fully Characterised Adenoma Markers

Figure 4:
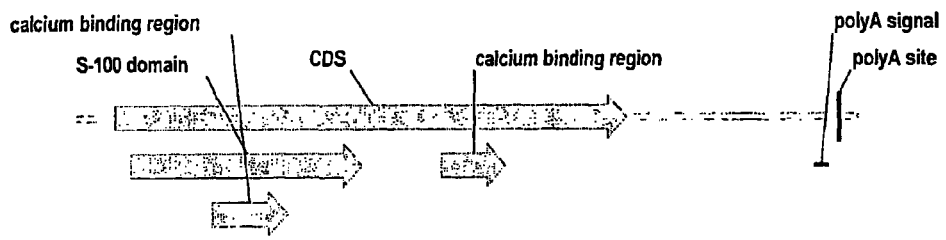
FIG. 4 is a schematic representation of an annotated view of S100P.
Figure 5:
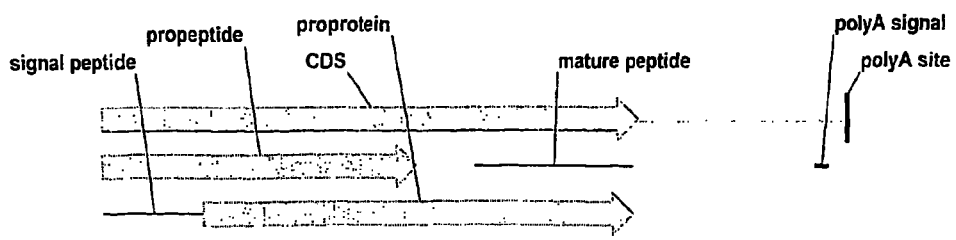
FIG. 5 is a schematic representation of an annotated view of Defensin α-6.

S100 Calcium Binding Protein P (S100P) (Seq Id Nos: 62 and 63)
Genbank accession: NM005980
Chromosome location: 4p16
Original Citation:
  Becker T, Gerke V, Kube E and Weber K. S100P, a novel Ca(2+)-binding protein from human placenta. cDNA cloning, recombinant protein expression and Ca2+ binding properties. Eur. J. Biochem. 207 (2), 541-547 (1992).
Transcript size: 439 bp
Annotated view: FIG. 4
Genbank protein accession: NP005971
Protein size: 95aa
Description:
  The protein encoded by this gene is a member of the S100 family of proteins containing 2 EF-hand calcium-binding motifs. S100 proteins are localized in the cytoplasm and/or nucleus of a wide range of cells, and are involved in the regulation of cellular processes such as cell cycle progression and differentiation. S100 genes include at least 13 members which are located as a cluster on chromosome 1q21. However, this gene is located at 4p16. This protein, in addition to binding Ca2+, also binds Zn2+ and Mg2+. S100p is up-regulated in inflammatory diseases of the bowel such as Crohn's disease and ulcerative colitis and overexpression has been linked to breast and prostate cancer progression using model systems Defensin α-6 (Paneth Cell-Specific) (Seq Id No: 49 and 50)
Genbank accession: NM001926
Chromosome location: 8pter-8p21
Original Citation:
  Jones D E and Bevins C L. Defensin-6 mRNA in human Paneth cells: implications for antimicrobial peptides in host defense of the human bowel. FEBS Lett. 315 (2), 187-192 (1993).
Annotated view: FIG. 5
Transcript size: 475 bp
Genbank protein accession: NP001917
Protein size: 100aa
Description:
  Defensins are a family of antimicrobial and cytotoxic peptides thought to be involved in host defense. They are abundant in phagocytic cells of haemopoietic origin and two forms (defensin α-5 and defensin α-6) are found in the secretory granules of Paneth cells in the small intestine. The genes for the haemopoietic and enteric defensins are located in the same region of chromosome 8. The finding of an abundant defensin α-6 mRNA in human Paneth cells supports the notion that these epithelial cells may play a key role in peptide-based host defense of the bowel. Defensin α-6 is over-expressed in Crohn's disease.

Figure 6:
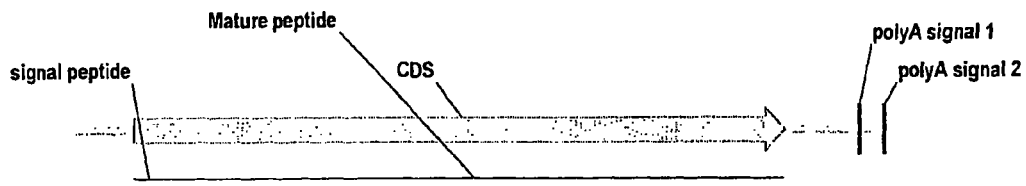
FIG. 6 is a schematic representation of an annotated view of GIF.

Gastric Intrinsic Factor (GIF) (Seq Id No 43 and 44)
Genbank accession: NM005142
Chromosome location: 11q13
Original Citation:
  Hewitt J E, Gordon M M, Taggart R T, Mohandas T K and Alpers D H. Human gastric intrinsic factor: characterization of cDNA and genomic clones and localization to human chromosome 11. Genomics 10 (2), 432-440 (1991)
Annotated view: FIG. 6
Transcript size: 1584 bp
Genbank protein accession: NP005133
Protein size: 417aa
Description:
  Gastric intrinsic factor (GIF) is a glycoprotein secreted by parietal cells of the gastric mucosa. GIF mediates transmembrane transport of Vitamin $B_{12}$ via receptors that function as oligomers in the plasma membrane. GIF-mediated import of Vitamin $B_{12}$ is limited to the apical membranes of epithelial cells. Deficiency of GIF results in pernicious anaemia.

Figure 7:
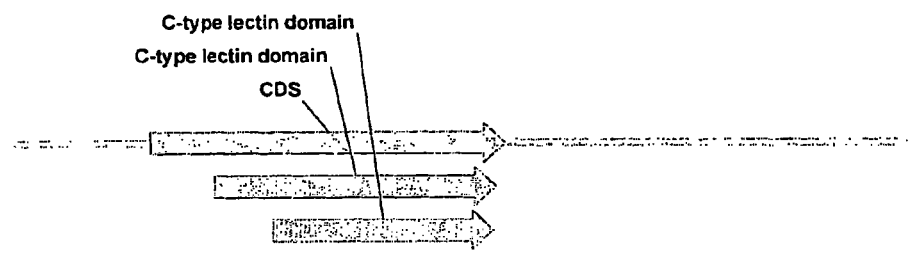
FIG. 7 is a schematic representation of an annotated view of Reg IV.

Regenerating Protein IV (RegIV) (Seq Id No: 38 and 39)
Genbank accession: NM032044
Chromosome location: 1q12-q21
Original Citation:
  Hartupee J C, Zhang H, Bonaldo M F, Soares M B and Dieckgraefe B K. Isolation and characterization of a cDNA encoding a novel member of the human regenerating protein family: Reg IV(1) Biochem. Biophys. Acta 1518 (3), 287-293 (2001).
Annotated view: FIG. 7
Transcript size: 1200 bp
Genbank protein accession: NP114433
Protein size: 158aa
Description:
  Reg and Reg-related genes constitute a multi-gene family belonging to the calcium (C-type) dependent lectin superfamily. Regenerating gene family members are expressed in the proximal gastrointestinal tract and ectopically at other sites in the setting of tissue injury. Reg IV has a highly restricted tissue expression pattern, with prominent expression in the gastrointestinal tract. Reg IV mRNA expression is significantly up-regulated by mucosal injury from active Crohn's disease or ulcerative colitis. Members of the Reg gene family are known to be up-regulated in colon carcinogenesis.

Figure 8:
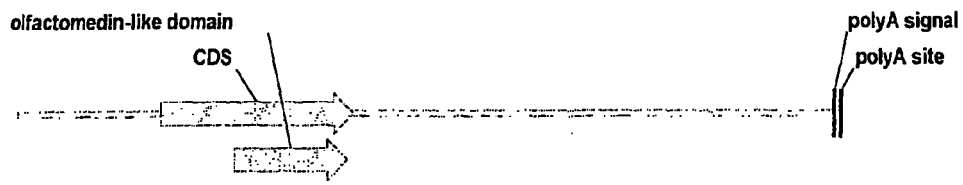
FIG. 8 is a schematic representation of an annotated view of GW112.

GW112 Protein (Seq Id No: 60 and 61)
Genbank accession: NM006418
Chromosome location: 13q14.2
Original Citation:
  Shinozaki S, Nakamura T, Iimura M, Kato Y, Iizuka B, Kobayashi M. and Hayashi N. Upregulation of Reg 1alpha and GW112 in the epithelium of inflamed colonic mucosa Gut 48 (5), 623-629 (2001).
Annotated view: FIG. 8
Transcript size: 2840 bp
Genbank protein accession: NP006409
Protein size: 218aa
Description:
  This gene was originally cloned from human myeloblasts and currently its function is unknown. GW112 is selectively expressed in inflamed colonic epithelium.

Claudin-2 (Seq Id No: 2 and 3)
Level of overexpression in adenomas: 250-fold
Genbank accession: NM020384

Figure 9:
FIG. 9 is a schematic representation of an annotated view of Claudin-2.
Figure 10:
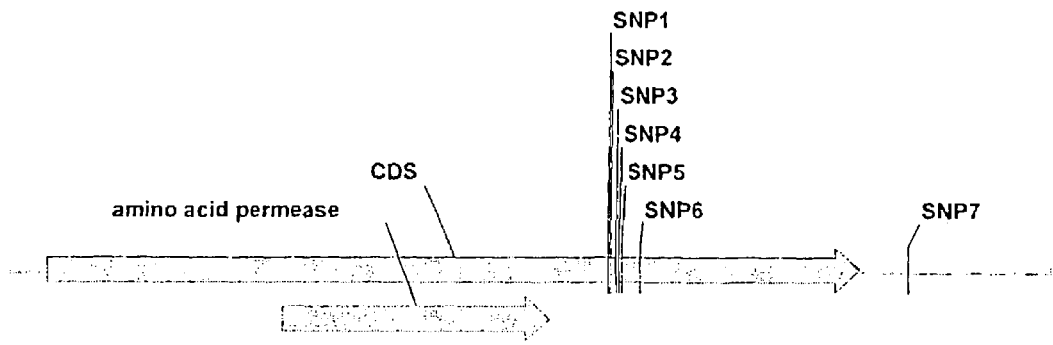
FIG. 10 is a schematic representation of an annotated view of SLC12A2.
Figure 11:
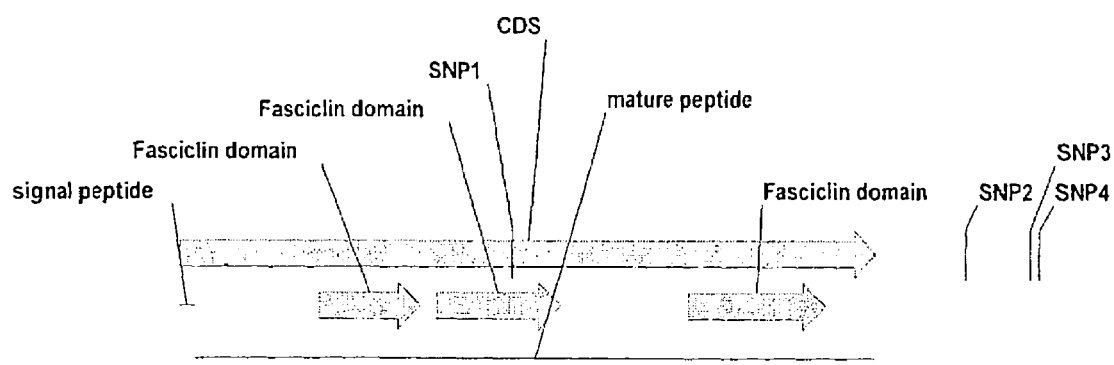
FIG. 11 is a schematic representation of an annotated view of TGFBI.
Figure 12:
FIG. 12 is a schematic representation of an annotated view of Transposon L1.1.

Chromosome location: Xq22.3-23
Annotated view: FIG. 9
Transcript size: 2782 bp
Genbank protein accession: NP065117
Protein size: 230aa
Description:
The claudins are a large family of transmembrane proteins that are part of the tight junction complex and they regulate epithelial barriers by forming structural components of a paracellular pore. Claudin-2 is found in the tight junctions of kidney, liver and intestine and is also involved in maintaining the blood-CSF barrier. The claudin-2 gene contains binding sites for and can be regulated by intestinal specific Cdx homeodomain proteins.
Solute Carrier Family 12, Member 2 (SLC12A2) (Seq Id No: 66 and 67)
Level of overexpression in adenomas: 30-fold
Genbank accession: NM001046
Chromosome location: 5q23.3
Original Citation:
Payne J A, Xu J C, Haas M, Lytle C Y, Ward D and Forbush B. Primary structure, functional expression, and chromosomal localization of the bumetamide-sensitive Na—K—Cl cotransporter in human colon. J. Biol. Chem. 270 (30), 17977-17985 (1995).
Annotated view: FIG. 10
Transcript size: 4375 bp
Genbank protein accession: NP001037
Protein size: 1212aa
Description:
Members of the solute carrier family are Na—K—Cl cotransporters and are important for the maintenance of water and electrolyte homeostasis and aid trans-cellular movement of sodium, potassium and chloride ions in both secretory and absorptive epithelia. Expression has been observed in the thick ascending limb of the Loop of Henle in mammalian kidney and a diverse array of secretory epithelia including the intestine. It is known to exist in two forms, with polarized membrane distribution, being exclusively basolateral in distribution within secretory epithelia, while in absorptive epithelia it is observed to localise to the apical membrane. It should be noted that the above reference denotes the characterisation of the basolateral isoform of the cotransporter from a human colonic cell line.
Transforming Growth Factor, Beta Induced (TGFBI) (Seq Id No: 56 and 57)
Level of overexpression in adenomas: 10-fold
Genbank accession: NM000358
Chromosome location: 5q31
Original Citation:
Skonier J, Neubauer M, Madisen L, Bennett K, Plowman G D and Purchio A F. cDNA cloning and sequence analysis of beta ig-h3, a novel gene induced in a human adenocarcinomna cell line after treatment with transforming growth factor-beta. DNA Cell Biol. 11 (7), 511-522 (1992).
Annotated view: FIG. 11
Transcript size: 2691 bp
Genbank protein accession: NP000349
Protein size: 683aa
Description:
Transforming growth factor, beta induced (TGFBI) is a protein which is induced in many cell types by TGF-β1 and is probably involved in mediating some of the signals of this growth modulator. TGFBI contains an amino-terminal secretory sequence and a ligand recognition site for several integrins at the carboxy-terminus. The TGFBI gene is located on chromosome 5q31, a region frequently deleted in preleukemic myelodysplasia and leukemia. The retinoblastoma gene protein (RB1) is known to negatively regulate the TGFBI gene as a mechanism to suppress cell growth. TGFBI has previously been shown to be up-regulated ≥20-fold in adenomatous and cancerous colonic epithelium. Six autosomal dominant corneal dystrophies are also caused by mutations in the TGFBI gene.
Transposon L1.1 (Seq Id No: 32, 33 and 34)
Level of overexpression in adenomas: 10-fold
Genbank accession: M80340
Chromosome location: not applicable
Original Citation:
Dombroski B A. Mathias S L, Nanthakumar E, Scott A F, Kazazian H H Jr. Isolation of an active human transposable element. Science 254(5039), 1805-1808 (1991).
Annotated view: FIG. 12
Transcript size: 6075 bp
Genbank protein accession: CDS1: AAA51621; CDS2: AAA51622
Protein size: CDS1: 41aa CDS2: 1275aa
Description:
L1 elements are retrotransposons and number from 20,000 to 50,000 in mammalian genomes making them a major component of highly repetitive DNA. A copy of the L1 element is made by the cellular RNA polymerase and is converted into double stranded DNA by a reverse transcriptase gene contained within the transposon. This copy is then inserted elsewhere in the genome. Transposable elements are thought to play an important role in evolution by creating new mutations and gene combinations and provide a mechanism to rapidly reorganise the genome. L1 elements may also be responsible for abnormal DNA rearrangement leading to carcinogenesis.
Overlapping Transcripts
The following sets of clones have been identified to overlap, at the nucleotide level, in part:
1-1d and 1-1g
11-20e and 3-19e
2-12f and 3-13e
8-12b and 5-12a
11-1 lb and 5-13E and 2-13B
2-17H and 2-17I-5
3-5C-3 and 3-19J-1 and 5-18F-2 and 5-19I Without limiting the present invention in any way, these overlapping nucleic acids may represent overlapping portions of the same transcript or they may represent the existence of multiple alternative transcripts, such as splice variants.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

| Markers with > 4.5 fold upregulation | | |
| --- | --- | --- |
| Rank | Clone Name | Fold Upregulation |
| 1 | 8-7bi | 296 |
| 2 | 11-10e | 246 |
| 3 | 11-5b | 141 |
| 4 | 8-2d | 50 |
| 5 | 12-2f | 45 |
| 6 | 4-14b | 33 |
| 7 | 6-12a | 30 |

TABLE 3-continued

Markers with > 4.5 fold upregulation

| Rank | Clone Name | Fold Upregulation |
|---|---|---|
| 8 | 1-6aii | 29 |
| 9 | 2-1c | 27 |
| 10 | 7-13b | 21 |
| 11 | 12-7c | 20 |
| 12 | 5-14j | 17 |
| 13 | 5-4a | 15 |
| 14 | 11-10b | 12 |
| 15 | 8-19a | 11 |
| 16 | 6-12b | 10 |
| 17 | 5-13d | 9 |
| 18 | 9-8a | 9 |
| 19 | 4-11e | 8 |
| 20 | 9-2d | 8 |
| 21 | 11-2d | 8 |
| 22 | 3-2c | 7 |
| 23 | 3-12eclone3 | 6 |
| 24 | 4-2a | 6 |
| 25 | 2-13aclone5 | 5 |
| 26 | 1-1g | 5 |
| 27 | 6-10d | 5 |
| 28 | 7-13dclone4 | 5 |

TABLE 4

Markers with 1.5-4.5 fold upregulation

| Rank | Clone Name | Fold Upregulation |
|---|---|---|
| 29 | 9-13c3 | 4 |
| 30 | 8-12b | 4 |
| 31 | humregA | 4 |
| 32 | 9-4gclone5 | 4 |
| 33 | 2-12eclone8 | 4 |
| 34 | 7-12a | 4 |
| 35 | 2-7gclone4 | 3 |
| 36 | 1-1d | 3 |
| 37 | 9-8g | 3 |
| 38 | 6-16a | 3 |
| 39 | 11-20e | 3 |
| 40 | 3-19e | 3 |
| 41 | 2-1g | 3 |
| 42 | 4-18d | 3 |
| 43 | 3-12a | 2 |
| 44 | 9-8f2clone5 | 2 |
| 45 | 5-2g | 2 |
| 46 | 3-5cclone4 | 2 |
| 47 | 3-16k | 2 |
| 48 | 8-17a | 2 |
| 49 | 6-18dclone7 | 2 |
| 50 | 5-2f | 2 |
| 51 | 6-17a | 2 |
| 52 | 2-10b | 2 |
| 53 | 2-12f | 2 |
| 54 | 2-5d | 2 |

TABLE 5

Markers with greater than 50% tissues upregulated greater than 5-fold

| Rank | Clone Name | % Disease > 5 Fold |
|---|---|---|
| 1 | 11-10e | 100% |
| 2 | 11-5b | 100% |
| 3 | 8-2d | 100% |
| 4 | 12-2f | 100% |
| 5 | 8-7bi | 96% |
| 6 | 4-14b | 94% |
| 7 | 5-4a | 94% |
| 8 | 1-6aii | 90% |
| 9 | 6-12a | 88% |
| 10 | 7-13b | 86% |
| 11 | 5-14j | 82% |
| 12 | 2-1c | 80% |
| 13 | 12-7c | 80% |
| 14 | 3-2c | 75% |
| 15 | 11-10b | 74% |
| 16 | 5-13d | 74% |
| 17 | 9-2d | 73% |
| 18 | 9-8a | 72% |
| 19 | 4-11e | 69% |
| 20 | 6-12b | 68% |
| 21 | 8-19a | 61% |
| 22 | 11-2d | 60% |
| 23 | 3-12eclone3 | 59% |
| 24 | 4-2a | 52% |

TABLE 6

Markers overexpressed > 5 fold AND with Normal tissues expressing less than 20% > 5 fold

| Rank | Clone Name | Fold Upregulation | % Normals > 5 fold |
|---|---|---|---|
| 1 | 11-10e | 246 | 14% |
| 2 | 11-5b | 141 | 14% |
| 3 | 8-2d | 50 | 19% |
| 4 | 12-2f | 45 | 19% |
| 5 | 4-14b | 33 | 14% |
| 6 | 6-12a | 30 | 19% |
| 7 | 1-6aii | 29 | 19% |
| 8 | 2-1c | 27 | 5% |
| 9 | 7-13b | 21 | 5% |
| 10 | 12-7c | 20 | 14% |
| 11 | 5-14j | 17 | 14% |
| 12 | 5-4a | 15 | 14% |
| 13 | 11-10b | 12 | 19% |
| 14 | 8-19a | 11 | 14% |
| 15 | 5-13d | 9 | 14% |
| 16 | 4-11e | 8 | 10% |
| 17 | 9-2d | 8 | 19% |
| 18 | 11-2d | 8 | 19% |
| 19 | 3-2c | 7 | 19% |
| 20 | 3-12eclone3 | 6 | 0% |
| 21 | 4-2a | 6 | 19% |
| 22 | 2-13aclone5 | 5 | 10% |
| 23 | 1-1g | 5 | 10% |
| 24 | 6-10d | 5 | 5% |
| 25 | 7-13dclone4 | 5 | 10% |

TABLE 7

Markers over-expressed > 5 fold in at least 50% of Adenoma tissues AND less than 20% of all Normal tissues

| Rank | Clone Name | % Disease > 5 fold | % Normals > 5 fold |
|---|---|---|---|
| 1 | 11-10e | 100% | 14% |
| 2 | 11-5b | 100% | 14% |
| 3 | 8-2d | 100% | 19% |
| 4 | 12-2f | 100% | 19% |
| 5 | 4-14b | 94% | 14% |
| 6 | 5-4a | 94% | 14% |
| 7 | 1-6aii | 90% | 19% |
| 8 | 6-12a | 88% | 19% |
| 9 | 7-13b | 86% | 5% |
| 10 | 5-14j | 82% | 14% |
| 11 | 2-1c | 80% | 5% |
| 12 | 12-7c | 80% | 14% |
| 13 | 3-2c | 75% | 19% |
| 14 | 5-13d | 74% | 14% |
| 15 | 11-10b | 74% | 19% |

TABLE 7-continued

Markers over-expressed > 5 fold in at least 50% of Adenoma tissues AND less than 20% of all Normal tissues

| Rank | Clone Name | % Disease > 5 fold | % Normals > 5 fold |
|---|---|---|---|
| 16 | 9-2d | 73% | 19% |
| 17 | 4-11e | 69% | 10% |
| 18 | 8-19a | 61% | 14% |
| 19 | 11-2d | 60% | 19% |
| 20 | 3-12eclone3 | 59% | 0% |
| 21 | 4-2a | 52% | 19% |

TABLE 9

Marker sets able to classify 70/71 tissues in groups of 3 & 4.

| Rank | Clone Name | | | |
|---|---|---|---|---|
| 1 | 8-2d | 4-14b | 4-18e | |
| 2 | 8-2d | 4-14b | 6-18dclone7 | 6-16a |
| 3 | 8-2d | 4-14b | 6-18dclone7 | 5-2g |
| 4 | 8-2d | 4-14b | 3-12eclone3 | 11-10a |
| 5 | 8-2d | 4-14b | 4-18e | 5-2g |
| 6 | 8-2d | 4-14b | 4-18e | 2-12f |
| 7 | 12-2f | 4-14b | 6-16a | 11-10a |

TABLE 10

Markers useful for classifying 70/71 in groups of 3 & 4

| (rank) | Clone Name |
|---|---|
| 1 | 8-2d (12-2f) |
| 2 | 4-14b |
| 3 | 4-18e |
| 4 | 6-18d Clone 7 |
| 5 | 6-16a |
| 6 | 5-2g |
| 7 | 11-10a |
| 8 | 3-12e Clone 3 (2-12f) |

TABLE 11

Marker sets of 3 able to classify 69/71 tissues

| Rank | Clone Name | | |
|---|---|---|---|
| 1 | 12-2f | 9-13c3 | 3-10eclone6 |
| 2 | 8-2d | 9-13c3 | 3-10eclone6 |
| 3 | 8-2d | 9-13c3 | 8-17a |
| 4 | 12-2f | 4-14b | 4-18e |
| 5 | 8-2d | 4-14b | 11-10a |
| 6 | 8-2d | 4-14b | 6-18dclone7 |

TABLE 12

Markers Useful for classifying 69/71 tissues in groups of 3

| (Rank) | Clone Name |
|---|---|
| 9 | 9-13c3 |
| 10 | 3-10e Clone 6 |
| 11 | 8-17a |

TABLE 13

Marker sets of 4 able to classify 69/71 tissues

| Rank | Clone Name | | | |
|---|---|---|---|---|
| 1 | 8-7bi | 8-2d | 4-14b | 11-10a |
| 2 | 8-2d | 1-6aii | 4-14b | 6-18dclone7 |
| 3 | 8-2d | 1-6aii | 4-18d | 11-10a |
| 4 | 8-2d | 12-2f | 4-14b | 6-18dclone7 |
| 5 | 8-2d | 12-2f | 4-14b | 9-8jsclone4 |
| 6 | 8-2d | 12-2f | 4-14b | 4-18e |
| 7 | 8-2d | 12-2f | 4-14b | 11-10a |
| 8 | 8-2d | 12-2f | 2-1c | 11-10a |
| 9 | 8-2d | 12-2f | 6-18dclone7 | 6-10d |
| 10 | 8-2d | 12-2f | 6-18dclone7 | 3-10eclone6 |
| 11 | 8-2d | 4-14b | 2-1c | 6-18dclone7 |
| 12 | 8-2d | 4-14b | 2-1c | 4-18e |
| 13 | 8-2d | 4-14b | 2-1c | 11-10a |
| 14 | 8-2d | 4-14b | 6-12b | 4-18e |
| 15 | 8-2d | 4-14b | 6-12b | 11-10a |
| 16 | 8-2d | 4-14b | 8-19a | 6-18dclone7 |
| 17 | 8-2d | 4-14b | 8-19a | 4-18e |
| 18 | 8-2d | 4-14b | 8-19a | 11-10a |
| 19 | 8-2d | 4-14b | 5-13d | 11-10a |
| 20 | 8-2d | 4-14b | 4-11e | 11-10a |
| 21 | 8-2d | 4-14b | 2-13aclone5 | 6-18dclone7 |
| 22 | 8-2d | 4-14b | 2-13aclone5 | 9-8jsclone4 |
| 23 | 8-2d | 4-14b | 2-13aclone5 | 4-18e |
| 24 | 8-2d | 4-14b | 2-13aclone5 | 11-10a |
| 25 | 8-2d | 4-14b | 6-18dclone7 | 4-18e |
| 26 | 8-2d | 4-14b | 6-18dclone7 | 2-12f |
| 27 | 8-2d | 4-14b | 6-18dclone7 | 11-10a |
| 28 | 8-2d | 4-14b | 6-18dclone7 | 2-5d |
| 29 | 8-2d | 4-14b | 1-1g | 11-10a |
| 30 | 8-2d | 4-14b | 6-16a | 4-18e |
| 31 | 8-2d | 4-14b | 6-16a | 11-10a |
| 32 | 8-2d | 4-14b | 3-12eclone3 | 9-8jsclone4 |
| 33 | 8-2d | 4-14b | 3-12eclone3 | 2-18fclone5 |
| 34 | 8-2d | 4-14b | 7-13dclone4 | 11-10a |
| 35 | 8-2d | 4-14b | 9-4gclone5 | 11-10a |
| 36 | 8-2d | 4-14b | 8-12b | 4-18e |
| 37 | 8-2d | 4-14b | 8-12b | 11-10a |
| 38 | 8-2d | 4-14b | 2-7gclone4 | 11-10a |
| 39 | 8-2d | 4-14b | 4-18e | 2-5d |
| 40 | 8-2d | 4-14b | 4-18e | 8-16b |
| 41 | 8-2d | 4-14b | 9-8g | 11-10a |
| 42 | 8-2d | 4-14b | 5-2g | 11-10a |
| 43 | 8-2d | 4-14b | 11-20e | 11-10a |
| 44 | 8-2d | 4-14b | 6-16cclone1 | 11-10a |
| 45 | 8-2d | 4-14b | 2-12f | 11-10a |
| 46 | 8-2d | 8-19a | 6-18dclone7 | 1-1d |
| 47 | 8-2d | 8-19a | 6-16a | 3-10eclone6 |
| 48 | 8-2d | 3-2c | 6-10d | 3-16bclone4 |
| 49 | 8-2d | 2-13aclone5 | 7-13dclone4 | 3-10eclone6 |
| 50 | 8-2d | 6-18dclone7 | 8-12b | 3-10eclone6 |
| 51 | 8-2d | 6-10d | 3-12eclone3 | 3-10eclone6 |
| 52 | 8-2d | 6-10d | 7-13dclone4 | 3-10eclone6 |
| 53 | 8-2d | 6-10d | 8-12b | 3-16bclone4 |
| 54 | 8-2d | 6-10d | 9-8g | 3-16bclone4 |
| 55 | 8-2d | 6-10d | 3-10eclone6 | 2-5d |
| 56 | 8-2d | 3-12eclone3 | 9-13c3 | 3-10eclone6 |
| 57 | 8-2d | 9-13c3 | 8-17a | 2-12f |
| 58 | 8-2d | 9-13c3 | 9-8g | 3-10eclone6 |
| 59 | 8-2d | 9-13c3 | 2-12f | 3-10eclone6 |
| 60 | 8-2d | 8-12b | 2-12f | 3-10eclone6 |
| 61 | 1-6aii | 12-2f | 4-14b | 6-18dclone7 |
| 62 | 1-6aii | 12-2f | 4-14b | 4-18e |
| 63 | 1-6aii | 12-2f | 4-14b | 11-10a |
| 64 | 1-6aii | 12-2f | 8-19a | 6-18dclone7 |
| 65 | 1-6aii | 12-2f | 9-8g | 3-10eclone6 |
| 66 | 1-6aii | 12-2f | 4-18d | 11-10a |
| 67 | 12-2f | 4-14b | 2-1c | 6-18dclone7 |
| 68 | 12-2f | 4-14b | 2-1c | 6-16cclone1 |
| 69 | 12-2f | 4-14b | 2-1c | 11-10a |
| 70 | 12-2f | 4-14b | 5-13d | 11-10a |
| 71 | 12-2f | 4-14b | 4-11e | 11-10a |
| 72 | 12-2f | 4-14b | 2-13aclone5 | 11-10a |
| 73 | 12-2f | 4-14b | 6-18dclone7 | 5-2g |
| 74 | 12-2f | 4-14b | 6-16a | 9-8jsclone4 |
| 75 | 12-2f | 4-14b | 3-12eclone3 | 2-18fclone5 |
| 76 | 12-2f | 4-14b | 3-12eclone3 | 11-10a |

TABLE 13-continued

Marker sets of 4 able to classify 69/71 tissues

| Rank | | Clone Name | | |
|---|---|---|---|---|
| 77 | 12-2f | 4-14b | 9-13c3 | 11-10a |
| 78 | 12-2f | 4-14b | 8-12b | 4-18e |
| 79 | 12-2f | 4-14b | 4-18e | 5-2g |
| 80 | 12-2f | 4-14b | 5-2g | 11-10a |
| 81 | 12-2f | 4-14b | 11-10a | 8-16b |
| 82 | 12-2f | 2-1c | 6-10d | 3-10eclone6 |
| 83 | 12-2f | 11-10b | 4-11e | 3-16bclone4 |
| 84 | 12-2f | 9-2d | 11-2d | 3-10eclone6 |
| 85 | 12-2f | 3-2c | 4-11e | 3-16bclone4 |
| 86 | 12-2f | 5-13d | 6-10d | 3-10eclone6 |
| 87 | 12-2f | 5-13d | 3-12eclone3 | 12-17a |
| 88 | 12-2f | 2-13aclone5 | 6-10d | 4-18e |
| 89 | 12-2f | 2-13aclone5 | 6-10d | 3-16bclone4 |
| 90 | 12-2f | 2-13aclone5 | 7-13dclone4 | 3-10eclone6 |
| 91 | 12-2f | 6-18dclone7 | 9-13c3 | 3-16bclone4 |
| 92 | 12-2f | 6-18dclone7 | 9-13c3 | 2-12f |
| 93 | 12-2f | 6-18dclone7 | 9-13c3 | 8-16b |
| 94 | 12-2f | 6-10d | 9-13c3 | 4-18e |
| 95 | 12-2f | 6-10d | 7-13dclone4 | 3-10eclone6 |
| 96 | 12-2f | 6-10d | 8-12b | 3-10eclone6 |
| 97 | 12-2f | 6-10d | 5-2g | 3-10eclone6 |
| 98 | 12-2f | 6-10d | 3-16bclone4 | 3-10eclone6 |
| 99 | 12-2f | 3-12eclone3 | 9-13c3 | 3-10eclone6 |
| 100 | 12-2f | 3-12eclone3 | 4-17d | 3-10eclone6 |
| 101 | 12-2f | 9-13c3 | 7-13dclone4 | 3-10eclone6 |
| 102 | 12-2f | 9-13c3 | 8-12b | 3-10eclone6 |
| 103 | 12-2f | 9-13c3 | 9-8g | 3-10eclone6 |
| 104 | 12-2f | 9-13c3 | 5-2g | 3-10eclone6 |
| 105 | 12-2f | 9-13c3 | 2-12f | 3-10eclone6 |
| 106 | 12-2f | 9-13c3 | 2-12f | 11-10a |
| 107 | 12-2f | 7-13dclone4 | 4-18e | 9-8g |
| 108 | 12-2f | 7-13dclone4 | 9-8g | 3-10eclone6 |

TABLE 14

Markers Useful for classifying 69/71 tissues in groups of 4

| (rank) | Clone Name |
|---|---|
| 12 | 6-10d |
| 13 | 2-13a Clone 5 |
| 14 | 1-6a ii |
| 15 | 2-1c |
| 16 | 7-13d Clone 4 |
| 17 | 8-12b |
| 18 | 3-16b Clone 4 |
| 19 | 9-8g |
| 20 | 8-19a |
| 21 | 5-13d (4-11e) |
| 22 | 9-8js Clone4 |
| 23 | 2-5d |
| 24 | 8-16b |
| 25 | 6-12b |
| 26 | 3-2c (11-10b, 9-2d, 11-2d) |
| 27 | 4-18d |
| 28 | 2-18f Clone 5 |
| 29 | 6-16c Clone 1 |
| 30 | 8-7 bi |
| 31 | 1-1g |
| 32 | 9-4g Clone5 |
| 33 | 2-7g Clone 4 |
| 34 | 1-1d |
| 35 | 11-20e |
| 36 | 4-17d |
| 37 | 12-17a |

TABLE 15

Marker sets of 3 that provide perfect classification of all tissues (69/69)

| Rank | | Clone Name | |
|---|---|---|---|
| 1 | 8-2d | 5-13d | 3-10eClone6 |
| 2 | 8-2d | 4-11e | 3-10eClone6 |
| 3 | 8-2d | 6-10d | 3-10eClone6 |
| 4 | 8-2d | 9-13c3 | 3-10eClone6 |
| 5 | 12-2f | 5-13d | 3-10eClone6 |
| 6 | 12-2f | 4-11e | 3-10eClone6 |
| 7 | 12-2f | 2-13aclone5 | 3-10eClone6 |
| 8 | 12-2f | 4-14b | 3-10eClone6 |

BIBLIOGRAPHY

Alon, A., Barkai, N., Nottermnan, D. A., Gish, K., Ybarra, S., Mach, D. and Levine, A. J. *Proc. Natl. Acad. Sci. USA:* 96, 6745-6750, June 1999

Becker T, Gerke V, Kube E and Weber K. *Eur. J. Biochem.* 207 (2), 541-547 (1992).

Bonner etal (1973) *J. Mol. Biol.* 81:123

Dombroski B A, Mathias S L, Nanthakumar E, Scott A F, Kazazian H H Jr. *Science* 254(5039), 1805-1808 (1991).

Douillard and Hoffman, Basic Facts about Hybridomas, in *Compendium of Immunology* Vol II, ed. by Schwartz, 1981;

Hartupee J C, Zhang H, Bonaldo M F, Soares M B and Dieckgraefe B K. *Biochem. Biophys. Acta* 1518 (3), 287-293 (2001).

Hewitt J E, Gordon M M, Taggart R T, Mohandas T K and Alpers D H. *Genomics* 10 (2), 432-440 (1991)

Kohler and Milstein, *Nature* 256: 495-499, 1975

Jones D E and Bevins C L. *FEBS Lett.* 315 (2), 187-192 (1993).

Kohonen. T. (1995) Self-Organizing Maps. Springer Verlad, Berlin. 17-18.

Li, L., Darden, T., Weinberg, C. Levine, A. and Pedersen, L. (2001) Gene Assessment and Sample classification for gene expression data using a genetic algorithm/k nearest neighbor method. Combinatorial Chemistry & High Throughput Screening, Vol. 4(8), 727-739.

Moore, A., Basilion, J., Chiocca, e., and Weissleder, R., Measuring Transferrin Receptor Gene Expression by NMR Imaging. BBA, 1402:239-249, 1988

Payne J A, Xu J C, Haas M, Lytle C Y, Ward D and Forbush B. *J. Biol. Chem.* 270 (30), 17977-17985 (1995).

Shinozaki S, Nakamura T, Iimura M, Kato Y, Iizuka B, Kobayashi M. and Hayashi N. Upregulation of Reg 1alpha and GW112 in the epithelium of inflamed colonic mucosa Gut 48 (5), 623-629 (2001).

Skonier J, Neubauer M, Madisen L, Bennett K, Plowman G D and Purchio A F. *DNA Cell Biol.* 11 (7), 511-522 (1992).

Wedemeyer, N., Potter, T., Wetzlich, S. and Gohde, W. Flow Cytometric Quantification of Competitive Reverse Transcriptase-PCR products, Clinical Chemistry 48:9 1398-1405, 2002

Weissleder, R., Moore, A., Ph. D., Mahmood-Bhorade, U., Benveniste, H., Chiocca, E. A., Basilion, J. P. High resolution in vivo imaging of transgene expression, Nature Medicine, 6:351-355, 200

Young, G., Rozen, P. and Levin, B., Early Detection and Screening for Colorectal Cancer. (1996.) Saunders, N.Y.

Young, G. P., Rozen, P. and Levin, B. Chapter 3: How Does Colorectal Cancer Develop? Colorectal cancer in Clinical Practice, Ed. Rozen, P., Young, G. P., Levin, P., Spann, S. J. Martin Dunitz 2002

The invention claimed is:

1. A method for determining an increased likelihood of the presence of colorectal adenoma in a human, said method comprising measuring the level of an mRNA which comprises the RNA equivalent of SEQ ID NO: 7 in a gastrointestinal tract sample from said human and determining an increased likelihood of the presence of colorectal adenoma when the level of said mRNA is increased in said human relative to the normal level of said mRNA in gastrointestinal tract samples from healthy individuals.

2. A method for determining an increased likelihood of the presence of colorectal adenoma in a human, said method comprising measuring the level of an mRNA which comprises the RNA equivalent of SEQ ID NO: 7 in a gastrointestinal tract sample from said human;

detecting the expression of at least one nucleic acid molecule in a blood, serum, stool or gastrointestinal tract sample, wherein said at least one nucleic acid molecule is selected from the following:

(i) nucleic acid molecules comprising a nucleotide sequence as set forth in any one of SEQ ID NOs: 1-2, SEQ ID NOs: 4-6, SEQ ID NOs: 8-32, SEQ ID NOs: 35-37, SEQ ID NO: 38, SEQ ID NOs: 40-43, SEQ ID NOs: 45-49, SEQ ID NOs: 51-56, SEQ ID NOs: 58-60, SEQ ID NO: 62, SEQ ID NOs: 64-66, SEQ ID NOs: 68-72 or SEQ ID NOs: 337-338; or (ii) a nucleic acid molecule comprising a nucleotide sequence complementary to any one or more of the sequences of (i); and determining an increased likelihood of the presence of colorectal adenoma when the level of said mRNA is increased in said human relative to the normal level of said mRNA in gastrointestinal tract samples from healthy individuals and when the expression of said at least one nucleic acid molecule is detected.

3. The method according to claim 2, wherein said at least one nucleic acid molecule includes two nucleic acid molecules which comprise a nucleotide sequence selected from the group consisting of SEQ ID NO: 14, SEQ ID NO: 16, SEQ ID NO: 24, SEQ ID NO: 65, SEQ ID NO: 19, SEQ ID NO: 1, SEQ ID NO: 53, SEQ ID NO: 72, SEQ ID NO: 11 and SEQ ID NO: 26.

4. The method according to claim 3, wherein said two nucleic acid molecules comprise the following nucleotide sequences, respectively:

(i) SEQ ID NO: 72 and SEQ ID NO: 11;
(ii) SEQ ID NO: 72 and SEQ ID NO: 26;
(iii) SEQ ID NO: 14 and SEQ ID NO: 16;
(iv) SEQ ID NO: 14 and SEQ ID NO: 1;
(v) SEQ ID NO: 14 and SEQ ID NO: 24; or
(vi) SEQ ID NO: 14 and SEQ ID NO: 16.

5. The method according to claim 2, wherein said at least one nucleic acid molecule includes two nucleic acid molecules which comprise the following nucleotide sequences, respectively:

(i) SEQ ID NO: 56 and SEQ ID NO: 11;
(ii) SEQ ID NO: 64 and SEQ ID NO: 11;
(iii) SEQ ID NO: 72 and SEQ ID NO: 11;
(iv) SEQ ID NO: 9 and SEQ ID NO: 11; or
(v) SEQ ID NO: 14 and SEQ ID NO: 11.

6. The method according to claim 2, wherein said at least one nucleic acid molecule includes three nucleic acid molecules which comprise a nucleotide sequence selected from the group consisting of SEQ ID NOs: 4-6, SEQ ID NO: 9, SEQ ID NO: 13, SEQ ID NO: 15, SEQ ID NOs: 21-22, SEQ ID NOs: 27-29, SEQ ID NOs: 30-31, SEQ ID NO: 36, SEQ ID NOs: 37-38, SEQ ID NO: 40, SEQ ID NO: 43, SEQ ID NOs: 48-49, SEQ ID NO: 52, SEQ ID NO: 56, SEQ ID NO: 59, SEQ ID NO: 64, SEQ ID NOs: 68-69, SEQ ID NO: 71 and SEQ ID NO: 337.

7. The method according to claim 2, wherein said at least one nucleic acid molecule includes three nucleic acid molecules which comprise the following nucleotide sequences, respectively:
(i) SEQ ID NO: 14, SEQ ID NO: 24 and SEQ ID NO: 65;
(ii) SEQ ID NO: 14, SEQ ID NO: 24 and SEQ ID NO: 19;
(iii) SEQ ID NO: 14, SEQ ID NO: 53 and SEQ ID NO: 1;
(iv) SEQ ID NO: 14, SEQ ID NO: 16 and SEQ ID NO: 19;
(v) SEQ ID NO: 14, SEQ ID NO: 16 and SEQ ID NO: 46; or
(vi) SEQ ID NO: 14, SEQ ID NO: 65 and SEQ ID NO: 1.

8. The method according to claim 2, wherein said at least one nucleic acid molecule includes at least three nucleic acid molecules which comprise the following nucleotide sequences, respectively:
(i) SEQ ID NO: 30, SEQ ID NO: 14 and SEQ ID NO: 1;
(ii) SEQ ID NO: 43, SEQ ID NO: 14 and SEQ ID NO: 24;
(iii) SEQ ID NO: 43, SEQ ID NO: 59 and SEQ ID NO: 1;
(iv) SEQ ID NO: 14, SEQ ID NO: 49 and SEQ ID NO: 24;
(v) SEQ ID NO: 14, SEQ ID NO: 49 and SEQ ID NO: 16;
(vi) SEQ ID NO: 14, SEQ ID NO: 49 and SEQ ID NO: 1;
(vii) SEQ ID NO: 14, SEQ ID NO: 21 and SEQ ID NO: 16;
(viii) SEQ ID NO: 14, SEQ ID NO: 21 and SEQ ID NO: 1;
(ix) SEQ ID NO: 14, SEQ ID NOs: 27-29 and SEQ ID NO: 24;
(x) SEQ ID NO: 14, SEQ ID NOs: 27-29 and SEQ ID NO: 16;
(xi) SEQ ID NO: 14, SEQ ID NOs: 27-29 and SEQ ID NO: 1;
(xii) SEQ ID NO: 14, SEQ ID NO: 56 and SEQ ID NO: 1;
(xiii) SEQ ID NO: 14, SEQ ID NO: 9 and SEQ ID NO: 24;
(xiv) SEQ ID NO: 14, SEQ ID NO: 9 and SEQ ID NO: 37;
(xv) SEQ ID NO: 14, SEQ ID NO: 9 and SEQ ID NO: 16;
(xvi) SEQ ID NO: 14, SEQ ID NO: 9 and SEQ ID NO: 1;
(xvii) SEQ ID NO: 14, SEQ ID NO: 24 and SEQ ID NO: 16;
(xviii) SEQ ID NO: 14, SEQ ID NO: 24 and SEQ ID NO: 46;
(xix) SEQ ID NO: 14, SEQ ID NO: 24 and SEQ ID NO: 1; or
(xx) SEQ ID NO: 14, SEQ ID NO: 24 and SEQ ID NO: 337.

9. The method according to claim 2, wherein said at least one nucleic acid molecule includes at least three nucleic acid molecules which comprise the following nucleotide sequences, respectively:
(i) SEQ ID NO: 14, SEQ ID NO: 5 and SEQ ID NO: 1;
(ii) SEQ ID NO: 14, SEQ ID NO: 65 and SEQ ID NO: 16;
(iii) SEQ ID NO: 14, SEQ ID NO: 65 and SEQ ID NO: 1;
(iv) SEQ ID NO: 14, SEQ ID NO: 53 and SEQ ID NO: 37;
(v) SEQ ID NO: 14, SEQ ID NO: 53 and SEQ ID NO: 48;
(vi) SEQ ID NO: 14, SEQ ID NO: 68 and SEQ ID NO: 1;
(vii) SEQ ID NO: 14, SEQ ID NO: 31 and SEQ ID NO: 1;
(viii) SEQ ID NO: 14, SEQ ID NO: 69 and SEQ ID NO: 16;
(ix) SEQ ID NO: 14, SEQ ID NO: 69 and SEQ ID NO: 1;
(x) SEQ ID NO: 14, SEQ ID NO: 52 and SEQ ID NO: 1;
(xi) SEQ ID NO: 14, SEQ ID NO: 16 and SEQ ID NO: 337;
(xii) SEQ ID NO: 14, SEQ ID NO: 16 and SEQ ID NO: 71;
(xiii) SEQ ID NO: 14, SEQ ID NO: 36 and SEQ ID NO: 1;
(xiv) SEQ ID NO: 14, SEQ ID NO: 19 and SEQ ID NO: 1;
(xv) SEQ ID NO: 14, SEQ ID NO: 40 and SEQ ID NO: 1;
(xvi) SEQ ID NO: 14, SEQ ID NO: 22 and SEQ ID NO: 1;
(xvii) SEQ ID NO: 14, SEQ ID NO: 46 and SEQ ID NO: 1;
(xviii) SEQ ID NOs: 27-29, SEQ ID NO: 24 and SEQ ID NO: 4;
(xix) SEQ ID NOs: 27-29, SEQ ID NO: 65 and SEQ ID NO: 11; or
(xx) SEQ ID NO: 38, SEQ ID NO: 64 and SEQ ID NO: 13.

10. The method according to claim 2, wherein said at least one nucleic acid molecule includes at least three nucleic acid molecules which comprise the following nucleotide sequences, respectively:
(i) SEQ ID NO: 9, SEQ ID NO: 68 and SEQ ID NO: 11;
(ii) SEQ ID NO: 24, SEQ ID NO: 69 and SEQ ID NO: 11;
(iii) SEQ ID NO: 64, SEQ ID NO: 53 and SEQ ID NO: 11;
(iv) SEQ ID NO: 64, SEQ ID NO: 68 and SEQ ID NO: 11;
(v) SEQ ID NO: 64, SEQ ID NO: 69 and SEQ ID NO: 13;
(vi) SEQ ID NO: 64, SEQ ID NO: 36 and SEQ ID NO: 13;
(vii) SEQ ID NO: 64, SEQ ID NO: 11 and SEQ ID NO: 337;
(viii) SEQ ID NO: 53, SEQ ID NO: 72 and SEQ ID NO: 11;
(ix) SEQ ID NO: 72, SEQ ID NO: 26 and SEQ ID NO: 46;
(x) SEQ ID NO: 72, SEQ ID NO: 36 and SEQ ID NO: 11;
(xi) SEQ ID NO: 72, SEQ ID NO: 46 and SEQ ID NO: 11;
(xii) SEQ ID NO: 69, SEQ ID NO: 46 and SEQ ID NO: 11;
(xiii) SEQ ID NO: 43, SEQ ID NO: 14 and SEQ ID NO: 24;
(xiv) SEQ ID NO: 43, SEQ ID NO: 14 and SEQ ID NO: 16;
(xv) SEQ ID NO: 43, SEQ ID NO: 14 and SEQ ID NO: 1;
(xvi) SEQ ID NO: 43, SEQ ID NOs: 27-29 and SEQ ID NO: 24;
(xvii) SEQ ID NO: 43, SEQ ID NO: 36 and SEQ ID NO: 11;
(xviii) SEQ ID NO: 43, SEQ ID NO: 59 and SEQ ID NO: 1;
(xix) SEQ ID NO: 14, SEQ ID NO: 49 and SEQ ID NO: 24; or
(xx) SEQ ID NO: 14, SEQ ID NO: 49 and SEQ ID NO: 22.

11. The method according to claim 2, wherein said at least one nucleic acid molecule includes three nucleic acid molecules which comprise the following nucleotide sequences, respectively:
(i) SEQ ID NO: 14, SEQ ID NO: 49 and SEQ ID NO: 1;
(ii) SEQ ID NO: 14, SEQ ID NO: 56 and SEQ ID NO: 1;
(iii) SEQ ID NO: 14, SEQ ID NO: 56 and SEQ ID NO: 1;
(iv) SEQ ID NO: 14, SEQ ID NO: 9 and SEQ ID NO: 1;
(v) SEQ ID NO: 14, SEQ ID NO: 24 and SEQ ID NO: 19;
(vi) SEQ ID NO: 14, SEQ ID NO: 65 and SEQ ID NO: 37;
(vii) SEQ ID NO: 14, SEQ ID NO: 53 and SEQ ID NO: 48;
(viii) SEQ ID NO: 14, SEQ ID NO: 53 and SEQ ID NO: 1;
(ix) SEQ ID NO: 14, SEQ ID NO: 72 and SEQ ID NO: 1;
(x) SEQ ID NO: 14, SEQ ID NO: 69 and SEQ ID NO: 16;
(xi) SEQ ID NO: 14, SEQ ID NO: 16 and SEQ ID NO: 19;
(xii) SEQ ID NO: 14, SEQ ID NO: 19 and SEQ ID NO: 1;
(xiii) SEQ ID NO: 14, SEQ ID NO: 1 and SEQ ID NO: 71;
(xiv) SEQ ID NO: 49, SEQ ID NO: 64 and SEQ ID NO: 11;
(xv) SEQ ID NO: 38, SEQ ID NO: 56 and SEQ ID NO: 13;
(xvi) SEQ ID NO: 38, SEQ ID NO: 56 and SEQ ID NO: 13;
(xvii) SEQ ID NO: 56, SEQ ID NO: 64 and SEQ ID NO: 11;
(xviii) SEQ ID NO: 56, SEQ ID NO: 53 and SEQ ID NO: 6;
(xix) SEQ ID NO: 9, SEQ ID NO: 64 and SEQ ID NO: 16; or
(xx) SEQ ID NO: 9, SEQ ID NO: 64 and SEQ ID NO: 13.

12. The method according to claim 2, wherein said at least one nucleic acid molecule includes three nucleic acid molecules which comprise the following nucleotide sequences, respectively:
(i) SEQ ID NO: 9, SEQ ID NO: 68 and SEQ ID NO: 11;
(ii) SEQ ID NO: 24, SEQ ID NO: 72 and SEQ ID NO: 13;
(iii) SEQ ID NO: 24, SEQ ID NO: 72 and SEQ ID NO: 46;
(iv) SEQ ID NO: 24, SEQ ID NO: 72 and SEQ ID NO: 71;
(v) SEQ ID NO: 64, SEQ ID NO: 72 and SEQ ID NO: 16;
(vi) SEQ ID NO: 64, SEQ ID NO: 68 and SEQ ID NO: 11;
(vii) SEQ ID NO: 64, SEQ ID NO: 69 and SEQ ID NO: 11;
(viii) SEQ ID NO: 64, SEQ ID NO: 19 and SEQ ID NO: 11;
(ix) SEQ ID NO: 64, SEQ ID NO: 13 and SEQ ID NO: 11;
(x) SEQ ID NO: 53, SEQ ID NO: 72 and SEQ ID NO: 11;
(xi) SEQ ID NO: 53, SEQ ID NO: 15 and SEQ ID NO: 11;
(xii) SEQ ID NO: 72, SEQ ID NO: 68 and SEQ ID NO: 11;
(xiii) SEQ ID NO: 72, SEQ ID NO: 69 and SEQ ID NO: 11;
(xiv) SEQ ID NO: 72, SEQ ID NO: 36 and SEQ ID NO: 11;
(xv) SEQ ID NO: 72, SEQ ID NO: 19 and SEQ ID NO: 11;
(xvi) SEQ ID NO: 72, SEQ ID NO: 46 and SEQ ID NO: 11;
(xvii) SEQ ID NO: 72, SEQ ID NO: 46 and SEQ ID NO: 1;
(xviii) SEQ ID NO: 68, SEQ ID NO: 16 and SEQ ID NO: 36; or
(xix) SEQ ID NO: 68, SEQ ID NO: 36 and SEQ ID NO: 11.

13. The method according to claim 2 wherein said detecting is directed to the expression product of said at least one nucleic acid molecule.

14. The method according to any one of claims 1 to 13, wherein said colorectal adenoma is a tubular adenoma, tubulovillous adenoma or villous adenoma.

* * * * *